(12) United States Patent
Kowalski et al.

(10) Patent No.: US 8,450,317 B2
(45) Date of Patent: May 28, 2013

(54) CXCR3 RECEPTOR ANTAGONISTS

(75) Inventors: Jennifer A. Kowalski, New Milford, CT (US); Daniel Richard Marshall, Norwalk, CT (US); Anthony S. Prokopowicz, III, Stormville, NY (US); Sabine Schlyer, New Milford, CT (US); Robert Sibley, North Haven, CT (US); Ronald John Sorcek, Bethel, CT (US); Di Wu, Danbury, CT (US); Frank Wu, Ridgefield, CT (US); Erick Richard Roush Young, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 260 days.

(21) Appl. No.: 12/768,268

(22) Filed: Apr. 27, 2010

(65) Prior Publication Data

US 2010/0280028 A1 Nov. 4, 2010

Related U.S. Application Data

(60) Provisional application No. 61/172,873, filed on Apr. 27, 2009, provisional application No. 61/319,482, filed on Mar. 31, 2010.

(51) Int. Cl.
*C07D 239/34* (2006.01)
*C07D 239/42* (2006.01)
*A61K 31/506* (2006.01)

(52) U.S. Cl.
USPC .............. 514/235.8; 514/252.18; 514/253.05; 514/253.06; 514/254.04; 514/254.05; 514/254.1; 544/121; 544/295; 544/363; 544/369; 544/370; 544/386

(58) Field of Classification Search
USPC ................. 544/121, 295, 363, 369, 370, 386; 514/235.8, 252.18, 253.05, 253.06, 254.04, 514/254.05, 254.1
See application file for complete search history.

(56) References Cited

U.S. PATENT DOCUMENTS

| | | |
|---|---|---|
| 2004/0192728 A1 | 9/2004 | Codd et al. |
| 2009/0099201 A1 | 4/2009 | Bolin et al. |
| 2009/0286766 A1 | 11/2009 | Sugasawa et al. |
| 2010/0273781 A1 | 10/2010 | Ginn et al. |
| 2013/0029971 A1 | 1/2013 | Ginn et al. |

FOREIGN PATENT DOCUMENTS

| | | |
|---|---|---|
| EP | 1505068 A1 | 2/2005 |
| EP | 2009005 A1 | 12/2008 |
| WO | WO 03/048164 * | 6/2003 |
| WO | 2007002742 A1 | 1/2007 |
| WO | WO 2007/100610 * | 9/2007 |
| WO | 2007123269 A1 | 11/2007 |
| WO | 2007127635 A2 | 11/2007 |
| WO | 2008054702 A1 | 5/2008 |
| WO | 2008148849 A2 | 12/2008 |
| WO | WO 2009/074300 * | 6/2009 |
| WO | 2009105435 A1 | 8/2009 |
| WO | 2010126811 A1 | 11/2010 |
| WO | 2010126851 A1 | 11/2010 |
| WO | 2011084985 A1 | 7/2011 |

OTHER PUBLICATIONS

Havlioglu et al., Slit Proteins potential endogenous modulators of inflammation, Neurovirology, 8, pp. 486-495, 2002.*
Chemical Abstract by IUPAC Chemical Data Series, http://www.iupac.org/goldbook/A00228.pdf (1997) p. 1.
Chemical Abstract by IUPAC Chemical Data Series, http://www.iupac.org/goldbook/A00464.pdf (1997) p. 1.
Chemical Abstract Registry No. 1025924-29-1, entered into the Registry File on Jun. 6, 2008, supplied by ChemZoo, Inc., p. 1.
Chemical Abstract Registry Na 1115906-32-5, entered into the Registry File on Mar. 5, 2009, supplied by Chemical Abstract Service, Columbus, Ohio, US p. 1.
Chemical Abstract Registry No. 1115906-35-8, entered into the Registry File on Mar. 5, 2009, supplied by Chemical Abstract Service, Columbus, Ohio, US p. 1.
Chemical Abstract Registry No. 1242874-28-7, entered into the Registry File on Sep. 27, 2010 supplied by Chemical Abstract Service, Columbus, Ohio, US p. 1.
Chemical Abstract Registry No. 1252349-95-3, entered into the Registry File on Nov. 10, 2010, supplied by Chemical Abstract Service, Columbus, Ohio, US p. 1.
Chemical Abstract Registry No. 903856-50-8, entered into the Registry File on Aug. 23, 2006, supplied by Chemical Abstract Service, Columbus, Ohio, US p. 1.
Chemical Abstract Registry No. 903858-09-3, entered into the Registry File on Aug. 23, 2006, supplied by Chemical Abstract Service, Columbus, Ohio, US p. 1.
Cheng, Cliff C., et al.; Puridine Carboxamides: Potent Palm Site Inhibitors of HCV NS5B Polymerase; ACS Medicinal Chemistry Letters (2010) vol. 1, No. 9 pp. 466-471.
International Search Report and Written Opinion for PCT/US2011/020191 mailed Apr. 12, 2011.
International Search Report for PCT/US2010/032347 mailed Jul. 23, 2010.
International Search Report for PCT/US2010/032477 mailed Jul. 16, 2010.

(Continued)

*Primary Examiner* — Deepak Rao
(74) *Attorney, Agent, or Firm* — Michael P. Morris; Edward S. Lazer

(57) ABSTRACT

The present invention relates to compounds of formula (I):

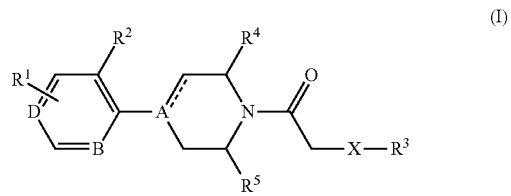

and pharmaceutically acceptable salts thereof, wherein $R^1$ to $R^5$, A, B, D and X are as defined herein. The invention also relates to pharmaceutical compositions comprising these compounds, methods of using these compounds in the treatment of various diseases and disorders, processes for preparing these compounds and intermediates useful in these processes.

5 Claims, No Drawings

OTHER PUBLICATIONS

Pease, James E., et al.; Chemokine Receptor Antagonists: Part 2; Expert Opinion on Therapeutic Patents (2009) vol. 19, No. 2 pp. 199-221.

Shin, Youseung, et al; Synthesis and SAR or Piperazine Amides as Novel c-jun N-Terminal Kinase (JNK) Inhibitors; Bioorganic & Medicinal Chemistry Letters (2009) vol. 19 pp. 3344-3347.

* cited by examiner

CXCR3 RECEPTOR ANTAGONISTS

FIELD OF THE INVENTION

This invention relates to heterocyclic compounds that are useful as antagonists of CXCR3 and are thus useful for treating a variety of diseases and disorders that are mediated or sustained through the interaction of CXCR3 and its ligands including multiple sclerosis, psoriasis, rheumatoid arthritis, inflammatory bowel disease and atherosclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemokine receptors, a subclass of the G-protein coupled receptors (GPCRs) are expressed on the surface of T-cells and other leukocytes. The interaction of chemokine receptors with their ligands plays an important role in the migration of leukocytes to sites of inflammation (A. D. Luster, New Engl. J. Med., 1998, 338, 436). The chemokine receptor CXCR3 is preferentially expressed on T helper (Th1) cells but is also found on natural killer cells and subsets of dendritic cells. Three major chemokine ligands for CXCR3 have been identified: Mig (Monokine Induced by γ-IFN/CXCL9), IP-10 (γ-interferon inducible protein) and I-TAC (IFN-Inducible T Cell α Chemoattractant/CXCR11) (K. E. Cole et al., J. Exp. Med., 1998, 187, 2009; Y. Weng et al., J. Biol. Chem., 1998, 273, 18288).

Histological evaluations of numerous inflammatory lesions, including those from patients with multiple sclerosis (T. L. Sorenson et al., J. Clin. Invest., 1999, 103, 807), rheumatoid arthritis (S. Qin et al., J. Clin. Invest., 1998, 101, 746), psoriasis (J. Flier et al., J. Pathol., 2001, 194, 398) and inflammatory bowel disease (Y. H. Yuan et al., Inflamm. Bowel Dis., 2001, 7, 281) have shown elevated expression of CXCR3 ligands accompanied by an increased frequency of T cells bearing CXCR3. This is in marked contrast to what is found in most normal tissues, where expression of CXCR3 and its ligands is extremely low. This correlative evidence suggests a role of CXCR3 in Th1-mediated chronic inflammation.

Studies with CXCR3 and IP-10 deficient mice also suggest a role for CXCR3 and IP-10 in Th1 mediated disease. For example, in one study CXCR3−/− mice showed significant resistance to allograft rejection (W. W. Hancock et al., J. Exp. Med., 2000, 192, 1515). In another study, IP-10 deficient mice showed protection against the development of colitis (U. P. Singh et al., J. Immunol., 2003, 171, 1401). Further evidence of a role for CXCR3 and IP-10 as mediators of disease is provided by studies utilizing blocking antibodies. For example in a rat model of adjuvant induced arthritis (I. Salomon et al., J. Immunol., 2002, 169, 2685) a DNA vaccine approach to overexpress self IP-10 was used to induce the production of self-IP-10 antibodies. These Abs are specific for IP-10 and do not cross react with other proinflammatory cytokines or chemokines including Mig and I-TAC. Pretreatment with this vaccine protected rats from the development of severe arthritis and reduced the time to remission of symptoms. In addition, affinity purified anti-IP-10 from vaccinated rats could therapeutically transfer protection to newly diseased rats. In another study, this vaccine approach was successful in suppressing disease in a mouse model of multiple sclerosis (G. Wildbaum et al., J. Immunol., 2002, 168, 5885).

In a study of pulmonary inflammation, (N. Li et al., Acta Pharmacol. Sinica, 2008, 29, 14) CXCR3 knockout mice showed alleviated inflammation compared to wild type mice in cigarette smoke induced pulmonary injury as well as lower influx of inflammatory T cells. Similarly, in a model of nephrotoxic nephritis, CXCR3 knockout mice showed reduced influx of T cells, less severe nephritis and improved renal function compared to wild type mice (U. Panzer et al., J. Am. Soc. Nephrol., 2007, 18, 2071). Thus CXCR3 may play a role in inflammatory pulmonary diseases such as COPD and inflammatory kidney disease.

Studies such as those cited above suggest that inhibitors of CXCR3 may be useful in treating inflammatory and autoimmune diseases in which CXCR3-mediated cellular recruitment plays a role, including multiple sclerosis, psoriasis, rheumatoid arthritis, inflammatory bowel disease, COPD and kidney disease.

Recent work has also implicated CXCR3 in the pathogenesis of atherosclerosis. In one study (F. Mach et al., J. Clin. Invest., 1999, 104, 1041) CXCR3 was found expressed in all T lymphocytes within human atherosclerotic lesions. The ligands IP10, Mig and I-TAC were all found within lesion-associated cells including endothelial and smooth muscle cells (Mig and I-TAC) and macrophages (IP10), suggesting these ligands play a role in recruitment of activated T lymphocytes within vascular wall lesions in atherogenesis. Left untreated and allowed to progress, atherosclerosis can result in narrowing of the lumen of the artery and plaque rupture which can lead to coronary heart disease, myocardial infarction and stroke (J. Sanz and Z. A. Fayad, Nature, 2008, 451, 953).

Further evidence has come from genetic deletion studies in mice. CXCR3 deletion on an ApoE$^{-/-}$ background resulted in a significant reduction in atherosclerotic lesion formation following ten weeks on a high cholesterol diet (N. R. Veillard et al., Circulation, 2005, 112, 870). Moreover, deletion of the CXCR3 ligand, IP-10 on an ApoE$^{-/-}$ background similarly reduced atherosclerotic lesion load (E. Heller et al., Circulation, 2006, 113, 2301). More recently, NBI-74330 a CXCR3 antagonist was dosed prophylactically in a LDL receptor knockout model. Similar to the CXCR3 deletion studies in the ApoE−/− results, NBI-74330 significantly attenuated atherosclerotic lesion formation (E. J. A. van Wanrooij et al., Arterioscler. Thromb. Vasc. Biol., 2008, 28, 251-257).

As a result of studies such as those cited above implicating the interaction of CXCR3 and its ligands in the etiology of various inflammatory and autoimmune diseases as well as atherosclerosis, considerable effort has been directed towards discovering antagonists of this interaction. A number of inhibitors have been reported in the scientific literature, including small molecule antagonists, antibodies and modified ligands (see for example J. C. Medina et al., Ann. Rep. Med. Chem., 2005, 40, 215). However, to date, no CXCR3 antagonist has been approved as a marketed drug.

BRIEF SUMMARY OF THE INVENTION

The present invention provides novel compounds which block the interaction of CXCR3 and its ligands and are thus useful for treating diseases and disorders that are mediated or sustained through the activity of CXCR3 including multiple sclerosis, psoriasis, rheumatoid arthritis, inflammatory bowel disease, COPD, kidney disease and atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest embodiment, the present invention relates compounds of formula (I):

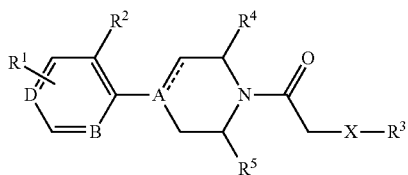

wherein:
A is C or N;
B is C or N;
D is C or N;
X is —NH—, —NHC(O)—, —N(CH$_3$)C(O)— or absent;
R$^1$ is H, —CN, halogen, —CF$_3$, —OCF$_3$, C$_{1-3}$alkyl, C$_{1-3}$alkoxy, —S(O)$_n$CH$_3$, amino, mono- or dimethylamino, —NHC(O)C$_{1-3}$alkyl, —NO$_2$, —C(O)NH$_2$, —C(O)NHC$_{1-3}$alkyl or —C(O)C$_{1-3}$alkyl;
R$^2$ is aryl or heteroaryl, each optionally substituted with one to three R$^6$;
R$^3$ is heteroaryl, heterocyclyl, aryl or C$_{3-10}$cycloalkyl each optionally substituted with one to three R$^7$;
R$^4$ and R$^5$ are each independently selected from H and C$_{1-2}$alkyl; or R$^4$ and R$^5$ may join to form an ethyl bridge;
each R$^6$ is independently —OH, oxo, hydroxyC$_{1-6}$alkyl, halogen, —(CH$_2$)$_m$—CN, nitro, C$_{1-6}$ alkyl, C$_{2-6}$ alkenyl, C$_{2-6}$ alkynyl, C$_{3-10}$ cycloalkyl, C$_{1-6}$ alkoxy, phenoxy, heteroaryl C$_{1-6}$ alkoxycarbonyl, carboxyl, —C(O)C$_{1-6}$alkyl, —(CH$_2$)$_m$—NR$_8$R$_9$, —S(O)$_n$C$_{1-6}$alkyl, —NHS(O)$_n$C$_{1-6}$alkyl, —NR$^8$C(O)C$_{1-6}$alkyl, —S(O)$_2$NR$_8$R$_9$, —C(O)NR$_8$R$_9$, heteroaryl, heterocyclyl, phenyl or benzyl, wherein each alkyl, alkenyl, alkynyl or alkoxy of said R$^6$ is optionally partially or fully halogenated and each heterocyclyl, heteroaryl, phenyl or benzyl of said R$^6$ is optionally substituted with one to three C$_{1-6}$ alkyl, C$_{1-6}$alkoxy(CH$_2$)$_m$, halogen, —CN, —CF$_3$, C$_{1-6}$ acyl, —NR$^8$R$^9$, C(O)NR$^8$R$^9$, —OH, hydroxyC$_{1-6}$alkyl, pyrrolidinyl or —S(O)$_n$C$_{1-6}$alkyl;
each R$^7$ is independently C$_{1-6}$ alkyl, C$_{2-6}$ alkenyl, C$_{2-6}$ alkynyl, C$_{3-10}$ cycloalkyl, C$_{1-6}$ alkoxy, halogen, oxo, —CN, carboxy, —(CH$_2$)$_m$—NR$_8$R$_9$, phenyl or heteroaryl, wherein each alkyl, alkenyl, alkynyl or alkoxy of said R$^7$ is optionally partially or fully halogenated and wherein two R$^7$ on adjacent carbon atoms of R$^3$ may join to form a three to seven member ring fused to R$^3$;
R$^8$ and R$^9$ are each independently hydrogen, C$_{1-6}$ alkyl, C$_{1-6}$ acyl, C$_{3-10}$ cycloalkyl, hydroxyC$_{1-6}$ alkyl, C$_{1-6}$ alkylC$_{1-6}$ alkoxy, C$_{1-6}$ alkylsulfonyl or C$_{1-6}$ alkoxycarbonyl;
m is 0-3;
n is 0-2; and
----- is a single bond if A is N and may be a single or double bond if A is C;
or the pharmaceutically acceptable salts thereof.

In another embodiment there is provided a compound of formula (I) as described above and wherein R$^3$ is aryl or heteroaryl, or the pharmaceutically acceptable salts thereof.

In another embodiment there is provided a compound of formula (I) as described in the broadest embodiment above wherein R$^2$ is aryl, and R$^3$ is aryl or heteroaryl, or the pharmaceutically acceptable salts thereof.

In another embodiment there is provided a compound of formula (I) as described in the broadest embodiment above wherein R$^2$ is heteroaryl, and R$^3$ is aryl or heteroaryl, or the pharmaceutically acceptable salts thereof.

In another embodiment there is provided a compound of formula (I) as described in the broadest embodiment above and wherein:
A is N; and
D is C;
or the pharmaceutically acceptable salts thereof.

In another embodiment there is provided a compound of formula (I) as described above and wherein:
B is C;
X is absent;
or the pharmaceutically acceptable salts thereof.

In another embodiment there is provided a compound of formula (I) as described in the broadest embodiment above and wherein:
B is C;
D is C;
R$^1$ is H, —CN, —F, —Cl, —CF$_3$, —CH$_3$, —OCH$_3$, —C(O)NHCH$_3$ or —S(O)$_2$CH$_3$;
R$^2$ is benzoimidazolyl, benzooxazolyl, benzo[b]thiophenyl, dibenzofuranyl, dibenzothiophenyl, furanyl, imidazolyl, 1H-imidazo[4,5-c]pyridinyl, indolyl, isoindolyl, isoquinolinyl, isoxazolyl, oxazolyl, phenyl, pyranyl, pyrazinyl, pyrazolyl, pyridazinyl, pyridinyl, pyrimidinyl, pyrrolyl, quinolinyl, thiadiazolyl, thiazolyl, thienyl or triazinyl, wherein each of the foregoing is optionally substituted by one to three R$^6$;
R$^3$ is benzoimidazolyl, benzo[d]isothiazolyl, benzo[b]thiophenyl, benzotriazolyl, furanyl, imidazo[4,5-b]pyridinyl, imidazolyl, indazolyl, indolyl, isoindolyl, isoquinolinyl, isothiazolyl, phenyl, phthalazinyl, pyrazolyl, pyridinyl, pyrrolo[2,3-b]pyridinyl, pyrrolo[2,3-c]pyridinyl, pyrrolo[3,2-c]pyridinyl, pyrrolo[3,2-b]pyridinyl, pyrrolo[2,3-d]pyrimidinyl, pyrrolyl, quinazolinyl, thiadiazolyl or thiazolyl wherein each of the foregoing is optionally substituted with one to three R$^7$;
R$^4$ and R$^5$ are H;
each R$^6$ is independently —OH, oxo, hydroxyC$_{1-6}$alkyl, halogen, —(CH$_2$)$_m$—CN, nitro, C$_{1-6}$ alkyl, C$_{2-6}$ alkenyl, C$_{2-6}$ alkynyl, C$_{3-10}$ cycloalkyl, C$_{1-6}$ alkoxy, phenoxy, pyridyloxy, C$_{1-6}$ alkoxycarbonyl, carboxyl, —C(O)C$_{1-6}$alkyl, —(CH$_2$)$_m$—NR$_8$R$_9$, —S(O)$_n$C$_{1-6}$alkyl, —NHS(O)$_2$C$_{1-6}$alkyl, —NHC(O)C$_{1-6}$alkyl, —S(O)$_2$NR$_8$R$_9$, —C(O)NR$_8$R$_9$, thienyl, morpholinyl, pyrroldinyl, piperidinyl, [1,3]-oxazepan-1-yl, piperazinyl, azabicyclo[2.2.1]heptyl, 2-oxa-5-azabicyclo[2.2.1]heptyl, octahydroisoquinolinyl, [1,4]-oxazepanyl, azetidinyl phenyl or benzyl, wherein each alkyl, alkenyl or alkynyl of said R$^6$ is optionally partially or fully halogenated and each heterocyclyl or phenyl of said R$^6$ is optionally substituted with one to three CH$_3$, —OCH$_3$, halogen, —CN, —CF$_3$, —C(O)CH$_3$, NR$^8$R$^9$, —C(O)NH$_2$, —C(O)NHCH$_3$, —OH, —CH$_2$OCH$_3$, —C(OH)(CH$_3$)CH$_3$, —SCH$_3$, pyrrolidinyl or —S(O)$_2$CH$_3$;
each R$^7$ is independently C$_{1-6}$ alkyl, C$_{2-6}$ alkenyl, C$_{2-6}$ alkynyl, C$_{3-10}$ cycloalkyl; alkoxy, halogen, oxo, —CN, carboxy, —(CH$_2$)$_m$—NR$_8$R$_9$, phenyl or pyridyl, wherein each alkyl, alkenyl or alkynyl of said R$^7$ is optionally partially or fully halogenated;
R$^8$ and R$^9$ are each independently hydrogen, C$_{1-6}$ alkyl, C$_{1-6}$ acyl or C$_{3-10}$ cycloalkyl;
or the pharmaceutically acceptable salts thereof.

In another embodiment there is provided a compound of formula (I) as described in the embodiment immediately above and wherein:

A is N;

X is —NH— or absent;

$R^1$ is H, —CN, —F, —Cl, —CF$_3$, —CH$_3$ or —OCH$_3$;

$R^2$ is benzoimidazolyl, benzooxazolyl, imidazolyl, 1H-imidazo[4,5-c]pyridinyl, indolyl, isoindolyl, isoquinolinyl, isoxazolyl, oxazolyl, phenyl, pyrazinyl, pyrazolyl, pyridazinyl, pyridinyl, pyrimidinyl, quinolinyl, thiadiazolyl, thiazolyl or thienyl, wherein each of the foregoing is optionally substituted by one to three $R^6$;

$R^3$ is benzoimidazolyl, benzotriazolyl, imidazolyl, imidazo[4,5-b]pyridinyl, indazolyl, indolyl, isoindolyl, isothiazolyl, pyrazolyl, pyridinyl, pyrrolo[2,3-b]pyridinyl, pyrrolo[2,3-b]pyridinyl, pyrrolo[3,2-c]pyridinyl, pyrrolo[3,2-b]pyridinyl, pyrrolo[2,3-d]pyrimidinyl, pyrrolyl, thiadiazolyl or thiazolyl wherein each of the foregoing is optionally substituted with one to three $R^7$;

each $R^6$ is independently —CH$_2$OH, —Cl, —F, —CN, oxo, C$_{1-6}$ alkyl, C$_{3-6}$ cycloalkyl, C$_{1-2}$ alkoxy, phenoxy, pyridyloxy, —C(O)CH$_3$, —(CH$_2$)$_m$—NR$_8$R$_9$, —S(O)$_n$CH$_3$, —NHS(O)$_2$CH$_3$, _NH(CO)CH$_3$, —S(O)$_2$NR$_8$R$_9$, —C(O)NR$_8$R$_9$, thienyl, morpholinyl, pyrrolidinyl, piperidinyl, [1,3]-oxazepan-1-yl, piperazinyl, phenyl or benzyl, wherein each alkyl of said $R^6$ is optionally partially or fully halogenated and each heterocyclyl or phenyl of said $R^6$ is optionally substituted with one to three CH$_3$, —OCH$_3$, halogen, —CN, —CF$_3$, N(CH$_3$)$_2$, —C(O)NH$_2$, —C(O)NHCH$_3$, —OH, —CH$_2$OCH$_3$, —C(OH)(CH$_3$)CH$_3$, pyrrolidinyl or S(O)$_2$CH$_3$;

each $R^7$ is independently C$_{1-3}$ alkyl, —OCH$_3$, CF$_3$, oxo, —CN, —Cl or —F;

$R^8$ and $R^9$ are each independently hydrogen, C$_{1-6}$ alkyl, C$_{1-3}$ acyl or C$_{3-6}$ cycloalkyl;

or the pharmaceutically acceptable salts thereof.

In another embodiment there is provided a compound of formula (I) as described in the embodiment immediately above and wherein:

X is absent;

$R^3$ is benzoimidazolyl, benzotriazolyl, imidazolyl, imidazo[4,5-b]pyridinyl, indazolyl, indolyl, isoindolyl, pyrazolyl, pyrrolo[2,3-b]pyridinyl, pyrrolo[2,3-b]pyridinyl, pyrrolo[3,2-c]pyridinyl, pyrrolo[3,2-b]pyridinyl or pyrrolyl, wherein each of the foregoing is optionally substituted with one to three $R^7$;

or the pharmaceutically acceptable salts thereof.

The following are representative compounds of the invention which can be made by the methods described in the general synthetic schemes, the synthetic examples, and known methods in the art.

TABLE I

| MOLECULAR STRUCTURE | CHEMICAL NAME | Observed MH+ |
|---|---|---|
| 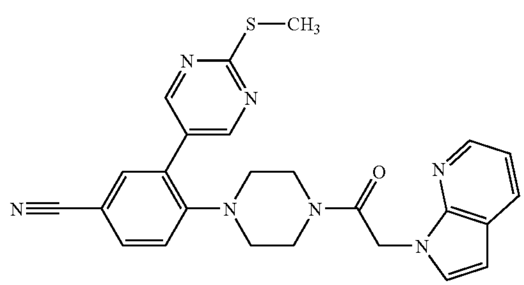 | 3-(2-Methylsulfanyl-pyrimidin-5-yl)-4-[4-(2-pyrrolo[2,3-b]pyridin-1-yl-acetyl)-piperazin-1-yl]-benzonitrile | 471 |
| 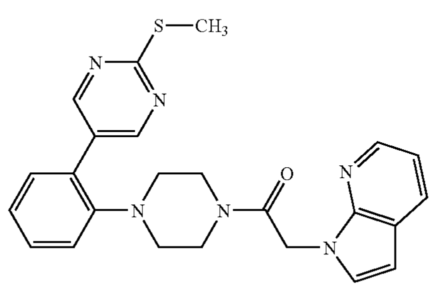 | 1-{4-[2-(2-Methylsulfanyl-pyrimidin-5-yl)-phenyl]-piperazin-1-yl}-2-pyrrolo[2,3-b]pyridin-1-yl-ethanone | 446 |
| 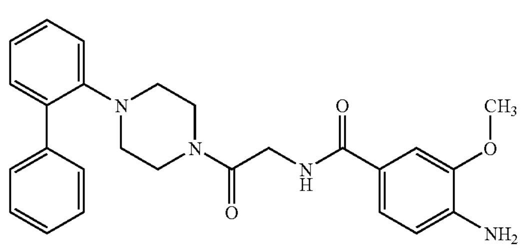 [SMILES: COc1cc(C(=O)NCC(=O)N2CCN(c3ccccc3-c3ccccc3)CC2)ccc1N] | 4-Amino-N-[2-(4-biphenyl-2-yl-piperazin-1-yl)-2-oxo-ethyl]-3-methoxy-benzamide | 446 |

TABLE I-continued

| MOLECULAR STRUCTURE | CHEMICAL NAME | Observed MH+ |
| --- | --- | --- |
| 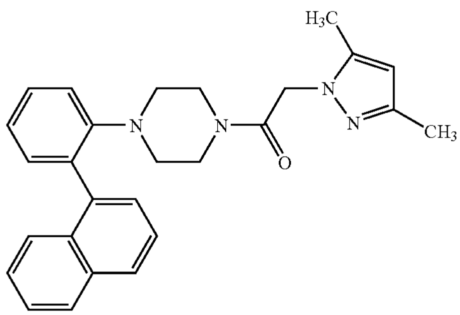 [SMILES: Cc1cc(C)n(CC(=O)N2CCN(c3ccccc3-c3cccc4ccccc34)CC2)n1] | 2-(3,5-Dimethyl-pyrazol-1-yl)-1-[4-(2-naphthalen-1-yl-phenyl)-piperazin-1-yl]-ethanone | 426 |
| 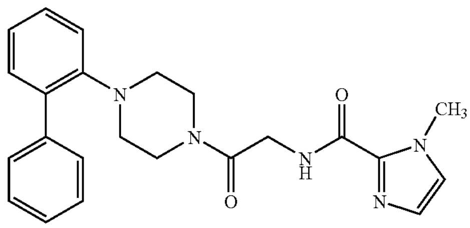 | 1-Methyl-1H-imidazole-2-carboxylic acid [2-(4-biphenyl-2-yl-piperazin-1-yl)-2-oxo-ethyl]-amide | 404 |
| 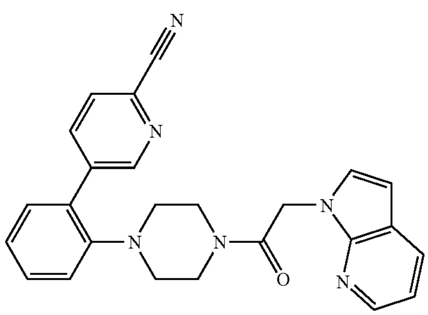 [SMILES: N#Cc1ccc(-c2ccccc2N2CCN(C(=O)Cn3ccc4cccnc43)CC2)cn1] | 5-{2-[4-(2-Pyrrolo[2,3-b]pyridin-1-yl-acetyl)-piperazin-1-yl]-phenyl}-pyridine-2-carbonitrile | 423 |
| 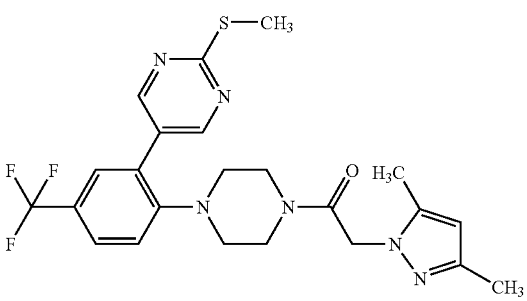 [SMILES: CSc1ncc(-c2cc(C(F)(F)F)ccc2N2CCN(C(=O)Cn3nc(C)cc3C)CC2)cn1] | 2-(3,5-Dimethyl-pyrazol-1-yl)-1-{4-[2-(2-methylsulfanyl-pyrimidin-5-yl)-4-trifluoromethyl-phenyl]-piperazin-1-yl}-ethanone | 492 |
| 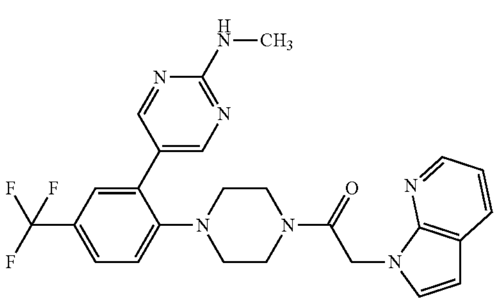 [SMILES: CNc1ncc(-c2cc(C(F)(F)F)ccc2N2CCN(C(=O)Cn3ccc4cccnc43)CC2)cn1] | 1-{4-[2-(2-Methylamino-pyrimidin-5-yl)-4-trifluoromethyl-phenyl]-piperazin-1-yl}-2-pyrrolo[2,3-b]pyridin-1-yl-ethanone | 497 |

TABLE I-continued

| MOLECULAR STRUCTURE | CHEMICAL NAME | Observed MH+ |
|---|---|---|
| 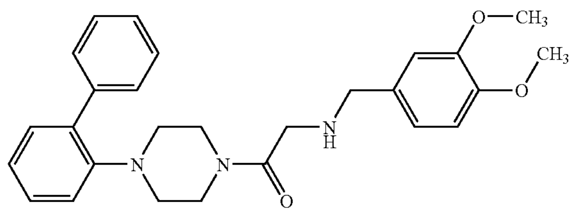 [SMILES: COc1ccc(CNCC(=O)N2CCN(c3ccccc3-c3ccccc3)CC2)cc1OC] | 1-(4-Biphenyl-2-yl-piperazin-1-yl)-2-(3,4-dimethoxy-benzylamino)-ethanone | 447 |
| 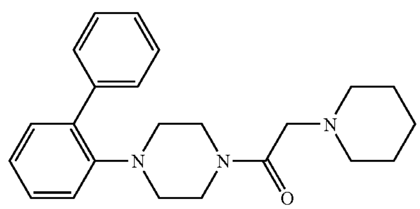 [SMILES: O=C(CN1CCCCC1)N1CCN(c2ccccc2-c2ccccc2)CC1] | 1-(4-Biphenyl-2-yl-piperazin-1-yl)-2-piperidin-1-yl-ethanone | 365 |
| 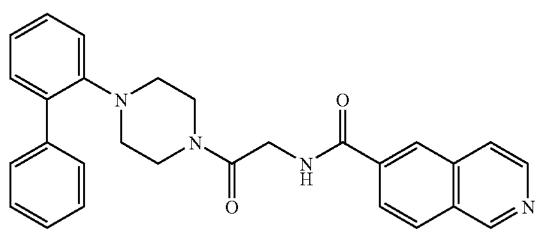 [SMILES: O=C(NCC(=O)N1CCN(c2ccccc2-c2ccccc2)CC1)c1ccc2cnccc2c1] | Isoquinoline-6-carboxylic acid [2-(4-biphenyl-2-yl-piperazin-1-yl)-2-oxo-ethyl]-amide | 451 |
| 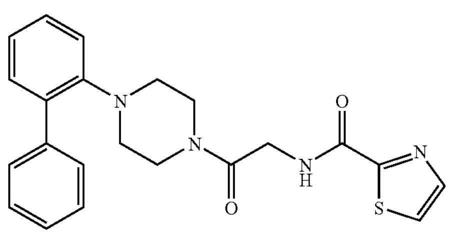 [SMILES: O=C(NCC(=O)N1CCN(c2ccccc2-c2ccccc2)CC1)c1nccs1] | Thiazole-2-carboxylic acid [2-(4-biphenyl-2-yl-piperazin-1-yl)-2-oxo-ethyl]-amide | 408 |
| 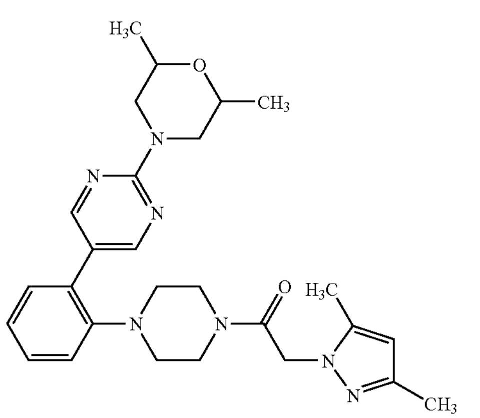 | 1-(4-{2-[2-(2,6-Dimethyl-morpholin-4-yl)-pyrimidin-5-yl]-phenyl}-piperazin-1-yl)-2-(3,5-dimethyl-pyrazol-1-yl)-ethanone | 491 |

TABLE I-continued

| MOLECULAR STRUCTURE | CHEMICAL NAME | Observed MH+ |
|---|---|---|
| 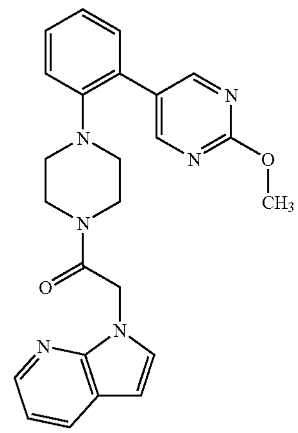 [SMILES: COc1ncc(-c2ccccc2N2CCN(C(=O)Cn3ccc4cccnc43)CC2)cn1] | 1-{4-[2-(2-Methoxy-pyrimidin-5-yl)phenyl]-piperazin-1-yl}-2-pyrrolo[2,3-b]pyridin-1-yl-ethanone | 429 |
| 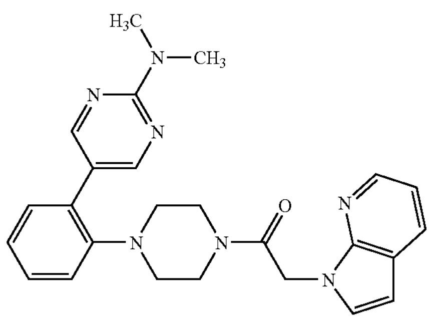 [SMILES: CN(C)c1ncc(-c2ccccc2N2CCN(C(=O)Cn3ccc4cccnc43)CC2)cn1] | 1-{4-[2-(2-Dimethylamino-pyrimidin-5-yl)-phenyl]-piperazin-1-yl}-2-pyrrolo[2,3-b]pyridin-1-yl-ethanone | 443 |
| 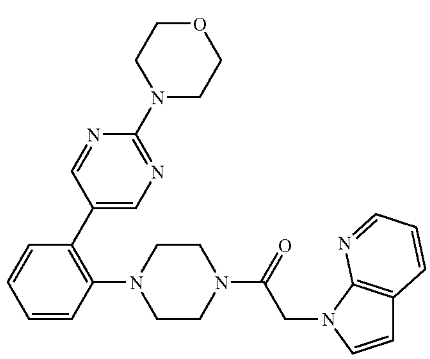 | 1-{4-[2-(2-Morpholin-4-yl-pyrimidin-5-yl)-phenyl]-piperazin-1-yl}-2-pyrrolo[2,3-b]pyridin-1-yl-ethanone | 485 |
| 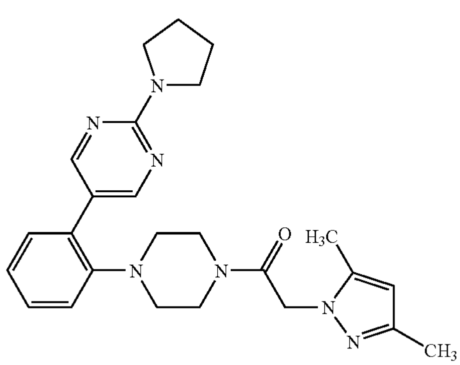 [SMILES: Cc1cc(C)n(CC(=O)N2CCN(c3ccccc3-c3cnc(N4CCCC4)nc3)CC2)n1] | 2-(3,5-Dimethyl-pyrazol-1-yl)-1-{4-[2-(2-pyrrolidin-1-yl-pyrimidin-5-yl)-phenyl]-piperazin-1-yl}-ethanone | 447 |

TABLE I-continued

| MOLECULAR STRUCTURE | CHEMICAL NAME | Observed MH+ |
|---|---|---|
| 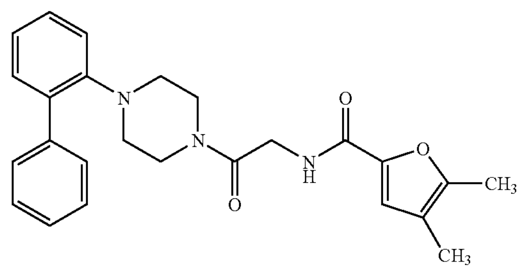 [SMILES: Cc1cc(C(=O)NCC(=O)N2CCN(c3ccccc3-c3ccccc3)CC2)oc1C] | 4,5-Dimethyl-furan-2-carboxylic acid [2-(4-biphenyl-2-yl-piperazin-1-yl)-2-oxo-ethyl]-amide | 418 |
| 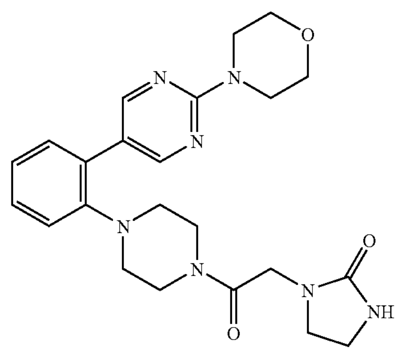 [SMILES: O=C(CN1CCNC1=O)N1CCN(c2ccccc2-c2cnc(N3CCOCC3)nc2)CC1] | 1-(2[{4-[2-(2-Morpholin-4-yl-pyrimidin-5-yl)-phenyl]-piperazin-1-yl}-2-oxo-ethyl)-imidazolidin-2-one | 452 |
| 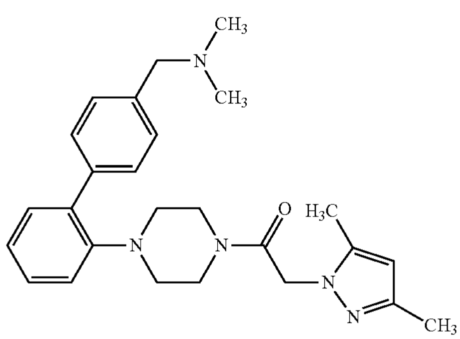 [SMILES: Cc1cc(C)n(CC(=O)N2CCN(c3ccccc3-c3ccc(CN(C)C)cc3)CC2)n1] | 1-[4-(4'-Dimethylaminomethyl-biphenyl-2-yl)-piperazin-1-yl]-2-(3,5-dimethyl-pyrazol-1-yl)-ethanone | 433 |
| 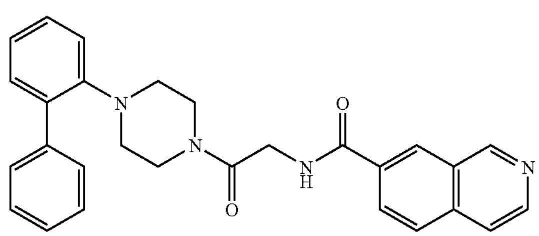 [SMILES: O=C(NCC(=O)N1CCN(c2ccccc2-c2ccccc2)CC1)c1ccc2ccncc2c1] | Isoquinoline-7-carboxylic acid [2-(4-biphenyl-2-yl-piperazin-1-yl)-2-oxo-ethyl]-amide | 451 |
| 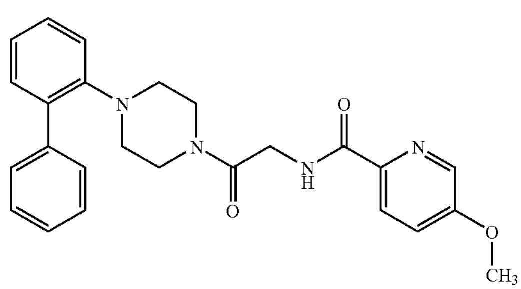 [SMILES: COc1ccc(C(=O)NCC(=O)N2CCN(c3ccccc3-c3ccccc3)CC2)nc1] | 5-Methoxy-pyridine-2-carboxylic acid [2-(4-biphenyl-2-yl-piperazin-1-yl)-2-oxo-ethyl]-amide | 432 |

TABLE I-continued

| MOLECULAR STRUCTURE | CHEMICAL NAME | Observed MH+ |
|---|---|---|
| 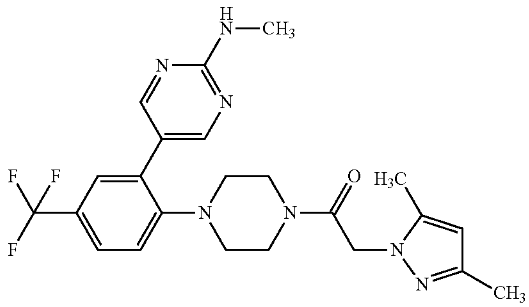 [SMILES: CNc1ncc(-c2cc(C(F)(F)F)ccc2N2CCN(C(=O)Cn3nc(C)cc3C)CC2)cn1] | 2-(3,5-Dimethyl-pyrazol-1-yl)-1-{4-[2-(2-methylamino-pyrimidin-5-yl)-4-trifluoromethyl-phenyl]-piperazin-1-yl}-ethanone | 475 |
| 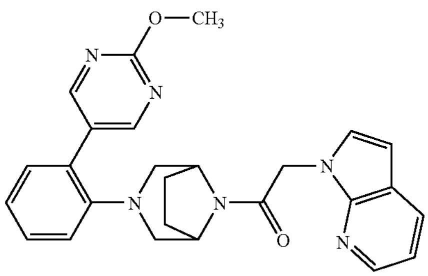 [SMILES: COc1ncc(-c2ccccc2N2CC3CCC(C2)N3C(=O)Cn2ccc3cccnc32)cn1] | 1-{3-[2-(2-Methoxy-pyrimidin-5-yl)-phenyl]-3,8-diaza-bicyclo[3.2.1]oct-8-yl}-2-pyrrolo[2,3-b]pyridin-1-yl-ethanone | 455 |
| 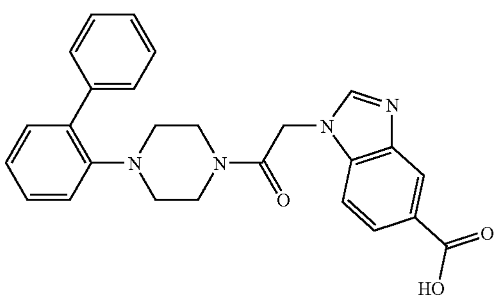 [SMILES: O=C(O)c1ccc2c(c1)ncn2CC(=O)N1CCN(c2ccccc2-c2ccccc2)CC1] | 1-[2-(4-Biphenyl-2-yl-piperazin-1-yl)-2-oxo-ethyl]-1H-benzoimidazole-5-carboxylic acid | 442 |
| 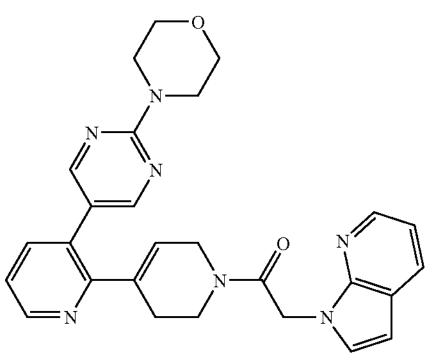 [SMILES: O=C(Cn1ccc2cccnc21)N1CC=C(c2ncccc2-c2cnc(N3CCOCC3)nc2)CC1] | 1-[3-(2-Morpholin-4-yl-pyrimidin-5-yl)-3',6'-dihydro-2'H-[2,4']bipyrimidinyl-1'-yl]-2-pyrrolo[2,3-b]pyridin-1-yl-ethanone | 483 |
| 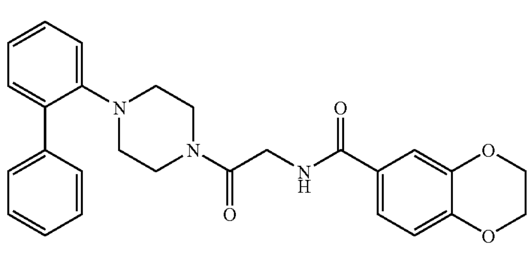 [SMILES: O=C(NCC(=O)N1CCN(c2ccccc2-c2ccccc2)CC1)c1ccc2c(c1)OCCO2] | 2,3-Dihydro-benzo[1,4]dioxine-6-carboxylic acid [2-(4-biphenyl-2-yl-piperazin-1-yl)-2-oxo-ethyl]-amide | 459 |

TABLE I-continued

| MOLECULAR STRUCTURE | CHEMICAL NAME | Observed MH+ |
|---|---|---|
| 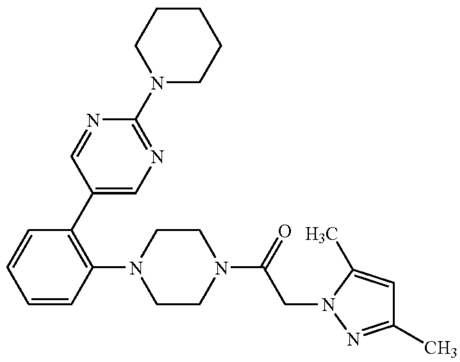 [SMILES: Cc1cc(C)n(CC(=O)N2CCN(c3ccccc3-c3cnc(N4CCCCC4)nc3)CC2)n1] | 2-(3,5-Dimethyl-pyrazol-1-yl)-1-{4-[2-(2-piperidin-1-yl-pyrimidin-5-yl)-phenyl]piperazin-1-yl}-ethanone | 461 |
| 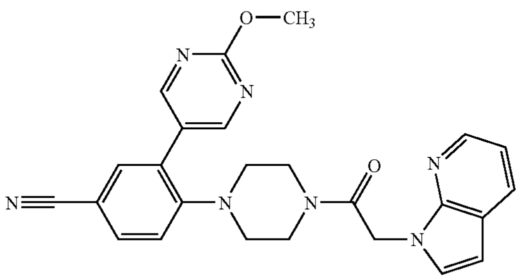 | 3-(2-methoxy-pyrimidin-5-yl)-4-[4-(2-pyrrolo[2,3-b]pyridin-1-yl-acetyl)-piperazin-1-yl]-benzonitrile | 455 |
| 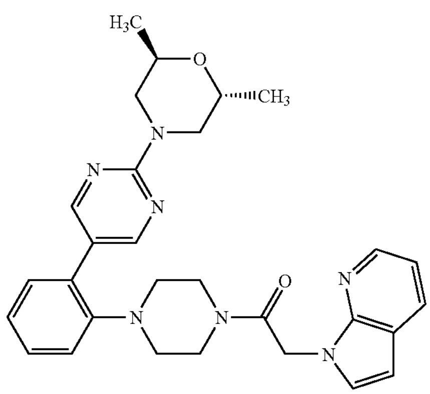 [SMILES: C[C@@H]1CN(c2ncc(-c3ccccc3N3CCN(C(=O)Cn4ccc5cccnc54)CC3)cn2)C[C@@H](C)O1] | 1-(4-{2-[2-((2R,6R)-2,6-Dimethyl-morpholin-4-yl)-pyrimidin-5-yl]-phenyl}-piperazin-1-yl)-2-pyrrolo[2,3-b]pyridin-1-yl-ethanone | 513 |
| 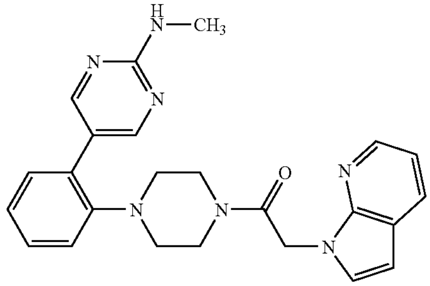 [SMILES: CNc1ncc(-c2ccccc2N2CCN(C(=O)Cn3ccc4cccnc43)CC2)cn1] | 1-{4-[2-(2-Methylamino-pyrimidin-5-yl)-phenyl]-piperazin-1-yl}-2-pyrrolo[2,3-b]pyridin-1-yl-ethanone | 429 |

TABLE I-continued

| MOLECULAR STRUCTURE | CHEMICAL NAME | Observed MH+ |
|---|---|---|
| 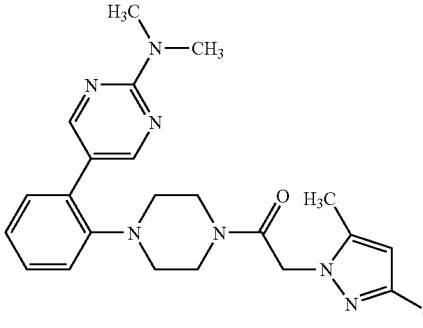 | 1-{4-[2-(2-Dimethylamino-pyrimidin-5-yl)-phenyl]-piperazin-1-yl}-2-(3,5-dimethyl-pyrazol-1-yl)-ethanone | 421 |
| 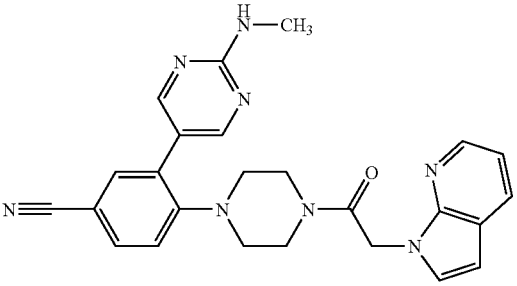 [SMILES: CNc1ncc(-c2cc(C#N)ccc2N2CCN(C(=O)Cn3ccc4cccnc43)CC2)cn1] | 3-(2-Methylamino-pyrimidin-5-yl)-4-[4-(2-pyrrolo[2,3-b]pyridin-1-yl-acetyl)-piperazin-1-yl]-benzonitrile | 454 |
| 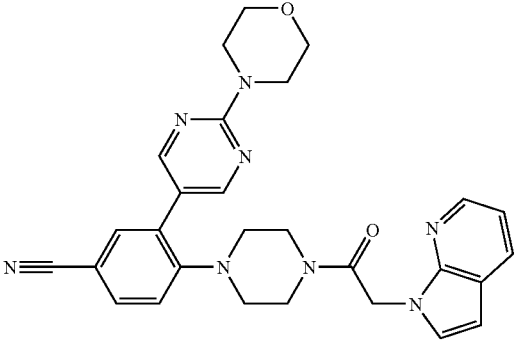 [SMILES: N#Cc1ccc(N2CCN(C(=O)Cn3ccc4cccnc43)CC2)c(-c2cnc(N3CCOCC3)nc2)c1] | 3-(2-Morpholin-4-yl-pyrimidin-5-yl)-4-[4-(2-pyrrolo[2,3-b]pyridin-1-yl-acetyl)-piperazin-1-yl]-benzonitrile | 510 |
| 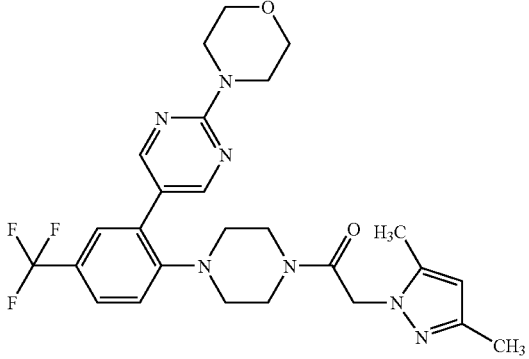 [SMILES: Cc1cc(C)n(CC(=O)N2CCN(c3ccc(C(F)(F)F)cc3-c3cnc(N4CCOCC4)nc3)CC2)n1] | 2-(3,5-Dimethyl-pyrazol-1-yl)-1-{4-[2-(2-morpholin-4-yl-pyrimidin-5-yl)-4-trifluoromethyl-phenyl]-piperazin-1-yl}-ethanone | 531 |
| 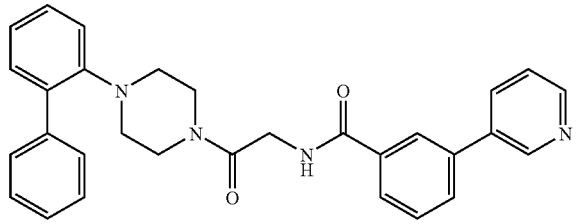 [SMILES: O=C(NCC(=O)N1CCN(c2ccccc2-c2ccccc2)CC1)c1cccc(-c2cccnc2)c1] | N-[2-(4-Biphenyl-2-yl-piperazin-1-yl)-2-oxo-ethyl]-3-pyridin-3-yl-benzamide | 477 |

TABLE I-continued

| MOLECULAR STRUCTURE | CHEMICAL NAME | Observed MH+ |
|---|---|---|
| 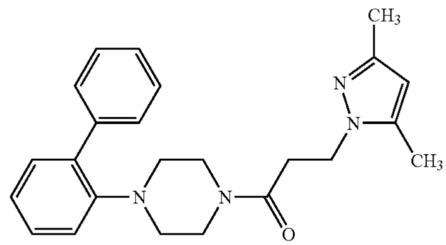 [SMILES: Cc1cc(C)n(CCC(=O)N2CCN(c3ccccc3-c3ccccc3)CC2)n1] | 1-(4-Biphenyl-2-yl-piperazin-1-yl)-3-(3,5-dimethyl-pyrazol-1-yl)-propan-1-one | 390 |
| 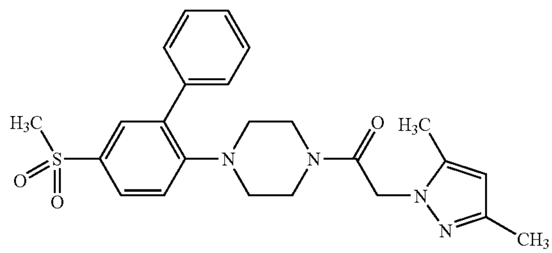 [SMILES: Cc1cc(C)n(CC(=O)N2CCN(c3ccc(S(C)(=O)=O)cc3-c3ccccc3)CC2)n1] | 2-(3,5-Dimethyl-pyrazol-1-yl)-1-[4-(5-methanesulfonyl-biphenyl-2-yl)-piperazin-1-yl]-ethanone | 454 |
| 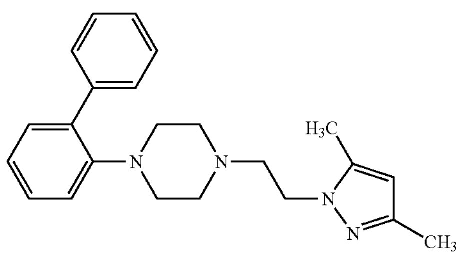 [SMILES: Cc1cc(C)n(CCN2CCN(c3ccccc3-c3ccccc3)CC2)n1] | 1-Biphenyl-2-yl-4-[2-(3,5-dimethyl-pyrazol-1-yl)-ethyl]-piperazine | 362 |
| 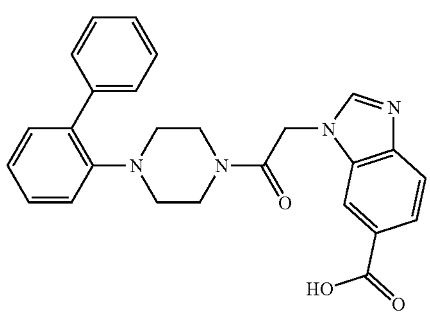 [SMILES: O=C(O)c1ccc2ncn(CC(=O)N3CCN(c4ccccc4-c4ccccc4)CC3)c2c1] | 3-[2-(4-Biphenyl-2-yl-piperazin-1-yl)-2-oxo-ethyl]-3H-benzoimidazole-5-carboxylic acid | 442 |
| 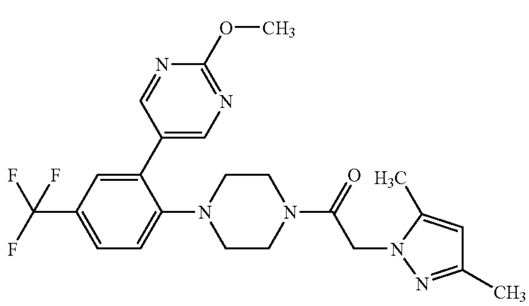 [SMILES: COc1ncc(-c2cc(C(F)(F)F)ccc2N2CCN(C(=O)Cn3nc(C)cc3C)CC2)cn1] | 2-(3,5-Dimethyl-pyrazol-1-yl)-1-{4-[2-(2-methoxy-pyrimidin-5-yl)-4-trifluoromethyl-phenyl]-piperazin-1-yl}-ethanone | 475 |

TABLE I-continued

| MOLECULAR STRUCTURE | CHEMICAL NAME | Observed MH+ |
|---|---|---|
| 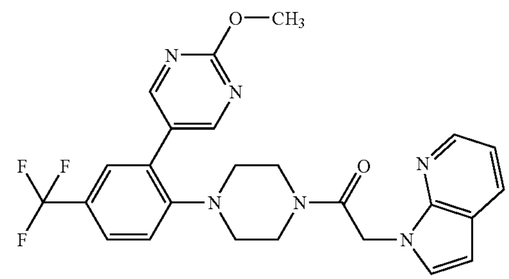 [SMILES: COc1ncc(-c2cc(C(F)(F)F)ccc2N2CCN(C(=O)Cn3ccc4cccnc43)CC2)cn1] | 1-{4-[2-(2-Methoxy-pyrimidin-5-yl)-4-trifluoromethyl-phenyl]-piperazin-1-yl}-2-pyrrolo[2,3-b]pyridin-1-yl-ethanone | 497 |
| 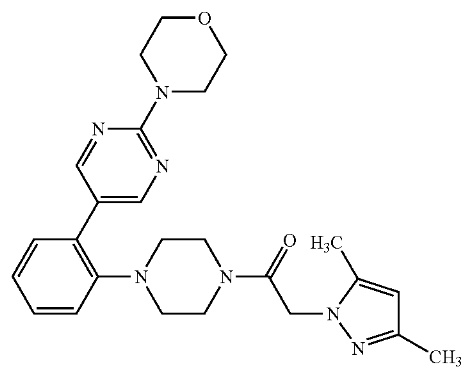 [SMILES: Cc1cc(C)n(CC(=O)N2CCN(c3ccccc3-c3cnc(N4CCOCC4)nc3)CC2)n1] | 2-(3,5-Dimethyl-pyrazol-1-yl)-1-{4-[2-(2-morpholin-4-yl-pyrimidin-5-yl)-phenyl]-piperazin-1-yl}-ethanone | 463 |
| 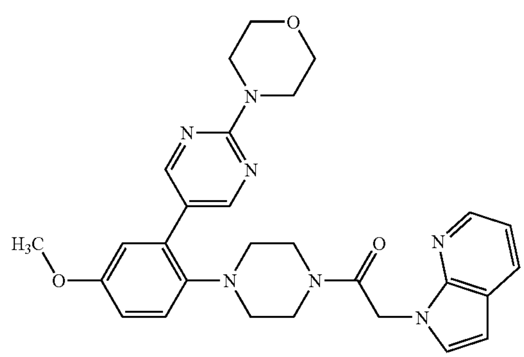 [SMILES: COc1ccc(N2CCN(C(=O)Cn3ccc4cccnc43)CC2)c(-c2cnc(N3CCOCC3)nc2)c1] | 1-{4-[4-Methoxy-2-(2-morpholin-4-yl-pyrimidin-5-yl)-phenyl]-piperazin-1-yl}-2-pyrrolo[2,3-b]pyridin-1-yl-ethanone | 515 |
| 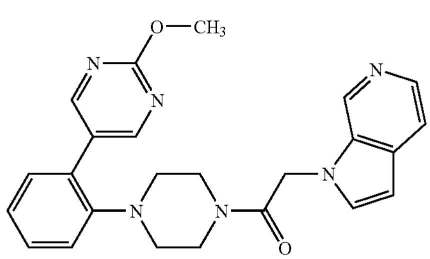 [SMILES: COc1ncc(-c2ccccc2N2CCN(C(=O)Cn3ccc4ccncc43)CC2)cn1] | 1-{4-[2-(2-Methoxy-pyrimidin-5-yl)-phenyl]-piperazin-1-yl}-2-pyrrolo[2,3-b]pyridin-1-yl-ethanone | 429 |
| 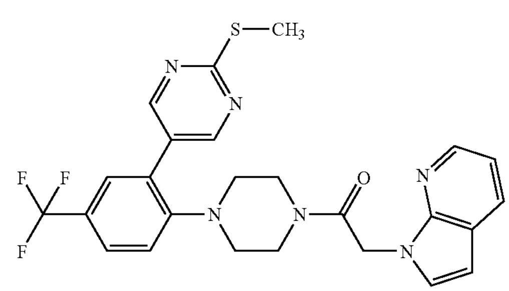 | 1-{4-[2-(2-Methylsulfanyl-pyrimidin-5-yl)-4-trifluoromethyl-phenyl]-piperazin-1-yl}-2-pyrrolo[2,3-b]pyridin-1-yl-ethanone | 514 |

TABLE I-continued

| MOLECULAR STRUCTURE | CHEMICAL NAME | Observed MH+ |
|---|---|---|
| 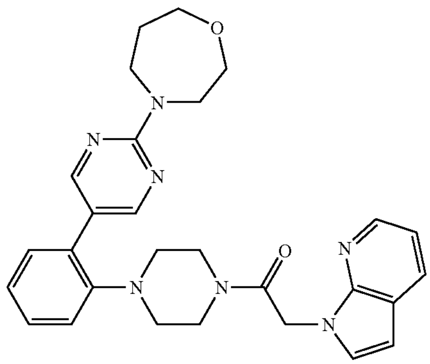 [SMILES: O=C(Cn1ccc2cccnc21)N1CCN(c2ccccc2-c2cnc(N3CCCOCC3)nc2)CC1] | 1-{4-[2-(2-[1,4]Oxazepan-4-yl-pyrimidin-5-yl)-phenyl]-piperazin-1-yl}-2-pyrrolo[2,3-b]]pyridin-1-yl-ethanone | 499 |
| 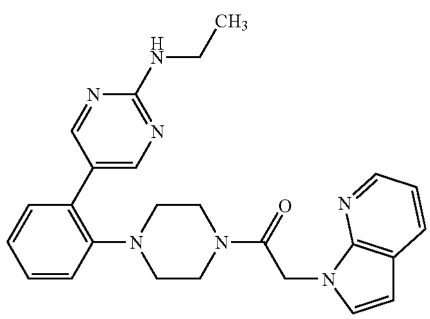 [SMILES: CCNc1ncc(-c2ccccc2N2CCN(C(=O)Cn3ccc4cccnc43)CC2)cn1] | 1-{4-[2-(2-Ethylamino-pyrimidin-5-yl)-phenyl]-piperazin-1-yl}-2-pyrrolo[2,3-b]pyridin-1-yl-ethanone | 443 |
| 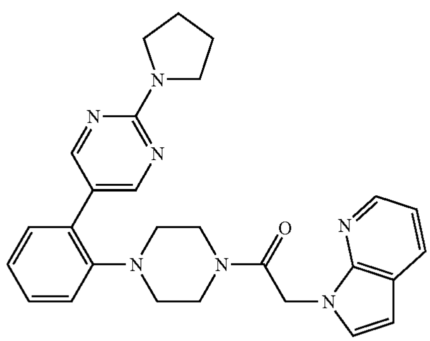 [SMILES: O=C(Cn1ccc2cccnc21)N1CCN(c2ccccc2-c2cnc(N3CCCC3)nc2)CC1] | 1-{4-[2-(2-Pyrrolidin-1-yl-pyrimidin-5-yl)-phenyl]-piperazin-1-yl}-2-pyrrolo[2,3-b]pyridin-1-yl-ethanone | 469 |
| 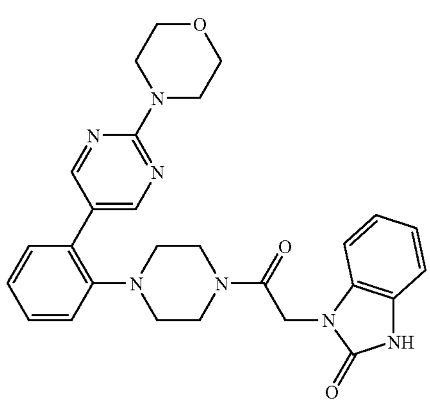 [SMILES: O=C(Cn1c(=O)[nH]c2ccccc21)N1CCN(c2ccccc2-c2cnc(N3CCOCC3)nc2)CC1] | 1-(2-{4-[2-(2-Morpholin-4-yl-pyrimidin-5-yl)-phenyl]-piperazin-1-yl}-2-oxo-ethyl)-1,3-dihydro-benzoimidazol-2-one | 501 |

TABLE I-continued

| MOLECULAR STRUCTURE | CHEMICAL NAME | Observed MH+ |
|---|---|---|
| 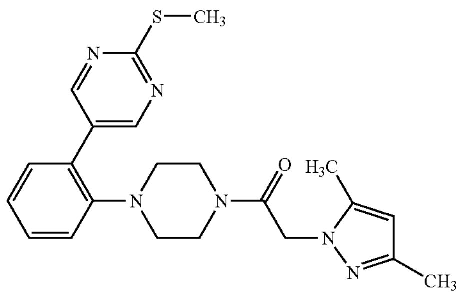 [SMILES: CSc1ncc(-c2ccccc2N2CCN(C(=O)Cn3nc(C)cc3C)CC2)cn1] | 2-(3,5-Dimethyl-pyrazol-1-yl)-1-{4-[2-(2-methylsulfanyl-pyrimidin-5-yl)-phenyl]-piperazin-1-yl}-ethanone | 424 |
| 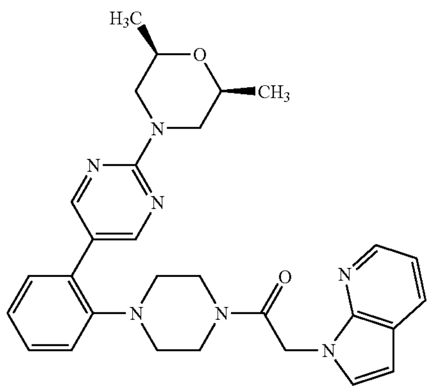 [SMILES: C[C@@H]1CN(c2ncc(-c3ccccc3N3CCN(C(=O)Cn4ccc5cccnc54)CC3)cn2)C[C@H](C)O1] | 1-(4-{2-[2-((2R,6S)-2,6-Dimethyl-morpholin-4-yl)-pyrimidin-5-yl]-phenyl}-piperazin-1-yl)-2-pyrrolo[2,3-b]pyridin-1-yl-ethanone | 513 |
| 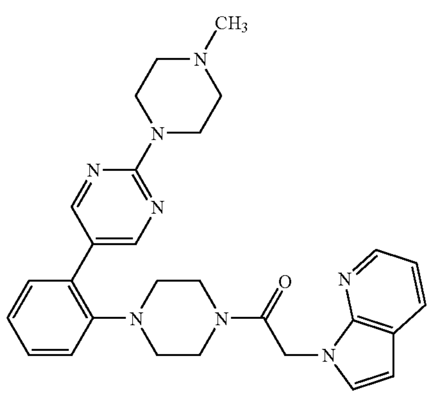 [SMILES: CN1CCN(c2ncc(-c3ccccc3N3CCN(C(=O)Cn4ccc5cccnc54)CC3)cn2)CC1] | 1-(4-{2-[2-(4-Methyl-piperazin-1-yl)-pyrimidin-5-yl]-phenyl}-piperazin-1-yl)-2-pyrrolo[2,3-b]pyridin-1-yl-ethanone | 498 |
| 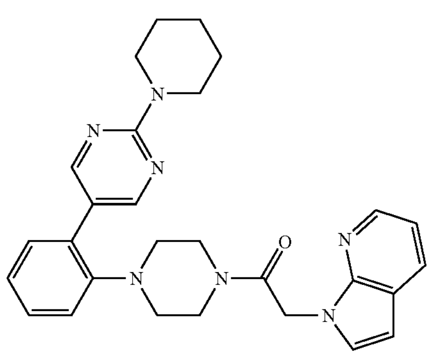 [SMILES: O=C(Cn1ccc2cccnc21)N1CCN(c2ccccc2-c2cnc(N3CCCCC3)nc2)CC1] | 1-{4-[2-(2-Piperidin-1-yl-pyrimidin-5-yl)-phenyl]-piperazin-1-yl}-2-pyrrol[2,3-b]pyridin-1-yl-ethanone | 483 |

TABLE I-continued

| MOLECULAR STRUCTURE | CHEMICAL NAME | Observed MH+ |
|---|---|---|
| 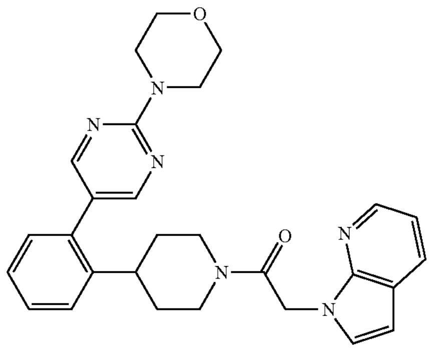 [SMILES: O=C(Cn1ccc2cccnc21)N1CCC(c2ccccc2-c2cnc(N3CCOCC3)nc2)CC1] | 1-{4-[2-(2-Morpholin-4-yl-pyrimidin-5-yl)-phenyl]-piperidin-1-yl}-2-pyrrolo[2,3-b]pyridin-1-yl-ethanone | 484 |
| 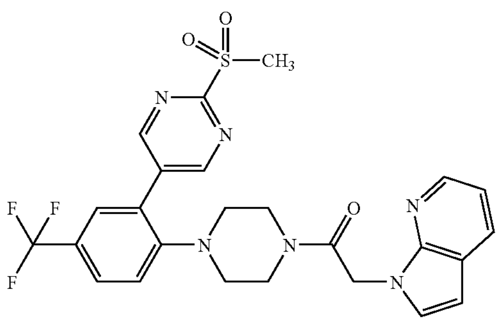 [SMILES: CS(=O)(=O)c1ncc(-c2cc(C(F)(F)F)ccc2N2CCN(C(=O)Cn3ccc4cccnc43)CC2)cn1] | 1-{4-[2-(2-Methanesulfonyl-pyrimidin-5-yl)-4-trifluoromethyl-phenyl]-piperazin-1-yl}-2-pyrrolo[2,3-b]pyridin-1-yl-ethanone | 546 |
| 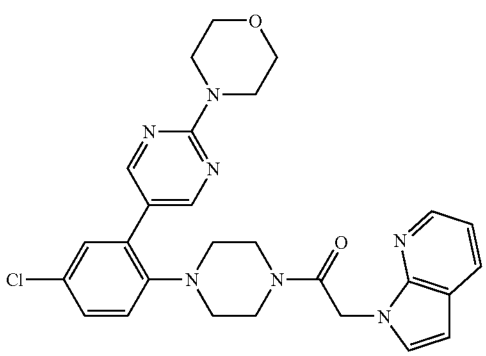 [SMILES: O=C(Cn1ccc2cccnc21)N1CCN(c2ccc(Cl)cc2-c2cnc(N3CCOCC3)nc2)CC1] | 1-{4-[4-Chloro-2-(2-morpholin-4-yl-pyrimidin-5-yl)-phenyl]-piperazin-1-yl}-2-pyrrolo[2,3-b]pyridin-1-yl-ethanone | 519 |
| 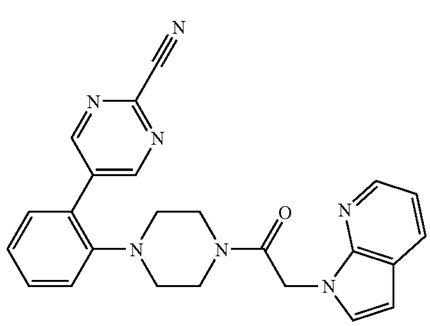 [SMILES: N#Cc1ncc(-c2ccccc2N2CCN(C(=O)Cn3ccc4cccnc43)CC2)cn1] | 5-{2-[4-(2-Pyrrolo[2,3-b]pyridin-1-yl-acetyl)-piperazin-1-yl]-phenyl}-pyrimidine-1-carbonitrile | 424 |

TABLE I-continued

| MOLECULAR STRUCTURE | CHEMICAL NAME | Observed MH+ |
|---|---|---|
| 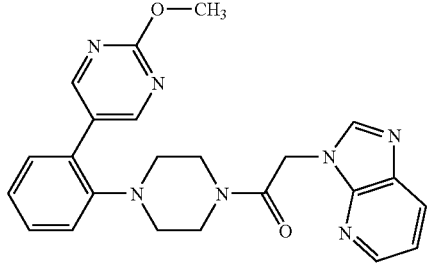 [SMILES: COc1ncc(-c2ccccc2N2CCN(C(=O)Cn3cnc4cccnc43)CC2)cn1] | 2-Imidazo[4,5-b]pyridin-3-yl-1-{4[[2-(2-methoxypyrimidin-5-yl)-phenyl]-piperazin-1-yl}-ethanone | 430 |
| 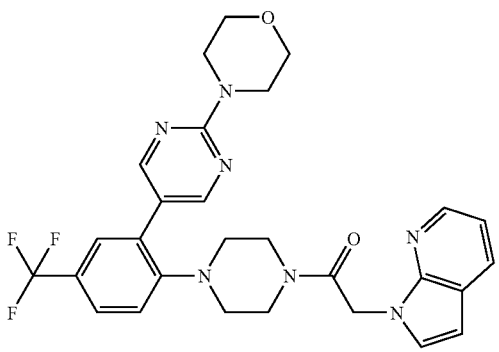 [SMILES: O=C(Cn1ccc2cccnc21)N1CCN(c2ccc(C(F)(F)F)cc2-c2cnc(N3CCOCC3)nc2)CC1] | 1-{4-[2-(2-Morpholin-4-yl-pyrimidin-5-yl)-4-trifluoromethyl-phenyl]-piperazin-1-yl}-2-pyrrolo[2,3-b]pyridin-1-yl-ethanone | 553 |
| 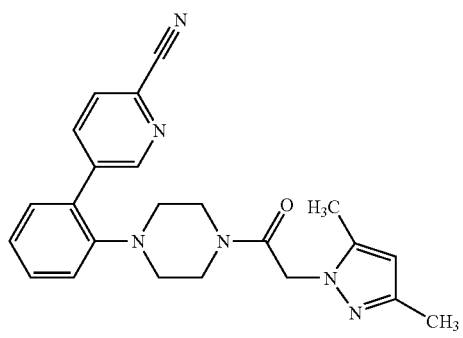 | 5-(2-{4-[2-(3,5-Dimethyl-pyrazol-1-yl)-acetyl]-piperazin-1-yl}-phenyl)-pyridine-2-carbonitrile | 401 |
| 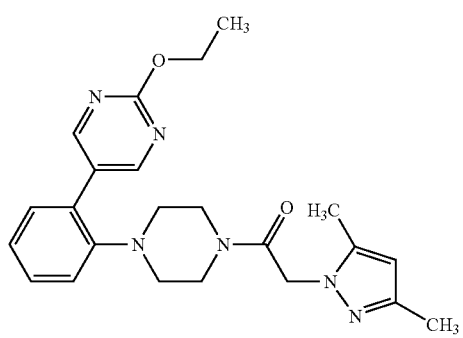 [SMILES: CCOc1ncc(-c2ccccc2N2CCN(C(=O)Cn3nc(C)cc3C)CC2)cn1] | 2-(3,5-Dimethyl-pyrazol-1-yl)-1-{4-[2-(2-ethoxy-pyrimidin-5-yl)-phenyl]-piperazin-1-yl}-ethanone | 422 |

TABLE I-continued

| MOLECULAR STRUCTURE | CHEMICAL NAME | Observed MH+ |
|---|---|---|
| 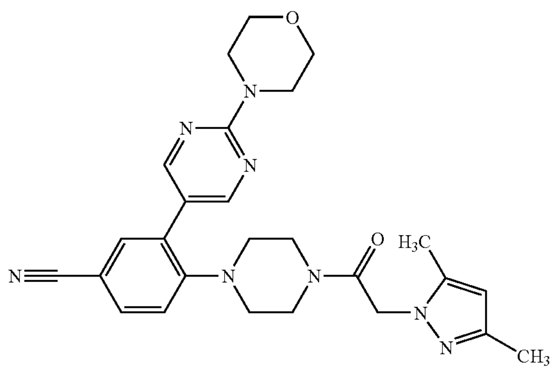 [SMILES: Cc1cc(C)n(CC(=O)N2CCN(c3ccc(C#N)cc3-c3cnc(N4CCOCC4)nc3)CC2)n1] | 4-{4-[2-(3,5-Dimethyl-pyrazol-1-yl)-acetyl]-piperazin-1-yl}-3-(2-morpholin-4-yl-pyrimidin-5-yl)-benzonitrile | 488 |
| 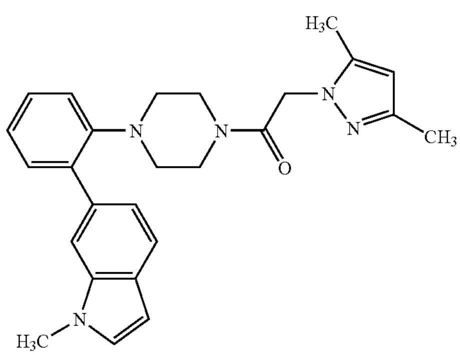 [SMILES: Cc1cc(C)n(CC(=O)N2CCN(c3ccccc3-c3ccc4ccn(C)c4c3)CC2)n1] | 2-(3,5-Dimethyl-pyrazol-1-yl)-1-{4-[2-(1-methyl-1H-indol-6-yl)-phenyl]-piperazin-1-yl}-ethanone | 429 |
| 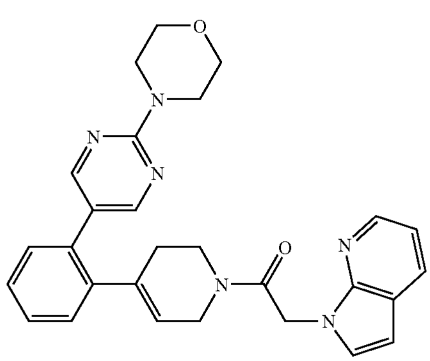 [SMILES: O=C(Cn1ccc2cccnc21)N1CC=C(c2ccccc2-c2cnc(N3CCOCC3)nc2)CC1] | 1-{4-[2-(2-Morpholin-4-yl-pyrimidin-5-yl)-phenyl]-3,6-dihydro-2H-pyridin-1-yl}-2-pyrrolo[2,3-b]pyridin-1-yl-ethanone | 482 |
| 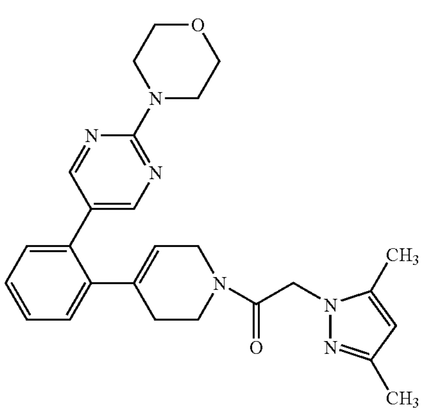 [SMILES: Cc1cc(C)n(CC(=O)N2CC=C(c3ccccc3-c3cnc(N4CCOCC4)nc3)CC2)n1] | 2-(3,5-Dimethyl-pyrazol-1-yl)-1-{4-[2-(2-morpholin-4-yl-pyrimidin-5-yl)-phenyl]-3,6-dihydro-2H-pyridin-1-yl}-ethanone | 460 |

TABLE I-continued

| MOLECULAR STRUCTURE | CHEMICAL NAME | Observed MH+ |
|---|---|---|
| 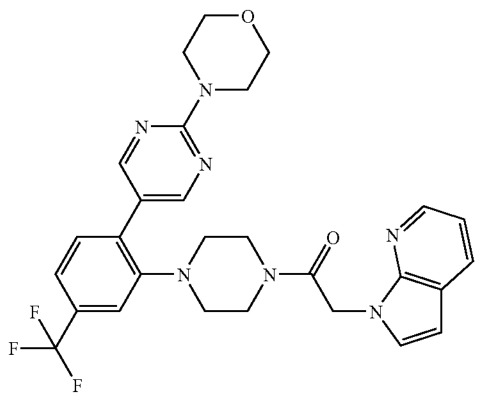 [SMILES: O=C(Cn1ccc2cccnc21)N1CCN(c2cc(C(F)(F)F)ccc2-c2cnc(N3CCOCC3)nc2)CC1] | 1-{4-[2-(2-Morpholin-4-yl-pyrimidin-5-yl)-5-trifluoromethyl-phenyl]-piperazin-1-yl}-2-pyrrolo[2,3-b]pyridin-1-yl-ethanone | 553 |
| 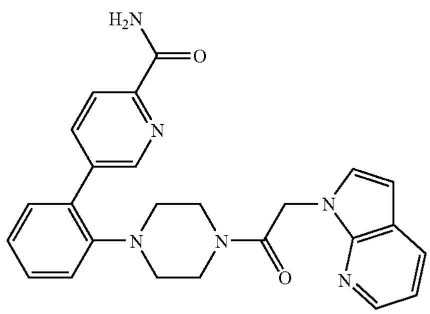 [SMILES: NC(=O)c1ccc(-c2ccccc2N2CCN(C(=O)Cn3ccc4cccnc43)CC2)cn1] | 5-{2-[4-(2-Pyrrolo[2,3-b]pyridin-1-yl-acetyl)-piperazin-1-yl]-phenyl}-pyridine-2-carboxylic acid amide | 441 |
| 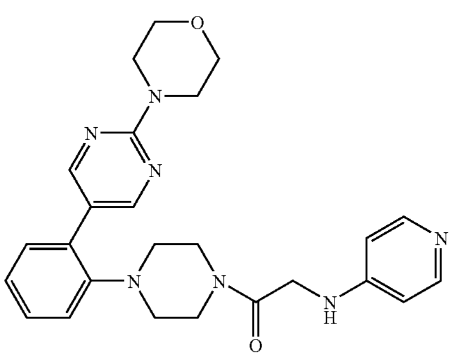 [SMILES: O=C(CNc1ccncc1)N1CCN(c2ccccc2-c2cnc(N3CCOCC3)nc2)CC1] | 1-{4-[2-(2-Morpholin-4-yl-pyrimidin-5-yl)-phenyl]-piperazin-1-yl}-2-(pyridin-4-ylamino)-ethanone | 461 |
| 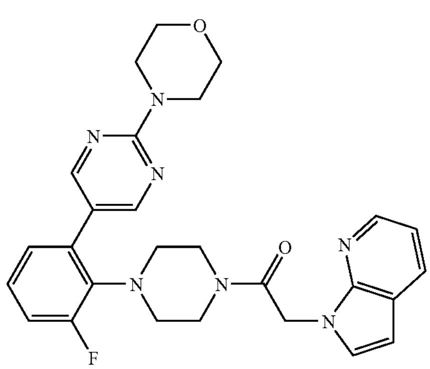 [SMILES: O=C(Cn1ccc2cccnc21)N1CCN(c2c(F)cccc2-c2cnc(N3CCOCC3)nc2)CC1] | 1-{4-[2-Fluoro-6-(2-morpholin-4-yl-pyrimidin-5-yl)-phenyl]-piperazin-1-yl}-2-pyrrolo[2,3-b]pyridin-1-yl-ethanone | 503 |

TABLE I-continued

| MOLECULAR STRUCTURE | CHEMICAL NAME | Observed MH+ |
|---|---|---|
| 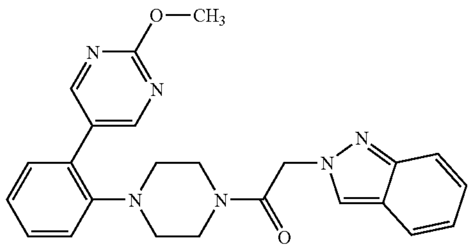 [SMILES: COc1ncc(-c2ccccc2N2CCN(C(=O)Cn3cc4ccccc4n3)CC2)cn1] | 2-Indazol-2-yl-1-{4-[2-(2-methoxy-pyrimidin-5-yl)-phenyl]-piperazin-1-yl}-ethanone | 429 |
| 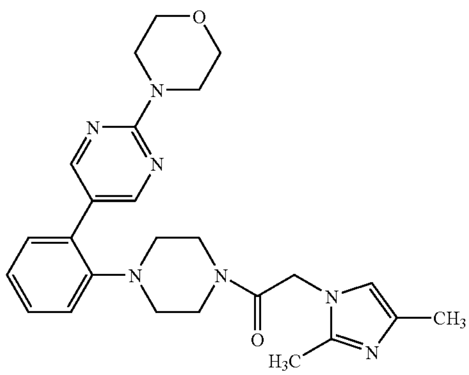 [SMILES: Cc1cn(CC(=O)N2CCN(c3ccccc3-c3cnc(N4CCOCC4)nc3)CC2)c(C)n1] | 2-(2,4-Dimethyl-imidazol-1-yl)-1-{4-[2-(2-morpholin-4-yl-pyrimidin-5-yl)-phenyl]-piperazin-1-yl}-ethanone | 463 |
| 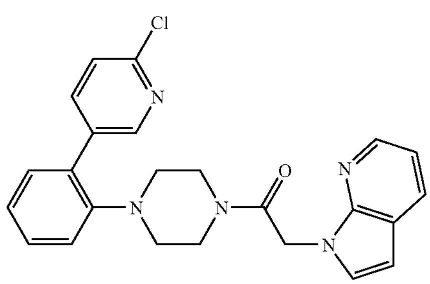 [SMILES: O=C(Cn1ccc2cccnc21)N1CCN(c2ccccc2-c2ccc(Cl)nc2)CC1] | 1-{4-[2-(6-Chloro-pyridin-3-yl)-phenyl]-piperazin-1-yl}-2-pyrrolo[2,3-b]pyridin-1-yl-ethanone | 433 |
| 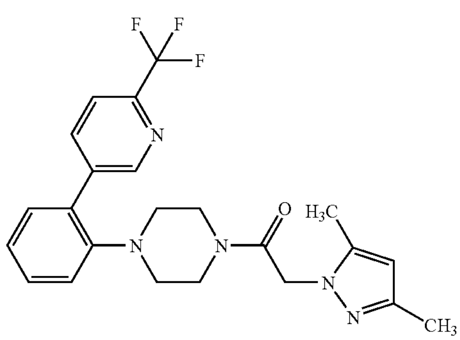 [SMILES: Cc1cc(C)n(CC(=O)N2CCN(c3ccccc3-c3ccc(C(F)(F)F)nc3)CC2)n1] | 2-(3,5-Dimethyl-pyrazol-1-yl)-1-{4-[2-(6-trifluoromethyl-pyridin-3-yl)-phenyl]-piperazin-1-yl}-ethanone | 444 |
| 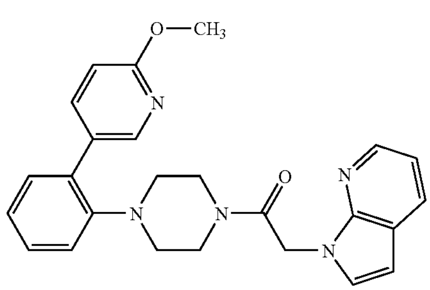 [SMILES: COc1ccc(-c2ccccc2N2CCN(C(=O)Cn3ccc4cccnc43)CC2)cn1] | 1-{4-[2-(6-Methoxy-pyridin-3-yl)-phenyl]-piperazin-1-yl}-2-pyrrolo[2,3-b]pyridin-1-yl-ethanone | 429 |

TABLE I-continued

| MOLECULAR STRUCTURE | CHEMICAL NAME | Observed MH+ |
|---|---|---|
| 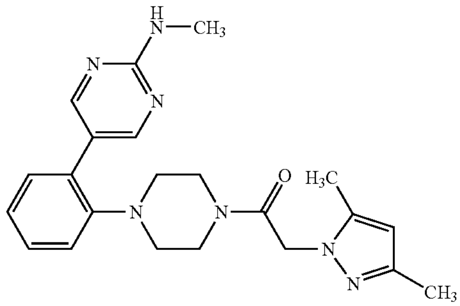 [SMILES: CNc1ncc(-c2ccccc2N2CCN(C(=O)Cn3nc(C)cc3C)CC2)cn1] | 2-(3,5-Dimethyl-pyrazol-1-yl)-1-{4-[2-(2-methylaminopyrimidin-5-yl)phenyl]-piperazin-1-yl}-ethanone | 407 |
| 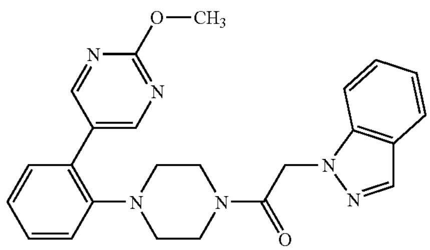 | 2-Indazol-1-yl-1-{4-[2-(2-methoxy-pyrimidin-5-yl)-phenyl]-piperazin-1-yl}-ethanone | 429 |
| 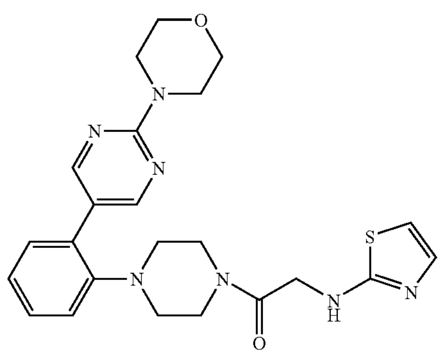 [SMILES: O=C(CNc1nccs1)N1CCN(c2ccccc2-c2cnc(N3CCOCC3)nc2)CC1] | 1-{4-[2-(2-Morpholin-4-yl-pyrimidin-5-yl)-phenyl]-piperazin-1-yl}-2-(thiazol-2-ylamino)-ethanone | 467 |
| 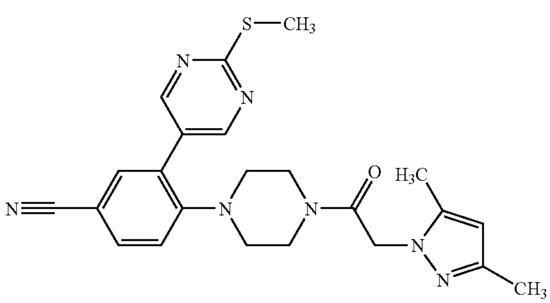 [SMILES: CSc1ncc(-c2cc(C#N)ccc2N2CCN(C(=O)Cn3nc(C)cc3C)CC2)cn1] | 4-{4-[2-(3,5-Dimethyl-pyrazol-1-yl)-acetyl]-piperazin-1-yl}-3-(2-methylsulfanyl-pyrimidin-5-yl)-benzonitrile | 449 |
| 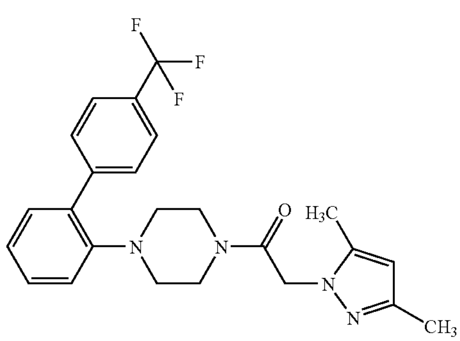 [SMILES: Cc1cc(C)n(CC(=O)N2CCN(c3ccccc3-c3ccc(C(F)(F)F)cc3)CC2)n1] | 2-(3,5-Dimethyl-pyrazol-1-yl)-1-[4-(4'-trifluoromethyl-biphenyl-2-yl)piperazin-1-yl]-ethanone | 443 |

TABLE I-continued

| MOLECULAR STRUCTURE | CHEMICAL NAME | Observed MH+ |
|---|---|---|
| 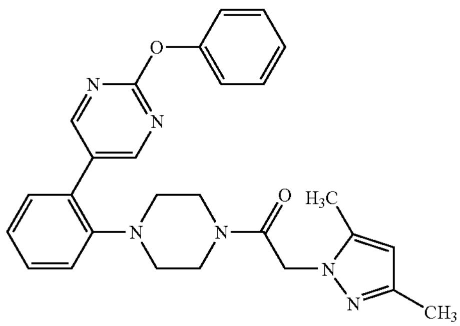 | 2-(3,5-Dimethyl-pyrazol-1-yl)-1-{4-[2-(2-phenoxy-pyrimidin-5-yl)-phenyl]-piperazin-1-yl}-ethanone | 470 |
| 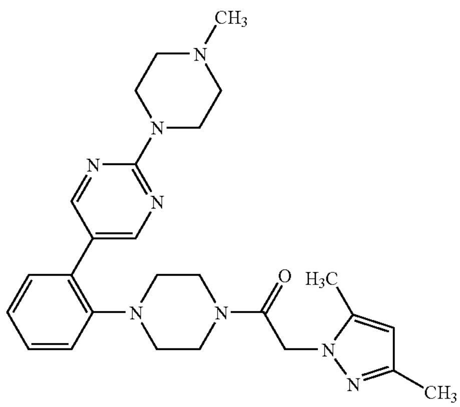 [SMILES: Cc1cc(C)n(CC(=O)N2CCN(c3ccccc3-c3cnc(N4CCN(C)CC4)nc3)CC2)n1] | 2-(3,5-Dimethyl-pyrazol-1-yl)-1-(4-{2-[2-(4-methyl-piperazin-1-yl)-pyrimidin-5-yl]-phenyl}-piperazin-1-yl)-ethanone | 476 |
| 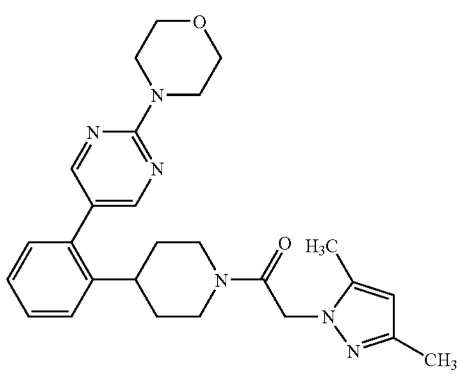 [SMILES: Cc1cc(C)n(CC(=O)N2CCC(c3ccccc3-c3cnc(N4CCOCC4)nc3)CC2)n1] | 2-(3,5-Dimethyl-pyrazol-1-yl)-1-{4-[2-(2-morpholin-4-yl-pyrimidin-5-yl)-phenyl]-piperidin-1-yl}-ethanone | 462 |
| 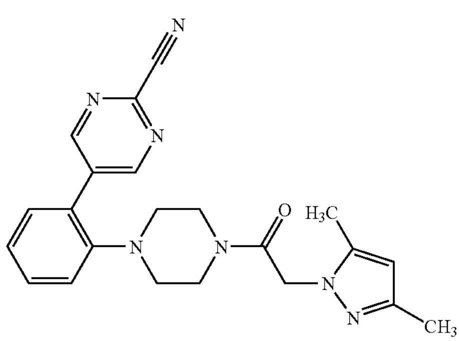 [SMILES: Cc1cc(C)n(CC(=O)N2CCN(c3ccccc3-c3cnc(C#N)nc3)CC2)n1] | 5-(2-{4-[2-(3,5-Dimethyl-pyrazol-1-yl)-acetyl]-piperazin-1-yl}-phenyl)-pyrimidine-2-carbonitrile | 402 |

TABLE I-continued

| MOLECULAR STRUCTURE | CHEMICAL NAME | Observed MH+ |
|---|---|---|
| 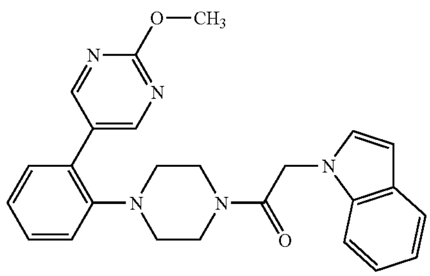 [SMILES: COc1ncc(-c2ccccc2N2CCN(C(=O)Cn3ccc4ccccc43)CC2)cn1] | 2-Indol-1-yl-1-{4-[2-(2-methoxy-pyrimidin-5-yl)-phenyl]-piperazin-1-yl}-ethanone | 428 |
| 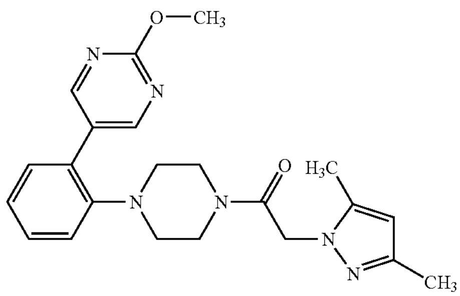 | 2-(3,5-Dimethyl-pyrazol-1-yl)-1-{4-[2-(2-methoxy-pyrimidin-5-yl)-phenyl]-piperazin-1-yl}-ethanone | 407 |
| 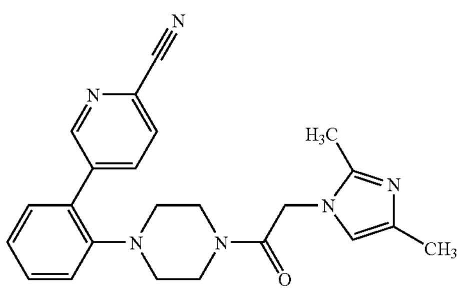 [SMILES: Cc1cn(CC(=O)N2CCN(c3ccccc3-c3ccc(C#N)nc3)CC2)c(C)n1] | 5-(2-{4-[2-(2,4-Dimethyl-imidazol-1-yl)-acetyl]-piperazin-1-yl}-phenyl)-pyridine-2-carbonitrile | 402 |
| 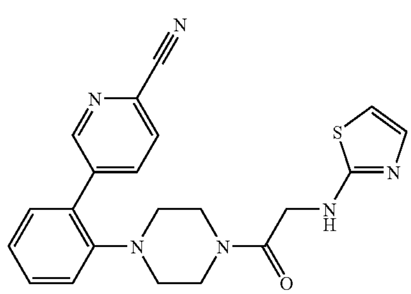 [SMILES: N#Cc1ccc(-c2ccccc2N2CCN(C(=O)CNc3nccs3)CC2)cn1] | 5-{2-{4-[2-(Thiazol-2-ylamino)-acetyl]-piperazin-1-yl}-phenyl)-pyridine-2-carbonitrile | 405 |
| 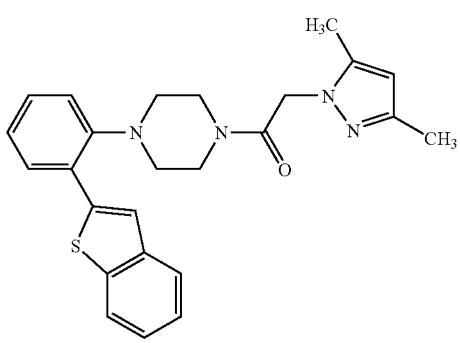 [SMILES: Cc1cc(C)n(CC(=O)N2CCN(c3ccccc3-c3cc4ccccc4s3)CC2)n1] | 1-[4-(2-Benzo[b]thiophen-2-yl-phenyl)-piperazin-1-yl]-2-(3,5-dimethyl-pyrazol-1-yl)-ethanone | 432 |

TABLE I-continued

| MOLECULAR STRUCTURE | CHEMICAL NAME | Observed MH+ |
|---|---|---|
| 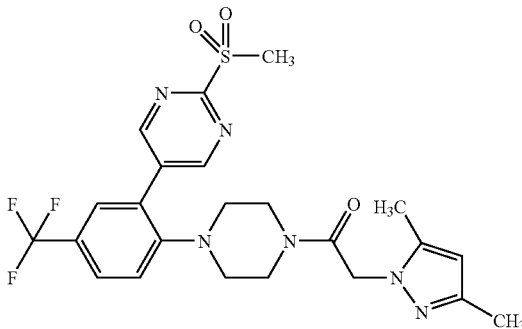 | 2-(3,5-Dimethyl-pyrazol-1-yl)-1-{4-[2-(2-methanesulfonyl-pyrimidin-5-yl)-4-trifluoromethyl-phenyl]-piperazin-1-yl}-ethanone | 524 |
| 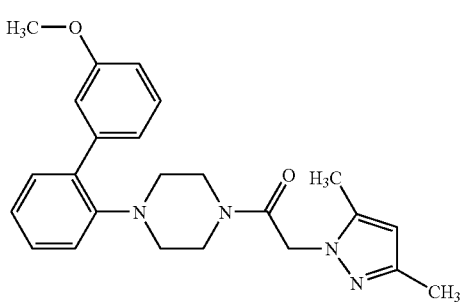 [SMILES: COc1cccc(-c2ccccc2N2CCN(C(=O)Cn3nc(C)cc3C)CC2)c1] | 2-(3,5-Dimethyl-pyrazol-1-yl)-1-[4-(3'-methoxy-biphenyl-2-yl)-piperazin-1-yl]-ethanone | 406 |
| 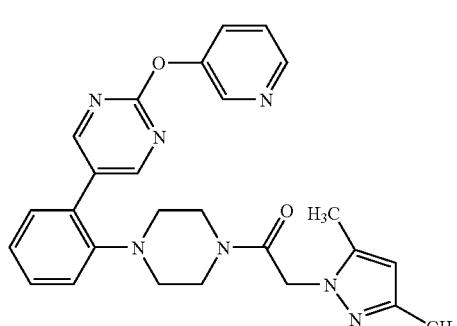 | 2-(3,5-Dimethyl-pyrazol-1-yl)-1-(4-{2-[2-(pyridin-3-yloxy)-pyrimidin-5-yl]-phenyl}-piperazin-1-yl)-ethanone | 471 |
| 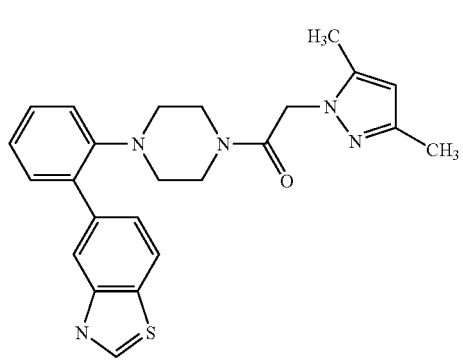 | 1-[4-(2-Benzothiazol-5-yl-phenyl)piperazin-1-yl]-2-(3,5-dimethyl-pyrazol-1-yl)-ethanone | 433 |

TABLE I-continued

| MOLECULAR STRUCTURE | CHEMICAL NAME | Observed MH+ |
|---|---|---|
| 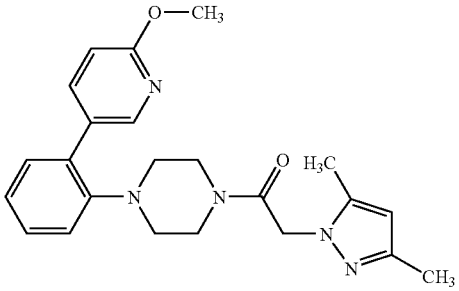 [SMILES: COc1ccc(-c2ccccc2N2CCN(C(=O)Cn3nc(C)cc3C)CC2)cn1] | 2-(3,5-Dimethyl-pyrazol-1-yl)-1-{4-[2-(6-methoxy-pyridin-3-yl)-phenyl]-piperazin-1-yl}-ethanone | 406 |
| 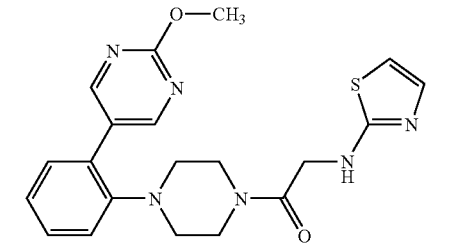 [SMILES: COc1ncc(-c2ccccc2N2CCN(C(=O)CNc3nccs3)CC2)cn1] | 1-{4-[2-(2-Methoxy-pyrimidin-5-yl)-phenyl]-piperazin-1-yl}-2-(thiazol-2-ylamino)-ethanone | 411 |
| 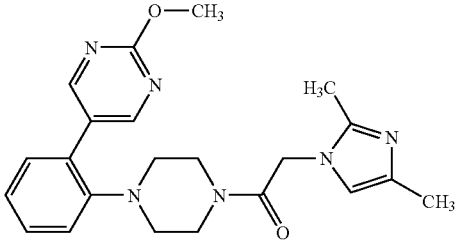 [SMILES: COc1ncc(-c2ccccc2N2CCN(C(=O)Cn3cc(C)nc3C)CC2)cn1] | 2-(2,4-Dimethyl-imidazol-1-yl)-1-{4-[2-(2-methoxy-pyrimidin-5-yl)-phenyl]-piperazin-1-yl}-ethanone | 407 |
| 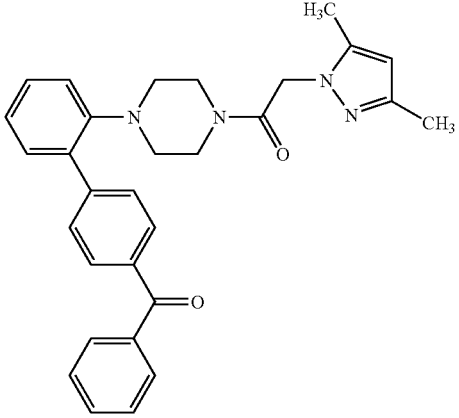 [SMILES: Cc1cc(C)n(CC(=O)N2CCN(c3ccccc3-c3ccc(C(=O)c4ccccc4)cc3)CC2)n1] | 1-[4-(4'-Benzoyl-biphenyl-2-yl)-piperazin-1-yl]-2-(3,5-dimethyl-pyrazol-1-yl)-ethanone | 480 |
| 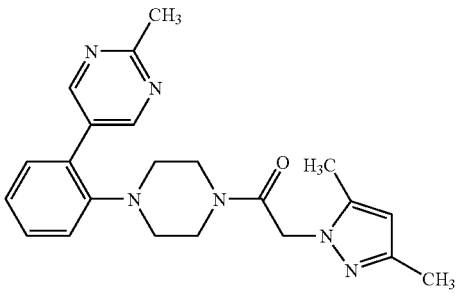 | 2-(3,5-Dimethyl-pyrazol-1-yl)-1-{4-[2-(2-methyl-pyrimidin-5-yl)-phenyl]-piperazin-1-yl}-ethanone | 391 |

TABLE I-continued

| MOLECULAR STRUCTURE | CHEMICAL NAME | Observed MH+ |
|---|---|---|
| 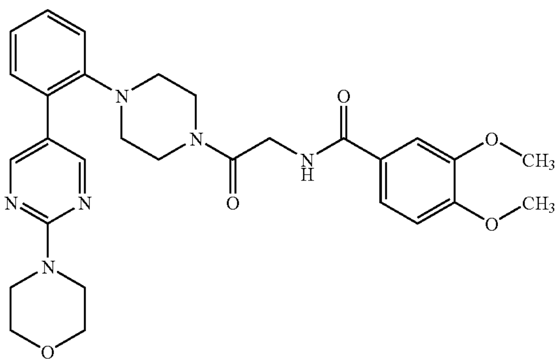 [SMILES: COc1ccc(C(=O)NCC(=O)N2CCN(c3ccccc3-c3cnc(N4CCOCC4)nc3)CC2)cc1OC] | 3,4-Dimethoxy-N-(2-{4-[2-(2-morpholin-4-yl-pyrimidin-5-yl)-phenyl]-piperazin-1-yl}-2-oxo-ethyl)-benzamide | 548 |
| 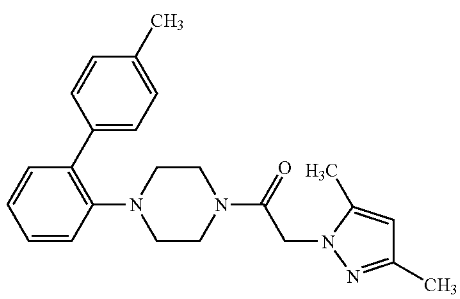 | 2-(3,5-Dimethyl-pyrazol-1-yl)-1-[4-(4'-methyl-biphenyl-2-yl)-piperazin-1-yl]-ethanone | 390 |
| 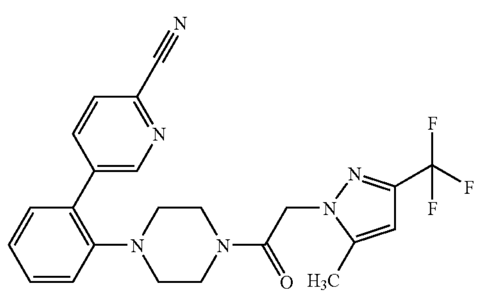 [SMILES: Cc1cc(C(F)(F)F)nn1CC(=O)N1CCN(c2ccccc2-c2ccc(C#N)nc2)CC1] | 5-(2-{4-[2-(5-methyl-3-trifluoromethyl-pyrazol-1-yl)-acetyl]-piperazin-1-yl}-phenyl)-pyridine-2-carbonitrile | 455 |
| 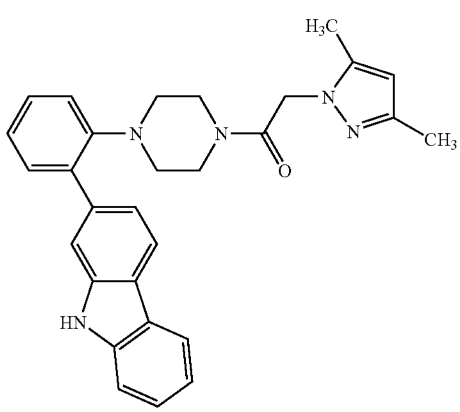 [SMILES: Cc1cc(C)n(CC(=O)N2CCN(c3ccccc3-c3ccc4c(c3)[nH]c3ccccc34)CC2)n1] | 1-{4-[2-(9H-Carbazol-2-yl)-phenyl]-piperazin-1-yl}-2-(3,5-dimethyl-pyrazol-1-yl)-ethanone | 465 |

TABLE I-continued
| MOLECULAR STRUCTURE | CHEMICAL NAME | Observed MH+ |
|---|---|---|
| 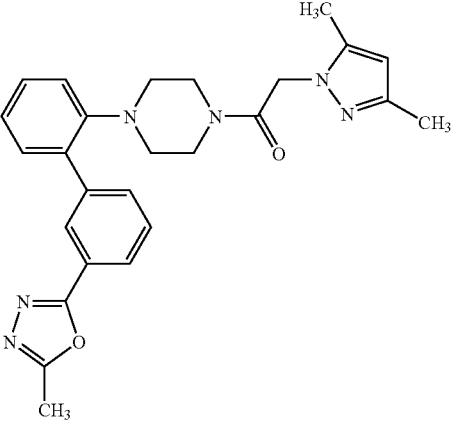 [SMILES: Cc1cc(C)n(CC(=O)N2CCN(c3ccccc3-c3cccc(-c4nnc(C)o4)c3)CC2)n1] | 2-(3,5-Dimethyl-pyrazol-1-yl)-1-{4-[3'-(5-methyl-[1,3,4]oxadiazol-2-yl)-biphenyl-2-yl]-piperazin-1-yl}-ethanone | 458 |
| 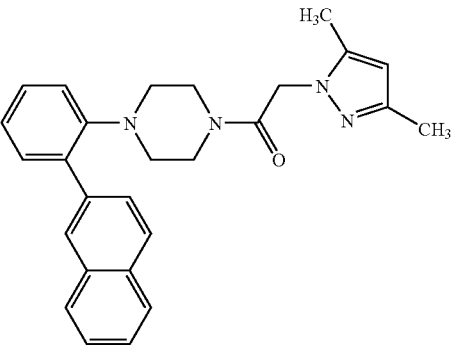 | 2-(3,5-Dimethyl-pyrazol-1-yl)-1-[4-(2-naphthalen-2-yl-phenyl)-piperazin-1-yl]-ethanone | 426 |
| 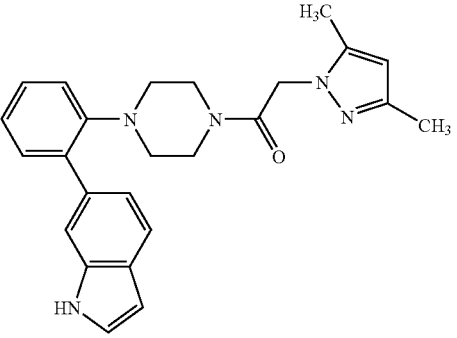 [SMILES: Cc1cc(C)n(CC(=O)N2CCN(c3ccccc3-c3ccc4cc[nH]c4c3)CC2)n1] | 2-(3,5-Dimethyl-pyrazol-1-yl)-1-{4-[2-(1H-indol-6-yl)-phenyl]-piperazin-1-yl}-ethanone | 415 |
| 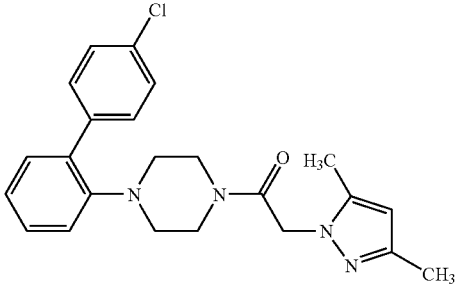 [SMILES: Cc1cc(C)n(CC(=O)N2CCN(c3ccccc3-c3ccc(Cl)cc3)CC2)n1] | 1-[4-(4'-Chloro-biphenyl-2-yl)-piperazin-1-yl]-2-(3,5-dimethyl-pyrazol-1-yl)-ethanone | 410 |

TABLE I-continued

| MOLECULAR STRUCTURE | CHEMICAL NAME | Observed MH+ |
|---|---|---|
| 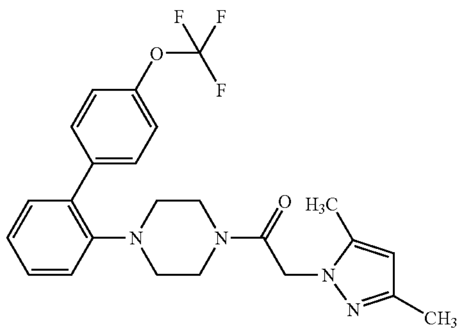 [SMILES: Cc1cc(C)n(CC(=O)N2CCN(c3ccccc3-c3ccc(OC(F)(F)F)cc3)CC2)n1] | 2-(3,5-Dimethyl-pyrazol-1-yl)-1-[4-(4'-trifluoromethoxy-biphenyl-2-yl)-piperazin-1-yl]-ethanone | 459 |
| 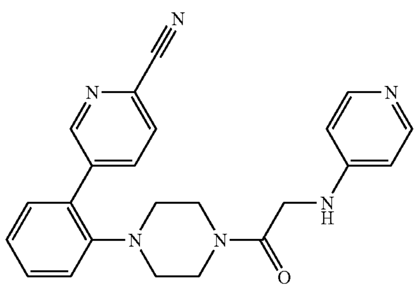 [SMILES: N#Cc1ccc(-c2ccccc2N2CCN(C(=O)CNc3ccncc3)CC2)cn1] | 5-(2-{4-[2-(Pyridin-4-ylamino)-acetyl]-piperazin-1-yl}-phenyl)-pyridine-2-carbonitrile | 399 |
| 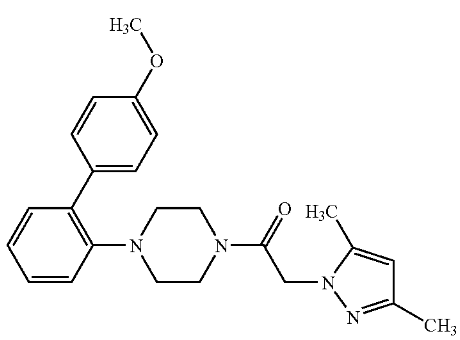 [SMILES: COc1ccc(-c2ccccc2N2CCN(C(=O)Cn3nc(C)cc3C)CC2)cc1] | 2-(3,5-Dimethyl-pyrazol-1-yl)-1-[4-(4'-methoxy-biphenyl-2-yl)-piperazin-1-yl]-ethanone | 406 |
| 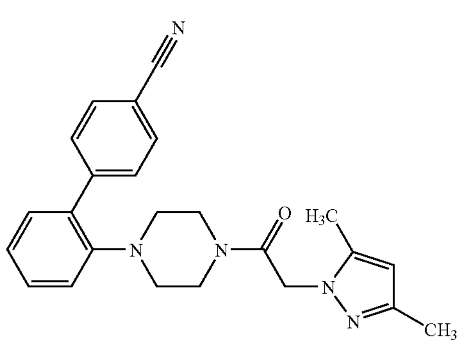 [SMILES: Cc1cc(C)n(CC(=O)N2CCN(c3ccccc3-c3ccc(C#N)cc3)CC2)n1] | 2'-{4-[2-(3,5-Dimethyl-pyrazol-1-yl)-acetyl]-piperazin-1-yl}-biphenyl-4-carbonitrile | 400 |

TABLE I-continued

| MOLECULAR STRUCTURE | CHEMICAL NAME | Observed MH+ |
|---|---|---|
| 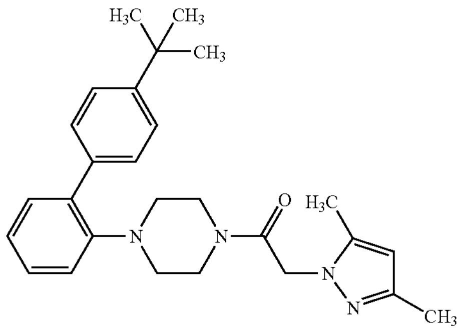 [SMILES: Cc1cc(C)n(CC(=O)N2CCN(c3ccccc3-c3ccc(C(C)(C)C)cc3)CC2)n1] | 1-[4-(4'-tert-Butyl-biphenyl-2-yl)-piperazin-1-yl]-2-(3,5-dimethyl-pyrazol-1-yl)-ethanone | 432 |
| 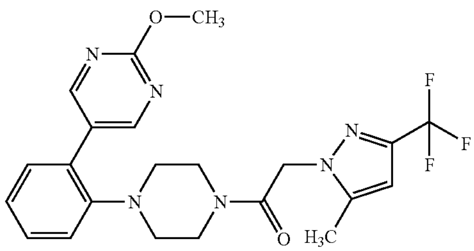 [SMILES: COc1ncc(-c2ccccc2N2CCN(C(=O)Cn3nc(C(F)(F)F)cc3C)CC2)cn1] | 1-{4-[2-(2-Methoxy-pyrimidin-5-yl)-phenyl]-piperazin-1-yl}-2-(5-methyl-3-trifluoromethyl-pyrazol-1-yl)-ethanone | 461 |
| 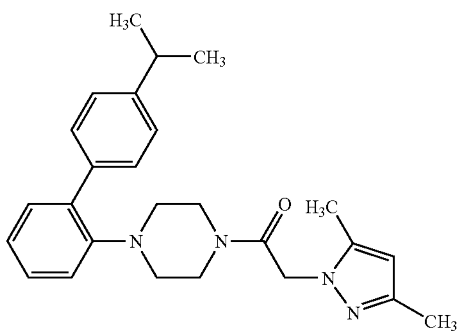 [SMILES: Cc1cc(C)n(CC(=O)N2CCN(c3ccccc3-c3ccc(C(C)C)cc3)CC2)n1] | 2-(3,5-Dimethyl-pyrazol-1-yl)-1-[4-(4'-isopropyl-biphenyl-2-yl)-piperazin-1-yl]-ethanone | 418 |
| 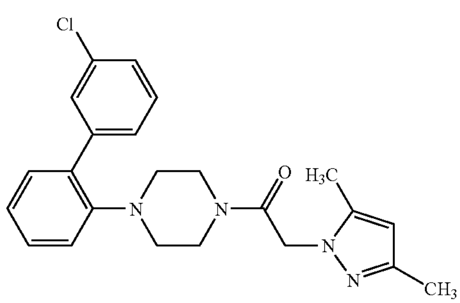 [SMILES: Cc1cc(C)n(CC(=O)N2CCN(c3ccccc3-c3cccc(Cl)c3)CC2)n1] | 1-[4-(3'-Chloro-biphenyl-2-yl)-piperazin-1-yl]-2-(3,5-dimethyl-pyrazol-1-yl)-ethanone | 410 |
| 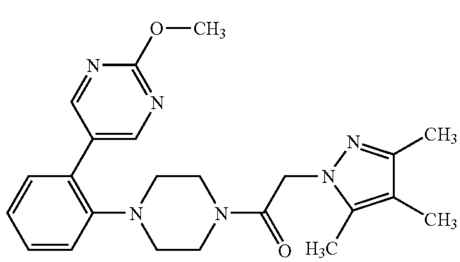 [SMILES: COc1ncc(-c2ccccc2N2CCN(C(=O)Cn3nc(C)c(C)c3C)CC2)cn1] | 1-{4-[2-(2-Methoxy-pyrimidin-5-yl)-phenyl]-piperazin-1-yl}-2-(3,4,5-trimethyl-pyrazol-1-yl)-ethanone | 421 |

TABLE I-continued

| MOLECULAR STRUCTURE | CHEMICAL NAME | Observed MH+ |
|---|---|---|
| 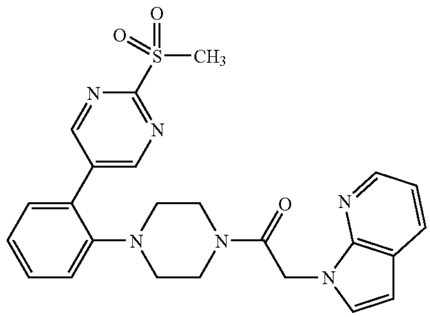 [SMILES: CS(=O)(=O)c1ncc(-c2ccccc2N2CCN(C(=O)Cn3ccc4cccnc43)CC2)cn1] | 1-{4-[2-(2-Methanesulfonyl-pyrimidin-5-yl)-phenyl]-piperazin-1-yl}-2-pyrrolo[2,3-b]pyridin-1-yl-ethanone | 478 |
| 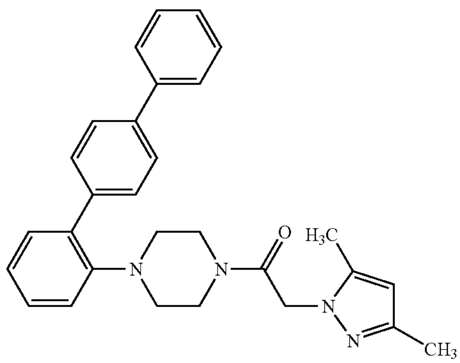 [SMILES: Cc1cc(C)n(CC(=O)N2CCN(c3ccccc3-c3ccc(-c4ccccc4)cc3)CC2)n1] | 2-(3,5-Dimethyl-pyrazol-1-yl)-1-(4-[1,1';4',1'']terphenyl-2-yl-piperazin-1-yl)-ethanone | 452 |
| 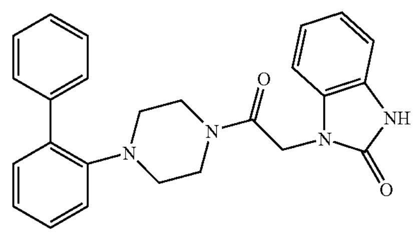 [SMILES: O=C(Cn1c(=O)[nH]c2ccccc21)N1CCN(c2ccccc2-c2ccccc2)CC1] | 1-[2-(4-Biphenyl-2-yl-piperazin-1-yl)-2-oxo-ethyl]-1,3-dihydro-benzoimidazol-2-one | 413 |
| 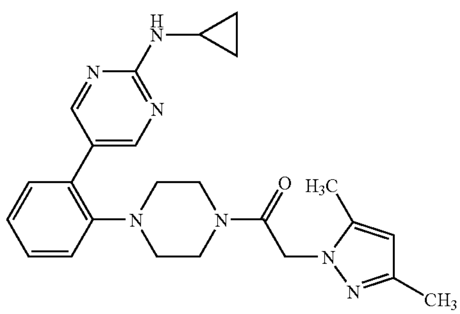 [SMILES: Cc1cc(C)n(CC(=O)N2CCN(c3ccccc3-c3cnc(NC4CC4)nc3)CC2)n1] | 1-{4-[2-(2-Cyclopropylamino-pyrimidin-5-yl)-phenyl]-piperazin-1-yl}-2-(3,5-dimethyl-pyrazol-1-yl)-ethanone | 433 |
| 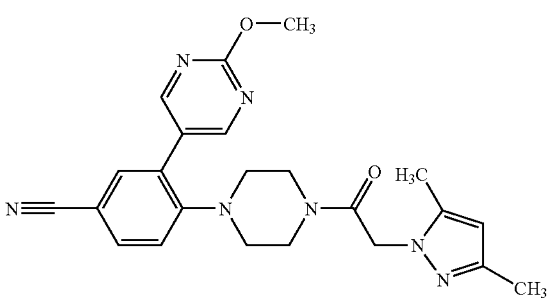 | 4-{4-[2-(3,5-Dimethyl-pyrazol-1-yl)-acetyl]-piperazin-1-yl}-3-(2-methoxy-pyrimidin-5-yl)-benzonitrile | 432 |

TABLE I-continued

| MOLECULAR STRUCTURE | CHEMICAL NAME | Observed MH+ |
|---|---|---|
| 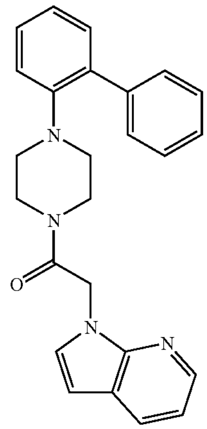 [SMILES: O=C(Cn1ccc2cccnc21)N1CCN(c2ccccc2-c2ccccc2)CC1] | 1-(4-Biphenyl-2-yl-piperazin-1-yl)-2-pyrrolo[2,3-b]pyridin-1-yl-ethanone | 397 |
| 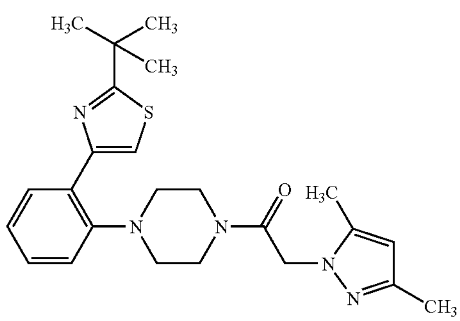 [SMILES: Cc1cc(C)n(CC(=O)N2CCN(c3ccccc3-c3csc(C(C)(C)C)n3)CC2)n1] | 1-{4-[2-(2-tert-Butyl-thiazol-4-yl)-phenyl]-piperazin-1-yl}-2-(3,5-dimethyl-pyrazol-1-yl)-ethanone | 439 |
| 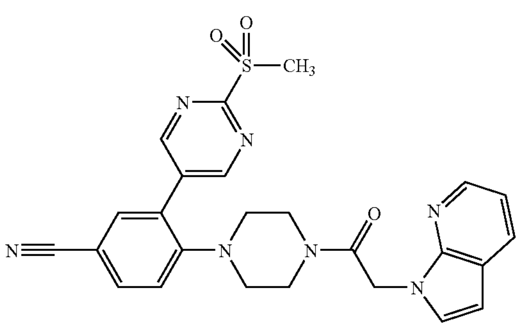 [SMILES: CS(=O)(=O)c1ncc(-c2cc(C#N)ccc2N2CCN(C(=O)Cn3ccc4cccnc43)CC2)cn1] | 3-(2-Methanesulfonyl-pyrimidin-5-yl)-4-[4-(2-pyrrolo[2,3-b]pyridin-1-yl-acetyl)-piperazin-1-yl]-benzonitrile | 503 |
| 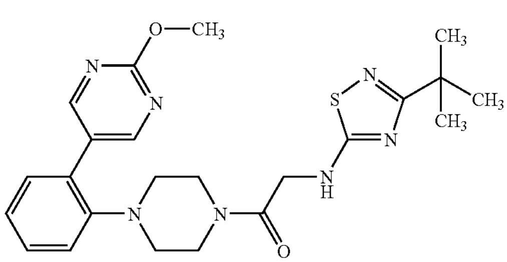 [SMILES: COc1ncc(-c2ccccc2N2CCN(C(=O)CNc3nc(C(C)(C)C)ns3)CC2)cn1] | 2-(3-tert-Butyl-[1,2,4]thiadiazol-5-ylamino)-1-{4-[2-(2-methoxy-pyrimidin-5-yl)-phenyl]-piperazin-1-yl}-ethanone | 468 |

TABLE I-continued

| MOLECULAR STRUCTURE | CHEMICAL NAME | Observed MH+ |
|---|---|---|
| 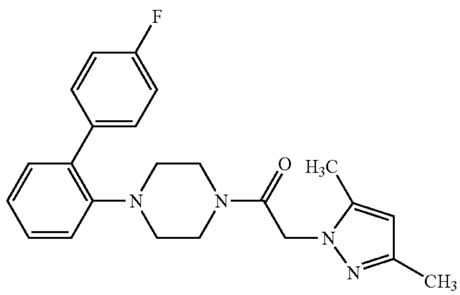 | 2-(3,5-Dimethyl-pyrazol-1-yl)-1-[4-(4'-fluoro-biphenyl-2-yl)-piperazin-1-yl]-ethanone | 393 |
| 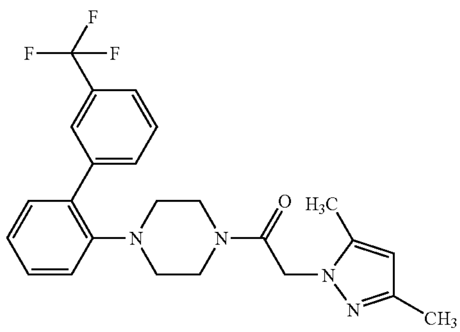 [SMILES: Cc1cc(C)n(CC(=O)N2CCN(c3ccccc3-c3cccc(C(F)(F)F)c3)CC2)n1] | 2-(3,5-Dimethyl-pyrazol-1-yl)-1-[4-(3'-trifluoromethyl-biphenyl-2-yl)-piperazin-1-yl]-ethanone | 443 |
| 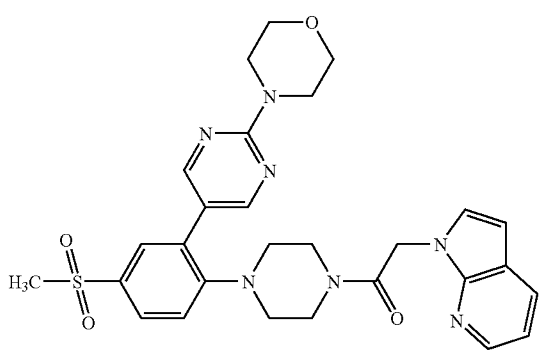 [SMILES: CS(=O)(=O)c1ccc(N2CCN(C(=O)Cn3ccc4cccnc43)CC2)c(-c2cnc(N3CCOCC3)nc2)c1] | 1-{4-[4-Methanesulfonyl-2-(2-morpholin-4-yl-pyrimidin-5-yl)-phenyl]-piperazin-1-yl}-2-pyrrolo[2,3-b]pyridin-1-yl-ethanone | 562 |
| 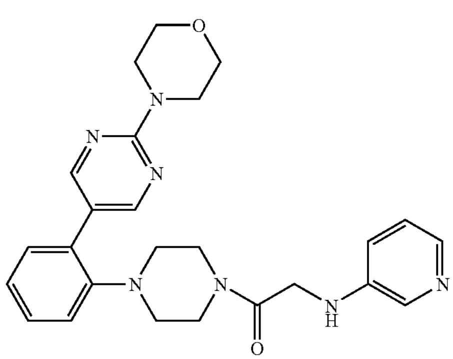 [SMILES: O=C(CNc1cccnc1)N1CCN(c2ccccc2-c2cnc(N3CCOCC3)nc2)CC1] | 1-{4-[2-(2-Morpholin-4-yl-pyrimidin-5-yl)-phenyl]-piperazin-1-yl}-2-(pyridin-3-ylamino)-ethanone | 461 |

TABLE I-continued

| MOLECULAR STRUCTURE | CHEMICAL NAME | Observed MH+ |
|---|---|---|
| 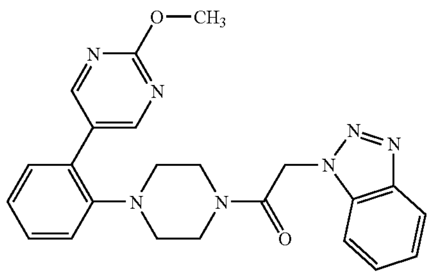 [SMILES: COc1ncc(-c2ccccc2N2CCN(C(=O)Cn3nnc4ccccc43)CC2)cn1] | 2-Benzotriazol-1-yl-1-{4-[2-(2-methoxy-pyrimidin-5-yl)-phenyl]-piperazin-1-yl}-ethanone | 430 |
| 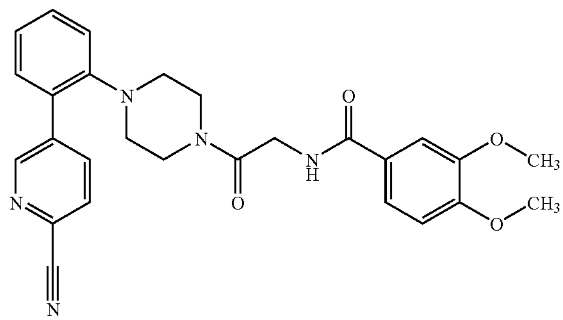 [SMILES: COc1ccc(C(=O)NCC(=O)N2CCN(c3ccccc3-c3ccc(C#N)nc3)CC2)cc1OC] | N-(2-{4-[2-(6-Cyano-pyridin-3-yl)-phenyl]-piperazin-1-yl}-2-oxo-ethyl)-3,4-dimethoxy-benzamide | 487 |
| 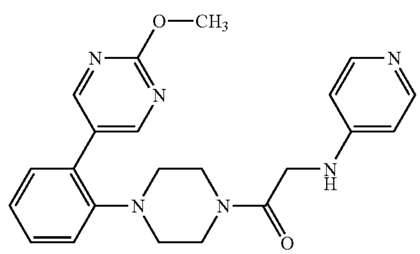 [SMILES: COc1ncc(-c2ccccc2N2CCN(C(=O)CNc3ccncc3)CC2)cn1] | 1-{4-[2-(2-Methoxy-pyrimidin-5-yl)-phenyl]-piperazin-1-yl}-2-(pyridin-4-ylamino)-ethanone | 405 |
| 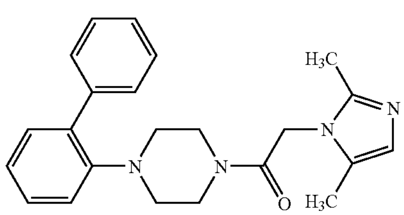 [SMILES: Cc1cnc(C)n1CC(=O)N1CCN(c2ccccc2-c2ccccc2)CC1] | 1-(4-Biphenyl-2-yl-piperazin-1-yl)-2-(2,5-dimethyl-imidazol-1-yl)-ethanone | 375 |
| 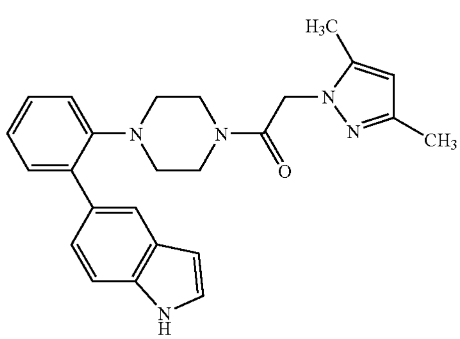 [SMILES: Cc1cc(C)n(CC(=O)N2CCN(c3ccccc3-c3ccc4[nH]ccc4c3)CC2)n1] | 2-(3,5-Dimethyl-pyrazol-1-yl)-1-{4-[2-(1H-indol-5-yl)-phenyl]-piperazin-1-yl}-ethanone | 415 |

TABLE I-continued

| MOLECULAR STRUCTURE | CHEMICAL NAME | Observed MH+ |
|---|---|---|
| 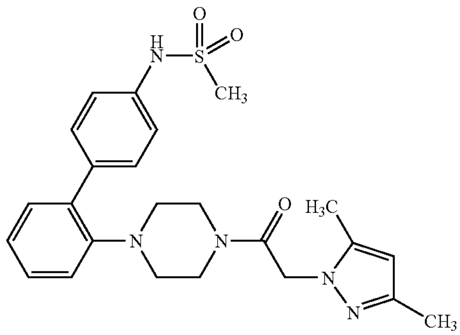 [SMILES: Cc1cc(C)n(CC(=O)N2CCN(c3ccccc3-c3ccc(NS(C)(=O)=O)cc3)CC2)n1] | N-(2'-{4-[2-(3,5-Dimethyl-pyrazol-1-yl)-acetyl]-piperazin-1-yl}-biphenyl-4-yl)-methanesulfonamide | 469 |
| 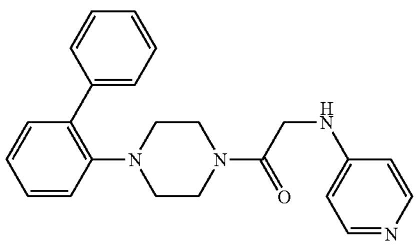 [SMILES: O=C(CNc1ccncc1)N1CCN(c2ccccc2-c2ccccc2)CC1] | 1-(4-Biphenyl-2-yl-piperazin-1-yl)-2-(pyridin-4-ylamino)-ethanone | 373 |
| 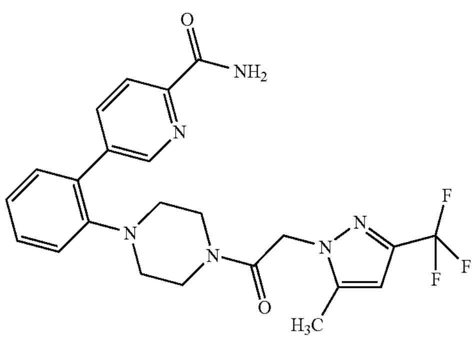 [SMILES: Cc1cc(C(F)(F)F)nn1CC(=O)N1CCN(c2ccccc2-c2ccc(C(N)=O)nc2)CC1] | 5-(2-{4-[2-(5-methyl-3-trifluoromethyl-pyrazol-1-yl)-acetyl]-piperazin-1-yl}-phenyl)-pyridine-2-carboxylic acid amide | 473 |
| 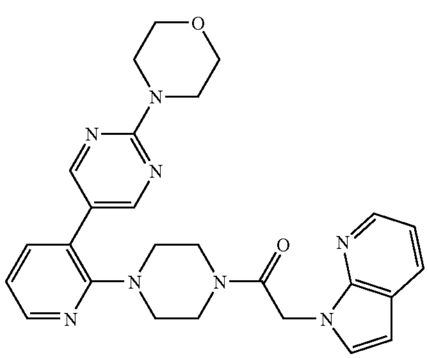 | 1-{4-[3-(2-Morpholin-4-yl-pyrimidin-5-yl)-pyridin-2-yl]-piperazin-1-yl}-2-pyrrolo[2,3-b]pyridin-1-yl-ethanone | 486 |
| 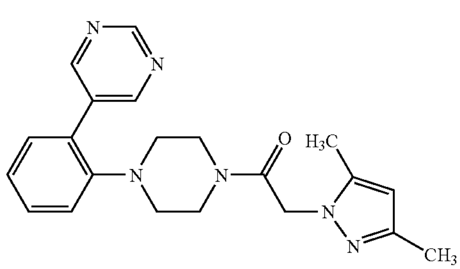 [SMILES: Cc1cc(C)n(CC(=O)N2CCN(c3ccccc3-c3cncnc3)CC2)n1] | 2-(3,5-Dimethyl-pyrazol-1-yl)-1-[4-(2-pyrimidin-5-yl-phenyl)-piperazin-1-yl]-ethanone | 377 |

TABLE I-continued

| MOLECULAR STRUCTURE | CHEMICAL NAME | Observed MH+ |
|---|---|---|
| 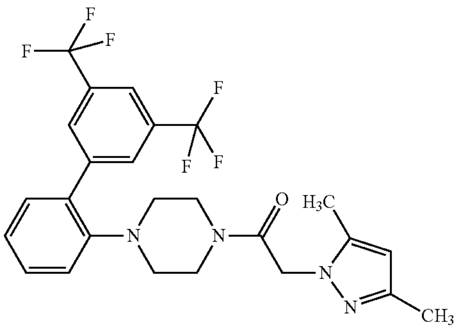 [SMILES: Cc1cc(C)n(CC(=O)N2CCN(c3ccccc3-c3cc(C(F)(F)F)cc(C(F)(F)F)c3)CC2)n1] | 1-[4-(3',5'-Bis-trifluoromethyl-biphenyl-2-yl)-piperazin-1-yl]-2-(3,5-dimethyl-pyrazol-1-yl)-ethanone | 511 |
| 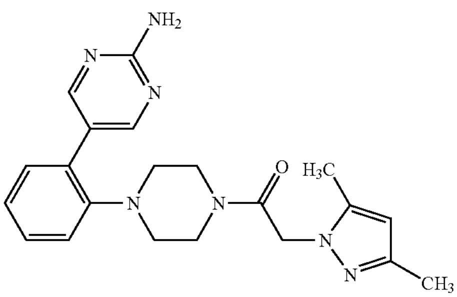 [SMILES: Cc1cc(C)n(CC(=O)N2CCN(c3ccccc3-c3cnc(N)nc3)CC2)n1] | 1-{4-[2-(2-Amino-pyrimidin-5-yl)-phenyl]-piperazin-1-yl}-2-(3,5-dimethyl-pyrazol-1-yl)-ethanone | 392 |
| 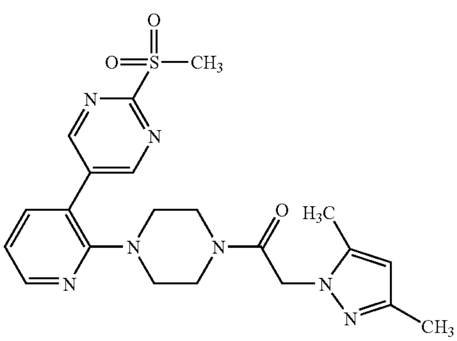 [SMILES: Cc1cc(C)n(CC(=O)N2CCN(c3ncccc3-c3cnc(S(C)(=O)=O)nc3)CC2)n1] | 2-(3,5-Dimethyl-pyrazol-1-yl)-1-[4-(4'-methanesulfonyl-biphenyl-2-yl)-piperazin-1-yl]-ethanone | 454 |
| 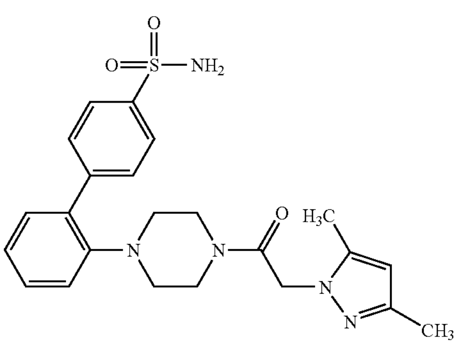 | 2'-{4-[2-(3,5-Dimethyl-pyrazol-1-yl)-acetyl]-piperazin-1-yl}-biphenyl-4-sulfonic acid amide | 455 |
| 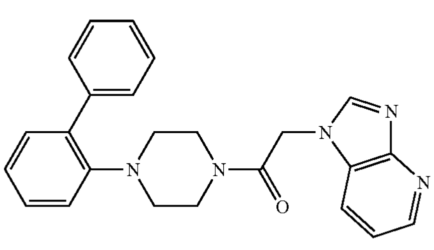 [SMILES: O=C(Cn1cnc2ncccc21)N1CCN(c2ccccc2-c2ccccc2)CC1] | 1-(4-Biphenyl-2-yl-piperazin-1-yl)-2-imidazo[4,5-b]pyridin-1-yl-ethanone | 398 |

TABLE I-continued

| MOLECULAR STRUCTURE | CHEMICAL NAME | Observed MH+ |
|---|---|---|
| 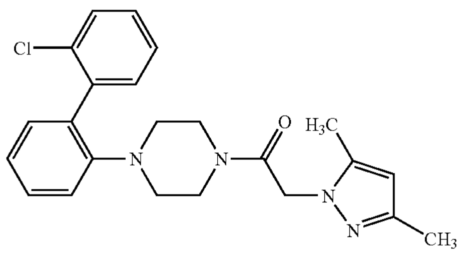 [SMILES: Cc1cc(C)n(CC(=O)N2CCN(c3ccccc3-c3ccccc3Cl)CC2)n1] | 1-[4-(2'-Chloro-biphenyl-2-yl)-piperazin-1-yl]-2-(3,5-dimethyl-pyrazol-1-yl)-ethanone | 410 |
| 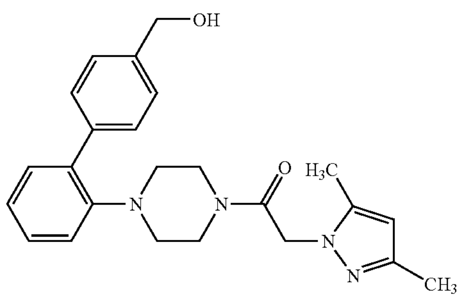 [SMILES: Cc1cc(C)n(CC(=O)N2CCN(c3ccccc3-c3ccc(CO)cc3)CC2)n1] | 2-(3,5-Dimethyl-pyrazol-1-yl)-1-[4-(4'-hydroxymethyl-biphenyl-2-yl)-piperazin-1-yl]-ethanone | 406 |
| 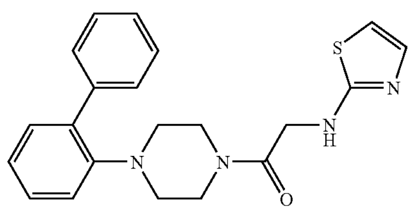 [SMILES: O=C(CNc1nccs1)N1CCN(c2ccccc2-c2ccccc2)CC1] | 1-(4-Biphenyl-2-yl-piperazin-1-yl)-2-(thiazol-2-ylamino)-ethanone | 379 |
| 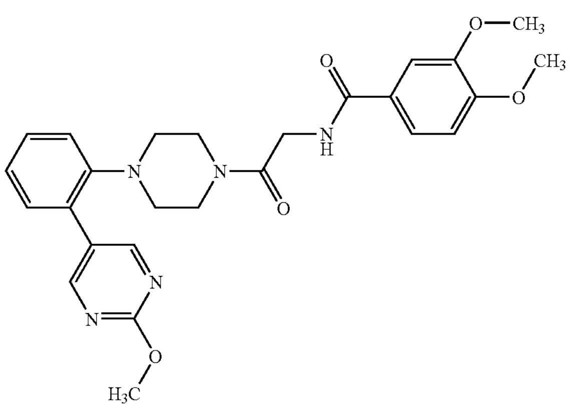 [SMILES: COc1ncc(-c2ccccc2N2CCN(C(=O)CNC(=O)c3ccc(OC)c(OC)c3)CC2)cn1] | 3,4-Dimethoxy-N-(2-{4-[2-(2-methoxy-pyrimidin-5-yl)-phenyl]-piperazin-1-yl}-2-oxo-ethyl)-benzamide | 493 |
| 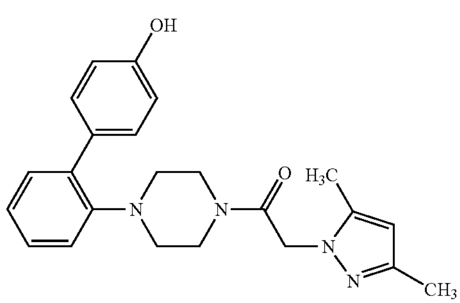 | 2-(3,5-Dimethyl-pyrazol-1-yl)-1-[4-(4'-hydroxy-biphenyl-2-yl)-piperazin-1-yl]-ethanone | 391 |

TABLE I-continued

| MOLECULAR STRUCTURE | CHEMICAL NAME | Observed MH+ |
|---|---|---|
| | 2-(3,5-Dimethyl-pyrazol-1-yl)-1-(4-[1,1';3',1"]terphenyl-2-yl-piperazin-1-yl)-ethanone | 452 |
| 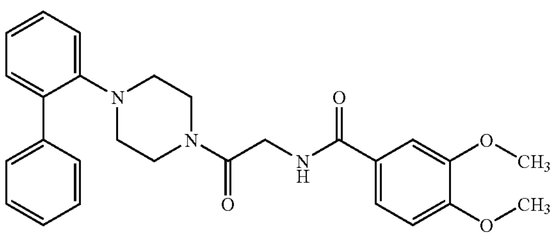 [SMILES: COc1ccc(C(=O)NCC(=O)N2CCN(c3ccccc3-c3ccccc3)CC2)cc1OC] | N-[2-(4-Biphenyl-2-yl-piperazin-1-yl)-2-oxo-ethyl]-3,4-dimethoxy-benzamide | 461 |
| 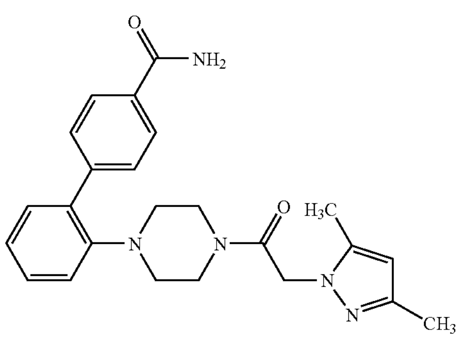 [SMILES: Cc1cc(C)n(CC(=O)N2CCN(c3ccccc3-c3ccc(C(N)=O)cc3)CC2)n1] | 2'-{4-[2-(3,5-Dimethyl-pyrazol-1-yl)-acetyl]-piperazin-1-yl}-biphenyl-4-carboxylic acid amide | 419 |
| 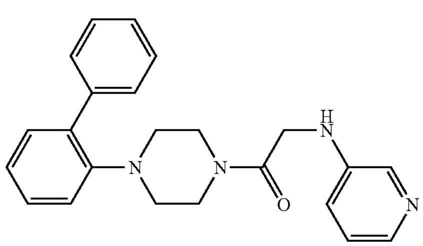 [SMILES: O=C(CNc1cccnc1)N1CCN(c2ccccc2-c2ccccc2)CC1] | 1-(4-Biphenyl-2-yl-piperazin-1-yl)-2-(pyridin-3-ylamino)-ethanone | 373 |
| 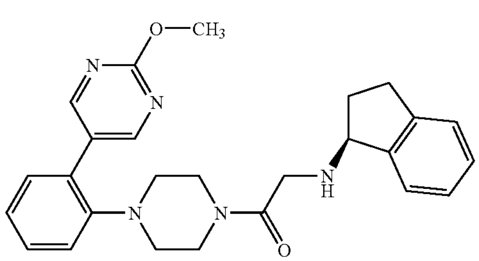 [SMILES: COc1ncc(-c2ccccc2N2CCN(C(=O)CN[C@H]3CCc4ccccc43)CC2)cn1] | 2-((S)-Indan-1-ylamino)-1-{4-[2-(2-methoxy-pyrimidin-5-yl)-phenyl]-piperazin-1-yl}-ethanone | 444 |

TABLE I-continued

| MOLECULAR STRUCTURE | CHEMICAL NAME | Observed MH+ |
|---|---|---|
| 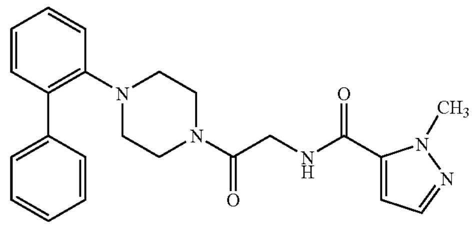 [SMILES: Cn1nccc1C(=O)NCC(=O)N1CCN(c2ccccc2-c2ccccc2)CC1] | 2-Methyl-2H-pyrazole-3-carboxylic acid [2-(4-biphenyl-2-yl-piperazin-1-yl)-2-oxo-ethyl]-amide | 405 |
| 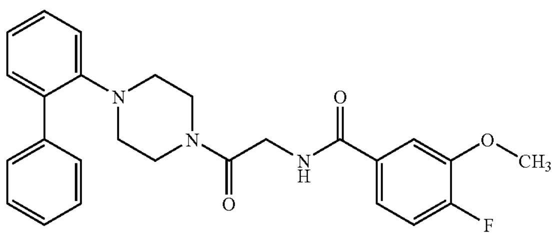 [SMILES: COc1cc(C(=O)NCC(=O)N2CCN(c3ccccc3-c3ccccc3)CC2)ccc1F] | N-[2-(4-Biphenyl-2-yl-piperazin-1-yl)-2-oxo-ethyl]-4-fluoro-3-methoxy-benzamide | 449 |
| 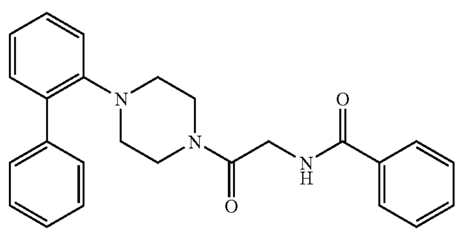 [SMILES: O=C(NCC(=O)N1CCN(c2ccccc2-c2ccccc2)CC1)c1ccccc1] | N-[2-(4-Biphenyl-2-yl-piperazin-1-yl)-2-oxo-ethyl]-benzamide | 401 |
| 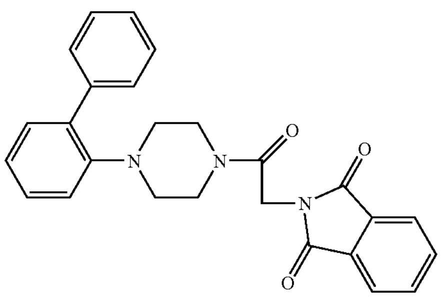 [SMILES: O=C(CN1C(=O)c2ccccc2C1=O)N1CCN(c2ccccc2-c2ccccc2)CC1] | 2-[2-(4-Biphenyl-2-yl-piperazin-1-yl)-2-oxo-ethyl]-isoindole-1,3-dione | 426 |
| 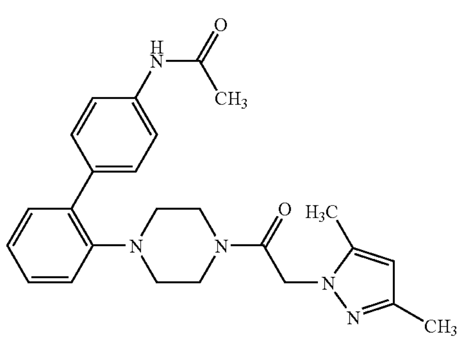 [SMILES: CC(=O)Nc1ccc(-c2ccccc2N2CCN(C(=O)Cn3nc(C)cc3C)CC2)cc1] | N-(2'-{4-[2-(3,5-Dimethyl-pyrazol-1-yl)-acetyl]-piperazin-1-yl}-biphenyl-4-yl)-acetamide | 433 |
| 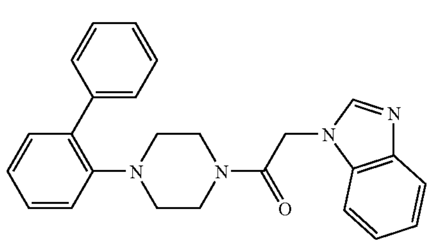 [SMILES: O=C(Cn1cnc2ccccc21)N1CCN(c2ccccc2-c2ccccc2)CC1] | 2-Benzoimidazol-1-yl-1-(4-biphenyl-2-yl-piperazin-1-yl)-ethanone | 397 |

TABLE I-continued

| MOLECULAR STRUCTURE | CHEMICAL NAME | Observed MH+ |
|---|---|---|
| 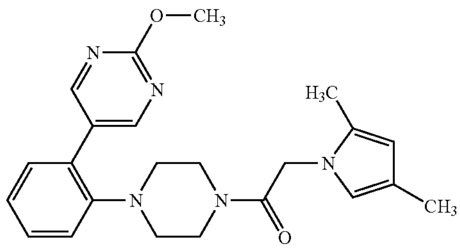 [SMILES: COc1ncc(-c2ccccc2N2CCN(C(=O)Cn3cc(C)cc3C)CC2)cn1] | 2-(2,4-Dimethyl-pyrrol-1-yl)-1-{4-[2-(2-methoxy-pyrimidin-5-yl)-phenyl]-piperazin-1-yl}-ethanone | 406 |
| 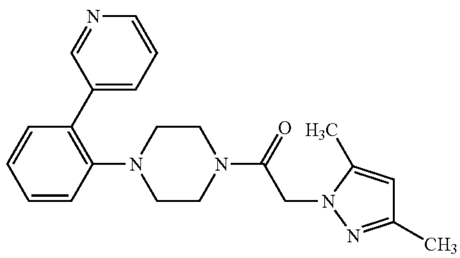 | 2-(3,5-Dimethyl-pyrazol-1-yl)-1-[4-(2-pyridin-3-yl-phenyl)-piperazin-1-yl]-ethanone | 376 |
| 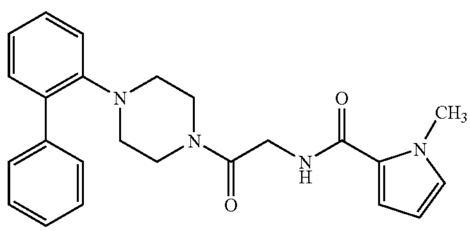 [SMILES: Cn1cccc1C(=O)NCC(=O)N1CCN(c2ccccc2-c2ccccc2)CC1] | 1-Methyl-1H-pyrrole-2-carboxylic acid [2-(4-biphenyl-2-yl-piperazin-1-yl)-2-oxo-ethyl]-amide | 403 |
| 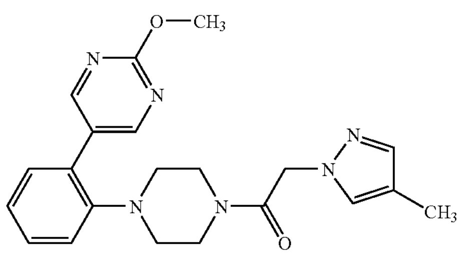 [SMILES: COc1ncc(-c2ccccc2N2CCN(C(=O)Cn3cc(C)cn3)CC2)cn1] | 1-{4-[2-(2-Methoxy-pyrimidin-5-yl)-phenyl]-piperazin-1-yl}-2-(4-methyl-pyrazol-1-yl)-ethanone | 393 |
| 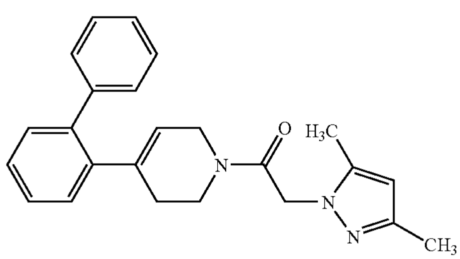 [SMILES: Cc1cc(C)n(CC(=O)N2CC=C(c3ccccc3-c3ccccc3)CC2)n1] | 1-(4-Biphenyl-2-yl-3,6-dihydro-2H-pyridin-1-yl)-2-(3,5-dimthyl-pyrazol-1-yl)-ethanone | 372 |
| 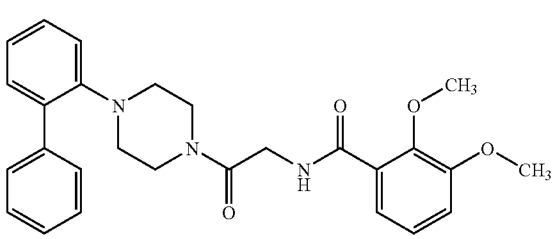 [SMILES: COc1cccc(C(=O)NCC(=O)N2CCN(c3ccccc3-c3ccccc3)CC2)c1OC] | N-[2-(4-Biphenyl-2-yl-piperazin-1-yl)-2-oxo-ethyl]-2,3-dimethoxy-benzamide | 461 |

TABLE I-continued

| MOLECULAR STRUCTURE | CHEMICAL NAME | Observed MH+ |
|---|---|---|
| 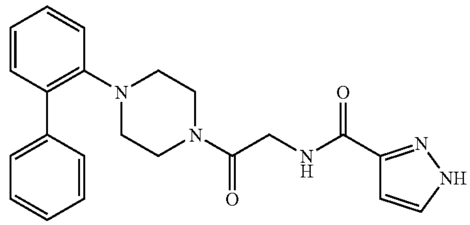 [SMILES: O=C(NCC(=O)N1CCN(c2ccccc2-c2ccccc2)CC1)c1cc[nH]n1] | 1H-Pyrazole-3-carboxylic acid [2-(4-biphenyl-2-yl-piperazin-1-yl)-2-oxo-ethyl]-amide | 390 |
| 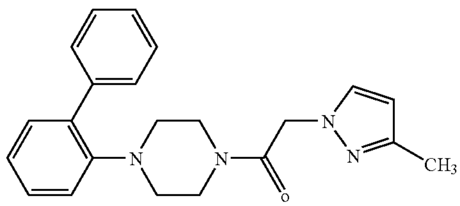 | 1-(4-Biphenyl-2-yl-piperazin-1-yl)-2-(3-methyl-pyrazol-1-yl)-ethanone | 361 |
| 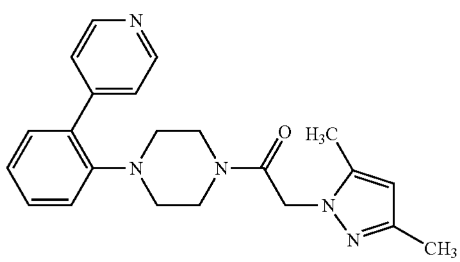 [SMILES: Cc1cc(C)n(CC(=O)N2CCN(c3ccccc3-c3ccncc3)CC2)n1] | 2-(3,5-Dimethyl-pyrazol-1-yl)-1-[4-(2-pyridin-4-yl-phenyl)-piperazin-1-yl]-ethanone | 376 |
| 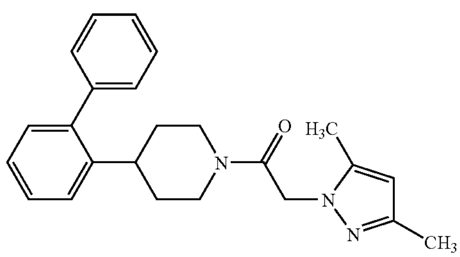 [SMILES: Cc1cc(C)n(CC(=O)N2CCC(c3ccccc3-c3ccccc3)CC2)n1] | 1-(4-Biphenyl-2-yl-piperidin-1-yl)-2-(3,5-dimethyl-pyrazol-1-yl)-ethanone | 374 |
| 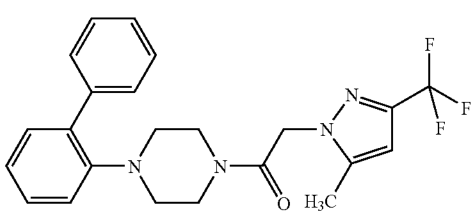 [SMILES: Cc1cc(C(F)(F)F)nn1CC(=O)N1CCN(c2ccccc2-c2ccccc2)CC1] | 1-(4-Biphenyl-2-yl-piperazin-1-yl)-2-(5-methyl-3-trifluoromethyl-pyrazol-1-yl)-ethanone | 429 |
| 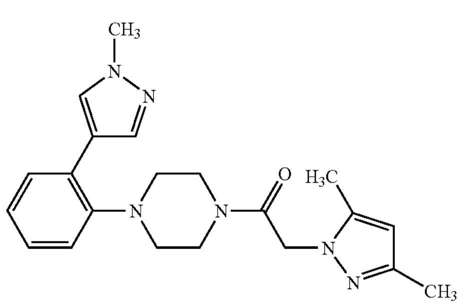 [SMILES: Cc1cc(C)n(CC(=O)N2CCN(c3ccccc3-c3cnn(C)c3)CC2)n1] | 2-(3,5-Dimethyl-pyrazol-1-yl)-1-{4-[2-(1-methyl-1H-pyrazol-4-yl)-phenyl]-piperazin-1-yl}-ethanone | 379 |

TABLE I-continued

| MOLECULAR STRUCTURE | CHEMICAL NAME | Observed MH+ |
|---|---|---|
| 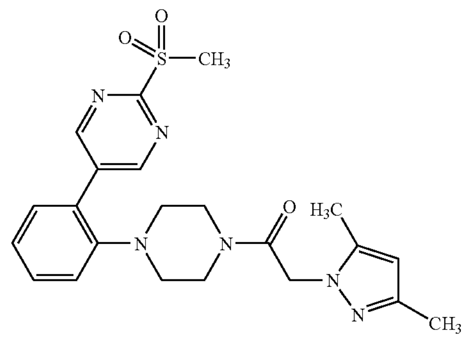 [SMILES: Cc1cc(C)n(CC(=O)N2CCN(c3ccccc3-c3cnc(S(C)(=O)=O)nc3)CC2)n1] | 2-(3,5-Dimethyl-pyrazol-1-yl)-1-{4-[2-(2-methanesulfonyl-pyrimidin-5-yl)-phenyl]-piperazin-1-yl}-ethanone | 456 |
| 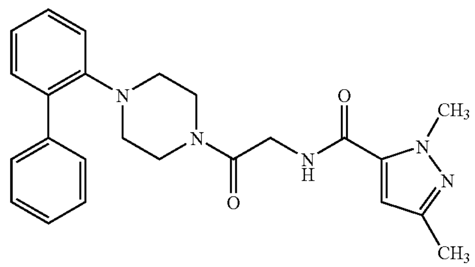 [SMILES: Cc1cc(C(=O)NCC(=O)N2CCN(c3ccccc3-c3ccccc3)CC2)n(C)n1] | 2,5-Dimethyl-2H-pyrrole-3-carboxylic acid [2-(4-biphenyl-2-yl-piperazin-1-yl)-2-oxo-ethyl]-amide | 419 |
| 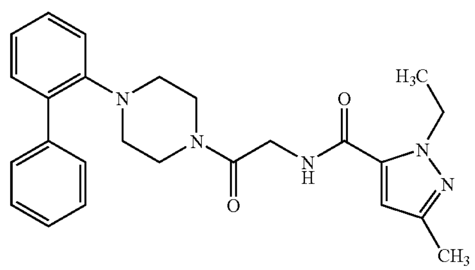 [SMILES: CCn1nc(C)cc1C(=O)NCC(=O)N1CCN(c2ccccc2-c2ccccc2)CC1] | 2-Ethyl-5-methyl-2H-pyrazole-3-carboxylic acid [2-(4-biphenyl-2-yl-piperazin-1-yl)-2-oxo-ethyl]-amide | 432 |
| 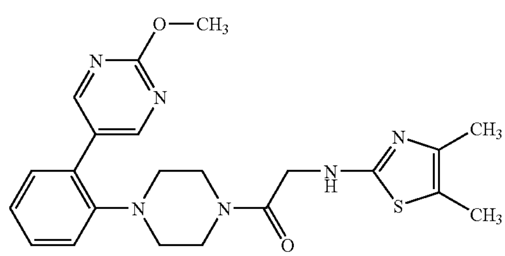 [SMILES: COc1ncc(-c2ccccc2N2CCN(C(=O)CNc3nc(C)c(C)s3)CC2)cn1] | 2-(4,5-Dimethyl-thiazol-2-ylamino)-1-{4-[2-(2-methoxy-pyrimidin-5-yl)-phenyl]-piperazin-1-yl}-ethanone | 439 |
| 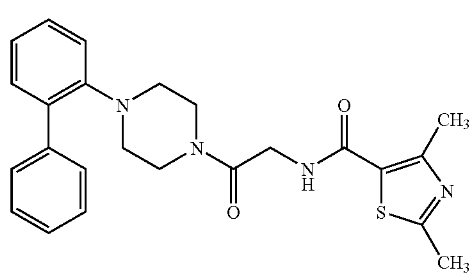 [SMILES: Cc1nc(C)c(C(=O)NCC(=O)N2CCN(c3ccccc3-c3ccccc3)CC2)s1] | 2,4-Dimethyl-thiazole-5-carboxylic acid [2-(4-biphenyl-2-yl-piperazin-1-yl)-2-oxo-ethyl]-amide | 435 |

TABLE I-continued

| MOLECULAR STRUCTURE | CHEMICAL NAME | Observed MH+ |
|---|---|---|
| 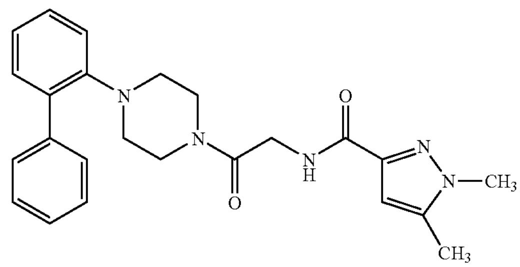 [SMILES: Cc1cc(C(=O)NCC(=O)N2CCN(c3ccccc3-c3ccccc3)CC2)nn1C] | 1,5-Dimethyl-1H-pyrazole-3-carboxylic acid [2-(4-biphenyl-2-yl-piperazin-1-yl)-2-oxo-ethyl]-amide | 419 |
| 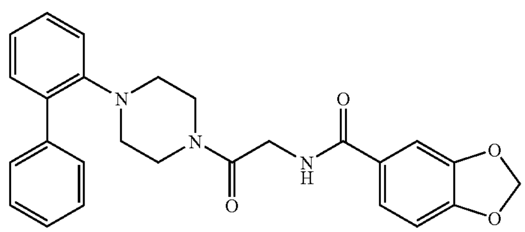 [SMILES: O=C(NCC(=O)N1CCN(c2ccccc2-c2ccccc2)CC1)c1ccc2c(c1)OCO2] | Benzo[1,3]dioxole-5-carboxylic acid [2-(4-biphenyl-2-yl-piperazin-1-yl)-2-oxo-ethyl]-amide | 445 |
| 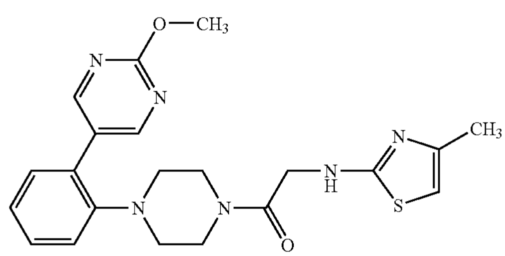 [SMILES: COc1ncc(-c2ccccc2N2CCN(C(=O)CNc3nc(C)cs3)CC2)cn1] | 1-{4-[2-(2-Methoxy-pyrimidin-5-yl)-phenyl]-piperazin-1-yl}-2-(4-methyl-thiazol-2-ylamino)-ethanone | 425 |
| 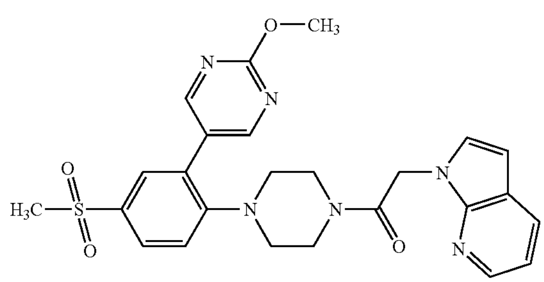 [SMILES: COc1ncc(-c2cc(S(C)(=O)=O)ccc2N2CCN(C(=O)Cn3ccc4cccnc43)CC2)cn1] | 1-{4-[4-Methanesulfonyl-2-(2-methoxy-pyrimidin-5-yl)-phenyl]-piperazin-1-yl}-2-pyrrolo[2,3-b]pyridin-1-yl-ethanone | 507 |
| 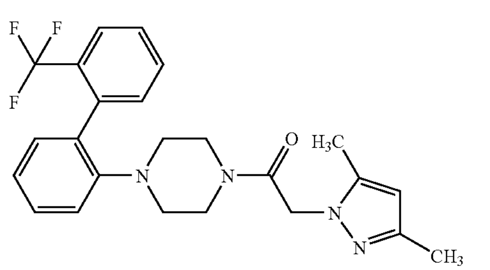 [SMILES: Cc1cc(C)n(CC(=O)N2CCN(c3ccccc3-c3ccccc3C(F)(F)F)CC2)n1] | 2-(3,5-Dimethyl-pyrazol-1-yl)-1-[4-(2'-trifluoromethyl-biphenyl-2-yl)-piperazin-1-yl]-ethanone | 443 |

TABLE I-continued

| MOLECULAR STRUCTURE | CHEMICAL NAME | Observed MH+ |
|---|---|---|
| 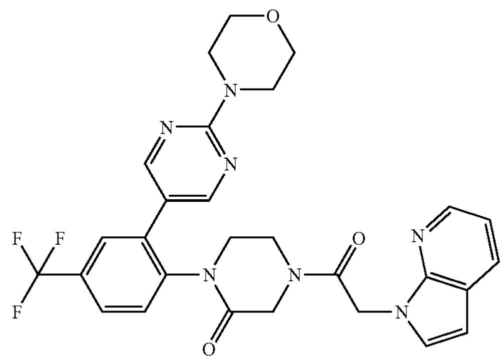 [SMILES: O=C(Cn1ccc2cccnc21)N1CCN(c2ccc(C(F)(F)F)cc2-c2cnc(N3CCOCC3)nc2)C(=O)C1] | 1-[2-(2-Morpholin-4-yl-pyrimidin-5-yl)-4-trifluoromethyl-phenyl]-4-(2-pyrrolo[2,3-b]pyridin-1-yl-acetyl)-piperazin-2-one | 567 |
| 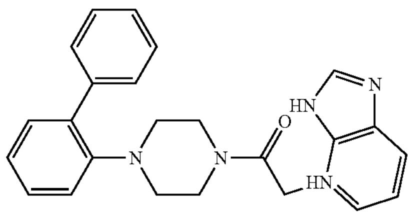 | 1-(4-Biphenyl-2-yl-piperazin-1-yl)-2-(3H-imidazo[4,5-b]pyridin-4-yl)-ethanone | 400 |
| 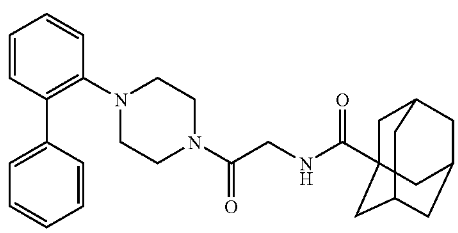 [SMILES: O=C(CNC(=O)C12CC3CC(CC(C3)C1)C2)N1CCN(c2ccccc2-c2ccccc2)CC1] | Adamantane-1-carboxylic acid [2-(4-biphenyl-2-yl-piperazin-1-yl)-2-oxo-ethyl]-amide | 459 |
| 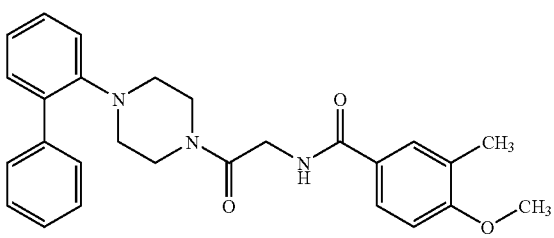 [SMILES: COc1ccc(C(=O)NCC(=O)N2CCN(c3ccccc3-c3ccccc3)CC2)cc1C] | N-[2-(4-Biphenyl-2-yl-piperazin-1-yl)-2-oxo-ethyl]-4-methoxy-3-methyl-benzamide | 445 |
| 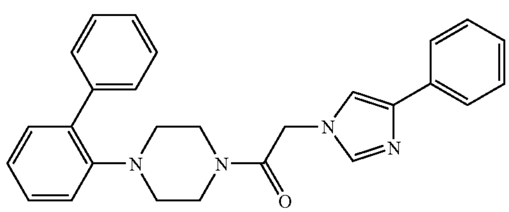 [SMILES: O=C(Cn1cnc(-c2ccccc2)c1)N1CCN(c2ccccc2-c2ccccc2)CC1] | 1-(4-Biphenyl-2-yl-piperazin-1-yl)-2-(4-phenyl-imidazol-1-yl)-ethanone | 423 |
| 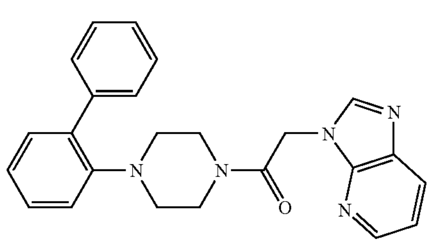 | 1-(4-Biphenyl-2-yl-piperazin-1-yl)-2-imidazo[4,5-b]pyridin-3-yl-ethanone | 398 |

TABLE I-continued

| MOLECULAR STRUCTURE | CHEMICAL NAME | Observed MH+ |
|---|---|---|
| 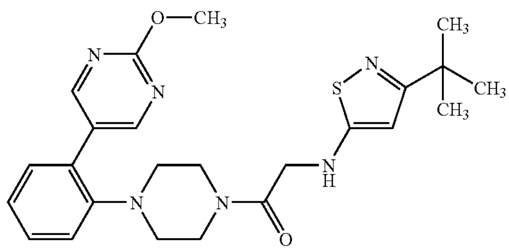 [SMILES: COc1ncc(-c2ccccc2N2CCN(C(=O)CNc3cc(C(C)(C)C)ns3)CC2)cn1] | 2-(3-tert-Butyl-isothiazol-5-ylamino)-1-{4-[2-(2-methoxy-pyrimidin-5-yl)-phenyl]-piperazin-1-yl}-ethanone | 467 |
| 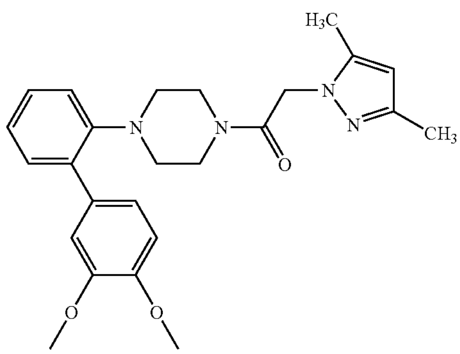 [SMILES: COc1ccc(-c2ccccc2N2CCN(C(=O)Cn3nc(C)cc3C)CC2)cc1OC] | 1-[4-(3',4'-Dimethoxy-biphenyl-2-yl)-piperazin-1-yl]-2-(3,5-dimethyl-pyrazol-1-yl)-ethanone | 435 |
| 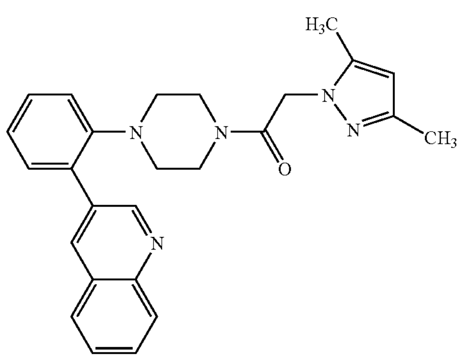 | 2-(3,5-Dimethyl-pyrazol-1-yl)-1-[4-(2-quinolin-3-yl-phenyl)-piperazin-1-yl]-ethanone | 426 |
| 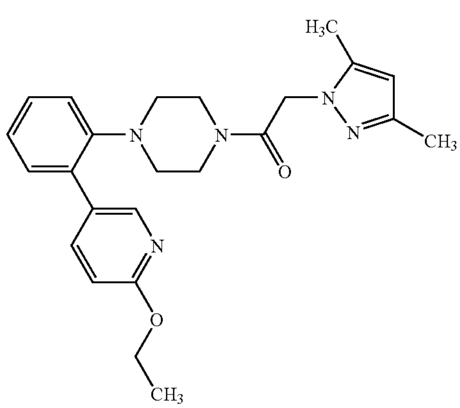 [SMILES: CCOc1ccc(-c2ccccc2N2CCN(C(=O)Cn3nc(C)cc3C)CC2)cn1] | 2-(3,5-Dimethyl-pyrazol-1-yl)-1-{4-[2-(6-ethoxy-pyridin-3-yl)-phenyl]-piperazin-1-yl}-ethanone | 420 |

TABLE I-continued
| MOLECULAR STRUCTURE | CHEMICAL NAME | Observed MH+ |
|---|---|---|
| 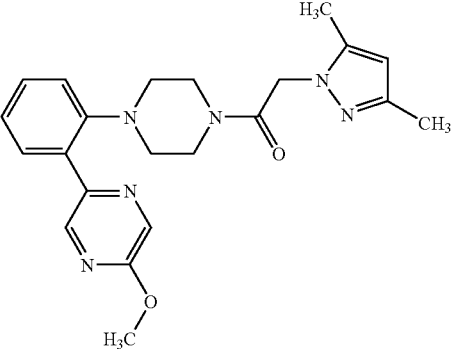 [SMILES: COc1cnc(-c2ccccc2N2CCN(C(=O)Cn3nc(C)cc3C)CC2)cn1] | 2-(3,5-Dimethyl-pyrazol-1-yl)-1-{4-[2-(5-methoxy-pyrazin-2-yl)-phenyl]-piperazin-1-yl}-ethanone | 407 |
| 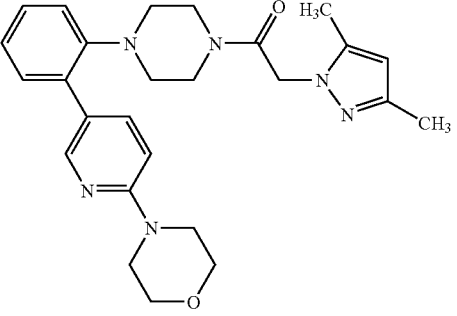 [SMILES: Cc1cc(C)n(CC(=O)N2CCN(c3ccccc3-c3ccc(N4CCOCC4)nc3)CC2)n1] | 2-(3,5-Dimethyl-pyrazol-1-yl)-1-{4-[2-(6-morpholin-4-yl-pyridin-3-yl)-phenyl]-piperazin-1-yl}-ethanone | 461 |
| 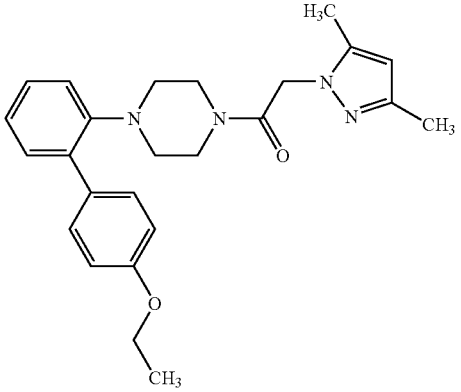 | 2-(3,5-Dimethyl-pyrazol-1-yl)-1-[4-(4'-ethoxy-biphenyl-2-yl)-piperazin-1-yl]-ethanone | 419 |
| 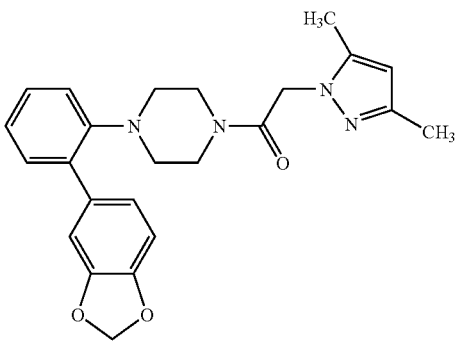 [SMILES: Cc1cc(C)n(CC(=O)N2CCN(c3ccccc3-c3ccc4c(c3)OCO4)CC2)n1] | 1-[4-(2-Benzo[1,3]dioxol-5-yl-phenyl)-piperazin-1-yl]-2-(3,5-dimethyl-pyrazol-1-yl)-ethanone | 419 |

TABLE I-continued

| MOLECULAR STRUCTURE | CHEMICAL NAME | Observed MH+ |
|---|---|---|
| 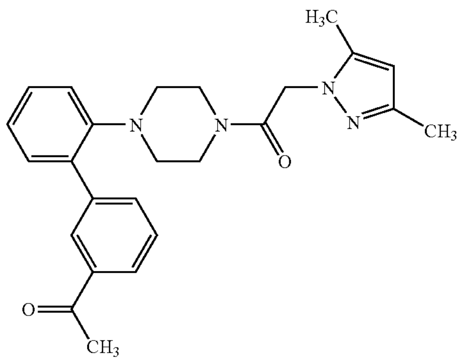 [SMILES: CC(=O)c1cccc(-c2ccccc2N2CCN(C(=O)Cn3nc(C)cc3C)CC2)c1] | 1-[4-(3'-Acetyl-biphenyl-2-yl)-piperazin-1-yl]-2-(3,5-dimethyl-pyrazol-1-yl)-ethanone | 417 |
| 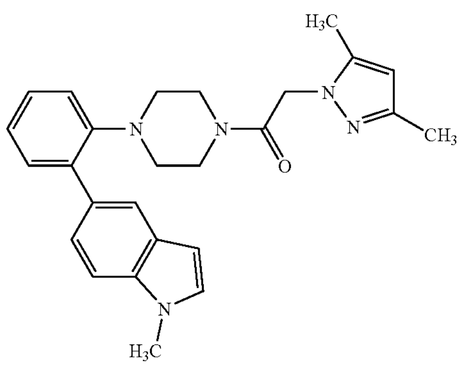 [SMILES: Cc1cc(C)n(CC(=O)N2CCN(c3ccccc3-c3ccc4c(ccn4C)c3)CC2)n1] | 2-(3,5-Dimethyl-pyrazol-1-yl)-1-{4-[2-(1-methyl-1H-indol-5-yl)-phenyl]-piperazin-1-yl}-ethanone | 428 |
| 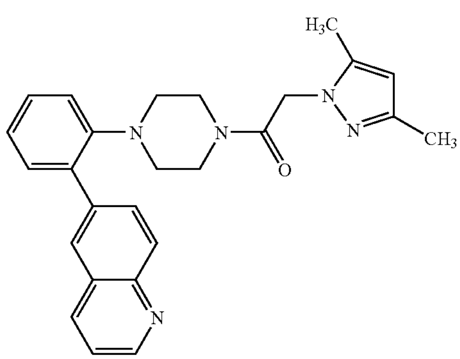 [SMILES: Cc1cc(C)n(CC(=O)N2CCN(c3ccccc3-c3ccc4ncccc4c3)CC2)n1] | 2-(3,5-Dimethyl-pyrazol-1-yl)-1-[4-(2-quinolin-6-yl-phenyl)-piperazin-1-yl]-ethanone | 426 |
| 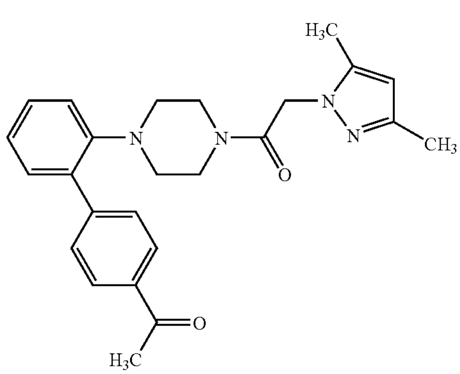 [SMILES: CC(=O)c1ccc(-c2ccccc2N2CCN(C(=O)Cn3nc(C)cc3C)CC2)cc1] | 1-[4-(4'-Acetyl-biphenyl-2-yl)-piperazin-1-yl]-2-(3,5-dimethyl-pyrazol-1-yl)-ethanone | 417 |

TABLE I-continued

| MOLECULAR STRUCTURE | CHEMICAL NAME | Observed MH+ |
|---|---|---|
| 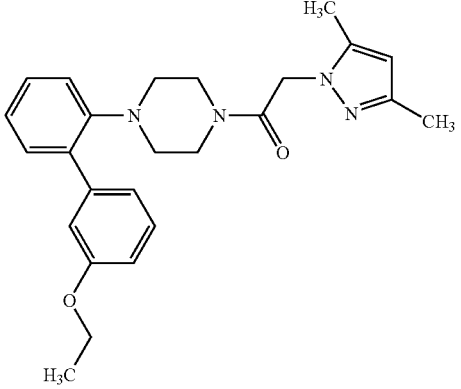 [SMILES: CCOc1cccc(-c2ccccc2N2CCN(C(=O)Cn3nc(C)cc3C)CC2)c1] | 2-(3,5-Dimethyl-pyrazol-1-yl)-1-[4-(3-ethoxy-biphenyl-2-yl)-piperazin-1-yl]-ethanone | 419 |
| 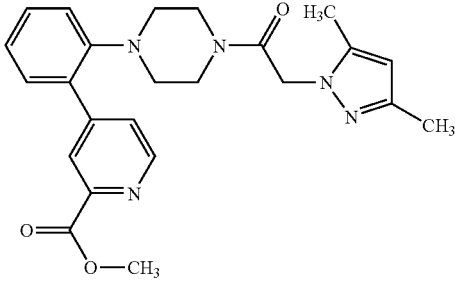 [SMILES: COC(=O)c1cc(-c2ccccc2N2CCN(C(=O)Cn3nc(C)cc3C)CC2)ccn1] | 4-(2-{4-[2-(3,5-Dimethyl-pyrazol-1-yl)-acetyl]-piperazin-1-yl}-phenyl)-pyridine-2-carboxylic acid methyl ester | 434 |
| 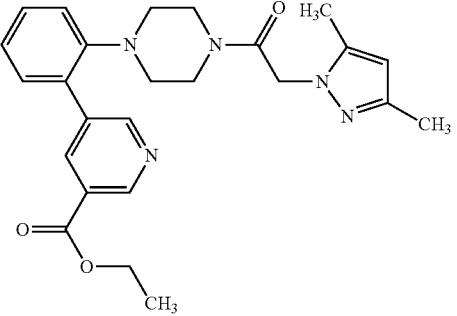 [SMILES: CCOC(=O)c1cncc(-c2ccccc2N2CCN(C(=O)Cn3nc(C)cc3C)CC2)c1] | 5-(2-{4-[2-(3,5-Dimethyl-pyrazol-1-yl)-acetyl]-piperazin-1-yl}-phenyl)-nicotinic acid ethyl ester | 448 |
| 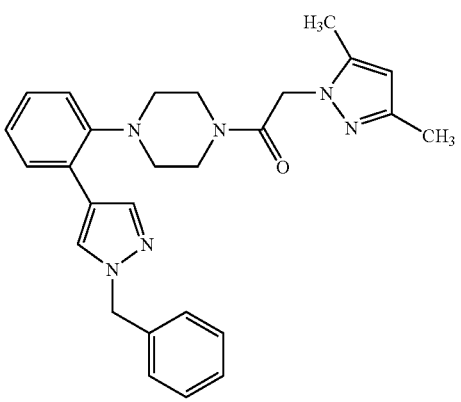 [SMILES: Cc1cc(C)n(CC(=O)N2CCN(c3ccccc3-c3cnn(Cc4ccccc4)c3)CC2)n1] | 1-{4-[2-(1-Benzyl-1H-pyrazol-4-yl)-phenyl]-piperazin-1-yl}-2-(3,5-dimthyl-pyrazol-1-yl)-ethanone | 455 |

TABLE I-continued
| MOLECULAR STRUCTURE | CHEMICAL NAME | Observed MH+ |
|---|---|---|
| 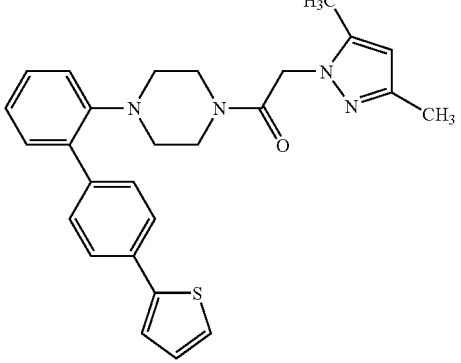 | 2-(3,5-Dimethyl-pyrazol-1-yl)-1-[4-(4'-thiophen-2-yl-biphenyl-2-yl)-piperazin-1-yl]-ethanone | 457 |
| 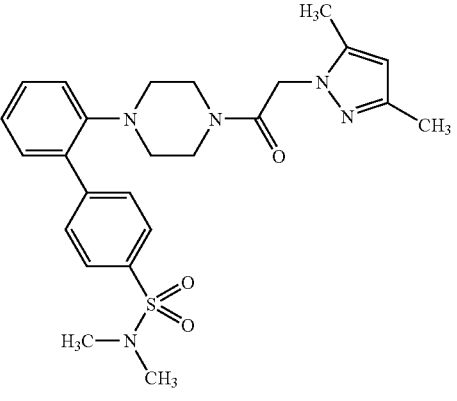 [SMILES: Cc1cc(C)n(CC(=O)N2CCN(c3ccccc3-c3ccc(S(=O)(=O)N(C)C)cc3)CC2)n1] | 2'-{4-[2-(3,5-Dimethyl-pyrazol-1-yl)-acetyl]-piperazin-1-yl}-biphenyl-4-sulfonoic acid dimethylamide | 482 |
| 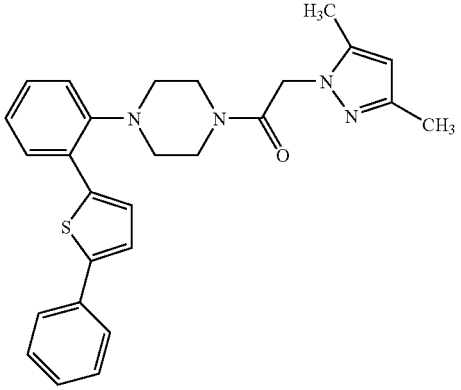 [SMILES: Cc1cc(C)n(CC(=O)N2CCN(c3ccccc3-c3ccc(-c4ccccc4)s3)CC2)n1] | 2-(3,5-Dimethyl-pyrazol-1-yl)-1-{4-[2-(5-phenyl-thiophen-2-yl)-phenyl]-piperazin-1-yl}-ethanone | 457 |
| 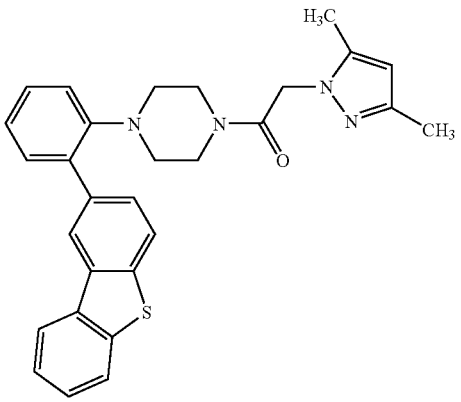 [SMILES: Cc1cc(C)n(CC(=O)N2CCN(c3ccccc3-c3ccc4sc5ccccc5c4c3)CC2)n1] | 1-[4-(2-Dibenzothiophen-2-yl-phenyl)-piperazin-1-yl]-2-(3,5-dimethyl-pyrazol-1-yl)-ethanone | 481 |

TABLE I-continued

| MOLECULAR STRUCTURE | CHEMICAL NAME | Observed MH+ |
|---|---|---|
| 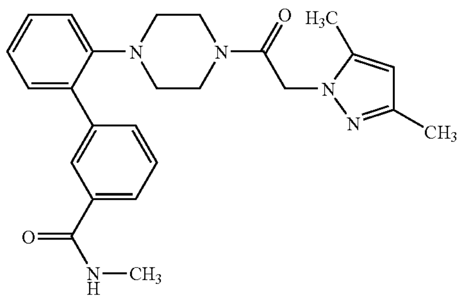 [SMILES: CNC(=O)c1cccc(-c2ccccc2N2CCN(C(=O)Cn3nc(C)cc3C)CC2)c1] | 2'-{4-[2-(3,5-Dimethyl-pyrazol-1-yl)-acetyl]-piperazin-1-yl}-biphenyl-3-carboxylic acid methylamide | 432 |
| 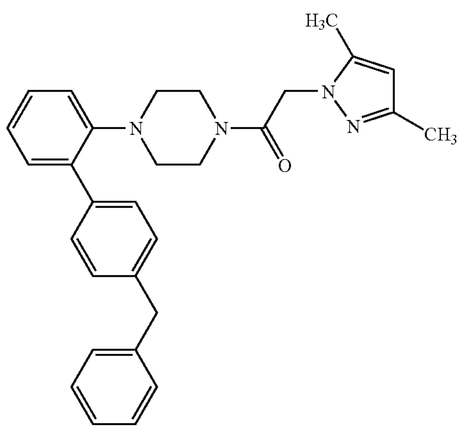 [SMILES: Cc1cc(C)n(CC(=O)N2CCN(c3ccccc3-c3ccc(Cc4ccccc4)cc3)CC2)n1] | 1-[4-(4'-Benzyl-biphenyl-2-yl)-piperazin-1-yl]-2-(3,5-dimethyl-pyrazol-1-yl)-ethanone | 465 |
| 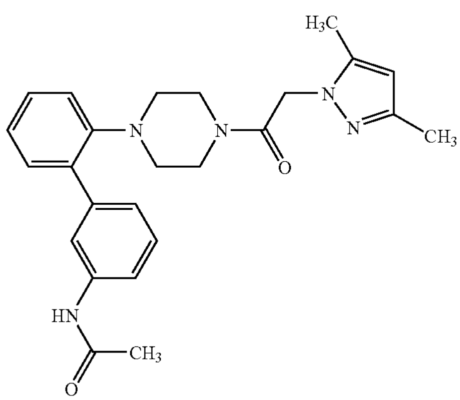 [SMILES: CC(=O)Nc1cccc(-c2ccccc2N2CCN(C(=O)Cn3nc(C)cc3C)CC2)c1] | N-(2'-{4-[2-(3,5-Dimethyl-pyrazol-1-yl)-acetyl]-piperazin-1-yl}-biphenyl-3-yl)-acetamide | 432 |
| 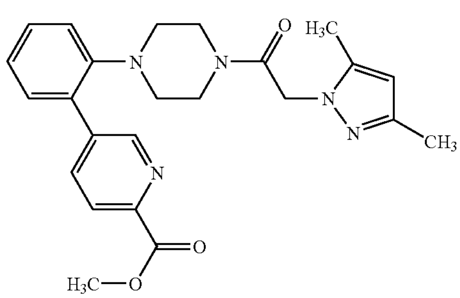 [SMILES: COC(=O)c1ccc(-c2ccccc2N2CCN(C(=O)Cn3nc(C)cc3C)CC2)cn1] | 5-(2-{4-[2-(3,5-Dimethyl-pyrazol-1-yl)-acetyl]-piperazin-1-yl}-phenyl)-pyridine-2-carboxylic acid methyl ester | 434 |

TABLE I-continued

| MOLECULAR STRUCTURE | CHEMICAL NAME | Observed MH+ |
|---|---|---|
| 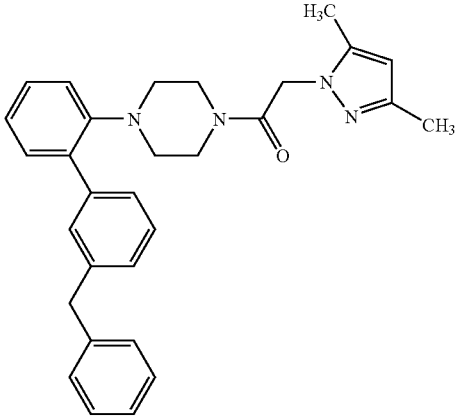 [SMILES: Cc1cc(C)n(CC(=O)N2CCN(c3ccccc3-c3cccc(Cc4ccccc4)c3)CC2)n1] | 1-[4-(3'-Benzyl-biphenyl-2-yl)-piperazin-1-yl]-2-(3,5-dimethyl-pyrazol-1-yl)-ethanone | 465 |
| 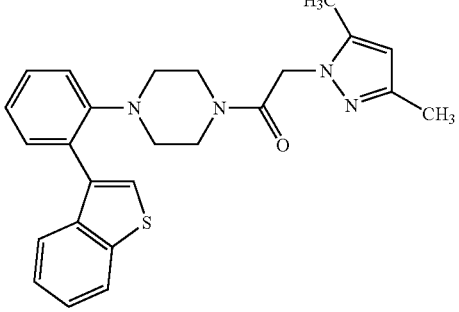 | 1-[4-(2-Benzo[b]thiophen-3-yl-phenyl)-piperazin-1-yl]-2-(3,5-dimethyl-pyrazol-1-yl)-ethanone | 431 |
| 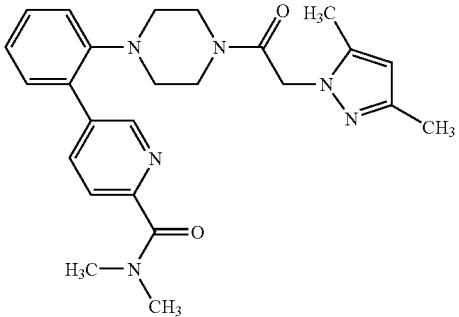 [SMILES: Cc1cc(C)n(CC(=O)N2CCN(c3ccccc3-c3ccc(C(=O)N(C)C)nc3)CC2)n1] | 2'-{4-[2-(3,5-Dimethyl-pyrazol-1-yl)-acetyl]-piperazin-1-yl}-biphenyl-4-carboxylic acid dimethylamide | 446 |
| 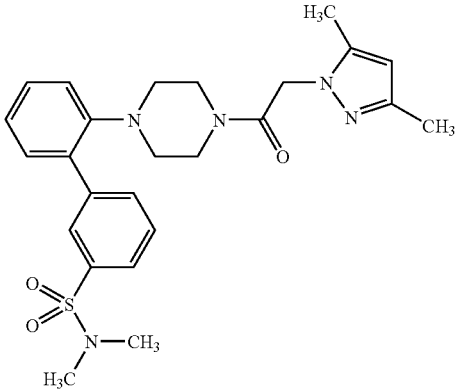 [SMILES: Cc1cc(C)n(CC(=O)N2CCN(c3ccccc3-c3cccc(S(=O)(=O)N(C)C)c3)CC2)n1] | 2'-{4-[2-(3,5-Dimethyl-pyrazol-1-yl)-acetyl]-piperazin-1-yl}-biphenyl-3-sulfonic acid dimethylamide | 482 |

TABLE I-continued

| MOLECULAR STRUCTURE | CHEMICAL NAME | Observed MH+ |
|---|---|---|
| 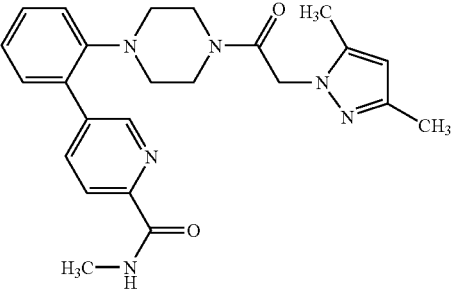 [SMILES: CNC(=O)c1ccc(-c2ccccc2N2CCN(C(=O)Cn3nc(C)cc3C)CC2)cn1] | 2'-{4[[2-(3,5-Dimethyl-pyrazol-1-yl)-acetyl]-piperazin-1-yl}-biphenyl-4-carboxylic acid methylamide | 432 |
| 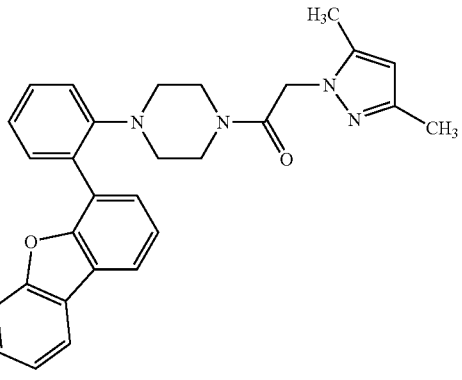 | 1-[4-(2-Dibenzofuran-4-yl-phenyl)-piperazin-1-yl]-2-(3,5-dimethyl-pyrazol-1-yl)-ethanone | 465 |
| 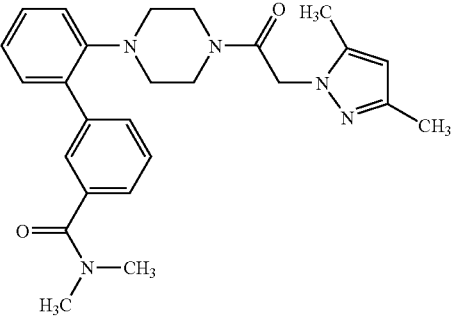 [SMILES: Cc1cc(C)n(CC(=O)N2CCN(c3ccccc3-c3cccc(C(=O)N(C)C)c3)CC2)n1] | 2'-{4-[2-(3,5-Dimethyl-pyrazol-1-yl)-acetyl]-piperazin-1-yl}-biphenyl-3-carboxylic acid dimethylamide | 446 |
| 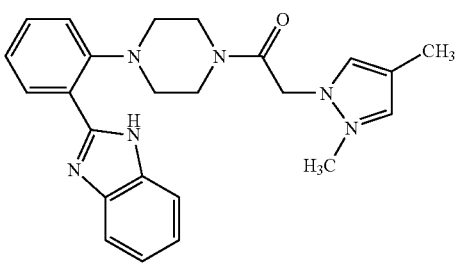 | 1-{4-[2-(1H-Benzoimidazol-2-yl)-phenyl]-piperazin-1-yl}-2-(3,5-dimethyl-pyrazol-1-yl)-ethanone | 415 |
| 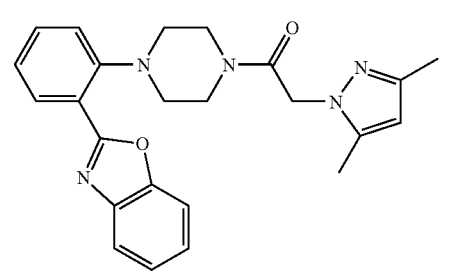 [SMILES: Cc1cc(C)n(CC(=O)N2CCN(c3ccccc3-c3nc4ccccc4o3)CC2)n1] | 1-[4-(2-Benzooxazol-2-yl-phenyl)-piperazin-1-yl]-2-(3,5-dimethyl-pyrazol-1-yl)-ethanone | 416 |

TABLE I-continued

| MOLECULAR STRUCTURE | CHEMICAL NAME | Observed MH+ |
|---|---|---|
| 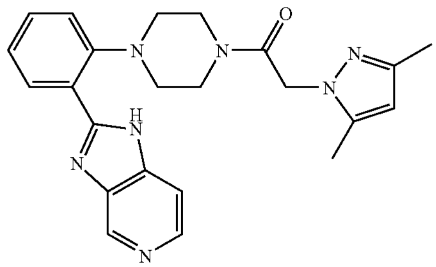 [SMILES: Cc1cc(C)n(CC(=O)N2CCN(c3ccccc3-c3nc4cnccc4[nH]3)CC2)n1] | 2-(3,5-Dimethyl-pyrazol-1-yl)-1-{4-[2-(1H-imidazo[4,5-c]pyridin-2-yl)-phenyl]-piperazin-1-yl}-ethanone | 416 |
| 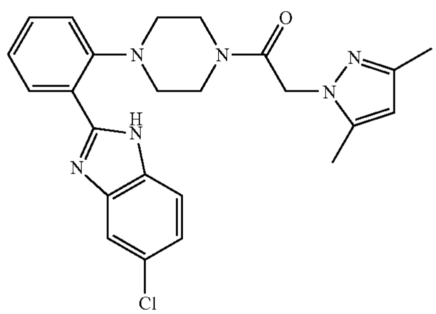 [SMILES: Cc1cc(C)n(CC(=O)N2CCN(c3ccccc3-c3nc4cc(Cl)ccc4[nH]3)CC2)n1] | 1-{4-[2-(5-Chloro-1H-benzoimidazol-2-yl)-phenyl]-piperazin-1-yl}-2-(3,5-dimethyl-pyrazol-1-yl)-ethanone | 449 |
| 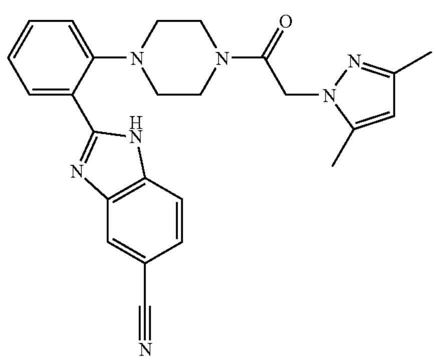 [SMILES: Cc1cc(C)n(CC(=O)N2CCN(c3ccccc3-c3nc4cc(C#N)ccc4[nH]3)CC2)n1] | 2-(2-{4-[2-(3,5-Dimethyl-pyrazol-1-yl)-acetyl]-piperazin-1-yl}-phenyl)-1H-benzoimidazole-5-carbonitrile | 440 |
| 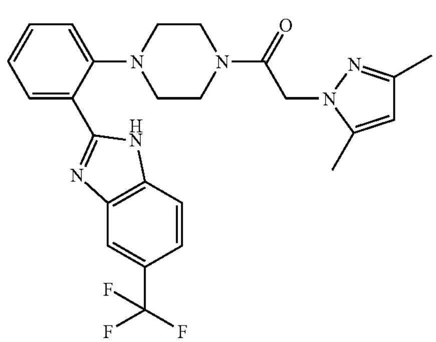 [SMILES: Cc1cc(C)n(CC(=O)N2CCN(c3ccccc3-c3nc4cc(C(F)(F)F)ccc4[nH]3)CC2)n1] | 2-(3,5-Dimethyl-pyrazol-1-yl)-1-{4-[2-(5-trifluoromethyl-1H-benzoimidazol-2-yl)-phenyl]-piperazin-1-yl}-ethanone | 483 |

TABLE I-continued

| MOLECULAR STRUCTURE | CHEMICAL NAME | Observed MH+ |
|---|---|---|
| 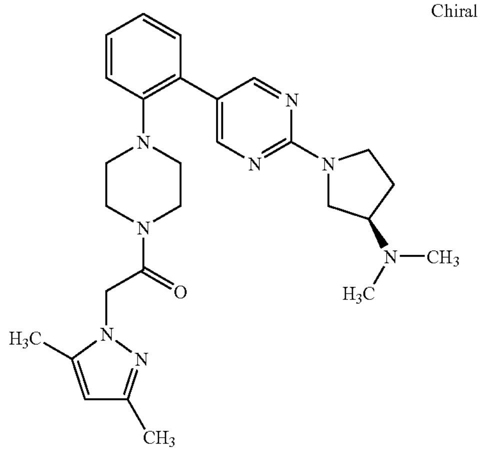 | 1-(4-{2-[2-((R)-3-Dimethylamino-pyrrolidin-1-yl)-pyrimidin-5-yl]-phenyl}-piperazin-1-yl)-2-(3,5-dimethyl-pyrazol-1-yl)-ethanone | 489 |
| 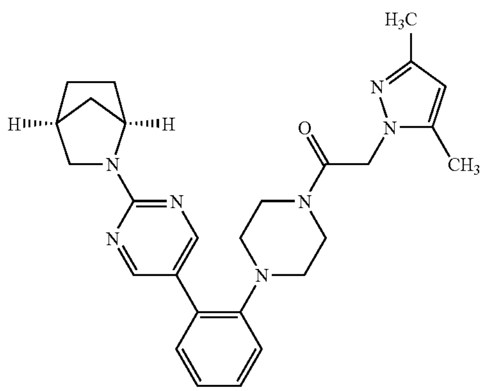 [SMILES: Cc1cc(C)n(CC(=O)N2CCN(c3ccccc3-c3cnc(N4C[C@H]5CC[C@@H]4C5)nc3)CC2)n1] | 1-(4-{2-[(1R,4S)-2-(2-Aza-bicyclo[2.2.1]hept-2-yl)-pyrimidin-5-yl]-phenyl}-piperazin-1-yl)-2-(3,5-dimethyl-pyrazol-1-yl)-ethanone | 472 |
| 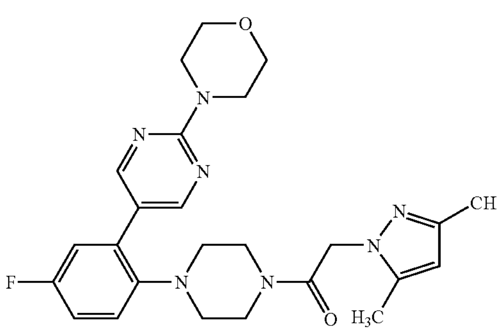 [SMILES: Cc1cc(C)n(CC(=O)N2CCN(c3ccc(F)cc3-c3cnc(N4CCOCC4)nc3)CC2)n1] | 2-(3,5-Dimethyl-pyrazol-1-yl)-1-{4-[4-fluoro-2-(2-morpholin-4-yl-pyrimidin-5-yl)-phenyl]-piperazin-1-yl}-ethanone | 481 |
| 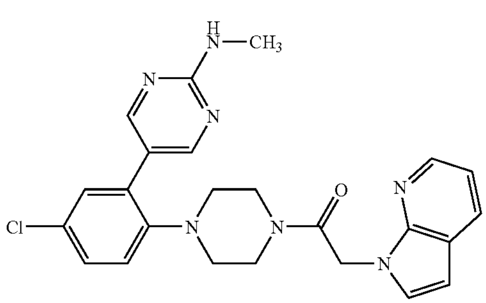 [SMILES: CNc1ncc(-c2cc(Cl)ccc2N2CCN(C(=O)Cn3ccc4cccnc43)CC2)cn1] | 1-{4-[4-Chloro-2-(2-methylamino-pyrimidin-5-yl)-phenyl]-piperazin-1-yl}-2-pyrrolo[2,3-b]pyridin-1-yl-ethanone | 462 |

TABLE I-continued

| MOLECULAR STRUCTURE | CHEMICAL NAME | Observed MH+ |
|---|---|---|
| 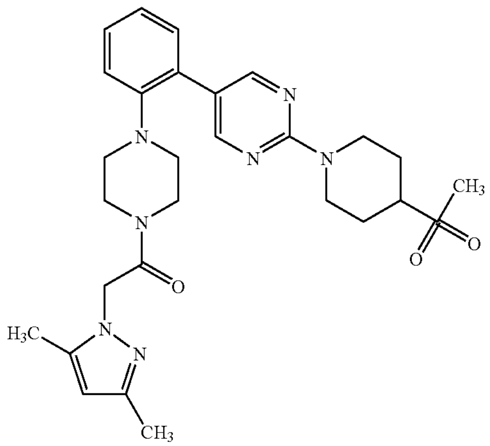 | 2-(3,5-Dimethyl-pyrazol-1-yl)-1-(4-{2-[2-(4-methanesulfonyl-piperidin-1-yl)-pyrimidin-5-yl]-phenyl}-piperazin-1-yl)-ethanone | 538 |
| 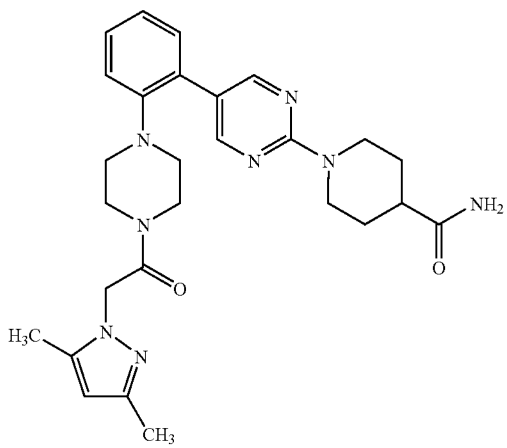 [SMILES: Cc1cc(C)n(CC(=O)N2CCN(c3ccccc3-c3cnc(N4CCC(C(N)=O)CC4)nc3)CC2)n1] | 1-[5-(2-{4-[2-(3,5-Dimethyl-pyrazol-1-yl)-acetyl]-piperazin-1-yl}-phenyl)-pyrimidin-2-yl]-piperidine-4-carboxylic acid amide | 503 |
| 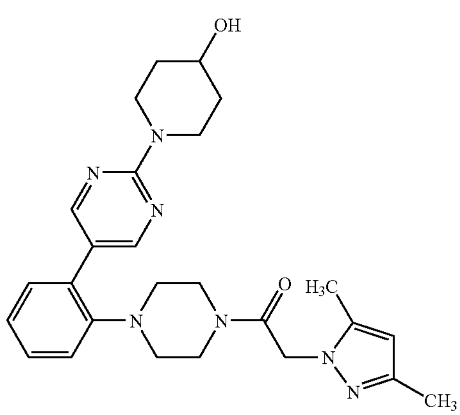 [SMILES: Cc1cc(C)n(CC(=O)N2CCN(c3ccccc3-c3cnc(N4CCC(O)CC4)nc3)CC2)n1] | 2-(3,5-Dimethyl-pyrazol-1-yl)-1-(4-{2-[2-(4-hydroxy-piperidin-1-yl)-pyrimidin-5-yl]-phenyl}-piperazin-1-yl)-ethanone | 476 |
| 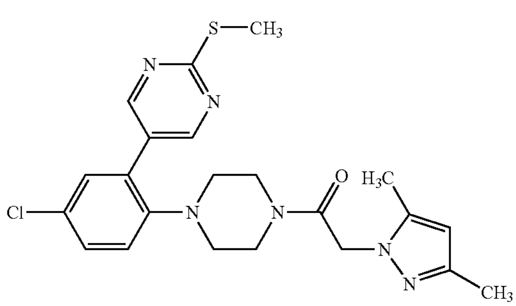 [SMILES: CSc1ncc(-c2cc(Cl)ccc2N2CCN(C(=O)Cn3nc(C)cc3C)CC2)cn1] | 1-{4-[4-Chloro-2-(2-methylsulfanyl-pyrimidin-5-yl)-phenyl]-piperazin-1-yl}-2-(3,5-dimethyl-pyrazol-1-yl)-ethanone | 459 |

TABLE I-continued

| MOLECULAR STRUCTURE | CHEMICAL NAME | Observed MH+ |
|---|---|---|
| 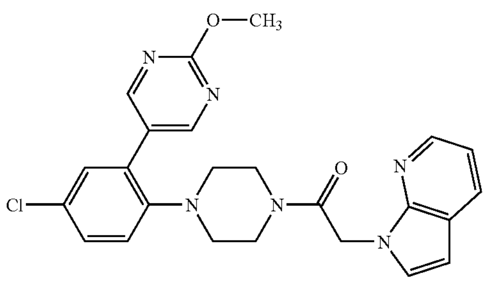 [SMILES: COc1ncc(-c2cc(Cl)ccc2N2CCN(C(=O)Cn3ccc4cccnc43)CC2)cn1] | 1-{4-[4-Chloro-2-(2-methoxy-pyrimidin-5-yl)-phenyl]-piperazin-1-yl}-2-pyrrolo[2,3-b]pyridin-1-yl-ethanone | 463 |
| 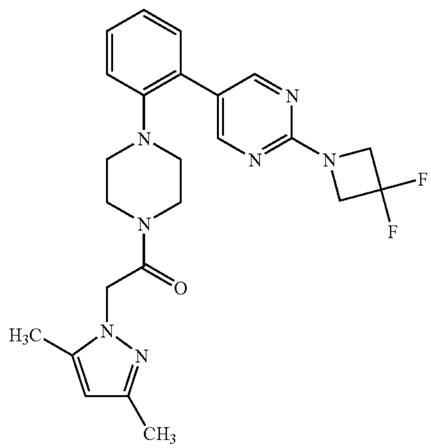 [SMILES: Cc1cc(C)n(CC(=O)N2CCN(c3ccccc3-c3cnc(N4CC(F)(F)C4)nc3)CC2)n1] | 1-(4-{2-[2-(3,3-Difluoro-azetidin-1-yl)-pyrimidin-5-yl]-phenyl}-piperazin-1-yl)-2-(3,5-dimethyl-pyrazol-1-yl)-ethanone | 468 |
| 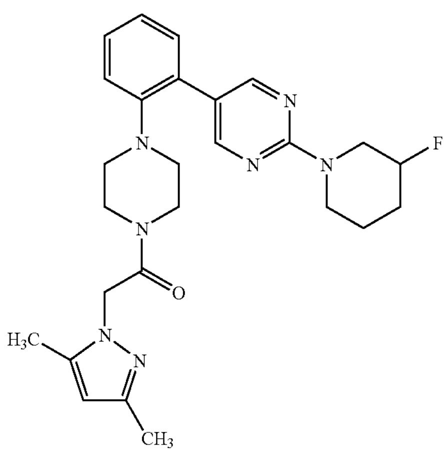 [SMILES: Cc1cc(C)n(CC(=O)N2CCN(c3ccccc3-c3cnc(N4CCCC(F)C4)nc3)CC2)n1] | 2-(3,5-Dimethyl-pyrazol-1-yl)-1-(4-{2-[2-(3-fluoro-piperidin-1-yl)-pyrimidin-5-yl]-phenyl}-piperazin-1-yl)-ethanone | 478 |
| 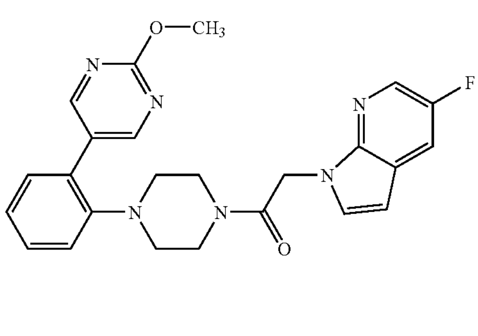 [SMILES: COc1ncc(-c2ccccc2N2CCN(C(=O)Cn3ccc4cc(F)cnc43)CC2)cn1] | 2-(5-Fluoro-pyrrolo[2,3-b]pyridin-1-yl)-1-{4-[2-(2-methoxy-pyrimidin-5-yl)-phenyl]-piperazin-1-yl}-ethanone | 447 |

TABLE I-continued
| MOLECULAR STRUCTURE | CHEMICAL NAME | Observed MH+ |
|---|---|---|
| 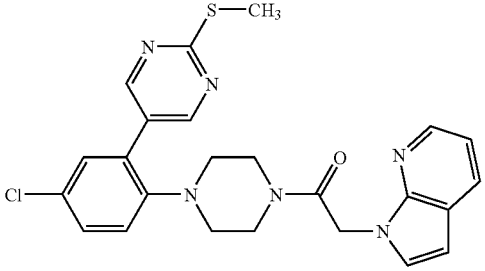 | 1-{4-[4-Chloro-2-(2-methylsulfanyl-pyrimidin-5-yl)-phenyl]-piperazin-1-yl}-2-pyrrolo[2,3-b]pyridin-1-yl-ethanone | 479 |
| 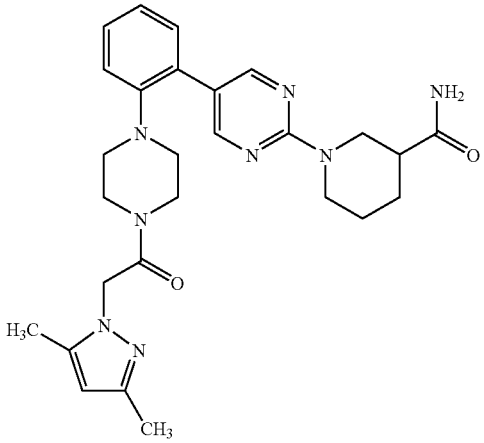 [SMILES: Cc1cc(C)n(CC(=O)N2CCN(c3ccccc3-c3cnc(N4CCCC(C(N)=O)C4)nc3)CC2)n1] | 1-[5-(2-{4-[2-(3,5-Dimethyl-pyrazol-1-yl)-acetyl]-piperazin-1-yl}-phenyl)-pyrimidin-2-yl]-piperidine-3-carboxylic acid amide | 504 |
| 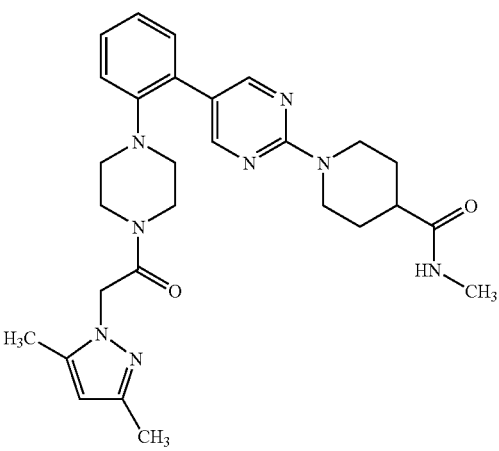 | 1-[5-(2-{4-[2-(3,5-Dimethyl-pyrazol-1-yl)-acetyl]-piperazin-1-yl}-phenyl)-pyrimidin-2-yl]-piperidine-4-carboxylic acid methylamide | 517 |

| MOLECULAR STRUCTURE | CHEMICAL NAME | Observed MH+ |
|---|---|---|
| 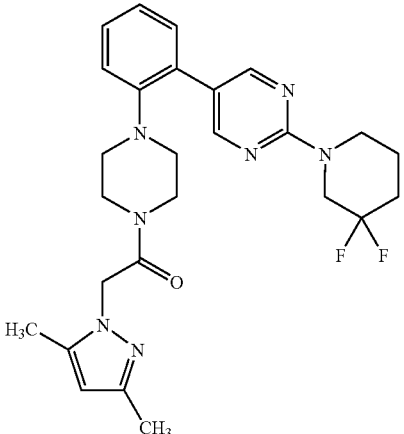 [SMILES: Cc1cc(C)n(CC(=O)N2CCN(c3ccccc3-c3cnc(N4CCCC(F)(F)C4)nc3)CC2)n1] | 1-(4-{2-[2-(3,3-Difluoro-piperidin-1-yl)-pyrimidin-5-yl]-phenyl}-piperazin-1-yl)-2-(3,5-dimethyl-pyrazol-1-yl)-ethanone | 496 |
| 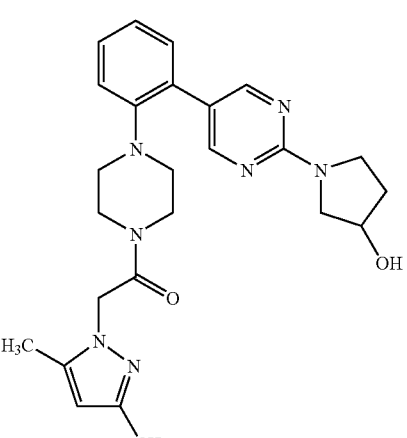 | 2-(3,5-Dimethyl-pyrazol-1-yl)-1-(4-{2-[2-(3-hydroxy-pyrrolidin-1-yl)-pyrimidin-5-yl]-phenyl}-piperazin-1-yl)-ethanone | 462 |
| 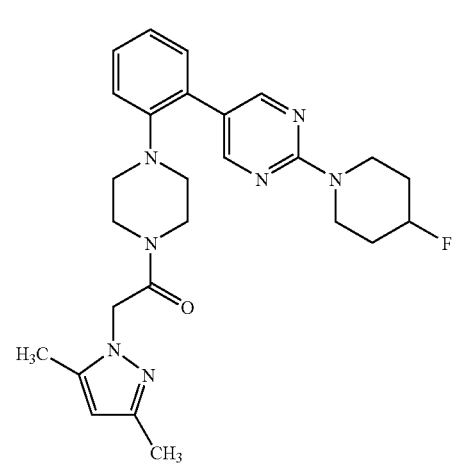 [SMILES: Cc1cc(C)n(CC(=O)N2CCN(c3ccccc3-c3cnc(N4CCC(F)CC4)nc3)CC2)n1] | 2-(3,5-Dimethyl-pyrazol-1-yl)-1-(4-{2-[2-(4-fluoro-piperidin-1-yl)-pyrimidin-5-yl]-phenyl}-piperazin-1-yl)-ethanone | 479 |

TABLE I-continued

| MOLECULAR STRUCTURE | CHEMICAL NAME | Observed MH+ |
|---|---|---|
| 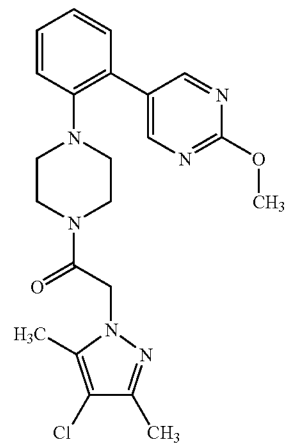 [SMILES: COc1ncc(-c2ccccc2N2CCN(C(=O)Cn3nc(C)c(Cl)c3C)CC2)cn1] | 2-(4-Chloro-3,5-dimethyl-pyrazol-1-yl)-1-{4-[2-(2-methoxy-pyrimidin-5-yl)-phenyl]-piperazin-1-yl}-ethanone | 442 |
| 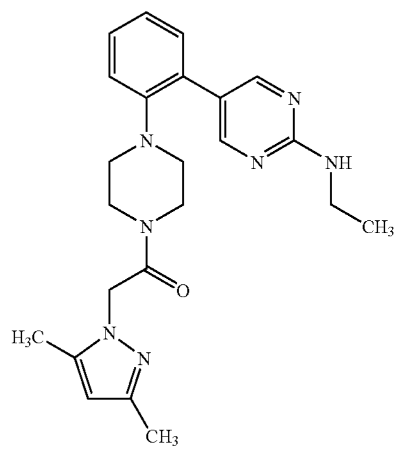 [SMILES: CCNc1ncc(-c2ccccc2N2CCN(C(=O)Cn3nc(C)cc3C)CC2)cn1] | 2-(3,5-Dimethyl-pyrazol-1-yl)-1-{4-[2-(2-ethylamino-pyrimidin-5-yl)-phenyl]-piperazin-1-yl}-ethanone | 420 |
| 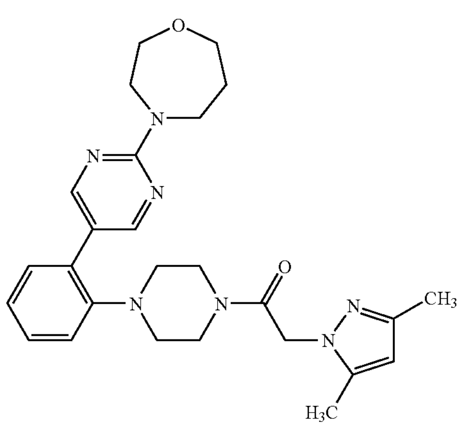 [SMILES: Cc1cc(C)n(CC(=O)N2CCN(c3ccccc3-c3cnc(N4CCCOCC4)nc3)CC2)n1] | 2-(3,5-Dimethyl-pyrazol-1-yl)-1-{4-[2-(2-[1,4]oxazepan-4-yl-pyrimidin-5-yl)-phenyl]-piperazin-1-yl}-ethanone | 476 |

TABLE I-continued

| MOLECULAR STRUCTURE | CHEMICAL NAME | Observed MH+ |
|---|---|---|
| 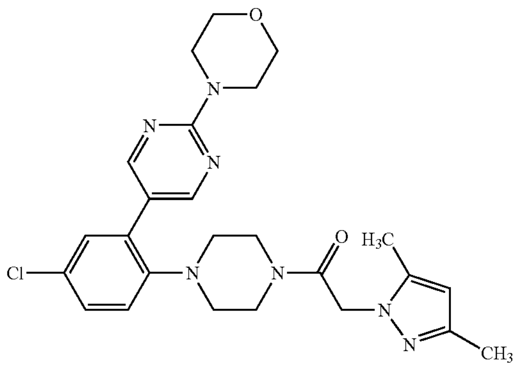 [SMILES: Cc1cc(C)n(CC(=O)N2CCN(c3ccc(Cl)cc3-c3cnc(N4CCOCC4)nc3)CC2)n1] | 1-{4-[4-Chloro-2-(2-morpholin-4-yl-pyrimidin-5-yl)-phenyl]-piperazin-1-yl}-2-(3,5-dimethyl-pyrazol-1-yl)-ethanone | 496 |
| 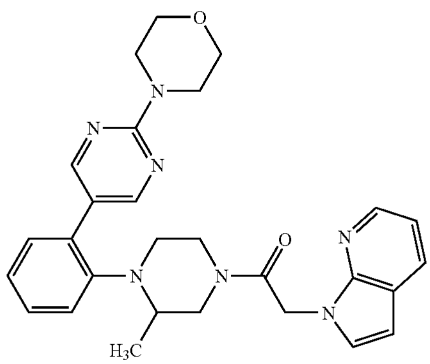 [SMILES: CC1CN(C(=O)Cn2ccc3cccnc32)CCN1c1ccccc1-c1cnc(N2CCOCC2)nc1] | 1-{3-Methyl-4-[2-(2-morpholin-4-yl-pyrimidin-5-yl)-phenyl]-piperazin-1-yl}-2-pyrrolo[2,3-b]pyridin-1-yl-ethanone | 497 |
| 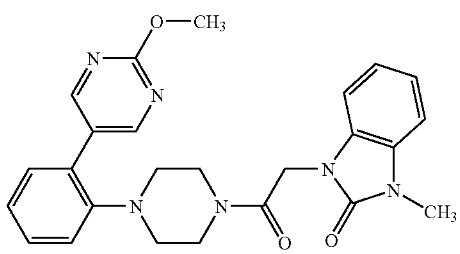 [SMILES: COc1ncc(-c2ccccc2N2CCN(C(=O)Cn3c(=O)n(C)c4ccccc43)CC2)cn1] | 1-(2-{4-[2-(2-Methoxy-pyrimidin-5-yl)-phenyl]-piperazin-1-yl}-2-oxo-ethyl)-3-methyl-1,3-dihydro-benzoimidazol-2-one | 460 |
| 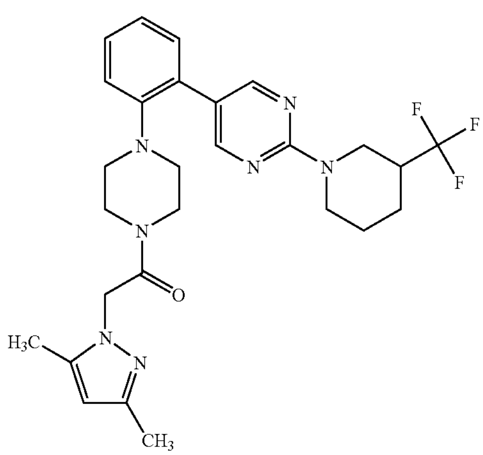 [SMILES: Cc1cc(C)n(CC(=O)N2CCN(c3ccccc3-c3cnc(N4CCCC(C(F)(F)F)C4)nc3)CC2)n1] | 2-(3,5-Dimthyl-pyrazol-1-yl)-1-(4-{2-[2-(3-trifluoromethyl-piperidin-1-yl)-pyrimidin-5-yl]-phenyl}-piperazin-1-yl)-ethanone | 528 |

TABLE I-continued

| MOLECULAR STRUCTURE | CHEMICAL NAME | Observed MH+ |
|---|---|---|
| 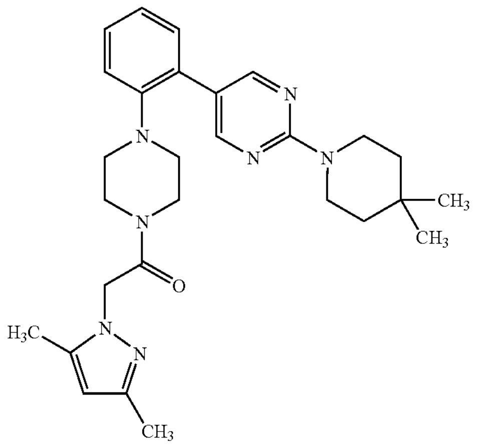 | 1-(4-{2-[2-(4,4-Dimethyl-piperidin-1-yl)-pyrimidin-5-yl]-phenyl}-piperazin-1-yl)-2-(3,5-dimethyl-pyrazol-1-yl)-ethanone | 488 |
| Chiral | 2-(3,5-Dimethyl-pyrazol-1-yl)-1-(4-{2-[2-((S)-2-methoxymethyl-pyrrolidin-1-yl)-pyrimidin-5-yl]-phenyl}-piperazin-1-yl)ethanone | 490 |
| 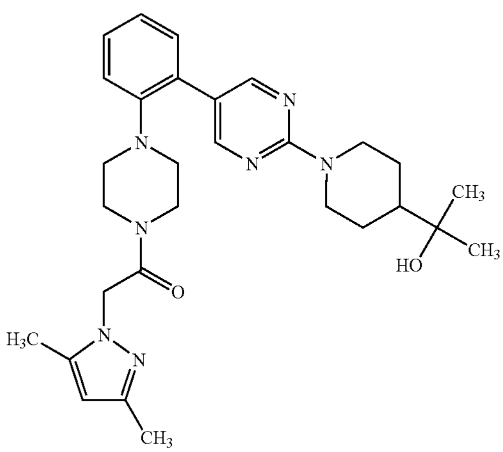 [SMILES: Cc1cc(C)n(CC(=O)N2CCN(c3ccccc3-c3cnc(N4CCC(C(C)(C)O)CC4)nc3)CC2)n1] | 2-(3,5-Dimethyl-pyrazol-1-yl)-1-[4-(2-{2-[4-(1-hydroxy-1-methyl-ethyl)-piperidin-1-yl]-pyrimidin-5-yl}-phenyl)-piperazin-1-yl]-ethanone | 518 |
| 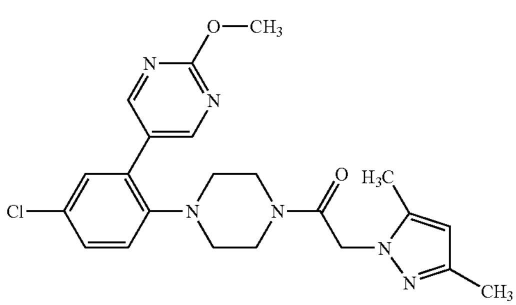 | 1-{4-[4-Chloro-2-(2-methoxy-pyrimidin-5-yl)-phenyl]-piperazin-1-yl}-2-(3,5-dimethyl-pyrazol-1-yl)-ethanone | 441 |

TABLE I-continued

| MOLECULAR STRUCTURE | CHEMICAL NAME | Observed MH+ |
|---|---|---|
| 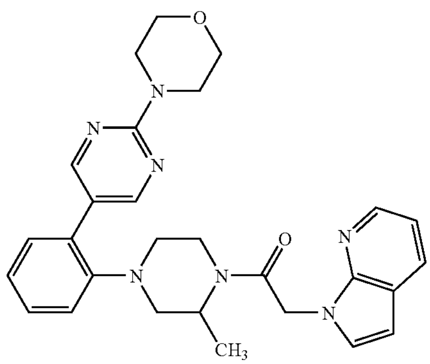 [SMILES: CC1CN(c2ccccc2-c2cnc(N3CCOCC3)nc2)CCN1C(=O)Cn1ccc2cccnc21] | 1-{2-Methyl-4-[2-(2-morpholin-4-yl-pyrimidin-5-yl)-phenyl]-piperazin-1-yl}-2-pyrrolo[2,3-b]pyridin-1-yl-ethanone | 497 |
| 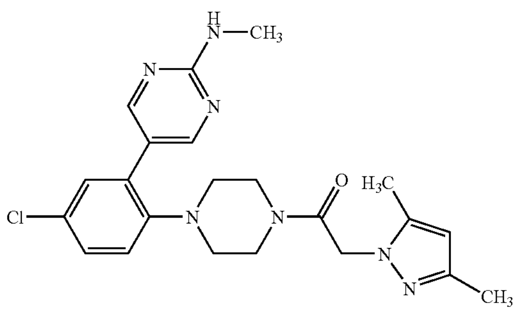 [SMILES: CNc1ncc(-c2cc(Cl)ccc2N2CCN(C(=O)Cn3nc(C)cc3C)CC2)cn1] | 1-{4-[4-Chloro-2-(2-methylamino-pyrimidin-5-yl)-phenyl]-piperazin-1-yl}-2-(3,5-dimethyl-pyrazol-1-yl)-ethanone | 440 |
| Chiral | 2-(3,5-Dimethyl-pyrazol-1-yl)-1-(4-{2-[(1S,4S)-2-(2-oxa-5-aza-bicyclo[2.2.1]hept-5-yl)-pyrimidin-5-yl]-phenyl}-piperazin-1-yl)-ethanone | 474 |
| 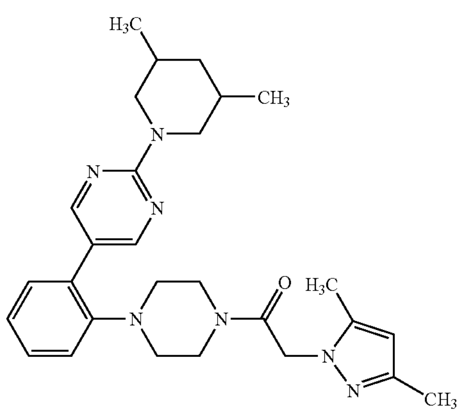 [SMILES: Cc1cc(C)n(CC(=O)N2CCN(c3ccccc3-c3cnc(N4CC(C)CC(C)C4)nc3)CC2)n1] | 1-(4-{2-[2-(3,5-Dimethyl-piperidin-1-yl)-pyrimidin-5-yl]-phenyl}-piperazin-1-yl)-2-(3,5-dimethyl-pyrazol-1-yl)-ethanone | 488 |

TABLE I-continued

| MOLECULAR STRUCTURE | CHEMICAL NAME | Observed MH+ |
|---|---|---|
| 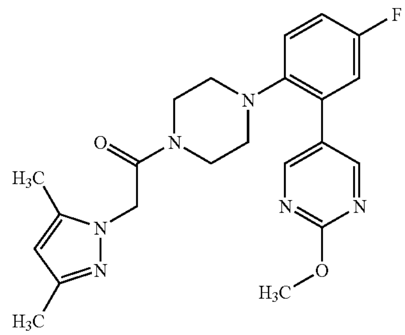 [SMILES: COc1ncc(-c2cc(F)ccc2N2CCN(C(=O)Cn3nc(C)cc3C)CC2)cn1] | 2-(3,5-Dimethyl-pyrazol-1-yl)-1-{4-[4-fluoro-2-(2-methoxy-pyrimidin-5-yl)-phenyl]-piperazin-1-yl}-ethanone | 425 |
| 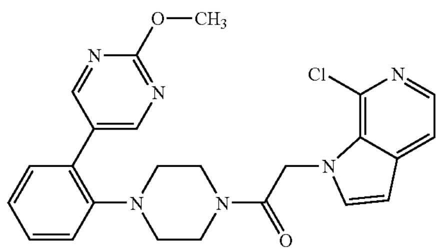 [SMILES: COc1ncc(-c2ccccc2N2CCN(C(=O)Cn3ccc4ccnc(Cl)c43)CC2)cn1] | 2-(7-Chloro-pyrrrolo[2,3-c]pyridin-1-yl)-1-{4-[2-(2-methoxy-pyrimidin-5-yl)-phenyl]-piperazin-1-yl}-ethanone | 464 |
| 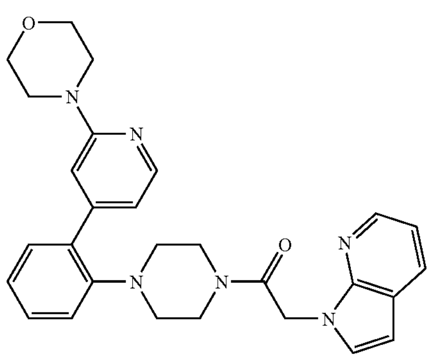 [SMILES: O=C(Cn1ccc2cccnc21)N1CCN(c2ccccc2-c2ccnc(N3CCOCC3)c2)CC1] | 1-{4-[2-(2-Morpholin-4-yl-pyridin-4-yl)-phenyl]-piperazin-1-yl}-2-pyrrolo[2,3-b]pyridin-1-yl-ethanone | 483 |
| 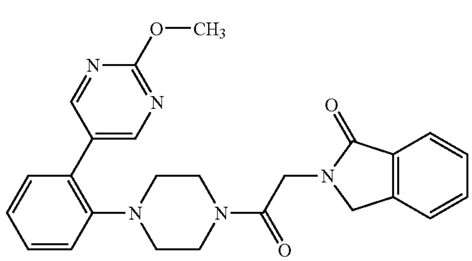 [SMILES: COc1ncc(-c2ccccc2N2CCN(C(=O)CN3Cc4ccccc4C3=O)CC2)cn1] | 2-(2-{4-[2-(2-Methoxy-pyrimidin-5-yl)-phenyl]-piperazin-1-yl}-2-oxo-ethyl)-2,3-dihydro-isoindol-1-one | 445 |

TABLE I-continued

| MOLECULAR STRUCTURE | CHEMICAL NAME | Observed MH+ |
|---|---|---|
| 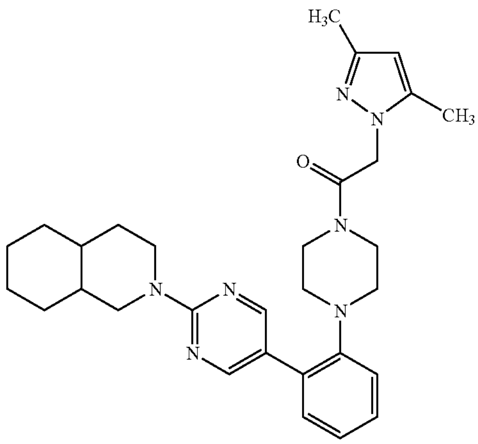 [SMILES: Cc1cc(C)n(CC(=O)N2CCN(c3ccccc3-c3cnc(N4CCC5CCCCC5C4)nc3)CC2)n1] | 2-(3,5-Dimethyl-pyrazol-1-yl)-1-(4-{2-[2-(octahydro-isoquinolin-2-yl)-pyrimidin-5-yl]-phenyl}-piperazin-1-yl)-ethanone | 514 |
| 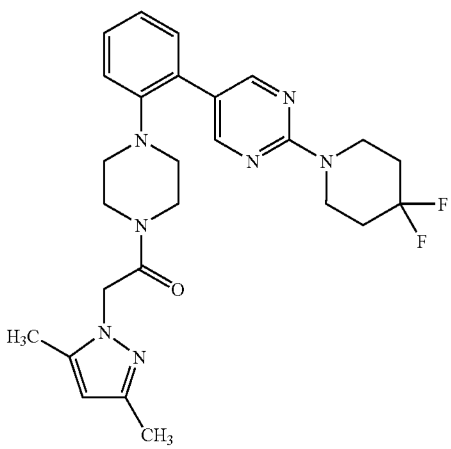 [SMILES: Cc1cc(C)n(CC(=O)N2CCN(c3ccccc3-c3cnc(N4CCC(F)(F)CC4)nc3)CC2)n1] | 1-(4-{2-[2-(4,4-Difluoro-piperidin-1-yl)-pyrimidin-5-yl]-phenyl}-piperazin-1-yl)-2-(3,5-dimethyl-pyrazol-1-yl)-ethanone | 496 |
| 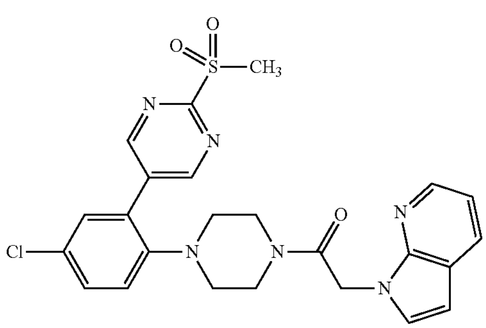 [SMILES: CS(=O)(=O)c1ncc(-c2cc(Cl)ccc2N2CCN(C(=O)Cn3ccc4cccnc43)CC2)cn1] | 1-{4-[4-Chloro-2-(2-methanesulfonyl-pyrimidin-5-yl)-phenyl]-piperazin-1-yl}-2-pyrrolo[2,3-b]pyridin-1-yl-ethanone | 511 |
| 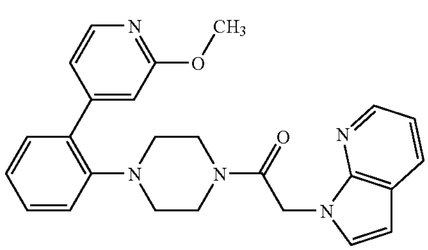 [SMILES: COc1cc(-c2ccccc2N2CCN(C(=O)Cn3ccc4cccnc43)CC2)ccn1] | 1-{4-[2-(2-Methoxy-pyridin-4-yl)-phenyl]-piperazin-1-yl}-2-pyrrolo[2,3-b]pyridin-1-yl-ethasnone | 428 |

TABLE I-continued

| MOLECULAR STRUCTURE | CHEMICAL NAME | Observed MH+ |
|---|---|---|
| 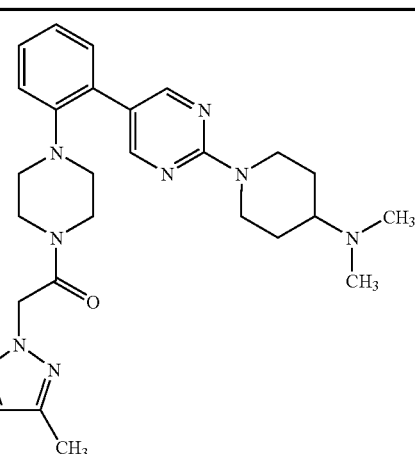 | 1-(4-{2-[2-(4-Dimethylamino-piperidin-1-yl)-pyrimidin-5-yl]-phenyl}-piperazin-1-yl)-2-(3,5-dimethyl-pyrazol-1-yl)-ethanone | 503 |
| 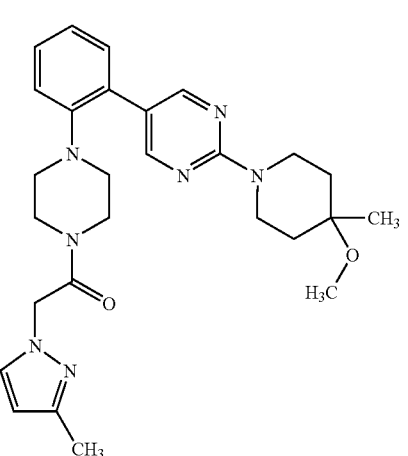 | 2-(3,5-Dimethylpyrazol-1-yl)-1-(4-{2-[2-(4-methoxy-4-methyl-[iperidin-1-yl)-pyrimidin-5-yl]-phenyl}-piperazin-1-yl)-ethanone | 504 |
| 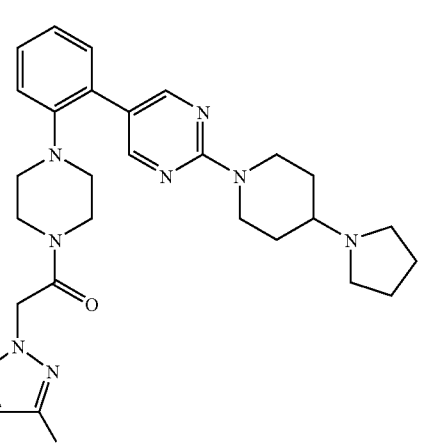 | 2-(3,5-Dimethyl-pyrazol-1-yl)-1-(4-{2-[2-(4-pyrrolidin-1-yl-piperidin-1-yl)-pyrimidin-5-yl]-phenyl}-piperazin-1-yl)-ethanone | 529 |
| 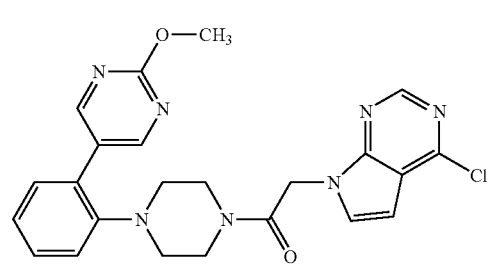 [SMILES: COc1ncc(-c2ccccc2N2CCN(C(=O)Cn3ccc4c(Cl)ncnc43)CC2)cn1] | 2-(4-Chloro-pyrrolo[2,3-d]pyrimidin-7-yl)-1-{4-[2-(2-methoxy-pyrimidin-5-yl)-phenyl]-piperazin-1-yl}-ethanone | 465 |

TABLE I-continued

| MOLECULAR STRUCTURE | CHEMICAL NAME | Observed MH+ |
|---|---|---|
| 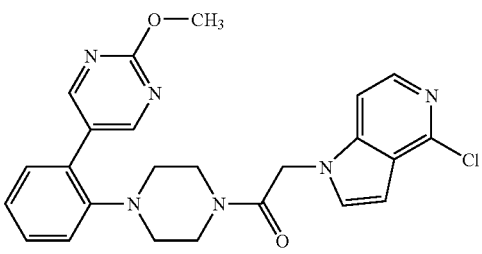 | 2-(4-Chloro-pyrrolo[3,2-c]pyridin-1-yl)-1-{4-[2-(2-methoxy-pyrimidin-5-yl)-phenyl]-piperazin-1-yl}-ethanone | 464 |
| 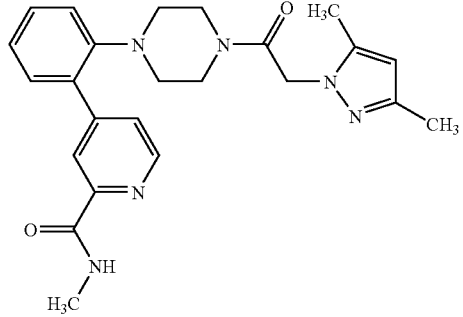 [SMILES: CNC(=O)c1cc(-c2ccccc2N2CCN(C(=O)Cn3nc(C)cc3C)CC2)ccn1] | 4-(2-{4-[2-(3,5-Dimethyl-pyrazol-1-yl)-acetyl]-piperazin-1-yl}-phenyl)-pyridine-2-carboxylic acid methylamide | 434 |
| 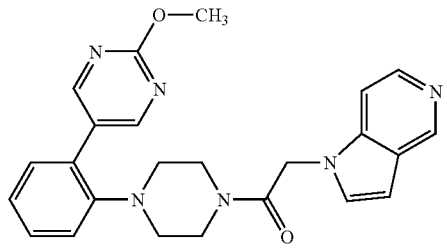 [SMILES: COc1ncc(-c2ccccc2N2CCN(C(=O)Cn3ccc4cnccc43)CC2)cn1] | 1-{4-[2-(2-Methoxy-pyrimidin-5-yl)-phenyl]-piperazin-1-yl)-2-pyrrolo[3,2-c]pyridin-1-yl-ethanone | 429 |
| 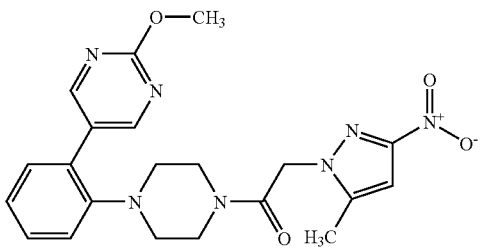 [SMILES: COc1ncc(-c2ccccc2N2CCN(C(=O)Cn3nc([N+](=O)[O-])cc3C)CC2)cn1] | 1-{4-[2-(2-Methoxy-pyrimidin-5-yl)-phenyl]-piperazin-1-yl}-2-(5-methyl-3-nitro-pyrazol-1-yl)-ethanone | 438 |
| 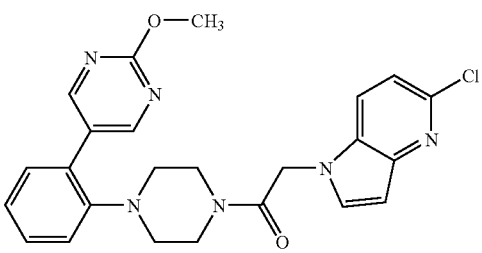 [SMILES: COc1ncc(-c2ccccc2N2CCN(C(=O)Cn3ccc4nc(Cl)ccc43)CC2)cn1] | 2-(5-Chloro-pyrrolo[3,2-b]pyridin-1-yl)-1-{4-[2-(2-methoxy-pyrimidin-5-yl)-phenyl]-piperazin-1-yl}-ethanone | 464 |

TABLE I-continued

| MOLECULAR STRUCTURE | CHEMICAL NAME | Observed MH+ |
|---|---|---|
| 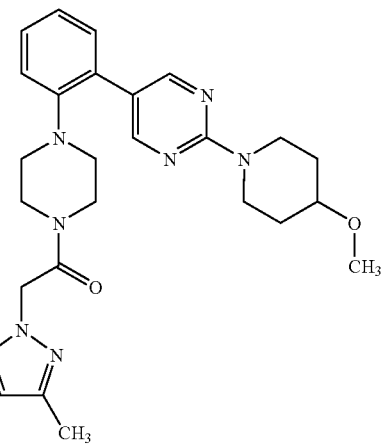 | 2-(3,5-Dimethyl-pyrazol-1-yl)--1-(4-{2-[2-(4-methoxy-piperidin-1-yl)-pyrimidin-5-yl]-phenyl}-piperazin-1-yl)-ethanone | 490 |
| 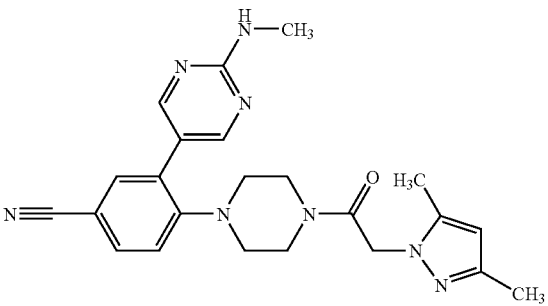 [SMILES: CNc1ncc(-c2cc(C#N)ccc2N2CCN(C(=O)Cn3nc(C)cc3C)CC2)cn1] | 4-{4-[2-(3,5-Dimethyl-pyrazol-1-yl)-acetyl]-piperazin-1-yl}-3-(2-methylamino-pyrimidin-5-yl)-benzonitrile | 431 |
| 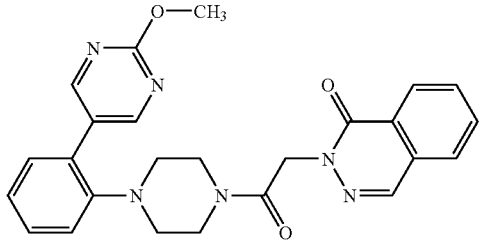 [SMILES: COc1ncc(-c2ccccc2N2CCN(C(=O)Cn3ncc4ccccc4c3=O)CC2)cn1] | 2-(2-{4-[2-(2-Methoxy-pyrimidin-5-yl)-phenyl]-piperazin-1-yl}-2-oxo-ethyl)-2H-phthalazin-1-one | 458 |
| 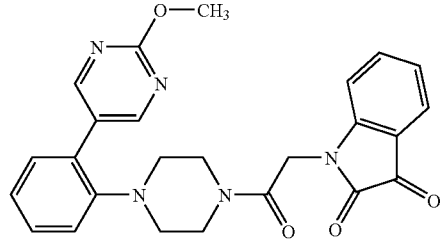 [SMILES: COc1ncc(-c2ccccc2N2CCN(C(=O)CN3C(=O)C(=O)c4ccccc43)CC2)cn1] | 1-(2-{4-[2-(2-Methoxy-pyrimidin-5-yl)-phenyl]-piperazin-1-yl}-2-oxo-ethyl)-1H-indole-2,3-dione | 458 |
| 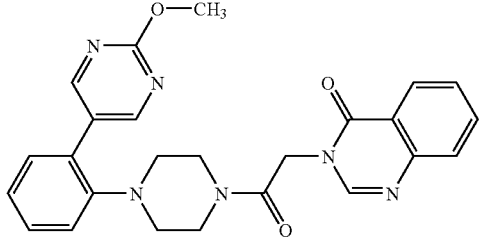 [SMILES: COc1ncc(-c2ccccc2N2CCN(C(=O)Cn3cnc4ccccc4c3=O)CC2)cn1] | 3-(2-{4-[2-(2-Methoxy-pyrimidin-5-yl)-phenyl]-piperazin-1-yl}-2-oxo-ethyl)-3H-quinazolin-4-one | 458 |

TABLE I-continued

| MOLECULAR STRUCTURE | CHEMICAL NAME | Observed MH+ |
|---|---|---|
| 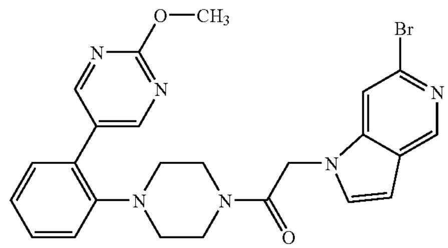 [SMILES: COc1ncc(-c2ccccc2N2CCN(C(=O)Cn3ccc4cnc(Br)cc43)CC2)cn1] | 2-(6-Bromo-pyrrolo[3,2-c]pyridin-1-yl)-1-{4-[2-(2-methoxy-pyrimidin-5-yl)-phenyl]-piperazin-1-yl}-ethanone | 508 |
| Chiral | 1-((S)-4-Biphenyl-2-yl-2-methyl-piperazin-1-yl)-2-(3,5-dimethyl-pyrazol-1-yl)-ethanone | 390 |
| 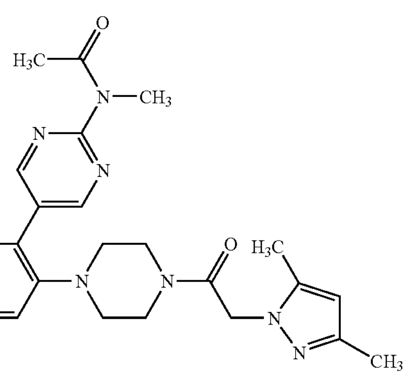 | N-[5-(2-{4-[2-(3,5-Dimethyl-pyrazol-1-yl)-acetyl]-piperazin-1-yl}-phenyl)-pyrimidin-2-yl]-N-methyl-acetamide | 448 |
| 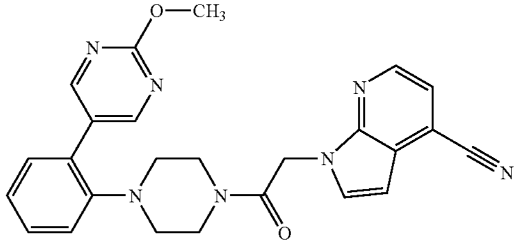 [SMILES: COc1ncc(-c2ccccc2N2CCN(C(=O)Cn3ccc4c(C#N)ccnc43)CC2)cn1] | 1-(2-{4-[2-(2-Methoxy-pyrimidin-5-yl)-phenyl]-piperazin-1-yl}-2-oxo-ethyl)-1H-pyrrolo[2,3-b]pyridine-4-carbonitrile | 455 |

TABLE I-continued

| MOLECULAR STRUCTURE | CHEMICAL NAME | Observed MH+ |
| --- | --- | --- |
| Chiral | (R)-1-[5-(2-{4-[2-(3,5-Dimethyl-pyrazol-1-yl)acetyl]-piperazin-1-yl}-phenyl)-pyrimidin-2-yl]-pyrrolidine-2-carboxylic acid amide | 489 |
| 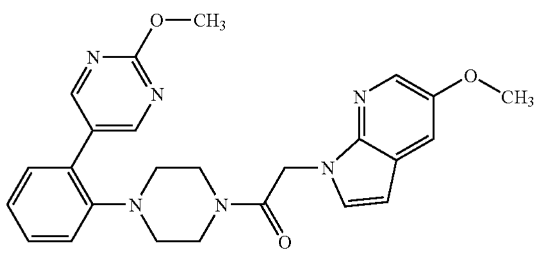 [SMILES: COc1cnc2c(ccn2CC(=O)N2CCN(c3ccccc3-c3cnc(OC)nc3)CC2)c1] | 1-{4-[2-(2-Methoxy-pyrimidin-5-yl)-phenyl]-piperazin-1-yl}-2-(5-methoxy-pyrrolo[2,3-b]pyridin-1-yl)-ethanone | 460 |
| 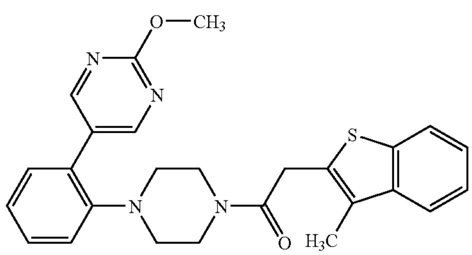 [SMILES: COc1ncc(-c2ccccc2N2CCN(C(=O)Cc3sc4ccccc4c3C)CC2)cn1] | 1-{4-[2-(2-Methoxy-pyrimidin-5-yl)-phenyl]-piperazin-1-yl}-2-(3-methyl-benzo[b]thiophen-2-yl)-ethanone | 460 |
| 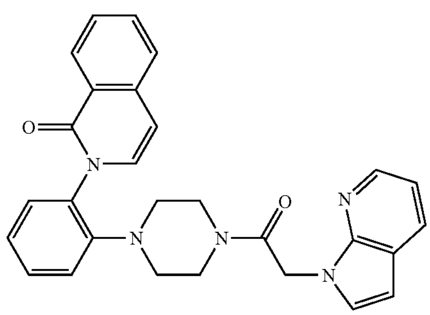 [SMILES: O=C(Cn1ccc2cccnc21)N1CCN(c2ccccc2-n2ccc3ccccc3c2=O)CC1] | 2-{2-[4-(2-Pyrrolo[2,3-b]pyridin-1-yl-acetyl)-piperazin-1-yl]-phenyl}-2H-isoquinolin-1-one | 464 |
| 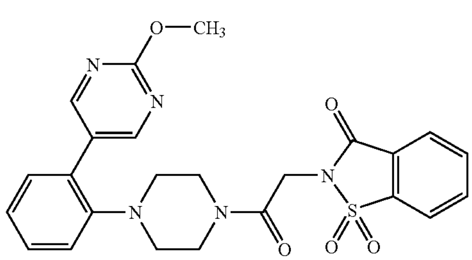 [SMILES: COc1ncc(-c2ccccc2N2CCN(C(=O)CN3C(=O)c4ccccc4S3(=O)=O)CC2)cn1] | 2-(2-{4-[2-(2-methoxy-pyrimidin-5-yl)-phenyl]-piperazin-1-yl}-2-oxo-ethyl)-1,1-dioxo-1,2-dihydro-1l6-benzo[d]isothiazol-3-one | 495 |

TABLE I-continued

| MOLECULAR STRUCTURE | CHEMICAL NAME | Observed MH+ |
|---|---|---|
| 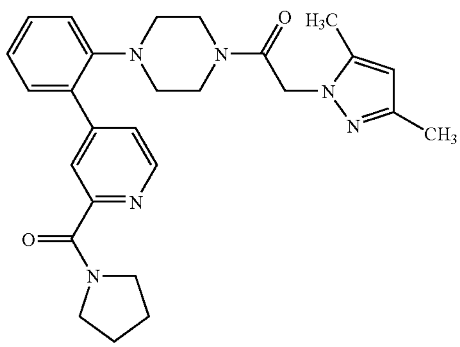 [SMILES: Cc1cc(C)n(CC(=O)N2CCN(c3ccccc3-c3ccnc(C(=O)N4CCCC4)c3)CC2)n1] | 2-(3,5-Dimethyl-pyrazol-1-yl)-1-(4-{2-[2-(pyrrolidine-1-carbonyl)-pyridin-4-yl]-phenyl}-piperazin-1-yl)-ethanone | 491 |
| 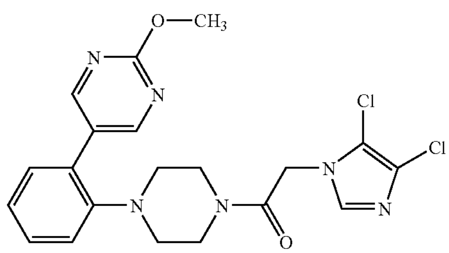 [SMILES: COc1ncc(-c2ccccc2N2CCN(C(=O)Cn3cnc(Cl)c3Cl)CC2)cn1] | 2-(4,5-Dichloro-imidazol-1-yl)-1-{4-[2-(2-methoxy-pyrimidin-5-yl)-phenyl]-piperazin-1-yl}-ethanone | 448 |
| 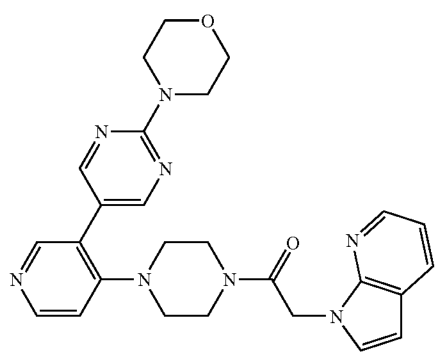 [SMILES: O=C(Cn1ccc2cccnc21)N1CCN(c2ccncc2-c2cnc(N3CCOCC3)nc2)CC1] | 1-{4-[3-(2-Morpholin-4-yl-pyrimidin-5-yl)-pyridin-4-yl]-piperazin-1-yl}-2-pyrrolo[2,3-b]pyridin-1-yl-ethanone | 486 |
| Chiral | 1-((R)-4-Biphenyl-2-yl-2-methyl-piperazin-1-yl)-2-(3,5-dimethyl-pyrazol-1-yl)-ethanone | 390 |
| Chiral | 1-((S)-4-Biphenyl-2-yl-2-methyl-piperazin-1-yl)-2-pyrrolo[2,3-b]pyridin-1-yl-ethanone | 412 |

TABLE I-continued

| MOLECULAR STRUCTURE | | CHEMICAL NAME | Observed MH+ |
|---|---|---|---|
| | Chiral | (S)-1-[5-(2-{4-[2-(3,5-Dimethyl-pyrazol-1-yl)-acetyl]-piperazin-1-yl}-phenyl)-pyrimidin-2-yl]-pyrrolidine-2-carboxylic acid methylamide | 503 |
| | | 2-{2-[4-(2-Pyrrolo[2,3-b]pyridin-1-yl-acetyl)-piperazin-1-yl]-phenyl}-isoindole-1,3-dione | 466 |
| | Chiral | 1-((R)-4-Biphenyl-2-yl-2-methyl-piperazin-1-yl)-2-pyrrolo[2,3-b]pyridin-1-yl-ethanone | 412 |
| | | 5-(2-{4-[2-(3,5-Dimethyl-pyrazol-1-yl)-acetyl]-piperazin-1-yl}-phenyl)-pyridine-2-carboxylic acid methylamide | 434 |
| | | 2-{2-[4-(2-Pyrrolo[2,3-b]pyridin-1-yl-acetyl)-piperazin-1-yl]-phenyl}-3,4-dihydro-2H-isoquinolin-1-one | 466 |

TABLE I-continued

| MOLECULAR STRUCTURE | CHEMICAL NAME | Observed MH+ |
|---|---|---|
| 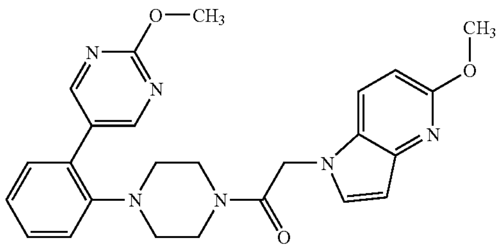 [SMILES: COc1ccc2c(ccn2CC(=O)N2CCN(c3ccccc3-c3cnc(OC)nc3)CC2)n1] | 1-{4-[2-(2-Methoxy-pyrimidin-5-yl)-phenyl]-piperazin-1-yl}-2-(5-methoxy-pyrrolo[3,2-b]pyridin-1-yl)-ethanone | 460 |
| 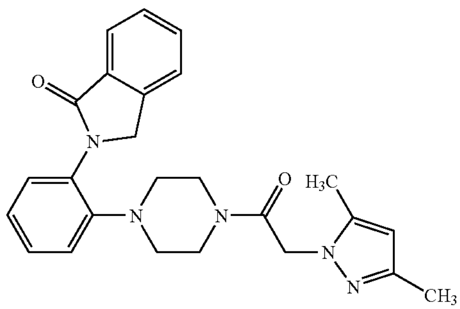 [SMILES: Cc1cc(C)n(CC(=O)N2CCN(c3ccccc3N3Cc4ccccc4C3=O)CC2)n1] | 2-(2-{4-[2-(3,5-Dimethyl-pyrazol-1-yl)-acetyl]-piperazin-1-yl}-phenyl)-2,3-dihydro-isoindol-1-one | 430 |
| 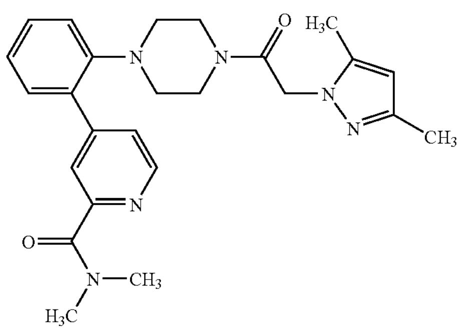 | 4-(2-{4-[2-(3,5-Dimethyl-pyrazol-1-yl)-acetyl]-piperazin-1-yl}-phenyl)-pyridine-2-carboxylic acid dimethylamide | 448 |
| 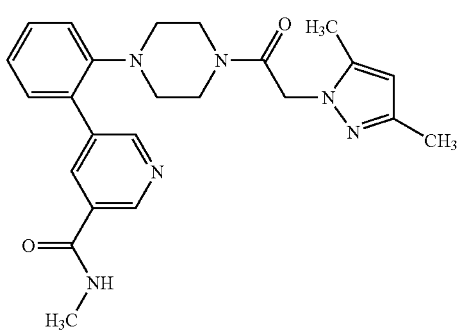 [SMILES: CNC(=O)c1cncc(-c2ccccc2N2CCN(C(=O)Cn3nc(C)cc3C)CC2)c1] | 5-(2-{4-[2-(3,5-Dimethyl-pyrazol-1-yl)-acetyl]-piperazin-1-yl}-phenyl)-N-methyl-nicotinamide | 434 |
| Chiral | 5-fluoro-N-(2-methoxypyridin-4-yl)-2-[(3S)-3-methyl-4-(1H-pyrrolo[2,3-c]pyridin-1-ylacetyl)piperazin-1-yl]benzamide | 503 |

TABLE I-continued

| MOLECULAR STRUCTURE | CHEMICAL NAME | Observed MH+ |
| --- | --- | --- |
| 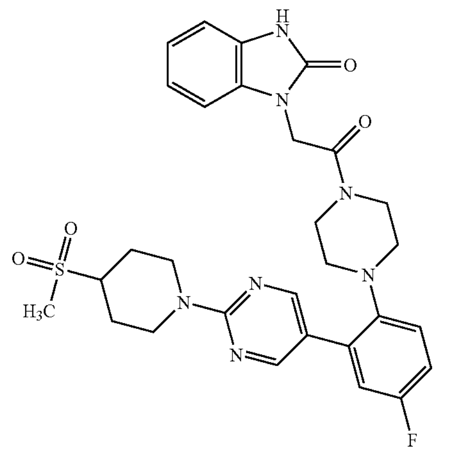 [SMILES: CS(=O)(=O)C1CCN(c2ncc(-c3cc(F)ccc3N3CCN(C(=O)Cn4c(=O)[nH]c5ccccc54)CC3)cn2)CC1] | 1-{2-[4-(4-fluoro-2-{2-[4-(methylsulfonyl)piperidin-1-yl[pyrimidin-5-yl}phenyl)piperazin-1-yl]-2-oxoethyl}-1,3-dihydro-2H-benzimidazol-2-one | 594 |
| 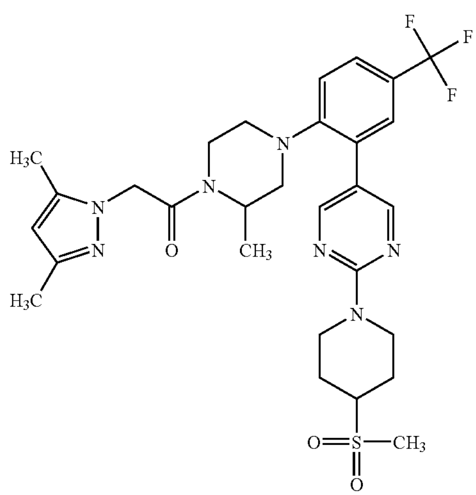 [SMILES: Cc1cc(C)n(CC(=O)N2CCN(c3ccc(C(F)(F)F)cc3-c3cnc(N4CCC(S(C)(=O)=O)CC4)nc3)CC2C)n1] | 2-(3,5-dimethyl-1H-pyrazol-1-yl)-1-{2-methyl-4-[2-{2-[4-(methylsulfonyl)piperidin-1-yl]pyrimidin-5-yl}-4-(trifluoromethyl)phenyl]piperazin-1-yl}ethanone | 620 |
| 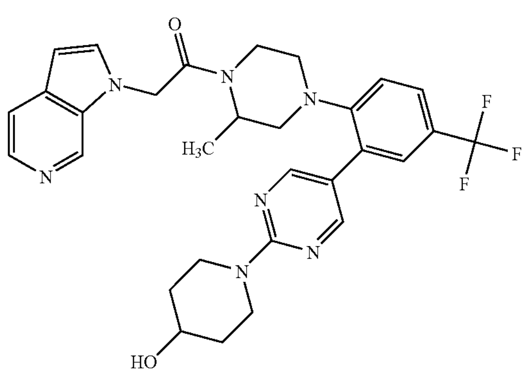 [SMILES: CC1CN(c2ccc(C(F)(F)F)cc2-c2cnc(N3CCC(O)CC3)nc2)CCN1C(=O)Cn1ccc2ccncc21] | 1-(4-{2-[2-(4-hydroxypiperidin-1-yl)pyrimidin-5-yl]-4-(trifluoromethyl)phenyl}-2-methylpiperazin-1-yl)-2-(1H-pyrrolo[2,3-c]pyridin-1-yl)ethanone | 580 |
| Chiral | 5-fluoro-2-[(3R)-4-(3H-imidazo[4,5-b]pyridin-3-ylacetyl)-3-methylpiperazin-1-yl]-N-(2-methoxypyridin-4-yl)benzamide | 504 |

TABLE I-continued

| MOLECULAR STRUCTURE | CHEMICAL NAME | Observed MH+ |
|---|---|---|
| 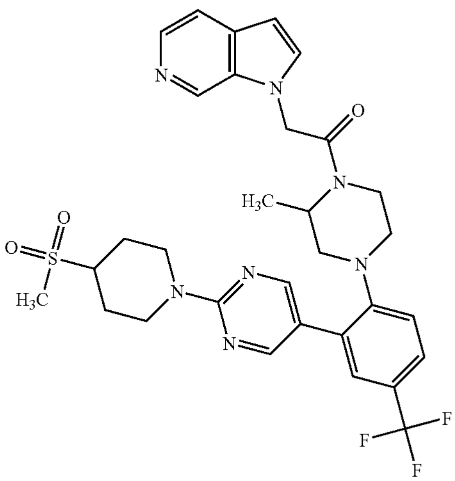 [SMILES: CC1CN(c2ccc(C(F)(F)F)cc2-c2cnc(N3CCC(S(C)(=O)=O)CC3)nc2)CCN1C(=O)Cn1ccc2ccncc21] | 1-{2-methyl-4-[2-{2-[4-(methylsulfonyl)piperidin-1-yl]pyrimidin-5-yl}-4-(trifluoromethyl)phenyl]piperazin-1-yl}-2-(1H-pyrrolo[2,3-c]pyridin-1-yl)ethanone | 642 |
| 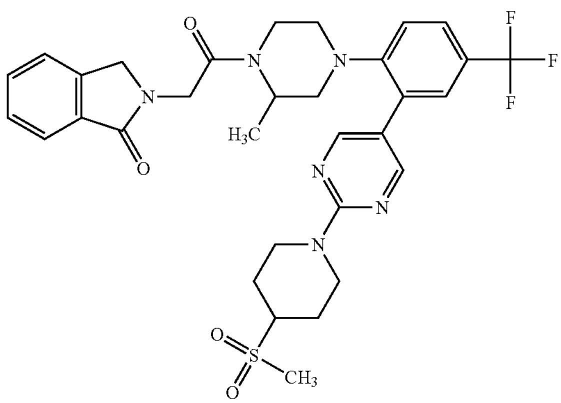 [SMILES: CC1CN(c2ccc(C(F)(F)F)cc2-c2cnc(N3CCC(S(C)(=O)=O)CC3)nc2)CCN1C(=O)CN1Cc2ccccc2C1=O] | 2-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-2,3-dihydro-1H-isoindol-1-one | 657 |
| Chiral | 5-fluoro-N-(2-methoxypyridin-4-yl)-2-{(3R)-3-methyl-4-[(1-oxo-1,3-dihydro-2H-isoindol-2-yl)acetyl]piperazin-1-yl}benzamide | 518 |

TABLE I-continued

| MOLECULAR STRUCTURE | CHEMICAL NAME | Observed MH+ |
|---|---|---|
| 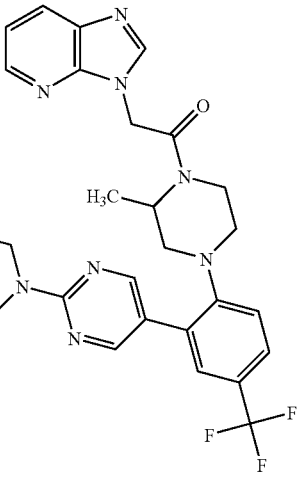 | 2-(3H-imidazo[4,5-b]pyridin-3-yl)-1-{2-methyl-4-[2-{2-[4-(methylsulfonyl)piperidin-1-yl]pyrimidin-5-yl}-4-(trifluoromethyl)phenyl]piperazin-1-yl}ethanone | 643 |
| 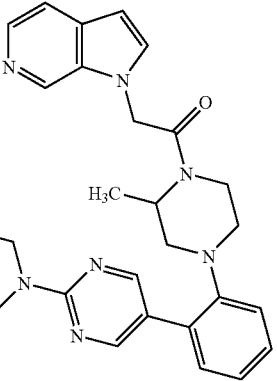 | 1-[2-methyl-4-(2-{2-[4-(methylsulfonyl)piperidin-1-yl]pyrimidin-5-yl}phenyl)piperazin-1-yl]-2-(1H-pyrrolo[2,3-c]pyridin-1-yl)ethanone | 574 |
| 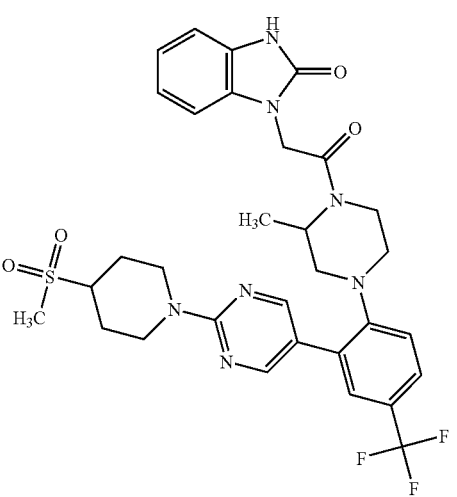 [SMILES: CC1CN(c2ccc(C(F)(F)F)cc2-c2cnc(N3CCC(S(C)(=O)=O)CC3)nc2)CCN1C(=O)Cn1c(=O)[nH]c2ccccc21] | 1-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-1,3-dihydro-2H-benzimidazol-2-one | 658 |

TABLE I-continued

| MOLECULAR STRUCTURE | CHEMICAL NAME | Observed MH+ |
|---|---|---|
| Chiral | 2-{(3R)-4-[(3,5-dimethyl-1H-pyrazol-1-yl)acetyl]-3-methylpiperazin-1-yl}-5-fluoro-N-(2-methoxypyridin-4-yl)benzamide | 481 |
| 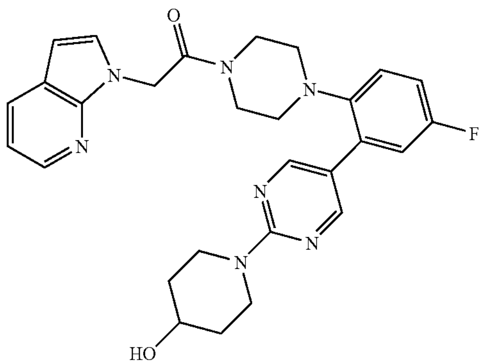 [SMILES: O=C(Cn1ccc2cccnc21)N1CCN(c2ccc(F)cc2-c2cnc(N3CCC(O)CC3)nc2)CC1] | 1-(4-{4-fluoro-2-[2-(4-hydroxypiperidin-1-yl)pyrimidin-5-yl]phenyl}piperazin-1-yl)-2-(1H-pyrrolo[2,3-b]pyridin-1-yl)ethanone | 516 |
| 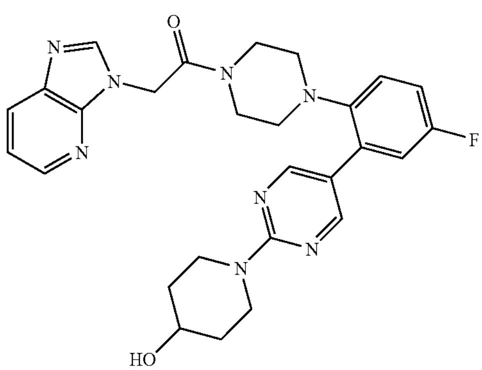 [SMILES: O=C(Cn1cnc2cccnc21)N1CCN(c2ccc(F)cc2-c2cnc(N3CCC(O)CC3)nc2)CC1] | 1-(4-{4-fluoro-2-[2-(4-hydroxypiperidin-1-yl)pyrimidin-5-yl]phenyl}piperazin-1-yl)-2-(3H-imidazo[4,5-b]pyridin-3-yl)ethanone | 517 |
| 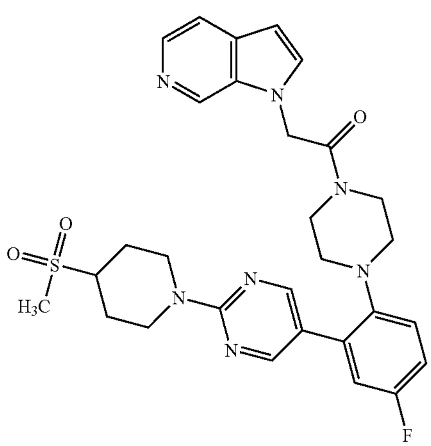 [SMILES: CS(=O)(=O)C1CCN(c2ncc(-c3cc(F)ccc3N3CCN(C(=O)Cn4ccc5ccncc54)CC3)cn2)CC1] | 1-[4-(4-fluoro-2-{2-[4-(methylsulfonyl)piperidin-1-yl]pyrimidin-5-yl}phenyl)piperazin-1-yl]-2-(1H-pyrrolo[2,3-c]pyridin-1-yl)ethanone | 578 |

TABLE I-continued

| MOLECULAR STRUCTURE | CHEMICAL NAME | Observed MH+ |
|---|---|---|
| 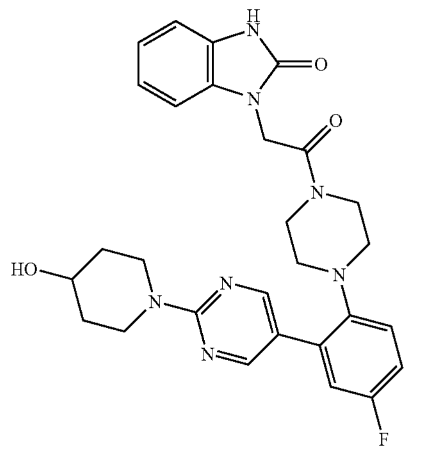 [SMILES: O=C(Cn1c(=O)[nH]c2ccccc21)N1CCN(c2ccc(F)cc2-c2cnc(N3CCC(O)CC3)nc2)CC1] | 1-[2-(4-{4-fluoro-2-[2-(4-hydroxypiperidin-1-yl)pyrimidin-5-yl]phenyl}piperazin-1-yl)-2-oxoethyl]-1,3-dihydro-2H-benzimidazol-2-one | 532 |
| | 1-[4-(4-fluoro-2-{2-[4-(methylsulfonyl)piperidin-1-yl]pyrimidin-5-yl}phenyl)-2-methylpiperazin-1-yl]-2-(1H-pyrrrolo[2,3-c]pyridin-1-yl)ethanone | 592 |
| 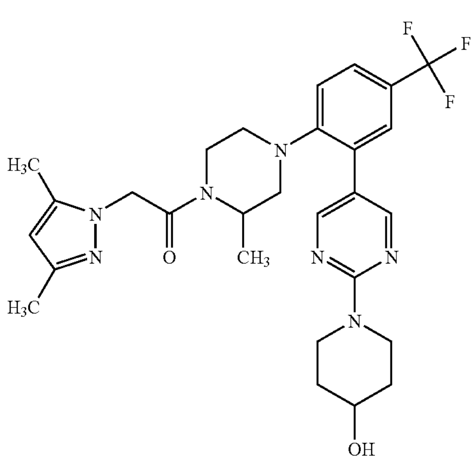 [SMILES: Cc1cc(C)n(CC(=O)N2CCN(c3ccc(C(F)(F)F)cc3-c3cnc(N4CCC(O)CC4)nc3)CC2C)n1] | 2-(3,5-dimethyl-1H-pyrazol-1-yl)-1-(4-{2-[2-(4-hydroxypiperidin-1-yl)pyrimidin-5-yl]-4-(trifluoromethyl)phenyl}-2-methylpiperazin-1-yl)ethanone | 558 |

TABLE I-continued

| MOLECULAR STRUCTURE | CHEMICAL NAME | Observed MH+ |
|---|---|---|
| 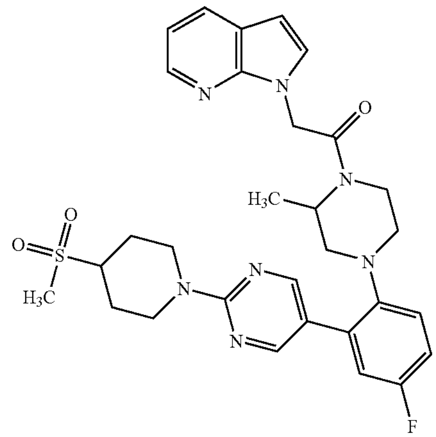 | 1-[4-(4-fluoro-2-{2-[4-(methylsulfonyl)piperidin-1-yl]pyrimidin-5-yl}phenyl)-2-methylpiperazin-1-yl]-2-(1H-pyrrolo[2,3-b]pyridin-1-yl)ethanone | 592 |
| Chiral | 5-fluoro-N-(2-methoxypyridin-4-yl)-2-{(3S)-3-methyl-4-[(2-oxopiperidin-1-yl)acetyl]piperazin-1-yl}benzamide | 484 |
| 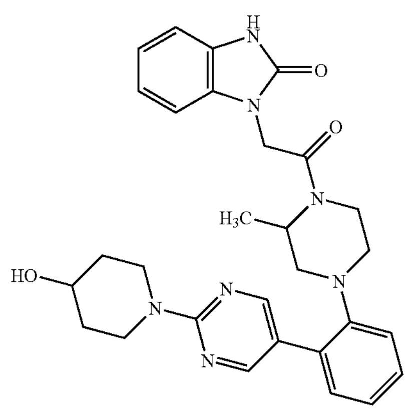 [SMILES: CC1CN(c2ccccc2-c2cnc(N3CCC(O)CC3)nc2)CCN1C(=O)Cn1c(=O)[nH]c2ccccc21] | 1-[2-(4-{2-[2-(4-hydroxypiperidin-1-yl)pyrimidin-5-yl]phenyl}-2-methylpiperazin-1-yl)-2-oxoethyl]-1,3-dihydro-2H-benzimidazol-2-one | 528 |
| 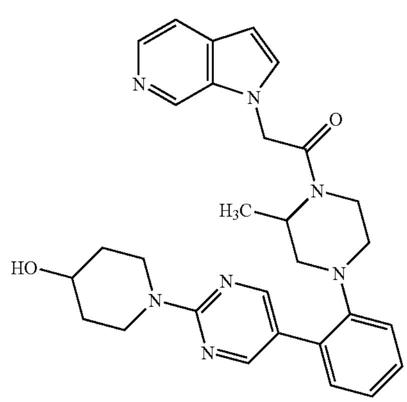 | 1-(4-{2-[2-(4-hydroxypiperidin-1-yl)pyrimidin-5-yl]phenyl}-2-methylpiperazin-1-yl)-2-(1H-pyrrolo[2,3-c]pyridin-1-yl)ethanone | 512 |

TABLE I-continued

| MOLECULAR STRUCTURE | | CHEMICAL NAME | Observed MH+ |
|---|---|---|---|
| | Chiral | 5-fluoro-N-(2-methoxypyridin-4-yl)-2-{(3R)-3-methyl-4-[(2-oxo-2,3-dihydro-1H-benzimidazol-1-yl)acetyl]piperazin-1-yl}benzamide | 519 |
| | Chiral | 5-fluoro-N-(2-methoxypyridin-4-yl)-2-[(3R)-3-methyl-4-(1H-pyrrolo[2,3-c]pyridin-1-ylacetyl)piperazin-1-yl]benzamide | 503 |
| | Chiral | 5-fluoro-N-(2-methoxypyridin-4-yl)-2-{(3R)-3-methyl-4-[N-methyl-N-(2-methylpropanoyl)glycyl]piperazin-1-yl}benzamide | 487 |
| | | 1-[4-(4-fluoro-2-{2-[4-(methylsulfonyl)piperidin-1-yl]pyrimidin-5-yl}phenyl)piperazin-1-yl]-2-(1H-pyrrolo[2,3-b]pyridin-1-yl)ethanone | 578 |

TABLE I-continued

| MOLECULAR STRUCTURE | CHEMICAL NAME | Observed MH+ |
|---|---|---|
| 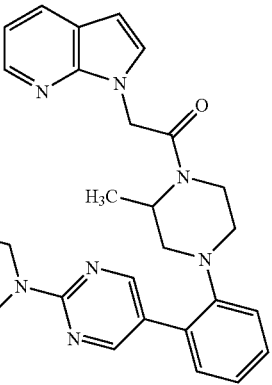 | 1-(4-{2-[2-(4-hydroxypiperidin-1-yl)pyrimidin-5-yl]phenyl}-2-methylpiperazin-1-yl)-2-(1H-pyrrolo[2,3-b]pyridin-1-yl)ethanone | 512 |
| 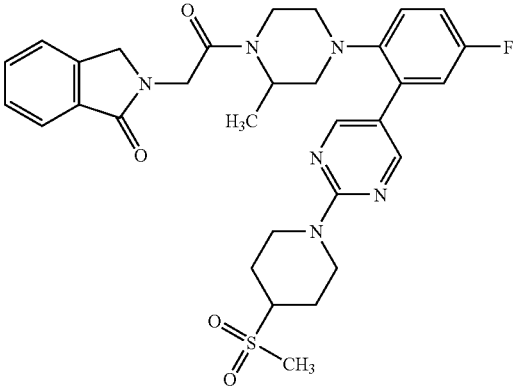 [SMILES: CC1CN(c2ccc(F)cc2-c2cnc(N3CCC(S(C)(=O)=O)CC3)nc2)CCN1C(=O)CN1Cc2ccccc2C1=O] | 2-{2-[4-(4-fluoro-2-{2-[4-(methylsulfonyl)piperidin-1-yl]pyrimidin-5-yl}phenyl)piperazin-1-yl]-2-oxoethyl}-2,3-dihydro-1H-isoindol-1-one | 593 |
| 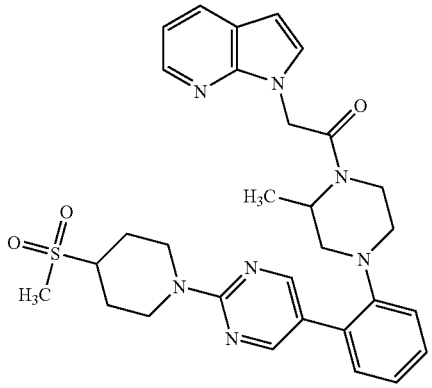 [SMILES: CC1CN(c2ccccc2-c2cnc(N3CCC(S(C)(=O)=O)CC3)nc2)CCN1C(=O)Cn1ccc2cccnc21] | 1-[2-methyl-4-(2-{2-[4-(methylsulfonyl)piperidin-1-yl]pyrimidin-5-yl}phenyl)piperazin-1-yl]-2-(1H-pyrrolo[2,3-b]pyridin-1-yl)ethanone | 574 |

TABLE I-continued

| MOLECULAR STRUCTURE | CHEMICAL NAME | Observed MH+ |
|---|---|---|
| 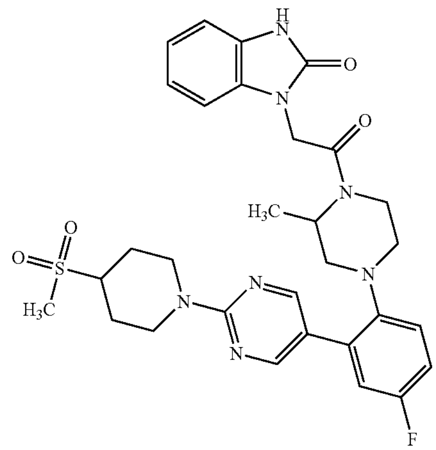 [SMILES: CC1CN(c2ccc(F)cc2-c2cnc(N3CCC(S(C)(=O)=O)CC3)nc2)CCN1C(=O)Cn1c(=O)[nH]c2ccccc21] | 1-{2-[4-(4-fluoro-2-{2-[4-(methylsulfonyl)piperidin-1-yl]pyrimidin-5-yl}phenyl)-2-methylpiperazin-1-yl]-2-oxoethyl}-1,3-dihydro-2H-benzimidazol-2-one | 608 |
| Chiral | 5-fluoro-N-(2-methoxypyridin-4-yl)-2-[(3R)-3-methyl-4-(1H-pyrrolo[2,3-b]pyridin-1-ylacetyl)piperazin-1-yl]benzamide | 503 |
| 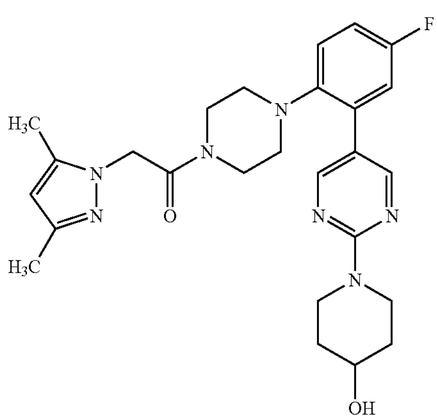 [SMILES: Cc1cc(C)n(CC(=O)N2CCN(c3ccc(F)cc3-c3cnc(N4CCC(O)CC4)nc3)CC2)n1] | 2-(3,5-dimethyl-1H-pyrazol-1-yl)-1-(4-{4-fluoro-2-[2-(4-hydroxypiperidin-1-yl)pyrimidin-5-yl]phenyl}piperazin-1-yl)ethanone | 494 |
| 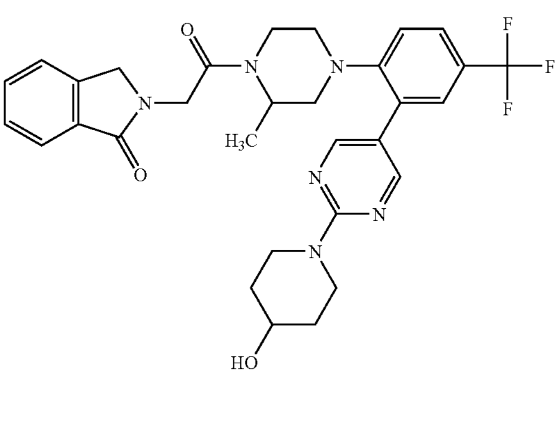 [SMILES: CC1CN(c2ccc(C(F)(F)F)cc2-c2cnc(N3CCC(O)CC3)nc2)CCN1C(=O)CN1Cc2ccccc2C1=O] | 2-[2-(4-{2-[2-(4-hydroxypiperidin-1-yl)pyrimidin-5-yl]-4-(trifluoromethyl)phenyl}-2-methylpiperazin-1-yl)-2-oxoethyl]-2,3-dihydro-1H-isoindol-2-one | 595 |

TABLE I-continued

| MOLECULAR STRUCTURE | CHEMICAL NAME | Observed MH+ |
|---|---|---|
| 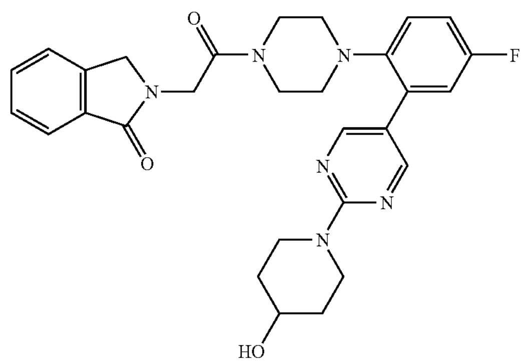 [SMILES: O=C(CN1Cc2ccccc2C1=O)N1CCN(c2ccc(F)cc2-c2cnc(N3CCC(O)CC3)nc2)CC1] | 2-[2-(4-{4-fluoro-2-[2-(4-hydroxypiperidin-1-yl)pyrimidin-5-yl]phenyl}piperazin-1-yl)-2-oxoethyl]-2,3-dihydro-1H-isoindol-2-one | 531 |
| 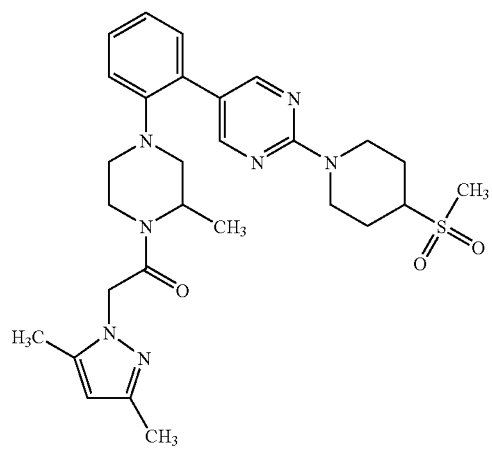 [SMILES: Cc1cc(C)n(CC(=O)N2CCN(c3ccccc3-c3cnc(N4CCC(S(C)(=O)=O)CC4)nc3)CC2C)n1] | 2-(3,5-dimethyl-1H-pyrazol-1-yl)-1-[2-methyl-4-(2-{2-[4-(methylsulfonyl)piperidin-1-yl]pyrimidin-5-yl}phenyl)piperazin-1-yl]ethanone | 552 |
| 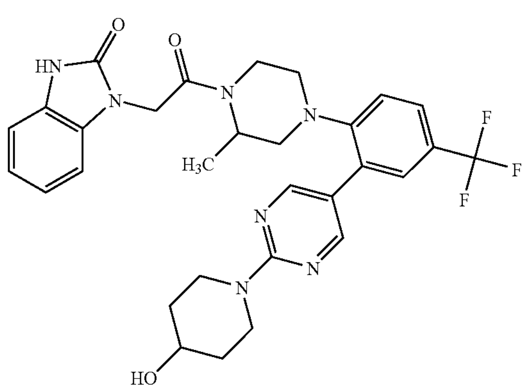 [SMILES: CC1CN(c2ccc(C(F)(F)F)cc2-c2cnc(N3CCC(O)CC3)nc2)CCN1C(=O)Cn1c(=O)[nH]c2ccccc21] | 1-[2-(4-{2-[2-(4-hydroxypiperidin-1-yl)pyrimidin-5-yl]-4-(trifluoromethyl)phenyl}-2-methylpiperazin-1-yl)-2-oxoethyl]-1,3-dihydro-2H-benzimidazol-2-one | 596 |
| Chiral | 5-fluoro-N-(2-methoxypyridin-4-yl)-2-{(3S)-3-methyl-4-[(2-oxo-2,3-dihydro-1H-benzimidazol-1-yl)acetyl]piperazin-1-yl}benzamide | 519 |

TABLE I-continued

| MOLECULAR STRUCTURE | CHEMICAL NAME | Observed MH+ |
|---|---|---|
| 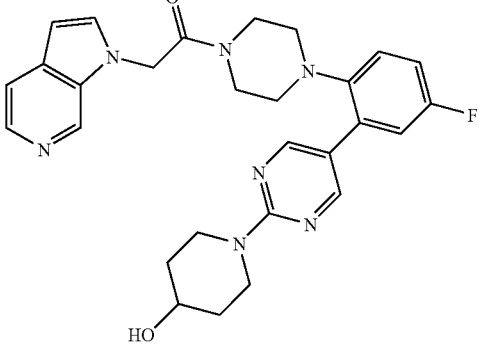 | 1-(4-{4-fluoro-2-[2-(4-hydroxypiperidin-1-yl)pyrimidin-5-yl]phenyl}piperazin-1-yl)-2-(1H-pyrrolo[2,3-c]pyridin-1-yl)ethanone | 516 |
| 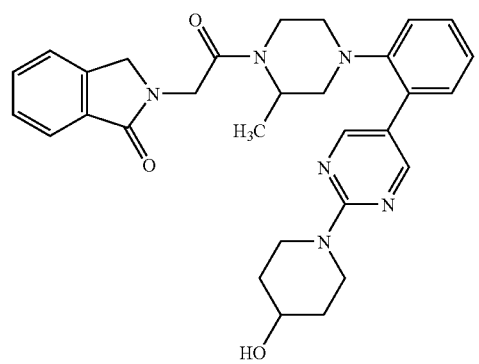 [SMILES: CC1CN(c2ccccc2-c2cnc(N3CCC(O)CC3)nc2)CCN1C(=O)CN1Cc2ccccc2C1=O] | 2-[2-(4-{2-[2-(4-hydroxypiperidin-1-yl)pyrimidin-5-yl]phenyl}-2-methylpiperazin-1-yl)-2-oxoethyl]-2,3-dihydro-1H-isoindol-1-one | 527 |
| 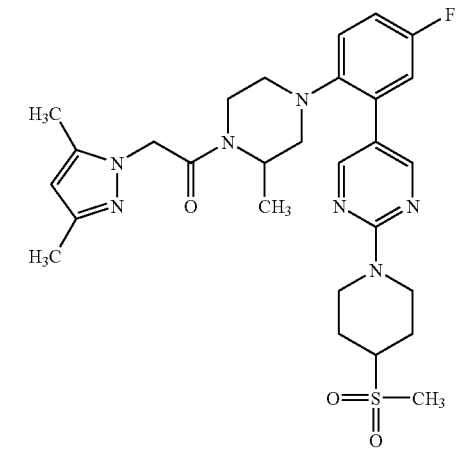 [SMILES: Cc1cc(C)n(CC(=O)N2CCN(c3ccc(F)cc3-c3cnc(N4CCC(S(C)(=O)=O)CC4)nc3)CC2C)n1] | 2-(3,5-dimethyl-1H-pyrazol-1-yl)-1-[4-(4-fluoro-2-{2-[4-(methylsulfonyl)piperidin-1-yl]pyrimidin-5-yl}phenyl)-2-methylpiperazain-1-yl]ethanone | 570 |
| 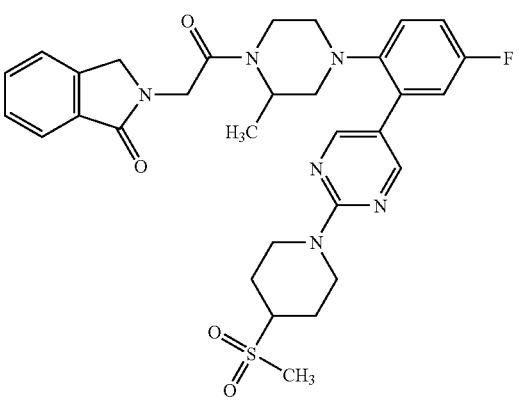 [SMILES: CC1CN(c2ccc(F)cc2-c2cnc(N3CCC(S(C)(=O)=O)CC3)nc2)CCN1C(=O)CN1Cc2ccccc2C1=O] | 2-{2-[4-(4-fluoro-2-{2-[4-(methylsulfonyl)piperidin-1-yl]pyrimidin-5-yl}phenyl)-2-methylpiperazin-1-yl]-2-oxoethyl}-2,3-dihydro-1H-isoindol-1-one | 607 |

TABLE I-continued

| MOLECULAR STRUCTURE | CHEMICAL NAME | Observed MH+ |
|---|---|---|
| Chiral | 5-fluoro-N-(2-methoxypyridin-4-yl)-2-{(3R)-3-methyl-4-[(2-oxopiperidin-1-yl)acetyl]piperazin-1-yl}benzamide | 484 |
| 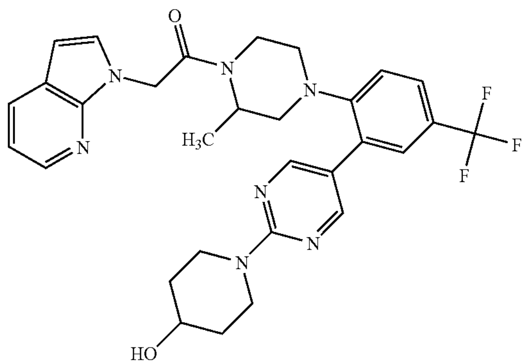 [SMILES: CC1CN(c2ccc(C(F)(F)F)cc2-c2cnc(N3CCC(O)CC3)nc2)CCN1C(=O)Cn1ccc2cccnc21] | 1-(4-{2-[2-(4-hydroxypiperidin-1-yl)pyrimidin-5-yl]-4-(trifluoromethyl)phenyl]-2-methylpiperazin-1-yl)-2-(1H-pyrrolo[2,3-b]pyridin-1-yl)ethanone | 580 |
| 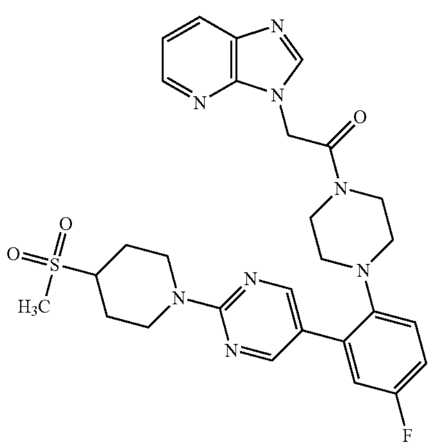 [SMILES: CS(=O)(=O)C1CCN(c2ncc(-c3cc(F)ccc3N3CCN(C(=O)Cn4cnc5cccnc54)CC3)cn2)CC1] | 1-[4-(4-fluoro-2-{2-[4-(methylsulfonyl)piperidin-1-yl]pyrimidin-5-yl}phenyl)piperazin-1-yl]-2-(3H-imidazo[4,5-b]pyridin-3-yl)ethanone | 579 |
| 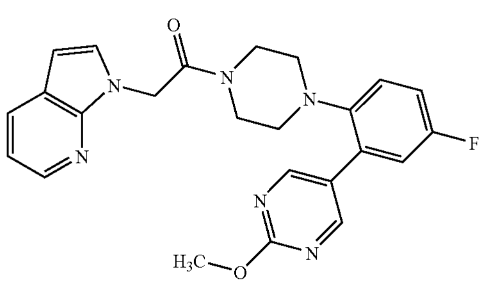 [SMILES: COc1ncc(-c2cc(F)ccc2N2CCN(C(=O)Cn3ccc4cccnc43)CC2)cn1] | 1-{4-[4-fluoro-2-(2-methoxypyrimidin-5-yl)phenyl]piperazin-1-yl}-2-(1H-pyrrolo[2,3-b]pyridin-1-yl)ethanone | 447 |

TABLE I-continued

| MOLECULAR STRUCTURE | CHEMICAL NAME | Observed MH+ |
|---|---|---|
| 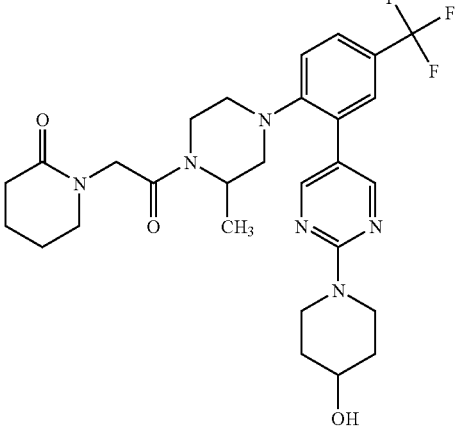 | 1-[2-(4-{2-[2-(4-hydroxypiperidin-1-yl)pyrimidin-5-yl]-4-(trifluoromethyl)phenyl}-2-methylpiperazin-1-yl)-2-oxoethyl]piperidin-2-one | 561 |
| 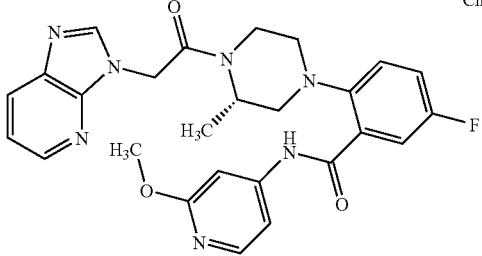 Chiral | 5-fluoro-2-[(3S)-4-(3H-imidazo[4,5-b]pyridin-3-ylacetyl)-3-methylpiperazin-1-yl]-N-(2-methoxypyridin-4-yl)benzamide | 504 |
| 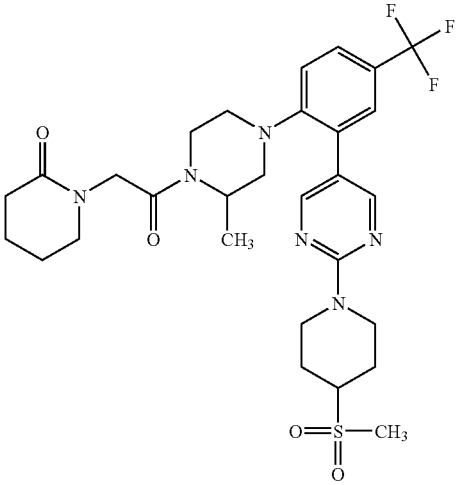 [SMILES: CC1CN(c2ccc(C(F)(F)F)cc2-c2cnc(N3CCC(S(C)(=O)=O)CC3)nc2)CCN1C(=O)CN1CCCCC1=O] | 1-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)piperidin-2-one | 623 |
| 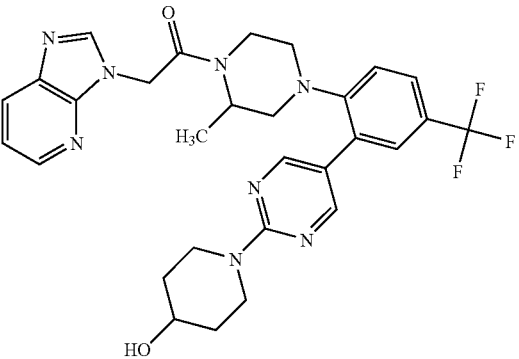 | 1-(4-{2-[2-(4-hydroxypiperidin-1-yl)pyrimidin-5-yl]-4-(trifluoromethyl)phenyl}-2-methylpiperazin-1-yl)-2-(3H-imidazo[4,5-b]pyridin-3-yl)ethanone | 581 |

TABLE I-continued

| MOLECULAR STRUCTURE | CHEMICAL NAME | Observed MH+ |
|---|---|---|
| 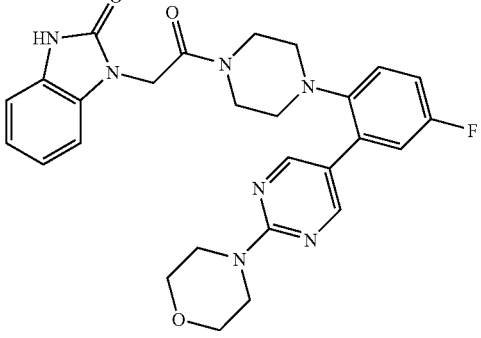 | 1-[2-(4-{4-fluoro-2-[2-(morpholin-4-yl)pyrimidin-5-yl]phenyl}piperazin-1-yl)-2-oxoethyl]-1,3-dihydro-2H-benzimidazol-2-one | 518 |
| 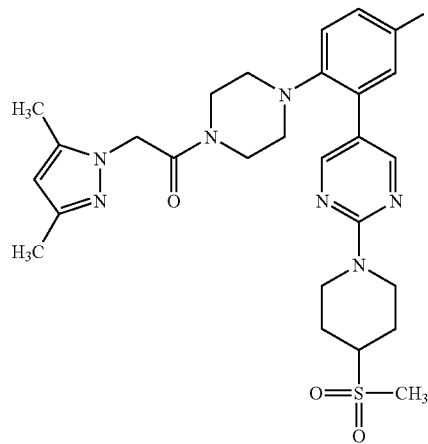 | 2-(3,5-dimethyl-1H-pyrazol-1-yl)-1-[4-(4-fluoro-2-{2-[4-(methylsulfonyl)piperidin-1-yl]pyrimidin-5-yl}phenyl)piperazin-1-yl]ethanone | 556 |
| 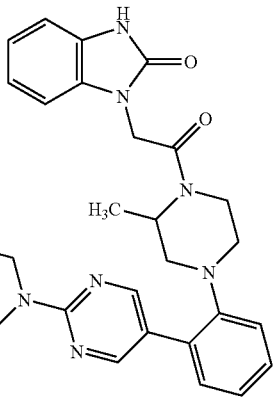 | 1-{2-[2-methyl-4-(2-{2-[4-(methylsulfonyl)piperidin-1-yl]pyrimidin-5-yl}phenyl)piperazin-1-yl]-2-oxoethyl}-1,3-dihydro-2H-benzimidazol-2-one | 590 |
| 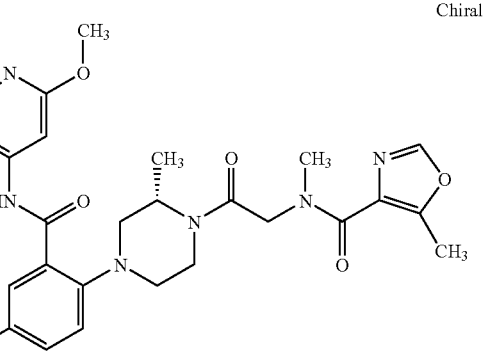 Chiral | N-{2-[(2S)-4-{4-fluoro-2-[(2-methoxypyridin-4-yl)carbamoyl]phenyl}-2-methylpiperazin-1-yl]-2-oxoethyl}-N,5-dimethyl-1,3-oxazole-4-carboxamide | 525 |

TABLE I-continued

| MOLECULAR STRUCTURE | | CHEMICAL NAME | Observed MH+ |
|---|---|---|---|
| | Chiral | 5-fluoro-N-(2-methoxypyridin-4-yl)-2-{(3S)-3-methyl-4-[N-methyl-N-(2-methylpropanoyl)glycyl]piperazin-1-yl}benzamide | 486 |
| | | 1-(4-{2-[2-(4-hydroxypiperidin-1-yl)pyrimidin-5-yl]phenyl}-2-methylpiperazin-1-yl)-2-(3H-imidazo[4,5-b]pyridin-3-yl)ethanone | 513 |
| | Chiral | 5-fluoro-2-{(3S)-3-methyl-4-[(2-oxo-2,3-dihydro-1H-benzimidazol-1-yl)acetyl]piperazin-1-yl}-N-(5-methyl-4,5,6,7-tetrahydro[1,3]thiazolo[5,4-c]pyridin-2-yl)benzamide | 564 |
| | Chiral | 2-{(3S)-4-[(3,5-dimethyl-1H-pyrazol-1-yl)acetyl]-3-methylpiperazin-1-yl}-5-fluoro-N-(2-methoxypyridin-4-yl)benzamide | 481 |

TABLE I-continued

| MOLECULAR STRUCTURE | | CHEMICAL NAME | Observed MH+ |
|---|---|---|---|
| | Chiral | N-{2-[(2R)-4-{4-fluoro-2-[(2-methoxypyridin-4-yl)carbamoyl]phenyl}-2-methylpiperazin-1-yl]-2-oxoethyl}-N,5-dimethyl-1,3-oxazole-4-carboxamide | 525 |
| | Chiral | 2-{(3S)-4-[(3,5-dimethyl-1H-pyrazol-1-yl)acetyl]-3-methylpiperazin-1-yl}-5-fluoro-N-(5-methyl-4,5,6,7-tetrahydro[1,3]thiazolo[5,4-c]pyridin-2-yl)benzamide | 526 |
| | | 1-[4-(4-fluoro-2-{2-[4-(methylsulfonyl)piperidin-1-yl]pyrimidin-5-yl}phenyl)-2-methylpiperazin-1-yl]-2-(3H-imidazo[4,5-b]pyridin-3-yl)ethanone | 593 |
| | | 1-(2-{4-[4-fluoro-2-(2-methoxypyrimidin-5-yl)phenyl]piperazin-1-yl}-2-oxoethyl)-1,3-dihydro-2H-benzimidazol-2-one | 463 |

TABLE I-continued

| MOLECULAR STRUCTURE | CHEMICAL NAME | Observed MH+ |
|---|---|---|
| Chiral | 5-fluoro-N-(2-methoxypyridin-4-yl)-2-{(3S)-3-methyl-4-[(1-oxo-1,3-dihydro-2H-isoindol-2-yl)acetyl]piperazin-1-yl}benzamide | 518 |
| 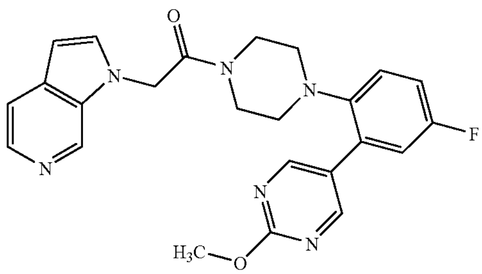 [SMILES: COc1ncc(-c2cc(F)ccc2N2CCN(C(=O)Cn3ccc4ccncc43)CC2)cn1] | 1-{4-[4-fluoro-2-(2-methoxypyrimidin-5-yl)phenyl]piperazin-1-yl}-2-(1H-pyrrolo[2,3-c]pyridin-1-yl)ethanone | 448 |
| 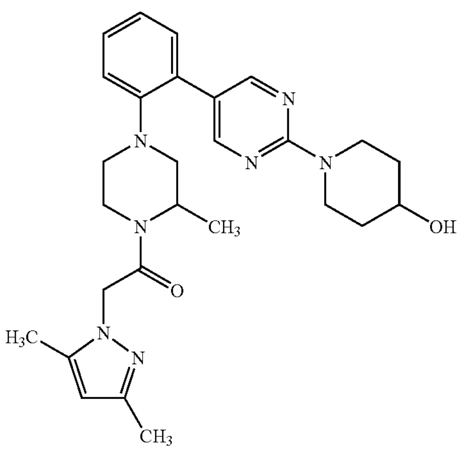 [SMILES: Cc1cc(C)n(CC(=O)N2CCN(c3ccccc3-c3cnc(N4CCC(O)CC4)nc3)CC2C)n1] | 2-(3,5-dimethyl-1H-pyrazol-1-yl)-1-(4-{2-[2-(4-hydroxypiperidin-1-yl)pyrimidin-5-yl]phenyl}-2-methylpiperazin-1-yl)ethanone | 490 |
| 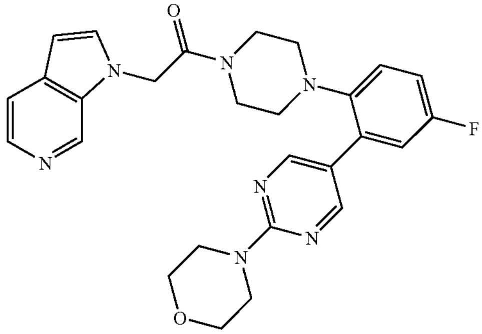 [SMILES: O=C(Cn1ccc2ccncc21)N1CCN(c2ccc(F)cc2-c2cnc(N3CCOCC3)nc2)CC1] | 1-(4-{4-fluoro-2-[2-(morpholin-4-yl)pyrimidin-5-yl]phenyl}piperazin-1-yl)-2-(1H-pyrrolo[2,3-c]pyridin-1-yl)ethanone | 502 |

TABLE I-continued

| MOLECULAR STRUCTURE | CHEMICAL NAME | Observed MH+ |
|---|---|---|
| 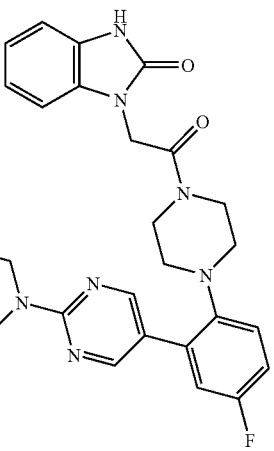 | 1-[2-(4-{4-fluoro-2-[2-(4-methylpiperazin-1-yl)pyrimidin-5-yl]phenyl}piperazin-1-yl)-2-oxoethyl]-1,3-dihydro-2H-benzimidazol-2-one | 531 |
| 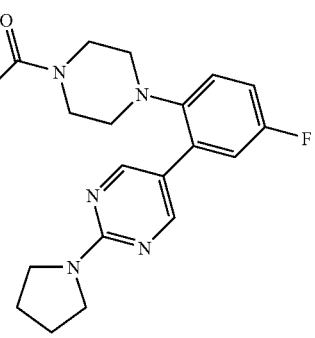 | 1-(4-{4-fluoro-2-[2-(pyrrolidin-1-yl)pyrimidin-5-yl]phenyl}piperazin-1-yl)-2-(3H-imidazo[4,5-b]pyridin-3-yl)ethanone | 487 |
| 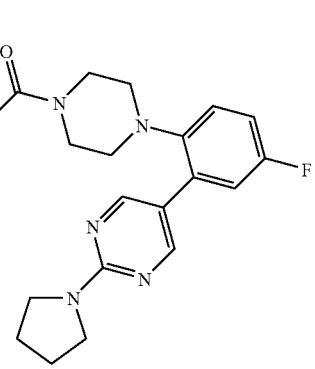 | 1-[2-(4-{4-fluoro-2-[2-(pyrrolidin-1-yl)pyrimidin-5-yl]phenyl}piperazin-1-yl)-2-oxoethyl]-1,3-dihydro-2H-benzimidazol-2-one | 502 |
| Chiral 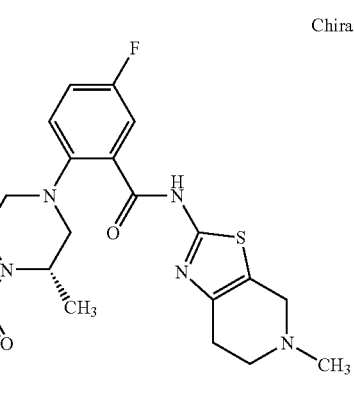 | 5-fluoro-2-{(3S)-3-methyl-4-[N-methyl-N-(2-methylpropanoyl)glycyl]piperazin-1-yl}-N-(5-methyl-4,5,6,7-tetrahydro[1,3]thiazolo[5,4-c]pyridin-2-yl)benzamide | 531 |

TABLE I-continued

| MOLECULAR STRUCTURE | CHEMICAL NAME | Observed MH+ |
|---|---|---|
| 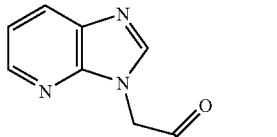 | 2-(3H-imidazo[4,5-b]pyridin-3-yl)-1-[2-methyl-4-(2-{2-[4-(methylsulfonyl)piperidin-1-yl]pyrimidin-5-yl}phenyl)piperazin-1-yl]ethanone | 575 |
| 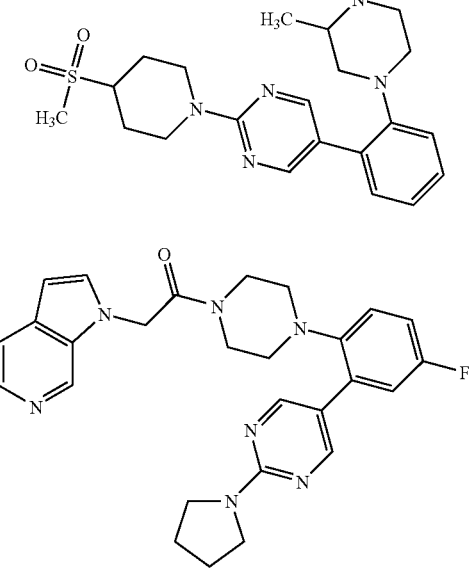 | 1-(4-{4-fluoro-2-[2-(pyrrolidin-1-yl)pyrimidin-5-yl]phenyl}piperazin-1-yl)-2-(1H-pyrrolo[2,3-c]pyridin-1-yl)ethanone | 486 |
| 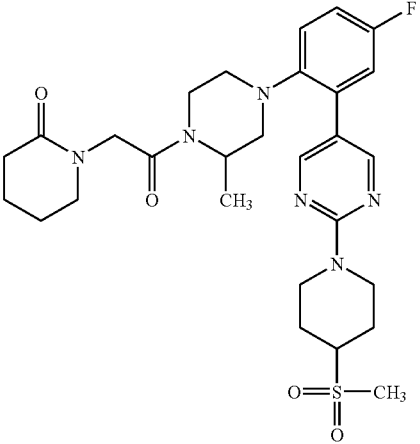 | 1-{2-[4-(4-fluoro-2-{2-[4-(methylsulfonyl)piperidin-1-yl]pyrimidin-5-yl}phenyl)-2-methylpiperazin-1-yl]-2-oxoethyl}piperidin-2-one | 573 |
| 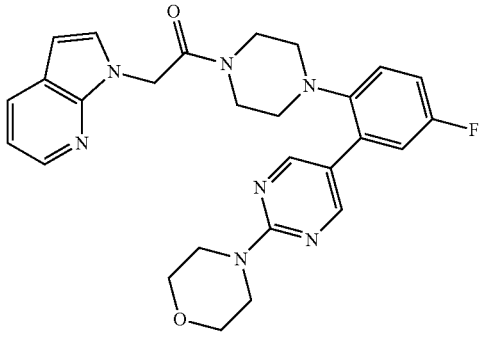 [SMILES: O=C(Cn1ccc2cccnc21)N1CCN(c2ccc(F)cc2-c2cnc(N3CCOCC3)nc2)CC1] | 1-(4-{4-fluoro-2-[2-(morpholin-4-yl)pyrimidin-5-yl]phenyl}piperazin-1-yl)-2-(1H-pyrrolo[2,3-b]pyridin-1-yl)ethanone | 502 |

TABLE I-continued

| MOLECULAR STRUCTURE | CHEMICAL NAME | Observed MH+ |
|---|---|---|
| 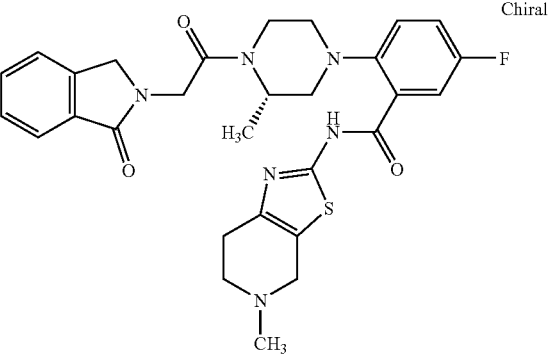 [SMILES: C[C@H]1CN(c2ccc(F)cc2C(=O)Nc2nc3c(s2)CN(C)CC3)CCN1C(=O)CN1Cc2ccccc2C1=O] Chiral | 5-fluoro-2-{(3S)-3-methyl-4-[(1-oxo-1,3-dihydro-2H-isoindol-2-yl)acetyl]piperazin-1-yl}-N-(5-methyl-4,5,6,7-tetrahydro[1,3]thiazolo[5,4-c]pyridin-2-yl)benzamide | 563 |
| 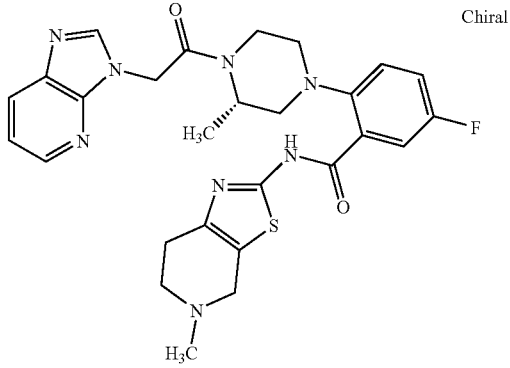 [SMILES: C[C@H]1CN(c2ccc(F)cc2C(=O)Nc2nc3c(s2)CN(C)CC3)CCN1C(=O)Cn1cnc2cccnc21] Chiral | 5-fluoro-2-[(3S)-4-(3H-imidazo[4,5-b]pyridin-3-ylacetyl)-3-methylpiperazin-1-yl]-N-(5-methyl-4,5,6,7-tetrahydro[1,3]thiazolo[5,4-c]pyridin-2-yl)benzamide | 549 |
| 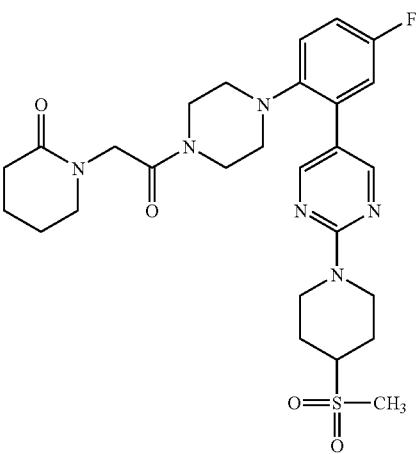 [SMILES: CS(=O)(=O)C1CCN(c2ncc(-c3cc(F)ccc3N3CCN(C(=O)CN4CCCCC4=O)CC3)cn2)CC1] | 1-{2-[4-(4-fluoro-2-{2-[4-(methylsulfonyl)piperidin-1-yl]pyrimidin-5-yl}phenyl)piperazin-1-yl]-2-oxoethyl}piperidin-2-one | 559 |

TABLE I-continued

| MOLECULAR STRUCTURE | CHEMICAL NAME | Observed MH+ |
|---|---|---|
| 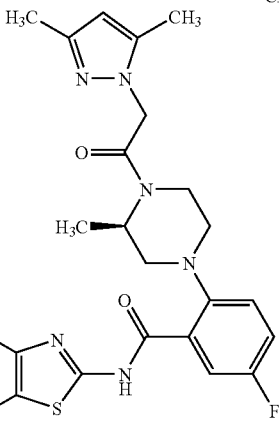 Chiral | 2-{(3R)-4-[(3,5-dimethyl-1H-pyrazol-1-yl)acetyl]-3-methylpiperazin-1-yl}-5-fluoro-N-(5-methyl-4,5,6,7-tetrahydro[1,3]thiazolo[5,4-c]pyridin-2-yl)benzamide | 526 |
| 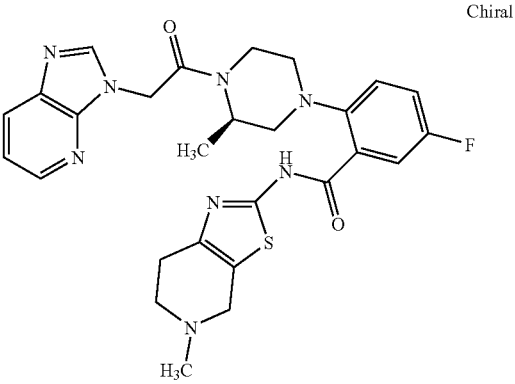 [SMILES: C[C@@H]1CN(c2ccc(F)cc2C(=O)Nc2nc3c(s2)CN(C)CC3)CCN1C(=O)Cn1cnc2cccnc21] Chiral | 5-fluoro-2-[(3R)-4-(3H-imidazo[4,5-b]pyridin-3-ylacetyl)-3-methylpiperazin-1-yl]-N-(5-methyl-4,5,6,7-tetrahydro[1,3]thiazolo[5,4-c]pyridin-2-yl)benzamide | 549 |
| 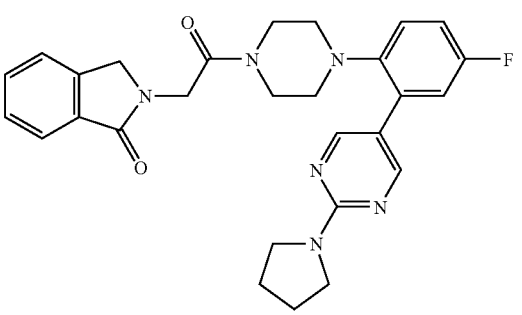 [SMILES: O=C(CN1Cc2ccccc2C1=O)N1CCN(c2ccc(F)cc2-c2cnc(N3CCCC3)nc2)CC1] | 2-[2-(4-{4-fluoro-2-[2-(pyrrolidin-1-yl)pyrimidin-5-yl]phenyl}piperazin-1-yl)-2-oxoethyl]-2,3-dihydro-1H-isoindol-1-one | 501 |
| 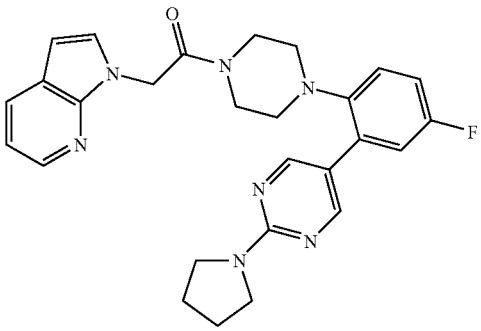 [SMILES: O=C(Cn1ccc2cccnc21)N1CCN(c2ccc(F)cc2-c2cnc(N3CCCC3)nc2)CC1] | 1-(4-{4-fluoro-2-[2-(pyrrolidin-1-yl)pyrimidin-5-yl]phenyl}piperazin-1-yl)-2-(1H-pyrrolo[2,3-b]pyridin-1-yl)ethanone | 486 |

TABLE I-continued

| MOLECULAR STRUCTURE | | CHEMICAL NAME | Observed MH+ |
|---|---|---|---|
| | Chiral | 5-fluoro-2-{(3R)-3-methyl-4-[(1-oxo-1,3-dihydro-2H-isoindol-2-yl)acetyl]piperazin-1-yl}-N-(5-methyl-4,5,6,7-tetrahydro[1,3]thiazolo[5,4-c]pyridin-2-yl)benzamide | 563 |
| | | 1-[2-(4-{4-fluoro-2-[2-(4-hydroxypiperidin-1-yl)pyrimidin-5-yl]phenyl}piperazin-1-yl)-2-oxoethyl]piperidin-2-one | 497 |
| | | 2-(3,5-dimethyl-1H-pyrazol-1-yl)-1-(4-{4-fluoro-2-[2-(pyrrolidin-1-yl)pyrimidin-5-yl]phenyl}piperazin-1-yl)ethanone | 464 |
| | Chiral | 5-fluoro-2-[(3S)-3-methyl-4-(1H-pyrrolo[2,3-b]pyridin-1-ylacetyl)piperazin-1-yl]-N-(5-methyl-4,5,6,7-tetrahydro[1,3]thiazolo[5,4-c]pyridin-2-yl)benzamide | 548 |

TABLE I-continued

| MOLECULAR STRUCTURE | CHEMICAL NAME | Observed MH+ |
|---|---|---|
| 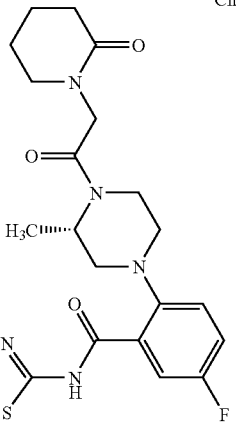 Chiral | 5-fluoro-2-{(3S)-3-methyl-4-[(2-oxopiperidin-1-yl)acetyl]piperazin-1-yl}-N-(5-methyl-4,5,6,7-tetrahydro[1,3]thiazolo[5,4-c]pyridin-2-yl)benzamide | 529 |
| 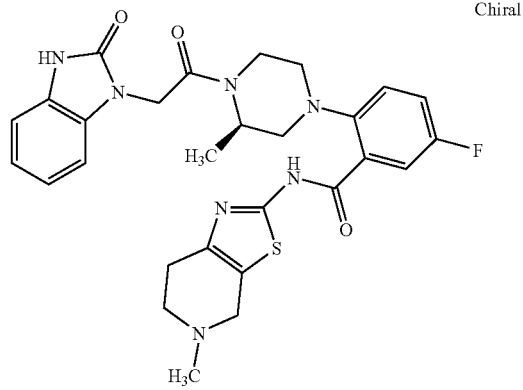 [SMILES: C[C@@H]1CN(c2ccc(F)cc2C(=O)Nc2nc3c(s2)CN(C)CC3)CCN1C(=O)Cn1c(=O)[nH]c2ccccc21] Chiral | 5-fluoro-2-{(3R)-3-methyl-4-[(2-oxo-2,3-dihydro-1H-benzimidazol-1-yl)acetyl]piperazin-1-yl}-N-(5-methyl-4,5,6,7-tetrahydro[1,3]thiazolo[5,4-c]pyridin-2-yl)benzamide | 564 |
| 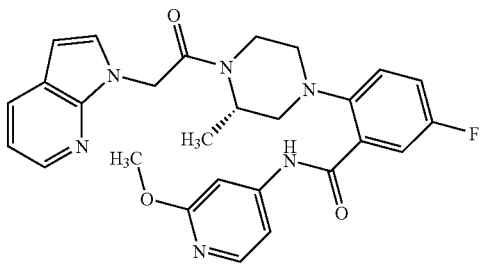 Chiral | 5-fluoro-N-(2-methoxypyridin-4-yl)-2-[(3S)-3-methyl-4-(1H-pyrrolo[2,3-b]pyridin-1-ylacetyl)piperazin-1-yl]benzamide | 503 |
| 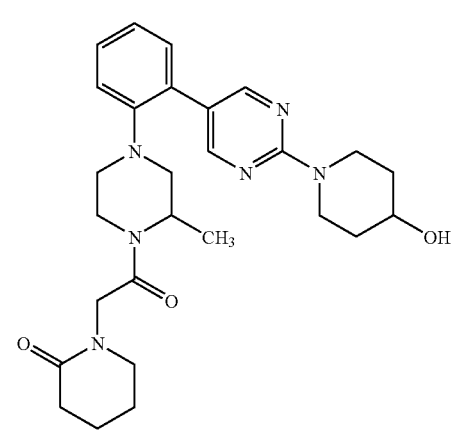 [SMILES: CC1CN(c2ccccc2-c2cnc(N3CCC(O)CC3)nc2)CCN1C(=O)CN1CCCCC1=O] | 1-[2-(4-{2-[2-(4-hydroxypiperidin-1-yl)pyrimidin-5-yl]phenyl}-2-methylpiperazin-1-yl)-2-oxoethyl]piperidin-2-one | 493 |

TABLE I-continued

| MOLECULAR STRUCTURE | | CHEMICAL NAME | Observed MH+ |
|---|---|---|---|
| 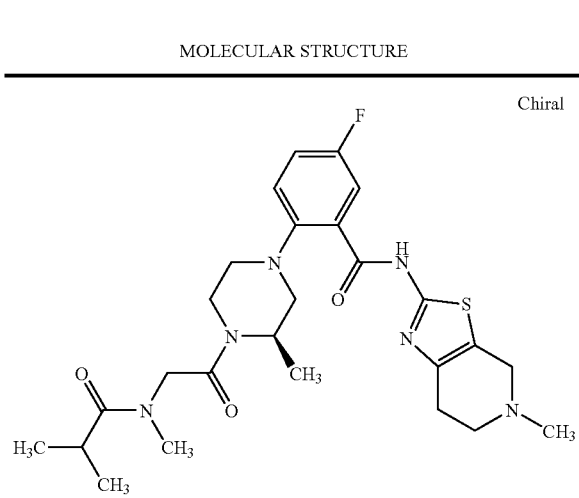 | Chiral | 5-fluoro-2-{(3R)-3-methyl-4-[N-methyl-N-(2-methylpropanoyl)glycyl]piperazin-1-yl}-N-(5-methyl-4,5,6,7-tetrahydro[1,3]thiazolo[5,4-c]pyridin-2-yl)benzamide | 531 |
| 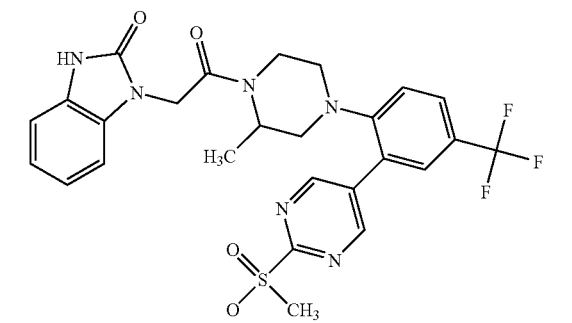 | | 1-[2-(2-methyl-4-{2-[2-(methylsulfonyl)pyrimidin-5-yl]-4-(trifluoromethyl)phenyl}piperazin-1-yl)-2-oxoethyl]-1,3-dihydro-2H-benzimidazol-2-one | 575 |
| 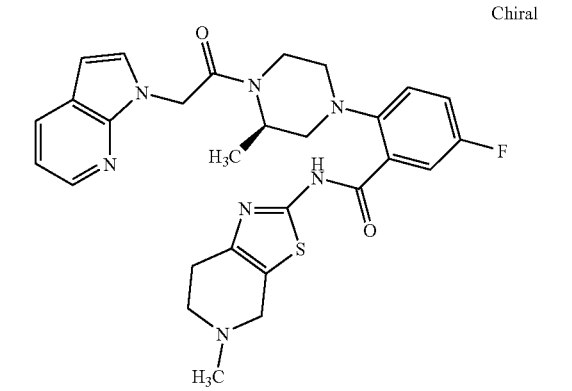 [SMILES: C[C@@H]1CN(c2ccc(F)cc2C(=O)Nc2nc3c(s2)CN(C)CC3)CCN1C(=O)Cn1ccc2cccnc21] | Chiral | 5-fluoro-2-[(3R)-3-methyl-4-(1H-pyrrolo[2,3-b]pyridin-1-ylacetyl)piperazin-1-yl]-N-(5-methyl-4,5,6,7-tetrahydro[1,3]thiazolo[5,4-c]pyridin-2-yl)benzamide | 548 |
| 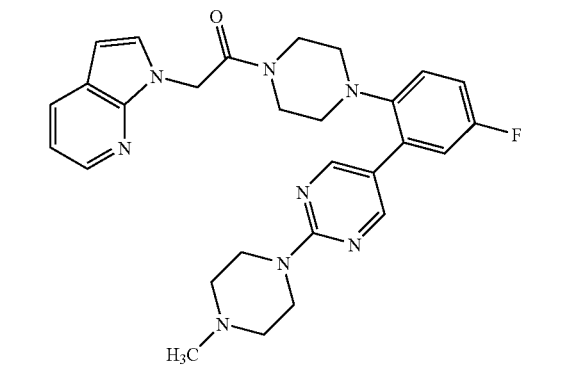 [SMILES: CN1CCN(c2ncc(-c3cc(F)ccc3N3CCN(C(=O)Cn4ccc5cccnc54)CC3)cn2)CC1] | | 1-(4-{4-fluoro-2-[2-(4-methylpiperazin-1-yl)pyrimidin-5-yl]phenyl}piperazin-1-yl)-2-(1H-pyrrolo[2,3-b]pyridin-1-yl)ethanone | 515 |

TABLE I-continued

| MOLECULAR STRUCTURE | | CHEMICAL NAME | Observed MH+ |
|---|---|---|---|
| 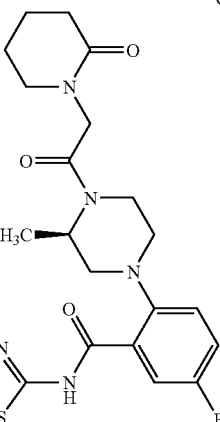 | Chiral | 5-fluoro-2-{(3R)-3-methyl-4-[(2-oxopiperidin-1-yl)acetyl]piperazin-1-yl}-N-(5-methyl-4,5,6,7-tetrahydro[1,3]thiazolo[5,4-c]pyridin-2-yl)benzamide | 529 |
| 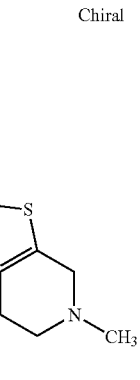 | Chiral | N-{2-[(2S)-4-{4-fluoro-2-[(5-methyl-4,5,6,7-tetrahydro[1,3]thiazolo[5,4-c]pyridin-2-yl)carbamoyl]phenyl}-2-methylpiperazin-1-yl]-2-oxoethyl}-N,5-dimethyl-1,3-oxazole-4-carboxamide | 570 |
| 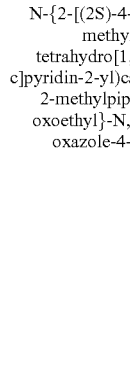 | | 2-[2-(4-{4-fluoro-2-[2-(morpholin-4-yl)pyrimidin-5-yl]phenyl}piperazin-1-yl)-2-oxoethyl]-2,3-dihydro-1H-isoindol-1-one | 517 |
| 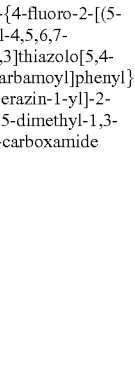 | | 1-[2-(4-{4-fluoro-2-[2-(pyrrolidin-1-yl)pyrimidin-5-yl]phenyl}piperazin-1-yl)-2-oxoethyl]piperidin-2-one | 467 |

TABLE I-continued

| MOLECULAR STRUCTURE | CHEMICAL NAME | Observed MH+ |
|---|---|---|
| 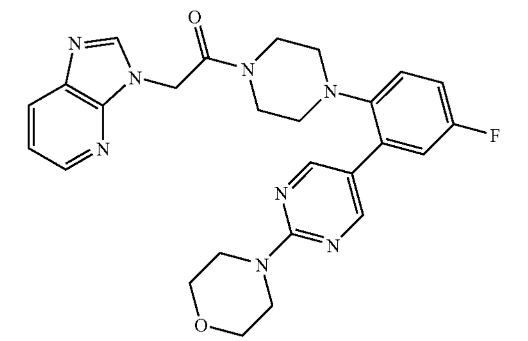 | 1-(4-{4-fluoro-2-[2-(morpholin-4-yl)pyrimidin-5-yl]phenyl}piperazin-1-yl)-2-(3H-imidazo[4,5-b]pyridin-3-yl)ethanone | 503 |
| 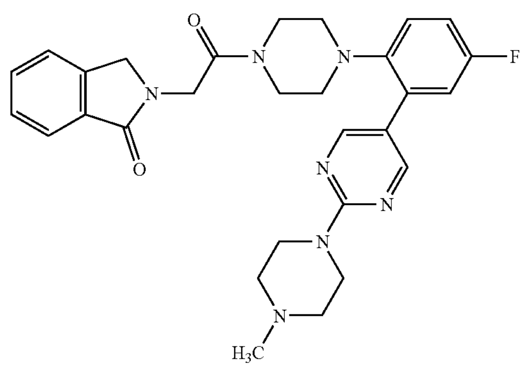 [SMILES: CN1CCN(c2ncc(-c3cc(F)ccc3N3CCN(C(=O)CN4Cc5ccccc5C4=O)CC3)cn2)CC1] | 2-[2-(4-{4-fluoro-2-[2-(4-methylpiperazin-1-yl)pyrimidin-5-yl]phenyl}piperazin-1-yl)-2-oxoethyl]-2,3-dihydro-1H-isoindol-1-one | 530 |
| 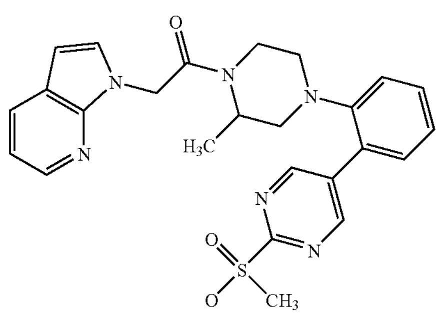 | 1-(2-methyl-4-{2-[2-(methylsulfonyl)pyrimidin-5-yl]phenyl}piperazin-1-yl)-2-(1H-pyrrolo[2,3-b]pyridin-1-yl)ethanone | 491 |
| 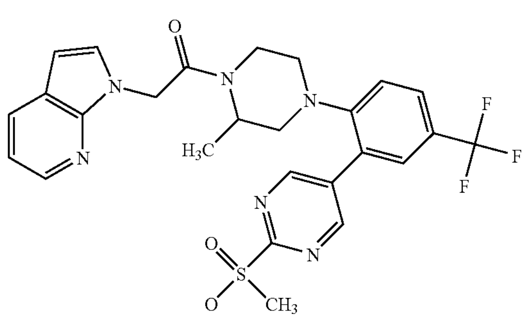 | 1-(2-methyl-4-{2-[2-(methylsulfonyl)pyrimidin-5-yl]-4-(trifluoromethyl)phenyl}piperazin-1-yl)-2-(1H-pyrrolo[2,3-b]pyridin-1-yl)ethanone | 559 |

TABLE I-continued

| MOLECULAR STRUCTURE | CHEMICAL NAME | Observed MH+ |
|---|---|---|
|  | 1-[2-(4-{4-fluoro-2-[2-(morpholin-4-yl)pyrimidin-5-yl]phenyl}piperazin-1-yl)-2-oxoethyl]piperidin-2-one | 483 |
|  | 1-{2-[2-methyl-4-(2-{2-[4-(methylsulfonyl)piperidin-1-yl]pyrimidin-5-yl}phenyl)piperazin-1-yl]-2-oxoethyl}piperidin-2-one | 555 |
| Chiral | N-{2-[(2R)-4-{4-fluoro-2-[(5-methyl-4,5,6,7-tetrahydro[1,3]thiazolo[5,4-c]pyridin-2-yl)carbamoyl]phenyl}-2-methylpiperazin-1-yl]-2-oxoethyl}-N,5-dimethyl-1,3-oxazole-4-carboxamide | 570 |

TABLE I-continued

| MOLECULAR STRUCTURE | CHEMICAL NAME | Observed MH+ |
|---|---|---|
| 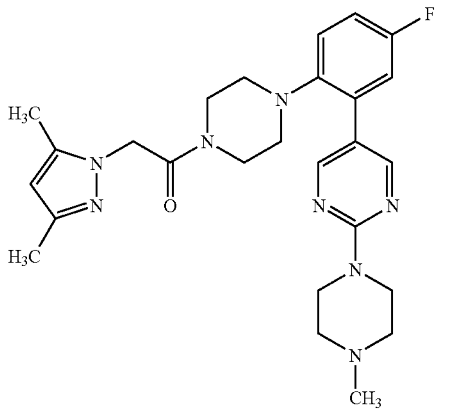 [SMILES: Cc1cc(C)n(CC(=O)N2CCN(c3ccc(F)cc3-c3cnc(N4CCN(C)CC4)nc3)CC2)n1] | 2-(3,5-dimethyl-1H-pyrazol-1-yl)-1-(4-{4-fluoro-2-[2-(4-methylpiperazin-1-yl)pyrimidin-5-yl]phenyl}piperazin-1-yl)ethanone | 493 |
| | 1-(4-{4-fluoro-2-[2-(4-methylpiperazain-1-yl)pyrimidin-5-yl]phenyl}piperazin-1-yl)-2-(3H-imidazo[4,5-b]pyridin-3-yl)ethanone | 516 |
| 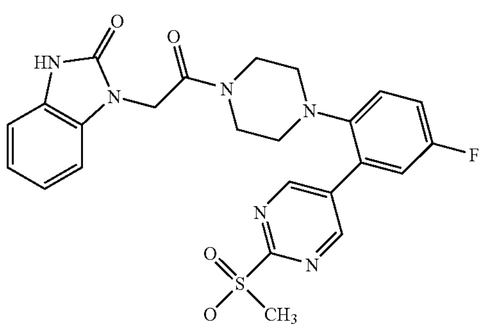 | 1-[2-(4-{4-fluoro-2-[2-(methylsulfonyl)pyrimidin-5-yl]phenyl}piperazin-1-yl)-2-oxoethyl]-1,3-dihydro-2H-benzimidazol-2-one | 511 |
| 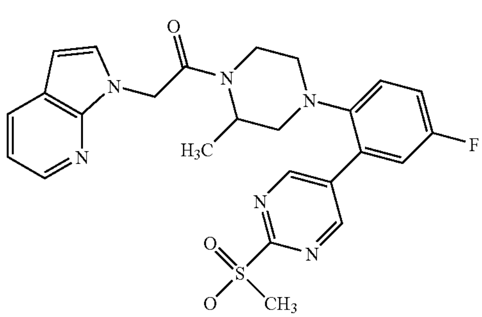 | 1-(4-{4-fluoro-2-[2-(methylsulfonyl)pyrimidin-5-yl]phenyl}-2-methylpiperazin-1-yl)-2-(1H-pyrrolo[2,3-b]pyridin-1-yl)ethanone | 509 |

TABLE I-continued

| MOLECULAR STRUCTURE | CHEMICAL NAME | Observed MH+ |
|---|---|---|
| 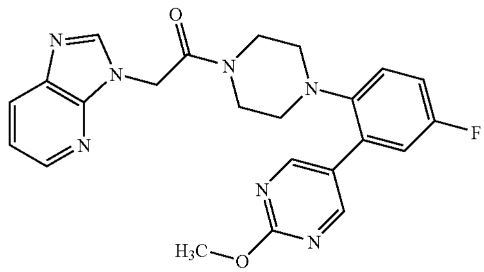 [SMILES: COc1ncc(-c2cc(F)ccc2N2CCN(C(=O)Cn3cnc4cccnc43)CC2)cn1] | 1-{4-[4-fluoro-2-(2-methoxypyrimidin-5-yl)phenyl]piperazin-1-yl}-2-(3H-imidazo[4,5-b]pyridin-3-yl)ethanone | 448 |
| 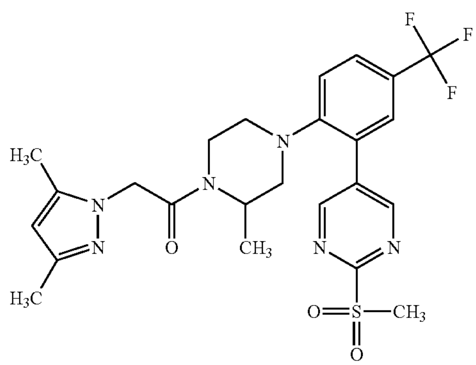 [SMILES: Cc1cc(C)n(CC(=O)N2CCN(c3ccc(C(F)(F)F)cc3-c3cnc(S(C)(=O)=O)nc3)CC2C)n1] | 2-(3,5-dimethyl-1H-pyrazol-1-yl)-1-(2-methyl-4-{2-[2-(methylsulfonyl)pyrimidin-5-yl]-4-(trifluoromethyl)phenyl}piperazin-1-yl)ethanone | 537 |
| 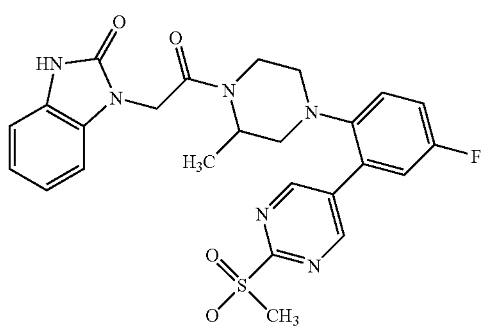 | 1-[2-(4-{4-fluoro-2-[2-(methylsulfonyl)pyrimidin-5-yl]phenyl}-2-methylpiperazin-1-yl)-2-oxoethyl]-1,3-dihydro-2H-benzimidazol-2-one | 525 |
| 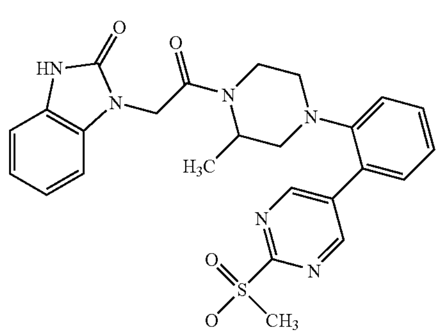 | 1-[2-(2-methyl-4-{2-[2-(methylsulfonyl)pyrimidin-5-yl]phenyl}piperazin-1-yl)-2-oxoethyl]-1,3-dihydro-2H-benzimidazol-2-one | 507 |

TABLE I-continued

| MOLECULAR STRUCTURE | CHEMICAL NAME | Observed MH+ |
|---|---|---|
| 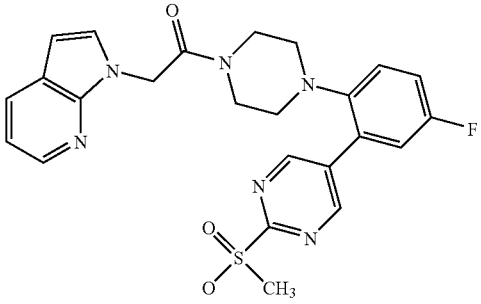 | 1-(4-{4-fluoro-2-[2-(methylsulfonyl)pyrimidin-5-yl]phenyl}piperazin-1-yl)-2-(1H-pyrrolo[2,3-b]pyridin-1-yl)ethanone | 495 |
| 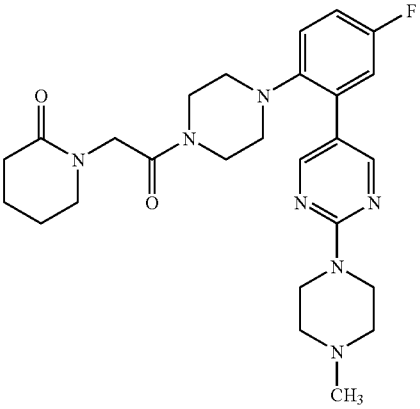 [SMILES: CN1CCN(c2ncc(-c3cc(F)ccc3N3CCN(C(=O)CN4CCCCC4=O)CC3)cn2)CC1] | 1-[2-(4-{4-fluoro-2-[2-(4-methylpiperazin-1-yl)pyrimidin-5-yl]phenyl}piperazin-1-yl)-2-oxoethyl]piperidin-2-one | 496 |
| 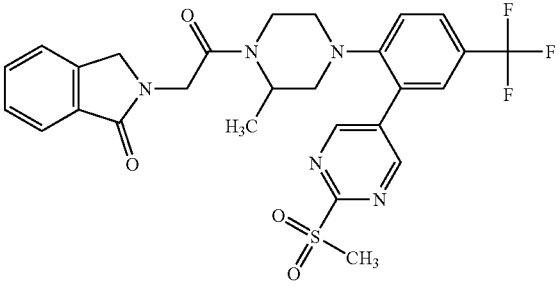 [SMILES: CC1CN(c2ccc(C(F)(F)F)cc2-c2cnc(S(C)(=O)=O)nc2)CCN1C(=O)CN1Cc2ccccc2C1=O] | 2-[2-(2-methyl-4-{2-[2-(methylsulfonyl)pyrimidin-5-yl]-4-(trifluoromethyl)phenyl]piperazin-1-yl)-2-oxoethyl]-2,3-dihydro-1H-isoindol-1-one | 574 |
| 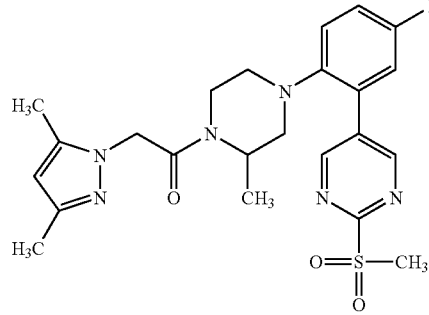 | 2-(3,5-dimethyl-1H-pyrazol-1-yl)-1-(4-{4-fluoro-2-[2-(methylsulfonyl)pyrimidin-5-yl]phenyl}-2-methylpiperazin-1-yl)ethanone | 487 |

TABLE I-continued

| MOLECULAR STRUCTURE | CHEMICAL NAME | Observed MH+ |
|---|---|---|
| 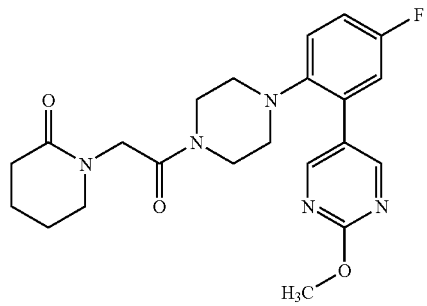 [SMILES: COc1ncc(-c2cc(F)ccc2N2CCN(C(=O)CN3CCCCC3=O)CC2)cn1] | 1-(2-{4-[4-fluoro-2-(2-methoxypyrimidin-5-yl)phenyl]piperazin-1-yl}-2-oxoethyl)piperidin-2-one | 428 |
| 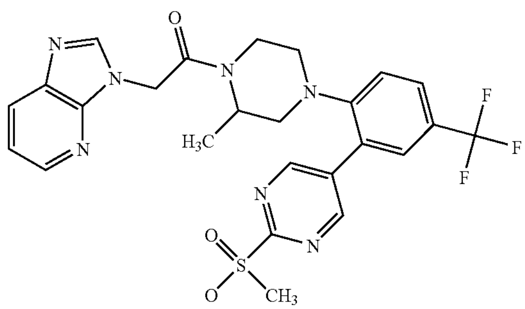 | 2-(3H-imidazo[4,5-b]pyridin-3-yl)-1-(2-methyl-4-{2-[2-(methylsulfonyl)pyrimidin-5-yl]-4-(trifluoromethyl)phenyl}piperazin-1-yl)ethanone | 560 |
| 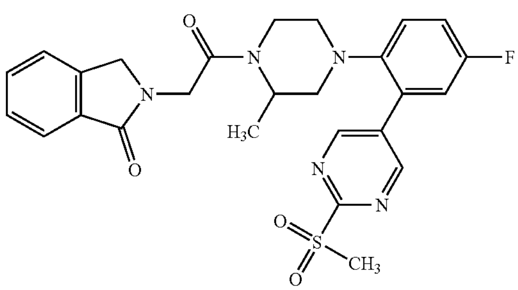 [SMILES: CC1CN(c2ccc(F)cc2-c2cnc(S(C)(=O)=O)nc2)CCN1C(=O)CN1Cc2ccccc2C1=O] | 2-[2-(4-{4-fluoro-2-[2-(methylsulfonyl)pyrimidin-5-yl]phenyl}-2-methylpiperazin-1-yl)-2-oxoethyl]-2,3-dihydro-1H-isoindol-1-one | 524 |
| 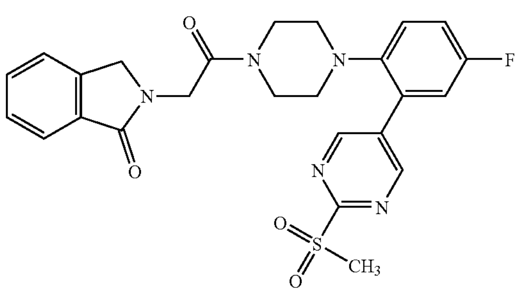 [SMILES: CS(=O)(=O)c1ncc(-c2cc(F)ccc2N2CCN(C(=O)CN3Cc4ccccc4C3=O)CC2)cn1] | 2-[2-(4-{4-fluoro-2-[2-(methylsulfonyl)pyrimidin-5-yl]phenyl}piperazin-1-yl)-2-oxoethyl]-2,3-dihydro-1H-isoindol-1-one | 510 |
| 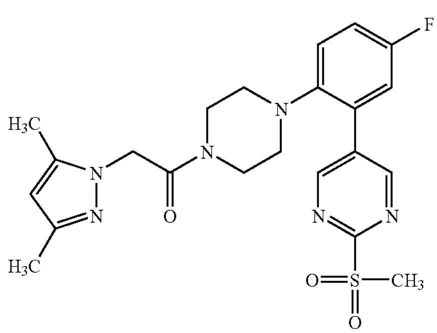 [SMILES: Cc1cc(C)n(CC(=O)N2CCN(c3ccc(F)cc3-c3cnc(S(C)(=O)=O)nc3)CC2)n1] | 2-(3,5-dimethyl-1H-pyrazol-1-yl)-1-(4-{4-fluoro-2-[2-(methylsulfonyl)pyrimidin-5-yl]phenyl}piperazin-1-yl)ethanone | 473 |

TABLE I-continued

| MOLECULAR STRUCTURE | CHEMICAL NAME | Observed MH+ |
|---|---|---|
| 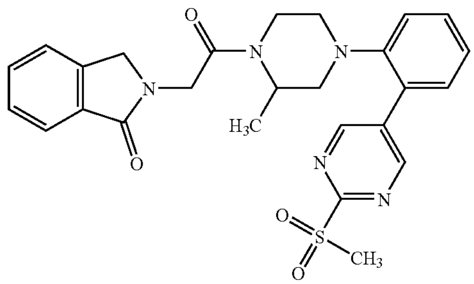 [SMILES: CC1CN(c2ccccc2-c2cnc(S(C)(=O)=O)nc2)CCN1C(=O)CN1Cc2ccccc2C1=O] | 2-[2-(2-methyl-4-{2-[2-(methylsulfonyl)pyrimidin-5-yl]phenyl}piperazin-1-yl)-2-oxoethyl]-2,3-dihydro-1H-isoindol-1-one | 506 |
| 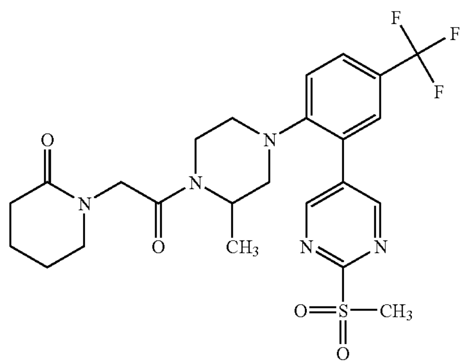 [SMILES: CC1CN(c2ccc(C(F)(F)F)cc2-c2cnc(S(C)(=O)=O)nc2)CCN1C(=O)CN1CCCCC1=O] | 1-[2-(2-methyl-4-{2-[2-(methylsulfonyl)pyrimidin-5-yl]-4-(trifluoromethyl)phenyl}piperazin-1-yl)-2-oxoethyl]piperidin-2-one | 540 |
| 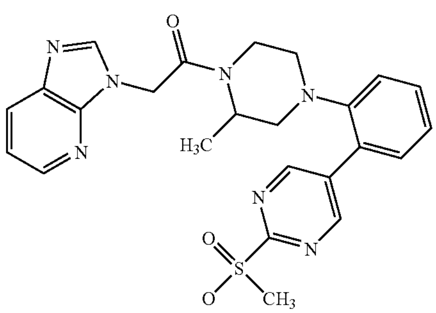 | 2-(3H-imidazo[4,5-b]pyridin-3-yl)-1-(2-methyl-4-{2-[2-(methylsulfonyl)pyrimidin-5-yl]phenyl}piperazin-1-yl)ethanone | 492 |
| 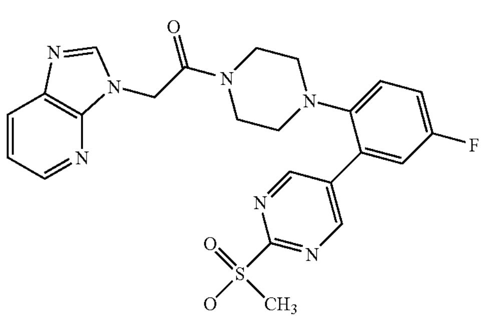 | 1-(4-{4-fluoro-2-[2-(methylsulfonyl)pyrimidin-5-yl]phenyl}piperazin-1-yl)-2-(3H-imidazo[4,5-b]pyridin-3-yl)ethanone | 496 |

TABLE I-continued

| MOLECULAR STRUCTURE | CHEMICAL NAME | Observed MH+ |
|---|---|---|
| 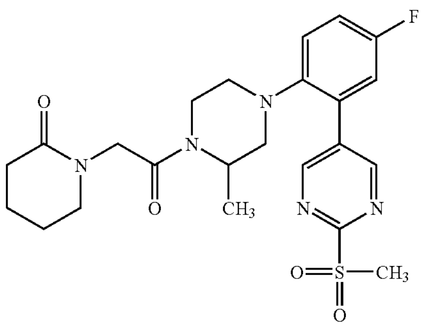 [SMILES: CC1CN(c2ccc(F)cc2-c2cnc(S(C)(=O)=O)nc2)CCN1C(=O)CN1CCCCC1=O] | 1-[2-(4-{4-fluoro-2-[2-(methylsulfonyl)pyrimidin-5-yl]phenyl}-2-methylpiperazin-1-yl)-2-oxoethyl]piperidin-2-one | 490 |
| 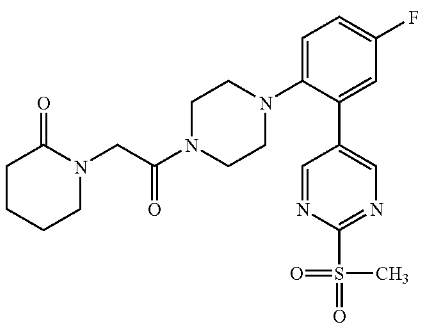 [SMILES: CS(=O)(=O)c1ncc(-c2cc(F)ccc2N2CCN(C(=O)CN3CCCCC3=O)CC2)cn1] | 1-[2-(4-{4-fluoro-2-[2-(methylsulfonyl)pyrimidin-5-yl]phenyl}piperazin-1-yl)-2-oxoethyl]piperidin-2-one | 476 |
| 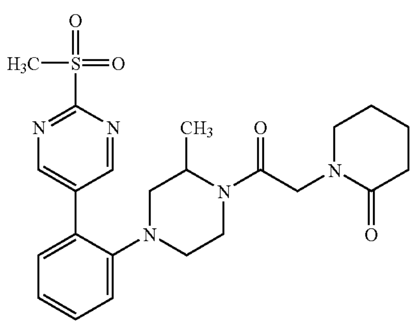 [SMILES: CC1CN(c2ccccc2-c2cnc(S(C)(=O)=O)nc2)CCN1C(=O)CN1CCCCC1=O] | 1-[2-(2-methyl-4-{2-[2-(methylsulfonyl)pyrimidin-5-yl]phenyl}piperazin-1-yl)-2-oxoethyl]piperidin-2-one | 472 |
| 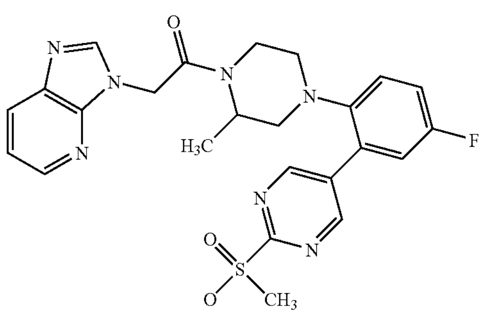 | 1-(4-[4-fluoro-2-[2-(methylsulfonyl)pyrimidin-5-yl]phenyl}-2-methylpiperazin-1-yl)-2-(3H-imidazo[4,5-b]pyridin-3-yl)ethanone | 510 |

In one embodiment, the invention relates to a compound selected from compounds described in Table 1, or the pharmaceutically acceptable salts thereof.

In another embodiment there is a compound selected from
3-(2-Methylsulfanyl-pyrimidin-5-yl)-4-[4-(2-pyrrolo[2,3-b]pyridin-1-yl-acetyl)-piperazin-1-yl]-benzonitrile;
1-{4-[2-(2-Methylsulfanyl-pyrimidin-5-yl)-phenyl]-piperazin-1-yl}-2-pyrrolo[2,3-b]pyridin-1-yl-ethanone;
5-{2-[4-(2-Pyrrolo[2,3-b]pyridin-1-yl-acetyl)-piperazin-1-yl]-phenyl}-pyridine-2-carbonitrile;
2-(3,5-Dimethyl-pyrazol-1-yl)-1-{4-[2-(2-methylsulfanyl-pyrimidin-5-yl)-4-trifluoromethyl-phenyl]-piperazin-1-yl}-ethanone;
1-{4-[2-(2-Methylamino-pyrimidin-5-yl)-4-trifluoromethyl-phenyl]-piperazin-1-yl}-2-pyrrolo[2,3-b]pyridin-1-yl-ethanone;
1-(4-{2-[2-(2,6-Dimethyl-morpholin-4-yl)-pyrimidin-5-yl]-phenyl}-piperazin-1-yl)-2-(3,5-dimethyl-pyrazol-1-yl)-ethanone;
1-{4-[2-(2-Methoxy-pyrimidin-5-yl)-phenyl]-piperazin-1-yl}-2-pyrrolo[2,3-b]pyridin-1-yl-ethanone;

1-{4-[2-(2-Dimethylamino-pyrimidin-5-yl)-phenyl]-piperazin-1-yl}-2-pyrrolo[2,3-b]pyridin-1-yl-ethanone;
1-{4-[2-(2-Morpholin-4-yl-pyrimidin-5-yl)-phenyl]-piperazin-1-yl}-2-pyrrolo[2,3-b]pyridin-1-yl-ethanone;
2-(3,5-Dimethyl-pyrazol-1-yl)-1-{4-[2-(2-pyrrolidin-1-yl-pyrimidin-5-yl)-phenyl]-piperazin-1-yl}-ethanone;
2-(3,5-Dimethyl-pyrazol-1-yl)-1-{4-[2-(2-methylamino-pyrimidin-5-yl)-4-trifluoromethyl-phenyl]-piperazin-1-yl}-ethanone;
1-{3-[2-(2-Methoxy-pyrimidin-5-yl)-phenyl]-3,8-diaza-bicyclo[3.2.1]oct-8-yl}-2-pyrrolo[2,3-b]pyridin-1-yl-ethanone;
2-(3,5-Dimethyl-pyrazol-1-yl)-1-{4-[2-(2-piperidin-1-yl-pyrimidin-5-yl)-phenyl]-piperazin-1-yl}-ethanone;
3-(2-Methoxy-pyrimidin-5-yl)-4-[4-(2-pyrrolo[2,3-b]pyridin-1-yl-acetyl)-piperazin-1-yl]-benzonitrile;
1-(4-{2-[2-((2R,6R)-2,6-Dimethyl-morpholin-4-yl)-pyrimidin-5-yl]-phenyl}-piperazin-1-yl)-2-pyrrolo[2,3-b]pyridin-1-yl-ethanone;
1-{4-[2-(2-Methylamino-pyrimidin-5-yl)-phenyl]-piperazin-1-yl}-2-pyrrolo[2,3-b]pyridin-1-yl-ethanone;
1-{4-[2-(2-Dimethylamino-pyrimidin-5-yl)-phenyl]-piperazin-1-yl}-2-(3,5-dimethyl-pyrazol-1-yl)-ethanone;
3-(2-Methylamino-pyrimidin-5-yl)-4-[4-(2-pyrrolo[2,3-b]pyridin-1-yl-acetyl)-piperazin-1-yl]-benzonitrile;
3-(2-Morpholin-4-yl-pyrimidin-5-yl)-4-[4-(2-pyrrolo[2,3-b]pyridin-1-yl-acetyl)-piperazin-1-yl]-benzonitrile;
2-(3,5-Dimethyl-pyrazol-1-yl)-1-{4-[2-(2-morpholin-4-yl-pyrimidin-5-yl)-4-trifluoromethyl-phenyl]-piperazin-1-yl}-ethanone;
2-(3,5-Dimethyl-pyrazol-1-yl)-1-{4-[2-(2-methoxy-pyrimidin-5-yl)-4-trifluoromethyl-phenyl]-piperazin-1-yl}-ethanone;
1-{4-[2-(2-Methoxy-pyrimidin-5-yl)-4-trifluoromethyl-phenyl]-piperazin-1-yl}-2-pyrrolo[2,3-b]pyridin-1-yl-ethanone;
2-(3,5-Dimethyl-pyrazol-1-yl)-1-{4-[2-(2-morpholin-4-yl-pyrimidin-5-yl)-phenyl]-piperazin-1-yl}-ethanone;
1-{4-[4-Methoxy-2-(2-morpholin-4-yl-pyrimidin-5-yl)-phenyl]-piperazin-1-yl}-2-pyrrolo[2,3-b]pyridin-1-yl-ethanone;
1-{4-[2-(2-Methoxy-pyrimidin-5-yl)-phenyl]-piperazin-1-yl}-2-pyrrolo[2,3-c]pyridin-1-yl-ethanone;
1-{4-[2-(2-Methylsulfanyl-pyrimidin-5-yl)-4-trifluoromethyl-phenyl]-piperazin-1-yl}-2-pyrrolo[2,3-b]pyridin-1-yl-ethanone;
1-{4-[2-(2-[1,4]Oxazepan-4-yl-pyrimidin-5-yl)-phenyl]-piperazin-1-yl}-2-pyrrolo[2,3-b]pyridin-1-yl-ethanone;
1-{4-[2-(2-Ethylamino-pyrimidin-5-yl)-phenyl]-piperazin-1-yl}-2-pyrrolo[2,3-b]pyridin-1-yl-ethanone;
1-{4-[2-(2-Pyrrolidin-1-yl-pyrimidin-5-yl)-phenyl]-piperazin-1-yl}-2-pyrrolo[2,3-b]pyridin-1-yl-ethanone;
1-(2-{4-[2-(2-Morpholin-4-yl-pyrimidin-5-yl)-phenyl]-piperazin-1-yl}-2-oxo-ethyl)-1,3-dihydro-benzoimidazol-2-one;
2-(3,5-Dimethyl-pyrazol-1-yl)-1-{4-[2-(2-methylsulfanyl-pyrimidin-5-yl)-phenyl]-piperazin-1-yl}-ethanone;
1-(4-{2-[2-((2R,6S)-2,6-Dimethyl-morpholin-4-yl)-pyrimidin-5-yl]-phenyl}-piperazin-1-yl)-2-pyrrolo[2,3-b]pyridin-1-yl-ethanone;
1-(4-{2-[2-(4-Methyl-piperazin-1-yl)-pyrimidin-5-yl]-phenyl}-piperazin-1-yl)-2-pyrrolo[2,3-b]pyridin-1-yl-ethanone;
1-{4-[2-(2-Piperidin-1-yl-pyrimidin-5-yl)-phenyl]-piperazin-1-yl}-2-pyrrolo[2,3-b]pyridin-1-yl-ethanone;
1-{4-[2-(2-Morpholin-4-yl-pyrimidin-5-yl)-phenyl]-piperidin-1-yl}-2-pyrrolo[2,3-b]pyridin-1-yl-ethanone;
1-{4-[2-(2-Methanesulfonyl-pyrimidin-5-yl)-4-trifluoromethyl-phenyl]-piperazin-1-yl}-2-pyrrolo[2,3-b]pyridin-1-yl-ethanone;
1-{4-[4-Chloro-2-(2-morpholin-4-yl-pyrimidin-5-yl)-phenyl]-piperazin-1-yl}-2-pyrrolo[2,3-b]pyridin-1-yl-ethanone;
5-{2-[4-(2-Pyrrolo[2,3-b]pyridin-1-yl-acetyl)-piperazin-1-yl]-phenyl}-pyrimidine-2-carbonitrile;
2-Imidazo[4,5-b]pyridin-3-yl-1-{4-[2-(2-methoxy-pyrimidin-5-yl)-phenyl]-piperazin-1-yl}-ethanone;
1-{4-[2-(2-Morpholin-4-yl-pyrimidin-5-yl)-4-trifluoromethyl-phenyl]-piperazin-1-yl}-2-pyrrolo[2,3-b]pyridin-1-yl-ethanone;
5-(2-{4-[2-(3,5-Dimethyl-pyrazol-1-yl)-acetyl]-piperazin-1-yl}-phenyl)-pyridine-2-carbonitrile;
2-(3,5-Dimethyl-pyrazol-1-yl)-1-{4-[2-(2-ethoxy-pyrimidin-5-yl)-phenyl]-piperazin-1-yl}-ethanone;
4-{4-[2-(3,5-Dimethyl-pyrazol-1-yl)-acetyl]-piperazin-1-yl}-3-(2-morpholin-4-yl-pyrimidin-5-yl)-benzonitrile;
2-(3,5-Dimethyl-pyrazol-1-yl)-1-{4-[2-(1-methyl-1H-indol-6-yl)-phenyl]-piperazin-1-yl}-ethanone;
1-{4-[2-(2-Morpholin-4-yl-pyrimidin-5-yl)-phenyl]-3,6-dihydro-2H-pyridin-1-yl}-2-pyrrolo[2,3-b]pyridin-1-yl-ethanone;
2-(3,5-Dimethyl-pyrazol-1-yl)-1-{4-[2-(2-morpholin-4-yl-pyrimidin-5-yl)-phenyl]-3,6-dihydro-2H-pyridin-1-yl}-ethanone;
1-{4-[2-(2-Morpholin-4-yl-pyrimidin-5-yl)-5-trifluoromethyl-phenyl]-piperazin-1-yl}-2-pyrrolo[2,3-b]pyridin-1-yl-ethanone;
5-{2-[4-(2-Pyrrolo[2,3-b]pyridin-1-yl-acetyl)-piperazin-1-yl]-phenyl}-pyridine-2-carboxylic acid amide;
1-{4-[2-(2-Morpholin-4-yl-pyrimidin-5-yl)-phenyl]-piperazin-1-yl}-2-(pyridin-4-ylamino)-ethanone;
1-{4-[2-Fluoro-6-(2-morpholin-4-yl-pyrimidin-5-yl)-phenyl]-piperazin-1-yl}-2-pyrrolo[2,3-b]pyridin-1-yl-ethanone;
2-Indazol-2-yl-1-{4-[2-(2-methoxy-pyrimidin-5-yl)-phenyl]-piperazin-1-yl}-ethanone;
2-(2,4-Dimethyl-imidazol-1-yl)-1-{4-[2-(2-morpholin-4-yl-pyrimidin-5-yl)-phenyl]-piperazin-1-yl}-ethanone;
1-{4-[2-(6-Chloro-pyridin-3-yl)-phenyl]-piperazin-1-yl}-2-pyrrolo[2,3-b]pyridin-1-yl-ethanone;
2-(3,5-Dimethyl-pyrazol-1-yl)-1-{4-[2-(6-trifluoromethyl-pyridin-3-yl)-phenyl]-piperazin-1-yl}-ethanone;
1-{4-[2-(6-Methoxy-pyridin-3-yl)-phenyl]-piperazin-1-yl}-2-pyrrolo[2,3-b]pyridin-1-yl-ethanone;
2-(3,5-Dimethyl-pyrazol-1-yl)-1-{4-[2-(2-methylamino-pyrimidin-5-yl)-phenyl]-piperazin-1-yl}-ethanone;
2-Indazol-1-yl-1-{4-[2-(2-methoxy-pyrimidin-5-yl)-phenyl]-piperazin-1-yl}-ethanone;
1-{4-[2-(2-Morpholin-4-yl-pyrimidin-5-yl)-phenyl]-piperazin-1-yl}-2-(thiazol-2-ylamino)-ethanone;
4-{4-[2-(3,5-Dimethyl-pyrazol-1-yl)-acetyl]-piperazin-1-yl}-3-(2-methylsulfanyl-pyrimidin-5-yl)-benzonitrile;
2-(3,5-Dimethyl-pyrazol-1-yl)-1-[4-(4'-trifluoromethyl-biphenyl-2-yl)-piperazin-1-yl]-ethanone;
2-(3,5-Dimethyl-pyrazol-1-yl)-1-{4-[2-(2-phenoxy-pyrimidin-5-yl)-phenyl]-piperazin-1-yl}-ethanone;
2-(3,5-Dimethyl-pyrazol-1-yl)-1-(4-{2-[2-(4-methyl-piperazin-1-yl)-pyrimidin-5-yl]-phenyl}-piperazin-1-yl)-ethanone;
2-(3,5-Dimethyl-pyrazol-1-yl)-1-{4-[2-(2-morpholin-4-yl-pyrimidin-5-yl)-phenyl]-piperidin-1-yl}-ethanone;
5-(2-{4-[2-(3,5-Dimethyl-pyrazol-1-yl)-acetyl]-piperazin-1-yl}-phenyl)-pyrimidine-2-carbonitrile;

2-Indol-1-yl-1-{4-[2-(2-methoxy-pyrimidin-5-yl)-phenyl]-piperazin-1-yl}-ethanone;
2-(3,5-Dimethyl-pyrazol-1-yl)-1-{4-[2-(2-methoxy-pyrimidin-5-yl)-phenyl]-piperazin-1-yl}-ethanone;
5-(2-{4-[2-(2,4-Dimethyl-imidazol-1-yl)-acetyl]-piperazin-1-yl}-phenyl)-pyridine-2-carbonitrile;
5-(2-{4-[2-(Thiazol-2-ylamino)-acetyl]-piperazin-1-yl}-phenyl)-pyridine-2-carbonitrile;
1-[4-(2-Benzo[b]thiophen-2-yl-phenyl)-piperazin-1-yl]-2-(3,5-dimethyl-pyrazol-1-yl)-ethanone;
2-(3,5-Dimethyl-pyrazol-1-yl)-1-{4-[2-(2-methanesulfonyl-pyrimidin-5-yl)-4-trifluoromethyl-phenyl]-piperazin-1-yl}-ethanone;
2-(3,5-Dimethyl-pyrazol-1-yl)-1-[4-(3'-methoxy-biphenyl-2-yl)-piperazin-1-yl]-ethanone;
2-(3,5-Dimethyl-pyrazol-1-yl)-1-(4-{2-[2-(pyridin-3-yloxy)-pyrimidin-5-yl]-phenyl}-piperazin-1-yl)-ethanone;
1-[4-(2-Benzothiazol-5-yl-phenyl)-piperazin-1-yl]-2-(3,5-dimethyl-pyrazol-1-yl)-ethanone;
2-(3,5-Dimethyl-pyrazol-1-yl)-1-{4-[2-(6-methoxy-pyridin-3-yl)-phenyl]-piperazin-1-yl}-ethanone;
1-{4-[2-(2-Methoxy-pyrimidin-5-yl)-phenyl]-piperazin-1-yl}-2-(thiazol-2-ylamino)-ethanone;
2-(2,4-Dimethyl-imidazol-1-yl)-1-{4-[2-(2-methoxy-pyrimidin-5-yl)-phenyl]-piperazin-1-yl}-ethanone;
1-[4-(4'-Benzoyl-biphenyl-2-yl)-piperazin-1-yl]-2-(3,5-dimethyl-pyrazol-1-yl)-ethanone;
2-(3,5-Dimethyl-pyrazol-1-yl)-1-{4-[2-(2-methyl-pyrimidin-5-yl)-phenyl]-piperazin-1-yl}-ethanone;
3,4-Dimethoxy-N-(2-{4-[2-(2-morpholin-4-yl-pyrimidin-5-yl)-phenyl]-piperazin-1-yl}-2-oxo-ethyl)-benzamide;
2-(3,5-Dimethyl-pyrazol-1-yl)-1-[4-(4'-methyl-biphenyl-2-yl)-piperazin-1-yl]-ethanone;
5-(2-{4-[2-(5-Methyl-3-trifluoromethyl-pyrazol-1-yl)-acetyl]-piperazin-1-yl}-phenyl)-pyridine-2-carbonitrile;
1-{4-[2-(9H-Carbazol-2-yl)-phenyl]-piperazin-1-yl}-2-(3,5-dimethyl-pyrazol-1-yl)-ethanone;
2-(3,5-Dimethyl-pyrazol-1-yl)-1-{4-[3'-(5-methyl-[1,3,4]oxadiazol-2-yl)-biphenyl-2-yl]-piperazin-1-yl}-ethanone;
2-(3,5-Dimethyl-pyrazol-1-yl)-1-[4-(2-naphthalen-2-yl-phenyl)-piperazin-1-yl]-ethanone;
2-(3,5-Dimethyl-pyrazol-1-yl)-1-{4-[2-(1H-indol-6-yl)-phenyl]-piperazin-1-yl}-ethanone;
1-[4-(4'-Chloro-biphenyl-2-yl)-piperazin-1-yl]-2-(3,5-dimethyl-pyrazol-1-yl)-ethanone;
2-(3,5-Dimethyl-pyrazol-1-yl)-1-[4-(4'-trifluoromethoxy-biphenyl-2-yl)-piperazin-1-yl]-ethanone;
5-(2-{4-[2-(Pyridin-4-ylamino)-acetyl]-piperazin-1-yl}-phenyl)-pyridine-2-carbonitrile;
2-(3,5-Dimethyl-pyrazol-1-yl)-1-[4-(4'-methoxy-biphenyl-2-yl)-piperazin-1-yl]-ethanone;
2'-{4-[2-(3,5-Dimethyl-pyrazol-1-yl)-acetyl]-piperazin-1-yl}-biphenyl-4-carbonitrile;
1-[4-(4'-tert-Butyl-biphenyl-2-yl)-piperazin-1-yl]-2-(3,5-dimethyl-pyrazol-1-yl)-ethanone;
1-{4-[2-(2-Methoxy-pyrimidin-5-yl)-phenyl]-piperazin-1-yl}-2-(5-methyl-3-trifluoromethyl-pyrazol-1-yl)-ethanone;
2-(3,5-Dimethyl-pyrazol-1-yl)-1-[4-(4'-isopropyl-biphenyl-2-yl)-piperazin-1-yl]-ethanone;
1-[4-(3'-Chloro-biphenyl-2-yl)-piperazin-1-yl]-2-(3,5-dimethyl-pyrazol-1-yl)-ethanone;
1-{4-[2-(2-Methoxy-pyrimidin-5-yl)-phenyl]-piperazin-1-yl}-2-(3,4,5-trimethyl-pyrazol-1-yl)-ethanone;
1-{4-[2-(2-Methanesulfonyl-pyrimidin-5-yl)-phenyl]-piperazin-1-yl}-2-pyrrolo[2,3-b]pyridin-1-yl-ethanone;
2-(3,5-Dimethyl-pyrazol-1-yl)-1-(4-[1,1';4',1"]terphenyl-2-yl-piperazin-1-yl)-ethanone;
1-[2-(4-Biphenyl-2-yl-piperazin-1-yl)-2-oxo-ethyl]-1,3-dihydro-benzoimidazol-2-one;
1-{4-[2-(2-Cyclopropylamino-pyrimidin-5-yl)-phenyl]-piperazin-1-yl}-2-(3,5-dimethyl-pyrazol-1-yl)-ethanone;
4-{4-[2-(3,5-Dimethyl-pyrazol-1-yl)-acetyl]-piperazin-1-yl}-3-(2-methoxy-pyrimidin-5-yl)-benzonitrile;
1-(4-Biphenyl-2-yl-piperazin-1-yl)-2-pyrrolo[2,3-b]pyridin-1-yl-ethanone;
1-{4-[2-(2-tert-Butyl-thiazol-4-yl)-phenyl]-piperazin-1-yl}-2-(3,5-dimethyl-pyrazol-1-yl)-ethanone;
3-(2-Methanesulfonyl-pyrimidin-5-yl)-4-[4-(2-pyrrolo[2,3-b]pyridin-1-yl-acetyl)-piperazin-1-yl]-benzonitrile;
2-(3-tert-Butyl-[1,2,4]thiadiazol-5-ylamino)-1-{4-[2-(2-methoxy-pyrimidin-5-yl)-phenyl]-piperazin-1-yl}-ethanone;
2-(3,5-Dimethyl-pyrazol-1-yl)-1-[4-(4'-fluoro-biphenyl-2-yl)-piperazin-1-yl]-ethanone;
2-(3,5-Dimethyl-pyrazol-1-yl)-1-[4-(3'-trifluoromethyl-biphenyl-2-yl)-piperazin-1-yl]-ethanone;
1-{4-[4-Methanesulfonyl-2-(2-morpholin-4-yl-pyrimidin-5-yl)-phenyl]-piperazin-1-yl}-2-pyrrolo[2,3-b]pyridin-1-yl-ethanone;
1-{4-[2-(2-Morpholin-4-yl-pyrimidin-5-yl)-phenyl]-piperazin-1-yl}-2-(pyridin-3-ylamino)-ethanone;
2-Benzotriazol-1-yl-1-{4-[2-(2-methoxy-pyrimidin-5-yl)-phenyl]-piperazin-1-yl}-ethanone;
N-(2-{4-[2-(6-Cyano-pyridin-3-yl)-phenyl]-piperazin-1-yl}-2-oxo-ethyl)-3,4-dimethoxy-benzamide;
1-{4-[2-(2-Methoxy-pyrimidin-5-yl)-phenyl]-piperazin-1-yl}-2-(pyridin-4-ylamino)-ethanone;
1-(4-Biphenyl-2-yl-piperazin-1-yl)-2-(2,5-dimethyl-imidazol-1-yl)-ethanone;
2-(3,5-Dimethyl-pyrazol-1-yl)-1-{4-[2-(1H-indol-5-yl)-phenyl]-piperazin-1-yl}-ethanone;
N-(2'-{4-[2-(3,5-Dimethyl-pyrazol-1-yl)-acetyl]-piperazin-1-yl}-biphenyl-4-yl)-methanesulfonamide;
1-(4-Biphenyl-2-yl-piperazin-1-yl)-2-(pyridin-4-ylamino)-ethanone;
5-(2-{4-[2-(5-Methyl-3-trifluoromethyl-pyrazol-1-yl)-acetyl]-piperazin-1-yl}-phenyl)-pyridine-2-carboxylic acid amide;
1-{4-[3-(2-Morpholin-4-yl-pyrimidin-5-yl)-pyridin-2-yl]-piperazin-1-yl}-2-pyrrolo[2,3-b]pyridin-1-yl-ethanone;
2-(3,5-Dimethyl-pyrazol-1-yl)-1-[4-(2-pyrimidin-5-yl-phenyl)-piperazin-1-yl]-ethanone;
1-[4-(3',5'-Bis-trifluoromethyl-biphenyl-2-yl)-piperazin-1-yl]-2-(3,5-dimethyl-pyrazol-1-yl)-ethanone;
1-{4-[2-(2-Amino-pyrimidin-5-yl)-phenyl]-piperazin-1-yl}-2-(3,5-dimethyl-pyrazol-1-yl)-ethanone;
2-(3,5-Dimethyl-pyrazol-1-yl)-1-[4-(4'-methanesulfonyl-biphenyl-2-yl)-piperazin-1-yl]-ethanone;
2'-{4-[2-(3,5-Dimethyl-pyrazol-1-yl)-acetyl]-piperazin-1-yl}-biphenyl-4-sulfonic acid amide;
1-(4-Biphenyl-2-yl-piperazin-1-yl)-2-imidazo[4,5-b]pyridin-1-yl-ethanone;
1-[4-(2'-Chloro-biphenyl-2-yl)-piperazin-1-yl]-2-(3,5-dimethyl-pyrazol-1-yl)-ethanone;
2-(3,5-Dimethyl-pyrazol-1-yl)-1-[4-(4'-hydroxymethyl-biphenyl-2-yl)-piperazin-1-yl]-ethanone;
1-(4-Biphenyl-2-yl-piperazin-1-yl)-2-(thiazol-2-ylamino)-ethanone;
3,4-Dimethoxy-N-(2-{4-[2-(2-methoxy-pyrimidin-5-yl)-phenyl]-piperazin-1-yl}-2-oxo-ethyl)-benzamide;
2-(3,5-Dimethyl-pyrazol-1-yl)-1-[4-(4'-hydroxy-biphenyl-2-yl)-piperazin-1-yl]-ethanone;

2-(3,5-Dimethyl-pyrazol-1-yl)-1-(4-[1,1';3',1"]terphenyl-2-yl-piperazin-1-yl)-ethanone;
1-[4-(3',4'-Dimethoxy-biphenyl-2-yl)-piperazin-1-yl]-2-(3,5-dimethyl-pyrazol-1-yl)-ethanone;
2-(3,5-Dimethyl-pyrazol-1-yl)-1-[4-(2-quinolin-3-yl-phenyl)-piperazin-1-yl]-ethanone;
2-(3,5-Dimethyl-pyrazol-1-yl)-1-{4-[2-(6-ethoxy-pyridin-3-yl)-phenyl]-piperazin-1-yl}-ethanone;
2-(3,5-Dimethyl-pyrazol-1-yl)-1-{4-[2-(5-methoxy-pyrazin-2-yl)-phenyl]-piperazin-1-yl}-ethanone;
2-(3,5-Dimethyl-pyrazol-1-yl)-1-{4-[2-(6-morpholin-4-yl-pyridin-3-yl)-phenyl]-piperazin-1-yl}-ethanone;
2-(3,5-Dimethyl-pyrazol-1-yl)-1-[4-(4'-ethoxy-biphenyl-2-yl)-piperazin-1-yl]-ethanone;
1-[4-(2-Benzo[1,3]dioxol-5-yl-phenyl)-piperazin-1-yl]-2-(3,5-dimethyl-pyrazol-1-yl)-ethanone;
1-[4-(3'-Acetyl-biphenyl-2-yl)-piperazin-1-yl]-2-(3,5-dimethyl-pyrazol-1-yl)-ethanone;
2-(3,5-Dimethyl-pyrazol-1-yl)-1-{4-[2-(1-methyl-1H-indol-5-yl)-phenyl]-piperazin-1-yl}-ethanone;
2-(3,5-Dimethyl-pyrazol-1-yl)-1-[4-(2-quinolin-6-yl-phenyl)-piperazin-1-yl]-ethanone;
1-[4-(4'-Acetyl-biphenyl-2-yl)-piperazin-1-yl]-2-(3,5-dimethyl-pyrazol-1-yl)-ethanone;
2-(3,5-Dimethyl-pyrazol-1-yl)-1-[4-(3'-ethoxy-biphenyl-2-yl)-piperazin-1-yl]-ethanone;
4-(2-{4-[2-(3,5-Dimethyl-pyrazol-1-yl)-acetyl]-piperazin-1-yl}-phenyl)-pyridine-2-carboxylic acid methyl ester;
5-(2-{4-[2-(3,5-Dimethyl-pyrazol-1-yl)-acetyl]-piperazin-1-yl}-phenyl)-nicotinic acid ethyl ester;
1-{4-[2-(1-Benzyl-1H-pyrazol-4-yl)-phenyl]-piperazin-1-yl}-2-(3,5-dimethyl-pyrazol-1-yl)-ethanone;
2-(3,5-Dimethyl-pyrazol-1-yl)-1-[4-(4'-thiophen-2-yl-biphenyl-2-yl)-piperazin-1-yl]-ethanone;
2'-{4-[2-(3,5-Dimethyl-pyrazol-1-yl)-acetyl]-piperazin-1-yl}-biphenyl-4-sulfonic acid dimethylamide;
2-(3,5-Dimethyl-pyrazol-1-yl)-1-{4-[2-(5-phenyl-thiophen-2-yl)-phenyl]-piperazin-1-yl}-ethanone;
1-[4-(2-Dibenzothiophen-2-yl-phenyl)-piperazin-1-yl]-2-(3,5-dimethyl-pyrazol-1-yl)-ethanone;
2'-{4-[2-(3,5-Dimethyl-pyrazol-1-yl)-acetyl]-piperazin-1-yl}-biphenyl-3-carboxylic acid methylamide;
1-[4-(4'-Benzyl-biphenyl-2-yl)-piperazin-1-yl]-2-(3,5-dimethyl-pyrazol-1-yl)-ethanone;
N-(2'-{4-[2-(3,5-Dimethyl-pyrazol-1-yl)-acetyl]-piperazin-1-yl}-biphenyl-3-yl)-acetamide;
5-(2-{4-[2-(3,5-Dimethyl-pyrazol-1-yl)-acetyl]-piperazin-1-yl}-phenyl)-pyridine-2-carboxylic acid methyl ester;
1-[4-(3'-Benzyl-biphenyl-2-yl)-piperazin-1-yl]-2-(3,5-dimethyl-pyrazol-1-yl)-ethanone;
1-[4-(2-Benzo[b]thiophen-3-yl-phenyl)-piperazin-1-yl]-2-(3,5-dimethyl-pyrazol-1-yl)-ethanone;
1-{4-[2-(1H-Benzoimidazol-2-yl)-phenyl]-piperazin-1-yl}-2-(3,5-dimethyl-pyrazol-1-yl)-ethanone;
1-[4-(2-Benzooxazol-2-yl-phenyl)-piperazin-1-yl]-2-(3,5-dimethyl-pyrazol-1-yl)-ethanone;
2-(3,5-Dimethyl-pyrazol-1-yl)-1-{4-[2-(1H-imidazo[4,5-c]pyridin-2-yl)-phenyl]-piperazin-1-yl}-ethanone;
1-{4-[2-(5-Chloro-1H-benzoimidazol-2-yl)-phenyl]-piperazin-1-yl}-2-(3,5-dimethyl-pyrazol-1-yl)-ethanone;
2-(2-{4-[2-(3,5-Dimethyl-pyrazol-1-yl)-acetyl]-piperazin-1-yl}-phenyl)-1H-benzoimidazole-5-carbonitrile;
2-(3,5-Dimethyl-pyrazol-1-yl)-1-{4-[2-(5-trifluoromethyl-1H-benzoimidazol-2-yl)-phenyl]-piperazin-1-yl}-ethanone;
1-(4-{2-[2-((R)-3-Dimethylamino-pyrrolidin-1-yl)-pyrimidin-5-yl]-phenyl}-piperazin-1-yl)-2-(3,5-dimethyl-pyrazol-1-yl)-ethanone;
1-(4-{2-[(1R,4S)-2-(2-Aza-bicyclo[2.2.1]hept-2-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-{4-[4-fluoro-2-(2-morpholin-4-yl-pyrimidin-5-yl)-phenyl]-piperazin-1-yl}-ethanone;
1-{4-[4-Chloro-2-(2-methylamino-pyrimidin-5-yl)-phenyl]-piperazin-1-yl}-2-pyrrolo[2,3-b]pyridin-1-yl-ethanone;
2-(3,5-Dimethyl-pyrazol-1-yl)-1-(4-{2-[2-(4-methanesulfonyl-piperidin-1-yl)-pyrimidin-5-yl]-phenyl}-piperazin-1-yl)-ethanone;
1-[5-(2-{4-[2-(3,5-Dimethyl-pyrazol-1-yl)-acetyl]-piperazin-1-yl}-phenyl)-pyrimidin-2-yl]-piperidine-4-carboxylic acid amide;
2-(3,5-Dimethyl-pyrazol-1-yl)-1-(4-{2-[2-(4-hydroxy-piperidin-1-yl)-pyrimidin-5-yl]-phenyl}-piperazin-1-yl)-ethanone;
1-{4-[4-Chloro-2-(2-methylsulfanyl-pyrimidin-5-yl)-phenyl]-piperazin-1-yl}-2-(3,5-dimethyl-pyrazol-1-yl)-ethanone;
1-{4-[4-Chloro-2-(2-methoxy-pyrimidin-5-yl)-phenyl]-piperazin-1-yl}-2-pyrrolo[2,3-b]pyridin-1-yl-ethanone;
1-(4-{2-[2-(3,3-Difluoro-azetidin-1-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-(4-{2-[2-(3-fluoro-piperidin-1-yl)-pyrimidin-5-yl]-phenyl}-piperazin-1-yl)-ethanone;
2-(5-Fluoro-pyrrolo[2,3-b]pyridin-1-yl)-1-{4-[2-(2-methoxy-pyrimidin-5-yl)-phenyl]-piperazin-1-yl}-ethanone;
1-{4-[4-Chloro-2-(2-methylsulfanyl-pyrimidin-5-yl)-phenyl]-piperazin-1-yl}-2-pyrrolo[2,3-b]pyridin-1-yl-ethanone;
1-[5-(2-{4-[2-(3,5-Dimethyl-pyrazol-1-yl)-acetyl]-piperazin-1-yl}-phenyl)-pyrimidin-2-yl]-piperidine-3-carboxylic acid amide;
1-[5-(2-{4-[2-(3,5-Dimethyl-pyrazol-1-yl)-acetyl]-piperazin-1-yl}-phenyl)-pyrimidin-2-yl]-piperidine-4-carboxylic acid methylamide;
1-(4-{2-[2-(3,3-Difluoro-piperidin-1-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-(4-{2-[2-(3-hydroxy-pyrrolidin-1-yl)-pyrimidin-5-yl]-phenyl}-piperazin-1-yl)-ethanone;
2-(3,5-Dimethyl-pyrazol-1-yl)-1-(4-{2-[2-(4-fluoro-piperidin-1-yl)-pyrimidin-5-yl]-phenyl}-piperazin-1-yl)-ethanone;
2-(4-Chloro-3,5-dimethyl-pyrazol-1-yl)-1-{4-[2-(2-methoxy-pyrimidin-5-yl)-phenyl]-piperazin-1-yl}-ethanone;
2-(3,5-Dimethyl-pyrazol-1-yl)-1-{4-[2-(2-ethylamino-pyrimidin-5-yl)-phenyl]-piperazin-1-yl}-ethanone;
2-(3,5-Dimethyl-pyrazol-1-yl)-1-{4-[2-(2-[1,4]oxazepan-4-yl-pyrimidin-5-yl)-phenyl]-piperazin-1-yl}-ethanone;
1-{4-[4-Chloro-2-(2-morpholin-4-yl-pyrimidin-5-yl)-phenyl]-piperazin-1-yl}-2-(3,5-dimethyl-pyrazol-1-yl)-ethanone;
1-{3-Methyl-4-[2-(2-morpholin-4-yl-pyrimidin-5-yl)-phenyl]-piperazin-1-yl}-2-pyrrolo[2,3-b]pyridin-1-yl-ethanone;
1-(2-{4-[2-(2-Methoxy-pyrimidin-5-yl)-phenyl]-piperazin-1-yl}-2-oxo-ethyl)-3-methyl-1,3-dihydro-benzoimidazol-2-one;

2-(3,5-Dimethyl-pyrazol-1-yl)-1-(4-{2-[2-(3-trifluoromethyl-piperidin-1-yl)-pyrimidin-5-yl]-phenyl}-piperazin-1-yl)-ethanone;

1-(4-{2-[2-(4,4-Dimethyl-piperidin-1-yl)-pyrimidin-5-yl]-phenyl}-piperazin-1-yl)-2-(3,5-dimethyl-pyrazol-1-yl)-ethanone;

2-(3,5-Dimethyl-pyrazol-1-yl)-1-(4-{2-[2-((S)-2-methoxymethyl-pyrrolidin-1-yl)-pyrimidin-5-yl]-phenyl}-piperazin-1-yl)-ethanone;

2-(3,5-Dimethyl-pyrazol-1-yl)-1-[4-(2-{2-[4-(1-hydroxy-1-methyl-ethyl)-piperidin-1-yl]-pyrimidin-5-yl}-phenyl)-piperazin-1-yl]-ethanone;

1-{4-[4-Chloro-2-(2-methoxy-pyrimidin-5-yl)-phenyl]-piperazin-1-yl}-2-(3,5-dimethyl-pyrazol-1-yl)-ethanone;

1-{2-Methyl-4-[2-(2-morpholin-4-yl-pyrimidin-5-yl)-phenyl]-piperazin-1-yl}-2-pyrrolo[2,3-b]pyridin-1-yl-ethanone;

1-{4-[4-Chloro-2-(2-methylamino-pyrimidin-5-yl)-phenyl]-piperazin-1-yl}-2-(3,5-dimethyl-pyrazol-1-yl)-ethanone;

2-(3,5-Dimethyl-pyrazol-1-yl)-1-(4-{2-[(1S,4S)-2-(2-oxa-5-aza-bicyclo[2.2.1]hept-5-yl)-pyrimidin-5-yl]-phenyl}-piperazin-1-yl)-ethanone;

1-(4-{2-[2-(3,5-Dimethyl-piperidin-1-yl)-pyrimidin-5-yl]-phenyl}-piperazin-1-yl)-2-(3,5-dimethyl-pyrazol-1-yl)-ethanone;

2-(3,5-Dimethyl-pyrazol-1-yl)-1-{4-[4-fluoro-2-(2-methoxy-pyrimidin-5-yl)-phenyl]-piperazin-1-yl}-ethanone;

2-(7-Chloro-pyrrolo[2,3-c]pyridin-1-yl)-1-{4-[2-(2-methoxy-pyrimidin-5-yl)-phenyl]-piperazin-1-yl}-ethanone;

1-{4-[2-(2-Morpholin-4-yl-pyridin-4-yl)-phenyl]-piperazin-1-yl}-2-pyrrolo[2,3-b]pyridin-1-yl-ethanone;

2-(2-{4-[2-(2-Methoxy-pyrimidin-5-yl)-phenyl]-piperazin-1-yl}-2-oxo-ethyl)-2,3-dihydro-isoindol-1-one;

2-(3,5-Dimethyl-pyrazol-1-yl)-1-(4-{2-[2-(octahydro-isoquinolin-2-yl)-pyrimidin-5-yl]-phenyl}-piperazin-1-yl)-ethanone;

1-(4-{2-[2-(4,4-Difluoro-piperidin-1-yl)-pyrimidin-5-yl]-phenyl}-piperazin-1-yl)-2-(3,5-dimethyl-pyrazol-1-yl)-ethanone;

1-{4-[4-Chloro-2-(2-methanesulfonyl-pyrimidin-5-yl)-phenyl]-piperazin-1-yl}-2-pyrrolo[2,3-b]pyridin-1-yl-ethanone;

1-{4-[2-(2-Methoxy-pyridin-4-yl)-phenyl]-piperazin-1-yl}-2-pyrrolo[2,3-b]pyridin-1-yl-ethanone;

1-(4-{2-[2-(4-Dimethylamino-piperidin-1-yl)-pyrimidin-5-yl]-phenyl}-piperazin-1-yl)-2-(3,5-dimethyl-pyrazol-1-yl)-ethanone;

2-(3,5-Dimethyl-pyrazol-1-yl)-1-(4-{2-[2-(4-methoxy-4-methyl-piperidin-1-yl)-pyrimidin-5-yl]-phenyl}-piperazin-1-yl)-ethanone;

2-(3,5-Dimethyl-pyrazol-1-yl)-1-(4-{2-[2-(4-pyrrolidin-1-yl-piperidin-1-yl)-pyrimidin-5-yl]-phenyl}-piperazin-1-yl)-ethanone;

2-(4-Chloro-pyrrolo[2,3-d]pyrimidin-7-yl)-1-{4-[2-(2-methoxy-pyrimidin-5-yl)-phenyl]-piperazin-1-yl}-ethanone;

2-{2-[4-(2-Pyrrolo[2,3-b]pyridin-1-yl-acetyl)-piperazin-1-yl]-phenyl}-2,3-dihydro-isoindol-1-one;

2-(4-Chloro-pyrrolo[3,2-c]pyridin-1-yl)-1-{4-[2-(2-methoxy-pyrimidin-5-yl)-phenyl]-piperazin-1-yl}-ethanone;

4-(2-{4-[2-(3,5-Dimethyl-pyrazol-1-yl)-acetyl]-piperazin-1-yl}-phenyl)-pyridine-2-carboxylic acid methylamide;

1-{4-[2-(2-Methoxy-pyrimidin-5-yl)-phenyl]-piperazin-1-yl}-2-pyrrolo[3,2-c]pyridin-1-yl-ethanone;

1-{4-[2-(2-Methoxy-pyrimidin-5-yl)-phenyl]-piperazin-1-yl}-2-(5-methyl-3-nitro-pyrazol-1-yl)-ethanone;

2-(5-Chloro-pyrrolo[3,2-b]pyridin-1-yl)-1-{4-[2-(2-methoxy-pyrimidin-5-yl)-phenyl]-piperazin-1-yl}-ethanone;

2-(3,5-Dimethyl-pyrazol-1-yl)-1-(4-{2-[2-(4-methoxy-piperidin-1-yl)-pyrimidin-5-yl]-phenyl}-piperazin-1-yl)-ethanone;

4-{4-[2-(3,5-Dimethyl-pyrazol-1-yl)-acetyl]-piperazin-1-yl}-3-(2-methylamino-pyrimidin-5-yl)-benzonitrile;

2-(2-{4-[2-(2-Methoxy-pyrimidin-5-yl)-phenyl]-piperazin-1-yl}-2-oxo-ethyl)-2H-phthalazin-1-one;

1-(2-{4-[2-(2-Methoxy-pyrimidin-5-yl)-phenyl]-piperazin-1-yl}-2-oxo-ethyl)-1H-indole-2,3-dione;

3-(2-{4-[2-(2-Methoxy-pyrimidin-5-yl)-phenyl]-piperazin-1-yl}-2-oxo-ethyl)-3H-quinazolin-4-one;

2-(6-Bromo-pyrrolo[3,2-c]pyridin-1-yl)-1-{4-[2-(2-methoxy-pyrimidin-5-yl)-phenyl]-piperazin-1-yl}-ethanone;

1-((S)-4-Biphenyl-2-yl-2-methyl-piperazin-1-yl)-2-(3,5-dimethyl-pyrazol-1-yl)-ethanone;

N-[5-(2-{4-[2-(3,5-Dimethyl-pyrazol-1-yl)-acetyl]-piperazin-1-yl}-phenyl)-pyrimidin-2-yl]-N-methyl-acetamide;

1-(2-{4-[2-(2-Methoxy-pyrimidin-5-yl)-phenyl]-piperazin-1-yl}-2-oxo-ethyl)-1H-pyrrolo[2,3-b]pyridine-4-carbonitrile;

(R)-1-[5-(2-{4-[2-(3,5-Dimethyl-pyrazol-1-yl)-acetyl]-piperazin-1-yl}-phenyl)-pyrimidin-2-yl]-pyrrolidine-2-carboxylic acid amide;

1-{4-[2-(2-Methoxy-pyrimidin-5-yl)-phenyl]-piperazin-1-yl}-2-(5-methoxy-pyrrolo[2,3-b]pyridin-1-yl)-ethanone;

1-{4-[2-(2-Methoxy-pyrimidin-5-yl)-phenyl]-piperazin-1-yl}-2-(3-methyl-benzo[b]thiophen-2-yl)-ethanone;

2-{2-[4-(2-Pyrrolo[2,3-b]pyridin-1-yl-acetyl)-piperazin-1-yl]-phenyl}-2H-isoquinolin-1-one;

2-(2-{4-[2-(2-Methoxy-pyrimidin-5-yl)-phenyl]-piperazin-1-yl}-2-oxo-ethyl)-1,1-dioxo-1,2-dihydro-1l6-benzo[d]isothiazol-3-one;

2-(3,5-Dimethyl-pyrazol-1-yl)-1-(4-{2-[2-(pyrrolidine-1-carbonyl)-pyridin-4-yl]-phenyl}-piperazin-1-yl)-ethanone;

2-(4,5-Dichloro-imidazol-1-yl)-1-{4-[2-(2-methoxy-pyrimidin-5-yl)-phenyl]-piperazin-1-yl}-ethanone;

1-{4-[3-(2-Morpholin-4-yl-pyrimidin-5-yl)-pyridin-4-yl]-piperazin-1-yl}-2-pyrrolo[2,3-b]pyridin-1-yl-ethanone;

1-((R)-4-Biphenyl-2-yl-2-methyl-piperazin-1-yl)-2-(3,5-dimethyl-pyrazol-1-yl)-ethanone;

1-((S)-4-Biphenyl-2-yl-2-methyl-piperazin-1-yl)-2-pyrrolo[2,3-b]pyridin-1-yl-ethanone;

(S)-1-[5-(2-{4-[2-(3,5-Dimethyl-pyrazol-1-yl)-acetyl]-piperazin-1-yl}-phenyl)-pyrimidin-2-yl]-pyrrolidine-2-carboxylic acid methylamide;

2-{2-[4-(2-Pyrrolo[2,3-b]pyridin-1-yl-acetyl)-piperazin-1-yl]-phenyl}-isoindole-1,3-dione;

1-((R)-4-Biphenyl-2-yl-2-methyl-piperazin-1-yl)-2-pyrrolo[2,3-b]pyridin-1-yl-ethanone;

5-(2-{4-[2-(3,5-Dimethyl-pyrazol-1-yl)-acetyl]-piperazin-1-yl}-phenyl)-pyridine-2-carboxylic acid methylamide;

5-fluoro-N-(2-methoxypyridin-4-yl)-2-[(3S)-3-methyl-4-(1H-pyrrolo[2,3-c]pyridin-1-ylacetyl)piperazin-1-yl]benzamide;

1-{2-[4-(4-fluoro-2-{2-[4-(methylsulfonyl)piperidin-1-yl]pyrimidin-5-yl}phenyl)piperazin-1-yl]-2-oxoethyl}-1,3-dihydro-2H-benzimidazol-2-one;

2-(3,5-dimethyl-1H-pyrazol-1-yl)-1-{2-methyl-4-[2-{2-[4-(methylsulfonyl)piperidin-1-yl]pyrimidin-5-yl}-4-(trifluoromethyl)phenyl]piperazin-1-yl}ethanone;

1-(4-{2-[2-(4-hydroxypiperidin-1-yl)pyrimidin-5-yl]-4-(trifluoromethyl)phenyl}-2-methylpiperazin-1-yl)-2-(1H-pyrrolo[2,3-c]pyridin-1-yl)ethanone;

5-fluoro-2-[(3R)-4-(3H-imidazo[4,5-b]pyridin-3-ylacetyl)-3-methylpiperazin-1-yl]-N-(2-methoxypyridin-4-yl)benzamide;

1-{2-methyl-4-[2-{2-[4-(methylsulfonyl)piperidin-1-yl]pyrimidin-5-yl}-4-(trifluoromethyl)phenyl]piperazin-1-yl}-2-(1H-pyrrolo[2,3-c]pyridin-1-yl)ethanone;

2-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-2,3-dihydro-1H-isoindol-1-one;

5-fluoro-N-(2-methoxypyridin-4-yl)-2-{(3R)-3-methyl-4-[(1-oxo-1,3-dihydro-2H-isoindol-2-yl)acetyl]piperazin-1-yl}benzamide;

2-(3H-imidazo[4,5-b]pyridin-3-yl)-1-{2-methyl-4-[2-{2-[4-(methylsulfonyl)piperidin-1-yl]pyrimidin-5-yl}-4-(trifluoromethyl)phenyl]piperazin-1-yl}ethanone;

1-[2-methyl-4-(2-{2-[4-(methylsulfonyl)piperidin-1-yl]pyrimidin-5-yl}phenyl)piperazin-1-yl]-2-(1H-pyrrolo[2,3-c]pyridin-1-yl)ethanone;

1-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-1,3-dihydro-2H-benzimidazol-2-one;

2-{(3R)-4-[(3,5-dimethyl-1H-pyrazol-1-yl)acetyl]-3-methylpiperazin-1-yl}-5-fluoro-N-(2-methoxypyridin-4-yl)benzamide;

1-(4-{4-fluoro-2-[2-(4-hydroxypiperidin-1-yl)pyrimidin-5-yl]phenyl}piperazin-1-yl)-2-(1H-pyrrolo[2,3-b]pyridin-1-yl)ethanone;

1-(4-{4-fluoro-2-[2-(4-hydroxypiperidin-1-yl)pyrimidin-5-yl]phenyl}piperazin-1-yl)-2-(3H-imidazo[4,5-b]pyridin-3-yl)ethanone;

1-[4-(4-fluoro-2-{2-[4-(methylsulfonyl)piperidin-1-yl]pyrimidin-5-yl}phenyl)piperazin-1-yl]-2-(1H-pyrrolo[2,3-c]pyridin-1-yl)ethanone;

1-[2-(4-{4-fluoro-2-[2-(4-hydroxypiperidin-1-yl)pyrimidin-5-yl]phenyl}piperazin-1-yl)-2-oxoethyl]-1,3-dihydro-2H-benzimidazol-2-one;

1-[4-(4-fluoro-2-{2-[4-(methylsulfonyl)piperidin-1-yl]pyrimidin-5-yl}phenyl)-2-methylpiperazin-1-yl]-2-(1H-pyrrolo[2,3-c]pyridin-1-yl)ethanone;

2-(3,5-dimethyl-1H-pyrazol-1-yl)-1-(4-{2-[2-(4-hydroxypiperidin-1-yl)pyrimidin-5-yl]-4-(trifluoromethyl)phenyl}-2-methylpiperazin-1-yl)ethanone;

1-[4-(4-fluoro-2-{2-[4-(methylsulfonyl)piperidin-1-yl]pyrimidin-5-yl}phenyl)-2-methylpiperazin-1-yl]-2-(1H-pyrrolo[2,3-b]pyridin-1-yl)ethanone;

5-fluoro-N-(2-methoxypyridin-4-yl)-2-{(3S)-3-methyl-4-[(2-oxopiperidin-1-yl)acetyl]piperazin-1-yl}benzamide;

1-[2-(4-{2-[2-(4-hydroxypiperidin-1-yl)pyrimidin-5-yl]phenyl}-2-methylpiperazin-1-yl)-2-oxoethyl]-1,3-dihydro-2H-benzimidazol-2-one;

1-(4-{2-[2-(4-hydroxypiperidin-1-yl)pyrimidin-5-yl]phenyl}-2-methylpiperazin-1-yl)-2-(1H-pyrrolo[2,3-c]pyridin-1-yl)ethanone;

5-fluoro-N-(2-methoxypyridin-4-yl)-2-{(3R)-3-methyl-4-[(2-oxo-2,3-dihydro-1H-benzimidazol-1-yl)acetyl]piperazin-1-yl}benzamide;

5-fluoro-N-(2-methoxypyridin-4-yl)-2-[(3R)-3-methyl-4-(1H-pyrrolo[2,3-c]pyridin-1-ylacetyl)piperazin-1-yl]benzamide;

5-fluoro-N-(2-methoxypyridin-4-yl)-2-{(3R)-3-methyl-4-[N-methyl-N-(2-methylpropanoyl)glycyl]piperazin-1-yl}benzamide;

1-[4-(4-fluoro-2-{2-[4-(methylsulfonyl)piperidin-1-yl]pyrimidin-5-yl}phenyl)piperazin-1-yl]-2-(1H-pyrrolo[2,3-b]pyridin-1-yl)ethanone;

1-(4-{2-[2-(4-hydroxypiperidin-1-yl)pyrimidin-5-yl]phenyl}-2-methylpiperazin-1-yl)-2-(1H-pyrrolo[2,3-b]pyridin-1-yl)ethanone;

2-{2-[4-(4-fluoro-2-{2-[4-(methylsulfonyl)piperidin-1-yl]pyrimidin-5-yl}phenyl)piperazin-1-yl]-2-oxoethyl}-2,3-dihydro-1H-isoindol-1-one;

1-[2-methyl-4-(2-{2-[4-(methylsulfonyl)piperidin-1-yl]pyrimidin-5-yl}phenyl)piperazin-1-yl]-2-(1H-pyrrolo[2,3-b]pyridin-1-yl)ethanone;

1-{2-[4-(4-fluoro-2-{2-[4-(methylsulfonyl)piperidin-1-yl]pyrimidin-5-yl}phenyl)-2-methylpiperazin-1-yl]-2-oxoethyl}-1,3-dihydro-2H-benzimidazol-2-one;

5-fluoro-N-(2-methoxypyridin-4-yl)-2-[(3R)-3-methyl-4-(1H-pyrrolo[2,3-b]pyridin-1-ylacetyl)piperazin-1-yl]benzamide;

2-(3,5-dimethyl-1H-pyrazol-1-yl)-1-(4-{4-fluoro-2-[2-(4-hydroxypiperidin-1-yl)pyrimidin-5-yl]phenyl}piperazin-1-yl)ethanone;

2-[2-(4-{2-[2-(4-hydroxypiperidin-1-yl)pyrimidin-5-yl]-4-(trifluoromethyl)phenyl}-2-methylpiperazin-1-yl)-2-oxoethyl]-2,3-dihydro-1H-isoindol-1-one;

2-[2-(4-{4-fluoro-2-[2-(4-hydroxypiperidin-1-yl)pyrimidin-5-yl]phenyl}piperazin-1-yl)-2-oxoethyl]-2,3-dihydro-1H-isoindol-1-one;

2-(3,5-dimethyl-1H-pyrazol-1-yl)-1-[2-methyl-4-(2-{2-[4-(methylsulfonyl)piperidin-1-yl]pyrimidin-5-yl}phenyl)piperazin-1-yl]ethanone;

1-[2-(4-{2-[2-(4-hydroxypiperidin-1-yl)pyrimidin-5-yl]-4-(trifluoromethyl)phenyl}-2-methylpiperazin-1-yl)-2-oxoethyl]-1,3-dihydro-2H-benzimidazol-2-one;

5-fluoro-N-(2-methoxypyridin-4-yl)-2-{(3S)-3-methyl-4-[(2-oxo-2,3-dihydro-1H-benzimidazol-1-yl)acetyl]piperazin-1-yl}benzamide;

1-(4-{4-fluoro-2-[2-(4-hydroxypiperidin-1-yl)pyrimidin-5-yl]phenyl}piperazin-1-yl)-2-(1H-pyrrolo[2,3-c]pyridin-1-yl)ethanone;

2-[2-(4-{2-[2-(4-hydroxypiperidin-1-yl)pyrimidin-5-yl]phenyl}-2-methylpiperazin-1-yl)-2-oxoethyl]-2,3-dihydro-1H-isoindol-1-one;

2-(3,5-dimethyl-1H-pyrazol-1-yl)-1-[4-(4-fluoro-2-{2-[4-(methylsulfonyl)piperidin-1-yl]pyrimidin-5-yl}phenyl)-2-methylpiperazin-1-yl]ethanone;

2-{2-[4-(4-fluoro-2-{2-[4-(methylsulfonyl)piperidin-1-yl]pyrimidin-5-yl}phenyl)-2-methylpiperazin-1-yl]-2-oxoethyl}-2,3-dihydro-1H-isoindol-1-one 5-fluoro-N-(2-methoxypyridin-4-yl)-2-{(3R)-3-methyl-4-[(2-oxopiperidin-1-yl)acetyl]piperazin-1-yl}benzamide;

1-(4-{2-[2-(4-hydroxypiperidin-1-yl)pyrimidin-5-yl]-4-(trifluoromethyl)phenyl}-2-methylpiperazin-1-yl)-2-(1H-pyrrolo[2,3-b]pyridin-1-yl)ethanone;

1-[4-(4-fluoro-2-{2-[4-(methylsulfonyl)piperidin-1-yl]pyrimidin-5-yl}phenyl)piperazin-1-yl]-2-(3H-imidazo[4,5-b]pyridin-3-yl)ethanone 1-{4-[4-fluoro-2-(2-methoxypyrimidin-5-yl)phenyl]piperazin-1-yl}-2-(1H-pyrrolo[2,3-b]pyridin-1-yl)ethanone;

1-[2-(4-{2-[2-(4-hydroxypiperidin-1-yl)pyrimidin-5-yl]-4-(trifluoromethyl)phenyl}-2-methylpiperazin-1-yl)-2-oxoethyl]piperidin-2-one 5-fluoro-2-[(3S)-4-(3H-imidazo[4,5-b]pyridin-3-ylacetyl)-3-methylpiperazin-1-yl]-N-(2-methoxypyridin-4-yl)benzamide;

1-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)piperidin-2-one;

1-(4-{2-[2-(4-hydroxypiperidin-1-yl)pyrimidin-5-yl]-4-(trifluoromethyl)phenyl}-2-methylpiperazin-1-yl)-2-(3H-imidazo[4,5-b]pyridin-3-yl)ethanone;

1-[2-(4-{4-fluoro-2-[2-(morpholin-4-yl)pyrimidin-5-yl] phenyl}piperazin-1-yl)-2-oxoethyl]-1,3-dihydro-2H-benzimidazol-2-one;

2-(3,5-dimethyl-1H-pyrazol-1-yl)-1-[4-(4-fluoro-2-{2-[4-(methylsulfonyl)piperidin-1-yl]pyrimidin-5-yl}phenyl) piperazin-1-yl]ethanone;

1-{2-[2-methyl-4-(2-{2-[4-(methylsulfonyl)piperidin-1-yl] pyrimidin-5-yl}phenyl)piperazin-1-yl]-2-oxoethyl}-1,3-dihydro-2H-benzimidazol-2-one;

N-{2-[(2S)-4-{4-fluoro-2-[(2-methoxypyridin-4-yl)carbamoyl]phenyl}-2-methylpiperazin-1-yl]-2-oxoethyl}-N,5-dimethyl-1,3-oxazole-4-carboxamide;

5-fluoro-N-(2-methoxypyridin-4-yl)-2-{(3S)-3-methyl-4-[N-methyl-N-(2-methylpropanoyl)glycyl]piperazin-1-yl}benzamide;

1-(4-{2-[2-(4-hydroxypiperidin-1-yl)pyrimidin-5-yl]phenyl}-2-methylpiperazin-1-yl)-2-(3H-imidazo[4,5-b]pyridin-3-yl)ethanone;

5-fluoro-2-{(3S)-3-methyl-4-[(2-oxo-2,3-dihydro-1H-benzimidazol-1-yl)acetyl]piperazin-1-yl}-N-(5-methyl-4,5,6,7-tetrahydro[1,3]thiazolo[5,4-c]pyridin-2-yl)benzamide;

2-{(3S)-4-[(3,5-dimethyl-1H-pyrazol-1-yl)acetyl]-3-methylpiperazin-1-yl}-5-fluoro-N-(2-methoxypyridin-4-yl) benzamide;

N-{2-[(2R)-4-{4-fluoro-2-[(2-methoxypyridin-4-yl)carbamoyl]phenyl}-2-methylpiperazin-1-yl]-2-oxoethyl}-N,5-dimethyl-1,3-oxazole-4-carboxamide;

2-{(3S)-4-[(3,5-dimethyl-1H-pyrazol-1-yl)acetyl]-3-methylpiperazin-1-yl}-5-fluoro-N-(5-methyl-4,5,6,7-tetrahydro[1,3]thiazolo[5,4-c]pyridin-2-yl)benzamide;

1-[4-(4-fluoro-2-{2-[4-(methylsulfonyl)piperidin-1-yl]pyrimidin-5-yl}phenyl)-2-methylpiperazin-1-yl]-2-(3H-imidazo[4,5-b]pyridin-3-yl)ethanone;

1-(2-{4-[4-fluoro-2-(2-methoxypyrimidin-5-yl)phenyl]piperazin-1-yl}-2-oxoethyl)-1,3-dihydro-2H-benzimidazol-2-one;

5-fluoro-N-(2-methoxypyridin-4-yl)-2-{(3S)-3-methyl-4-[(1-oxo-1,3-dihydro-2H-isoindol-2-yl)acetyl]piperazin-1-yl}benzamide;

1-{4-[4-fluoro-2-(2-methoxypyrimidin-5-yl)phenyl]piperazin-1-yl}-2-(1H-pyrrolo[2,3-c]pyridin-1-yl)ethanone;

2-(3,5-dimethyl-1H-pyrazol-1-yl)-1-(4-{2-[2-(4-hydroxypiperidin-1-yl)pyrimidin-5-yl]phenyl}-2-methylpiperazin-1-yl)ethanone;

1-(4-{4-fluoro-2-[2-(morpholin-4-yl)pyrimidin-5-yl] phenyl}piperazin-1-yl)-2-(1H-pyrrolo[2,3-c]pyridin-1-yl)ethanone;

1-[2-(4-{4-fluoro-2-[2-(4-methylpiperazin-1-yl)pyrimidin-5-yl]phenyl}piperazin-1-yl)-2-oxoethyl]-1,3-dihydro-2H-benzimidazol-2-one;

1-(4-{4-fluoro-2-[2-(pyrrolidin-1-yl)pyrimidin-5-yl] phenyl}piperazin-1-yl)-2-(3H-imidazo[4,5-b]pyridin-3-yl)ethanone;

1-[2-(4-{4-fluoro-2-[2-(pyrrolidin-1-yl)pyrimidin-5-yl] phenyl}piperazin-1-yl)-2-oxoethyl]-1,3-dihydro-2H-benzimidazol-2-one;

5-fluoro-2-{(3S)-3-methyl-4-[N-methyl-N-(2-methylpropanoyl)glycyl]piperazin-1-yl}-N-(5-methyl-4,5,6,7-tetrahydro[1,3]thiazolo[5,4-c]pyridin-2-yl)benzamide;

2-(3H-imidazo[4,5-b]pyridin-3-yl)-1-[2-methyl-4-(2-{2-[4-(methylsulfonyl)piperidin-1-yl]pyrimidin-5-yl}phenyl) piperazin-1-yl]ethanone;

1-(4-{4-fluoro-2-[2-(pyrrolidin-1-yl)pyrimidin-5-yl] phenyl}piperazin-1-yl)-2-(1H-pyrrolo[2,3-c]pyridin-1-yl)ethanone;

1-{2-[4-(4-fluoro-2-{2-[4-(methylsulfonyl)piperidin-1-yl] pyrimidin-5-yl}phenyl)-2-methylpiperazin-1-yl]-2-oxoethyl}piperidin-2-one;

1-(4-{4-fluoro-2-[2-(morpholin-4-yl)pyrimidin-5-yl] phenyl}piperazin-1-yl)-2-(1H-pyrrolo[2,3-b]pyridin-1-yl)ethanone;

5-fluoro-2-{(3S)-3-methyl-4-[(1-oxo-1,3-dihydro-2H-isoindol-2-yl)acetyl]piperazin-1-yl}-N-(5-methyl-4,5,6,7-tetrahydro[1,3]thiazolo[5,4-c]pyridin-2-yl)benzamide;

5-fluoro-2-[(3S)-4-(3H-imidazo[4,5-b]pyridin-3-ylacetyl)-3-methylpiperazin-1-yl]-N-(5-methyl-4,5,6,7-tetrahydro [1,3]thiazolo[5,4-c]pyridin-2-yl)benzamide;

1-{2-[4-(4-fluoro-2-{2-[4-(methylsulfonyl)piperidin-1-yl] pyrimidin-5-yl}phenyl)piperazin-1-yl]-2-oxoethyl}piperidin-2-one;

2-{(3R)-4-[(3,5-dimethyl-1H-pyrazol-1-yl)acetyl]-3-methylpiperazin-1-yl}-5-fluoro-N-(5-methyl-4,5,6,7-tetrahydro[1,3]thiazolo[5,4-c]pyridin-2-yl)benzamide;

5-fluoro-2-[(3R)-4-(3H-imidazo[4,5-b]pyridin-3-ylacetyl)-3-methylpiperazin-1-yl]-N-(5-methyl-4,5,6,7-tetrahydro [1,3]thiazolo[5,4-c]pyridin-2-yl)benzamide;

2-[2-(4-{4-fluoro-2-[2-(pyrrolidin-1-yl)pyrimidin-5-yl] phenyl}piperazin-1-yl)-2-oxoethyl]-2,3-dihydro-1H-isoindol-1-one;

1-(4-{4-fluoro-2-[2-(pyrrolidin-1-yl)pyrimidin-5-yl] phenyl}piperazin-1-yl)-2-(1H-pyrrolo[2,3-b]pyridin-1-yl)ethanone;

5-fluoro-2-{(3R)-3-methyl-4-[(1-oxo-1,3-dihydro-2H-isoindol-2-yl)acetyl]piperazin-1-yl}-N-(5-methyl-4,5,6,7-tetrahydro[1,3]thiazolo[5,4-c]pyridin-2-yl)benzamide;

1-[2-(4-{4-fluoro-2-[2-(4-hydroxypiperidin-1-yl)pyrimidin-5-yl]phenyl}piperazin-1-yl)-2-oxoethyl]piperidin-2-one;

2-(3,5-dimethyl-1H-pyrazol-1-yl)-1-(4-{4-fluoro-2-[2-(pyrrolidin-1-yl)pyrimidin-5-yl]phenyl}piperazin-1-yl)ethanone;

5-fluoro-2-[(3S)-3-methyl-4-(1H-pyrrolo[2,3-b]pyridin-1-ylacetyl)piperazin-1-yl]-N-(5-methyl-4,5,6,7-tetrahydro [1,3]thiazolo[5,4-c]pyridin-2-yl)benzamide;

5-fluoro-2-{(3S)-3-methyl-4-[(2-oxopiperidin-1-yl)acetyl] piperazin-1-yl}-N-(5-methyl-4,5,6,7-tetrahydro[1,3]thiazolo[5,4-c]pyridin-2-yl)benzamide;

5-fluoro-2-{(3R)-3-methyl-4-[(2-oxo-2,3-dihydro-1H-benzimidazol-1-yl)acetyl]piperazin-1-yl}-N-(5-methyl-4,5,6,7-tetrahydro[1,3]thiazolo[5,4-c]pyridin-2-yl)benzamide;

5-fluoro-N-(2-methoxypyridin-4-yl)-2-[(3S)-3-methyl-4-(1H-pyrrolo[2,3-b]pyridin-1-ylacetyl)piperazin-1-yl]benzamide;

1-[2-(4-{2-[2-(4-hydroxypiperidin-1-yl)pyrimidin-5-yl] phenyl}-2-methylpiperazin-1-yl)-2-oxoethyl]piperidin-2-one;

5-fluoro-2-{(3R)-3-methyl-4-[N-methyl-N-(2-methylpropanoyl)glycyl]piperazin-1-yl}-N-(5-methyl-4,5,6,7-tetrahydro[1,3]thiazolo[5,4-c]pyridin-2-yl)benzamide;

1-[2-(2-methyl-4-{2-[2-(methylsulfonyl)pyrimidin-5-yl]-4-(trifluoromethyl)phenyl}piperazin-1-yl)-2-oxoethyl]-1,3-dihydro-2H-benzimidazol-2-one;

5-fluoro-2-[(3R)-3-methyl-4-(1H-pyrrolo[2,3-b]pyridin-1-ylacetyl)piperazin-1-yl]-N-(5-methyl-4,5,6,7-tetrahydro [1,3]thiazolo[5,4-c]pyridin-2-yl)benzamide;

1-(4-{4-fluoro-2-[2-(4-methylpiperazin-1-yl)pyrimidin-5-yl]phenyl}piperazin-1-yl)-2-(1H-pyrrolo[2,3-b]pyridin-1-yl)ethanone;

5-fluoro-2-{(3R)-3-methyl-4-[(2-oxopiperidin-1-yl)acetyl] piperazin-1-yl}-N-(5-methyl-4,5,6,7-tetrahydro[1,3]thiazolo[5,4-c]pyridin-2-yl)benzamide;

N-{2-[(2S)-4-{4-fluoro-2-[(5-methyl-4,5,6,7-tetrahydro[1,3]thiazolo[5,4-c]pyridin-2-yl)carbamoyl]phenyl}-2-methylpiperazin-1-yl]-2-oxoethyl}-N,5-dimethyl-1,3-oxazole-4-carboxamide;

2-[2-(4-{4-fluoro-2-[2-(morpholin-4-yl)pyrimidin-5-yl]phenyl}piperazin-1-yl)-2-oxoethyl]-2,3-dihydro-1H-isoindol-1-one;

1-[2-(4-{4-fluoro-2-[2-(pyrrolidin-1-yl)pyrimidin-5-yl]phenyl}piperazin-1-yl)-2-oxoethyl]piperidin-2-one;

1-(4-{4-fluoro-2-[2-(morpholin-4-yl)pyrimidin-5-yl]phenyl}piperazin-1-yl)-2-(3H-imidazo[4,5-b]pyridin-3-yl)ethanone;

2-[2-(4-{4-fluoro-2-[2-(4-methylpiperazin-1-yl)pyrimidin-5-yl]phenyl}piperazin-1-yl)-2-oxoethyl]-2,3-dihydro-1H-isoindol-1-one;

1-(2-methyl-4-{2-[2-(methylsulfonyl)pyrimidin-5-yl]phenyl}piperazin-1-yl)-2-(1H-pyrrolo[2,3-b]pyridin-1-yl)ethanone;

1-(2-methyl-4-{2-[2-(methylsulfonyl)pyrimidin-5-yl]-4-(trifluoromethyl)phenyl}piperazin-1-yl)-2-(1H-pyrrolo[2,3-b]pyridin-1-yl)ethanone;

1-[2-(4-{4-fluoro-2-[2-(morpholin-4-yl)pyrimidin-5-yl]phenyl}piperazin-1-yl)-2-oxoethyl]piperidin-2-one;

1-{2-[2-methyl-4-(2-{2-[4-(methylsulfonyl)piperidin-1-yl]pyrimidin-5-yl}phenyl)piperazin-1-yl]-2-oxoethyl}piperidin-2-one;

N-{2-[(2R)-4-{4-fluoro-2-[(5-methyl-4,5,6,7-tetrahydro[1,3]thiazolo[5,4-c]pyridin-2-yl)carbamoyl]phenyl}-2-methylpiperazin-1-yl]-2-oxoethyl}-N,5-dimethyl-1,3-oxazole-4-carboxamide;

2-(3,5-dimethyl-1H-pyrazol-1-yl)-1-(4-{4-fluoro-2-[2-(4-methylpiperazin-1-yl)pyrimidin-5-yl]phenyl}piperazin-1-yl)ethanone;

1-(4-{4-fluoro-2-[2-(4-methylpiperazin-1-yl)pyrimidin-5-yl]phenyl}piperazin-1-yl)-2-(3H-imidazo[4,5-b]pyridin-3-yl)ethanone;

1-[2-(4-{4-fluoro-2-[2-(methylsulfonyl)pyrimidin-5-yl]phenyl}piperazin-1-yl)-2-oxoethyl]-1,3-dihydro-2H-benzimidazol-2-one;

1-(4-{4-fluoro-2-[2-(methylsulfonyl)pyrimidin-5-yl]phenyl}-2-methylpiperazin-1-yl)-2-(1H-pyrrolo[2,3-b]pyridin-1-yl)ethanone;

1-{4-[4-fluoro-2-(2-methoxypyrimidin-5-yl)phenyl]piperazin-1-yl}-2-(3H-imidazo[4,5-b]pyridin-3-yl)ethanone;

2-(3,5-dimethyl-1H-pyrazol-1-yl)-1-(2-methyl-4-{2-[2-(methylsulfonyl)pyrimidin-5-yl]-4-(trifluoromethyl)phenyl}piperazin-1-yl)ethanone;

1-[2-(4-{4-fluoro-2-[2-(methylsulfonyl)pyrimidin-5-yl]phenyl}-2-methylpiperazin-1-yl)-2-oxoethyl]-1,3-dihydro-2H-benzimidazol-2-one;

1-[2-(2-methyl-4-{2-[2-(methylsulfonyl)pyrimidin-5-yl]phenyl}piperazin-1-yl)-2-oxoethyl]-1,3-dihydro-2H-benzimidazol-2-one;

1-(4-{4-fluoro-2-[2-(methylsulfonyl)pyrimidin-5-yl]phenyl}piperazin-1-yl)-2-(1H-pyrrolo[2,3-b]pyridin-1-yl)ethanone;

1-[2-(4-{4-fluoro-2-[2-(4-methylpiperazin-1-yl)pyrimidin-5-yl]phenyl}piperazin-1-yl)-2-oxoethyl]piperidin-2-one;

2-[2-(2-methyl-4-{2-[2-(methylsulfonyl)pyrimidin-5-yl]-4-(trifluoromethyl)phenyl}piperazin-1-yl)-2-oxoethyl]-2,3-dihydro-1H-isoindol-1-one;

2-(3,5-dimethyl-1H-pyrazol-1-yl)-1-(4-{4-fluoro-2-[2-(methylsulfonyl)pyrimidin-5-yl]phenyl}-2-methylpiperazin-1-yl)ethanone;

1-(2-{4-[4-fluoro-2-(2-methoxypyrimidin-5-yl)phenyl]piperazin-1-yl}-2-oxoethyl)piperidin-2-one;

2-(3H-imidazo[4,5-b]pyridin-3-yl)-1-(2-methyl-4-{2-[2-(methylsulfonyl)pyrimidin-5-yl]-4-(trifluoromethyl)phenyl}piperazin-1-yl)ethanone;

2-[2-(4-{4-fluoro-2-[2-(methylsulfonyl)pyrimidin-5-yl]phenyl}-2-methylpiperazin-1-yl)-2-oxoethyl]-2,3-dihydro-1H-isoindol-1-one;

2-[2-(4-{4-fluoro-2-[2-(methylsulfonyl)pyrimidin-5-yl]phenyl}piperazin-1-yl)-2-oxoethyl]-2,3-dihydro-1H-isoindol-1-one;

2-(3,5-dimethyl-1H-pyrazol-1-yl)-1-(4-{4-fluoro-2-[2-(methylsulfonyl)pyrimidin-5-yl]phenyl}piperazin-1-yl)ethanone;

2-[2-(2-methyl-4-{2-[2-(methylsulfonyl)pyrimidin-5-yl]phenyl}piperazin-1-yl)-2-oxoethyl]-2,3-dihydro-1H-isoindol-1-one;

1-[2-(2-methyl-4-{2-[2-(methylsulfonyl)pyrimidin-5-yl]-4-(trifluoromethyl)phenyl}piperazin-1-yl)-2-oxoethyl]piperidin-2-one;

2-(3H-imidazo[4,5-b]pyridin-3-yl)-1-(2-methyl-4-{2-[2-(methylsulfonyl)pyrimidin-5-yl]phenyl}piperazin-1-yl)ethanone;

1-(4-{4-fluoro-2-[2-(methylsulfonyl)pyrimidin-5-yl]phenyl}piperazin-1-yl)-2-(3H-imidazo[4,5-b]pyridin-3-yl)ethanone;

1-[2-(4-{4-fluoro-2-[2-(methylsulfonyl)pyrimidin-5-yl]phenyl}-2-methylpiperazin-1-yl)-2-oxoethyl]piperidin-2-one;

1-[2-(4-{4-fluoro-2-[2-(methylsulfonyl)pyrimidin-5-yl]phenyl}piperazin-1-yl)-2-oxoethyl]piperidin-2-one;

1-[2-(2-methyl-4-{2-[2-(methylsulfonyl)pyrimidin-5-yl]phenyl}piperazin-1-yl)-2-oxoethyl]piperidin-2-one;

1-(4-{4-fluoro-2-[2-(methylsulfonyl)pyrimidin-5-yl]phenyl}-2-methylpiperazin-1-yl)-2-(3H-imidazo[4,5-b]pyridin-3-yl)ethanone;

and the pharmaceutically acceptable salts thereof.

In another embodiment, the invention relates to a compound selected from:

3-(2-Methylsulfanyl-pyrimidin-5-yl)-4-[4-(2-pyrrolo[2,3-b]pyridin-1-yl-acetyl)-piperazin-1-yl]-benzonitrile;

1-{4-[2-(2-Methylsulfanyl-pyrimidin-5-yl)-phenyl]-piperazin-1-yl}-2-pyrrolo[2,3-b]pyridin-1-yl-ethanone;

4-Amino-N-[2-(4-biphenyl-2-yl-piperazin-1-yl)-2-oxo-ethyl]-3-methoxy-benzamide;

2-(3,5-Dimethyl-pyrazol-1-yl)-1-[4-(2-naphthalen-1-yl-phenyl)-piperazin-1-yl]-ethanone;

1-Methyl-1H-imidazole-2-carboxylic acid [2-(4-biphenyl-2-yl-piperazin-1-yl)-2-oxo-ethyl]-amide;

5-{2-[4-(2-Pyrrolo[2,3-b]pyridin-1-yl-acetyl)-piperazin-1-yl]-phenyl}-pyridine-2-carbonitrile;

2-(3,5-Dimethyl-pyrazol-1-yl)-1-{4-[2-(2-methylsulfanyl-pyrimidin-5-yl)-4-trifluoromethyl-phenyl]-piperazin-1-yl}-ethanone;

1-{4-[2-(2-Methylamino-pyrimidin-5-yl)-4-trifluoromethyl-phenyl]-piperazin-1-yl}-2-pyrrolo[2,3-b]pyridin-1-yl-ethanone;

1-(4-Biphenyl-2-yl-piperazin-1-yl)-2-(3,4-dimethoxy-benzylamino)-ethanone 1-(4-Biphenyl-2-yl-piperazin-1-yl)-2-piperidin-1-yl-ethanone;

Isoquinoline-6-carboxylic acid [2-(4-biphenyl-2-yl-piperazin-1-yl)-2-oxo-ethyl]-amide;

Thiazole-2-carboxylic acid [2-(4-biphenyl-2-yl-piperazin-1-yl)-2-oxo-ethyl]-amide;

1-(4-{2-[2-(2,6-Dimethyl-morpholin-4-yl)-pyrimidin-5-yl]-phenyl}-piperazin-1-yl)-2-(3,5-dimethyl-pyrazol-1-yl)-ethanone;

1-{4-[2-(2-Methoxy-pyrimidin-5-yl)-phenyl]-piperazin-1-yl}-2-pyrrolo[2,3-b]pyridin-1-yl-ethanone;
1-{4-[2-(2-Dimethylamino-pyrimidin-5-yl)-phenyl]-piperazin-1-yl}-2-pyrrolo[2,3-b]pyridin-1-yl-ethanone;
1-{4-[2-(2-Morpholin-4-yl-pyrimidin-5-yl)-phenyl]-piperazin-1-yl}-2-pyrrolo[2,3-b]pyridin-1-yl-ethanone;
2-(3,5-Dimethyl-pyrazol-1-yl)-1-{4-[2-(2-pyrrolidin-1-yl-pyrimidin-5-yl)-phenyl]-piperazin-1-yl}-ethanone;
4,5-Dimethyl-furan-2-carboxylic acid [2-(4-biphenyl-2-yl-piperazin-1-yl)-2-oxo-ethyl]-amide;
1-(2-{4-[2-(2-Morpholin-4-yl-pyrimidin-5-yl)-phenyl]-piperazin-1-yl}-2-oxo-ethyl)-imidazolidin-2-one;
1-[4-(4'-Dimethylaminomethyl-biphenyl-2-yl)-piperazin-1-yl]-2-(3,5-dimethyl-pyrazol-1-yl)-ethanone;
Isoquinoline-7-carboxylic acid [2-(4-biphenyl-2-yl-piperazin-1-yl)-2-oxo-ethyl]-amide;
5-fluoro-N-(2-methoxypyridin-4-yl)-2-[(3S)-3-methyl-4-(1H-pyrrolo[2,3-c]pyridin-1-ylacetyl)piperazin-1-yl]benzamide;
1-{2-[4-(4-fluoro-2-{2-[4-(methylsulfonyl)piperidin-1-yl]pyrimidin-5-yl}phenyl)piperazin-1-yl]-2-oxoethyl}-1,3-dihydro-2H-benzimidazol-2-one;
2-(3,5-dimethyl-1H-pyrazol-1-yl)-1-{2-methyl-4-[2-{2-[4-(methylsulfonyl)piperidin-1-yl]pyrimidin-5-yl}-4-(trifluoromethyl)phenyl]piperazin-1-yl}ethanone;
1-(4-{2-[2-(4-hydroxypiperidin-1-yl)pyrimidin-5-yl]-4-(trifluoromethyl)phenyl}-2-methylpiperazin-1-yl)-2-(1H-pyrrolo[2,3-c]pyridin-1-yl)ethanone;
5-fluoro-2-[(3R)-4-(3H-imidazo[4,5-b]pyridin-3-ylacetyl)-3-methylpiperazin-1-yl]-N-(2-methoxypyridin-4-yl)benzamide;
1-{2-methyl-4-[2-{2-[4-(methylsulfonyl)piperidin-1-yl]pyrimidin-5-yl}-4-(trifluoromethyl)phenyl]piperazin-1-yl}-2-(1H-pyrrolo[2,3-c]pyridin-1-yl)ethanone;
2-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-2,3-dihydro-1H-isoindol-1-one;
5-fluoro-N-(2-methoxypyridin-4-yl)-2-{(3R)-3-methyl-4-[(1-oxo-1,3-dihydro-2H-isoindol-2-yl)acetyl]piperazin-1-yl}benzamide;
2-(3H-imidazo[4,5-b]pyridin-3-yl)-1-{2-methyl-4-[2-{2-[4-(methylsulfonyl)piperidin-1-yl]pyrimidin-5-yl}-4-(trifluoromethyl)phenyl]piperazin-1-yl}ethanone;
1-[2-methyl-4-(2-{2-[4-(methylsulfonyl)piperidin-1-yl]pyrimidin-5-yl}phenyl)piperazin-1-yl]-2-(1H-pyrrolo[2,3-c]pyridin-1-yl)ethanone;
1-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-1,3-dihydro-2H-benzimidazol-2-one;
2-{(3R)-4-[(3,5-dimethyl-1H-pyrazol-1-yl)acetyl]-3-methylpiperazin-1-yl}-5-fluoro-N-(2-methoxypyridin-4-yl)benzamide;
1-(4-{4-fluoro-2-[2-(4-hydroxypiperidin-1-yl)pyrimidin-5-yl]phenyl}piperazin-1-yl)-2-(1H-pyrrolo[2,3-b]pyridin-1-yl)ethanone;
1-(4-{4-fluoro-2-[2-(4-hydroxypiperidin-1-yl)pyrimidin-5-yl]phenyl}piperazin-1-yl)-2-(3H-imidazo[4,5-b]pyridin-3-yl)ethanone;
1-[4-(4-fluoro-2-{2-[4-(methylsulfonyl)piperidin-1-yl]pyrimidin-5-yl}phenyl)piperazin-1-yl]-2-(1H-pyrrolo[2,3-c]pyridin-1-yl)ethanone;
1-[2-(4-{4-fluoro-2-[2-(4-hydroxypiperidin-1-yl)pyrimidin-5-yl]phenyl}piperazin-1-yl)-2-oxoethyl]-1,3-dihydro-2H-benzimidazol-2-one;
1-[4-(4-fluoro-2-{2-[4-(methylsulfonyl)piperidin-1-yl]pyrimidin-5-yl}phenyl)-2-methylpiperazin-1-yl]-2-(1H-pyrrolo[2,3-c]pyridin-1-yl)ethanone;
2-(3,5-dimethyl-1H-pyrazol-1-yl)-1-(4-{2-[2-(4-hydroxypiperidin-1-yl)pyrimidin-5-yl]-4-(trifluoromethyl)phenyl}-2-methylpiperazin-1-yl)ethanone;
1-[4-(4-fluoro-2-{2-[4-(methylsulfonyl)piperidin-1-yl]pyrimidin-5-yl}phenyl)-2-methylpiperazin-1-yl]-2-(1H-pyrrolo[2,3-b]pyridin-1-yl)ethanone;
5-fluoro-N-(2-methoxypyridin-4-yl)-2-{(3S)-3-methyl-4-[(2-oxopiperidin-1-yl)acetyl]piperazin-1-yl}benzamide;
1-[2-(4-{2-[2-(4-hydroxypiperidin-1-yl)pyrimidin-5-yl]phenyl}-2-methylpiperazin-1-yl)-2-oxoethyl]-1,3-dihydro-2H-benzimidazol-2-one;
1-(4-{2-[2-(4-hydroxypiperidin-1-yl)pyrimidin-5-yl]phenyl}-2-methylpiperazin-1-yl)-2-(1H-pyrrolo[2,3-c]pyridin-1-yl)ethanone;
5-fluoro-N-(2-methoxypyridin-4-yl)-2-{(3R)-3-methyl-4-[(2-oxo-2,3-dihydro-1H-benzimidazol-1-yl)acetyl]piperazin-1-yl}benzamide;
5-fluoro-N-(2-methoxypyridin-4-yl)-2-[(3R)-3-methyl-4-(1H-pyrrolo[2,3-c]pyridin-1-ylacetyl)piperazin-1-yl]benzamide;
5-fluoro-N-(2-methoxypyridin-4-yl)-2-{(3R)-3-methyl-4-[N-methyl-N-(2-methylpropanoyl)glycyl]piperazin-1-yl}benzamide;
1-[4-(4-fluoro-2-{2-[4-(methylsulfonyl)piperidin-1-yl]pyrimidin-5-yl}phenyl)piperazin-1-yl]-2-(1H-pyrrolo[2,3-b]pyridin-1-yl)ethanone;
1-(4-{2-[2-(4-hydroxypiperidin-1-yl)pyrimidin-5-yl]phenyl}-2-methylpiperazin-1-yl)-2-(1H-pyrrolo[2,3-b]pyridin-1-yl)ethanone;
2-{2-[4-(4-fluoro-2-{2-[4-(methylsulfonyl)piperidin-1-yl]pyrimidin-5-yl}phenyl)piperazin-1-yl]-2-oxoethyl}-2,3-dihydro-1H-isoindol-1-one;
1-[2-methyl-4-(2-{2-[4-(methylsulfonyl)piperidin-1-yl]pyrimidin-5-yl}phenyl)piperazin-1-yl]-2-(1H-pyrrolo[2,3-b]pyridin-1-yl)ethanone;
1-{2-[4-(4-fluoro-2-{2-[4-(methylsulfonyl)piperidin-1-yl]pyrimidin-5-yl}phenyl)-2-methylpiperazin-1-yl]-2-oxoethyl}-1,3-dihydro-2H-benzimidazol-2-one;
5-fluoro-N-(2-methoxypyridin-4-yl)-2-[(3R)-3-methyl-4-(1H-pyrrolo[2,3-b]pyridin-1-ylacetyl)piperazin-1-yl]benzamide;
2-(3,5-dimethyl-1H-pyrazol-1-yl)-1-(4-{4-fluoro-2-[2-(4-hydroxypiperidin-1-yl)pyrimidin-5-yl]phenyl}piperazin-1-yl)ethanone;
2-[2-(4-{2-[2-(4-hydroxypiperidin-1-yl)pyrimidin-5-yl]-4-(trifluoromethyl)phenyl}-2-methylpiperazin-1-yl)-2-oxoethyl]-2,3-dihydro-1H-isoindol-1-one;
2-[2-(4-{4-fluoro-2-[2-(4-hydroxypiperidin-1-yl)pyrimidin-5-yl]phenyl}piperazin-1-yl)-2-oxoethyl]-2,3-dihydro-1H-isoindol-1-one;
2-(3,5-dimethyl-1H-pyrazol-1-yl)-1-[2-methyl-4-(2-{2-[4-(methylsulfonyl)piperidin-1-yl]pyrimidin-5-yl}phenyl)piperazin-1-yl]ethanone;
1-[2-(4-{2-[2-(4-hydroxypiperidin-1-yl)pyrimidin-5-yl]-4-(trifluoromethyl)phenyl}-2-methylpiperazin-1-yl)-2-oxoethyl]-1,3-dihydro-2H-benzimidazol-2-one;
5-fluoro-N-(2-methoxypyridin-4-yl)-2-{(3S)-3-methyl-4-[(2-oxo-2,3-dihydro-1H-benzimidazol-1-yl)acetyl]piperazin-1-yl}benzamide;
1-(4-{4-fluoro-2-[2-(4-hydroxypiperidin-1-yl)pyrimidin-5-yl]phenyl}piperazin-1-yl)-2-(1H-pyrrolo[2,3-c]pyridin-1-yl)ethanone;
2-[2-(4-{2-[2-(4-hydroxypiperidin-1-yl)pyrimidin-5-yl]phenyl}-2-methylpiperazin-1-yl)-2-oxoethyl]-2,3-dihydro-1H-isoindol-1-one;

2-(3,5-dimethyl-1H-pyrazol-1-yl)-1-[4-(4-fluoro-2-{2-[4-(methylsulfonyl)piperidin-1-yl]pyrimidin-5-yl}phenyl)-2-methylpiperazin-1-yl]ethanone;

2-{2-[4-(4-fluoro-2-{2-[4-(methylsulfonyl)piperidin-1-yl]pyrimidin-5-yl}phenyl)-2-methylpiperazin-1-yl]-2-oxoethyl}-2,3-dihydro-1H-isoindol-1-one;

5-fluoro-N-(2-methoxypyridin-4-yl)-2-{(3R)-3-methyl-4-[(2-oxopiperidin-1-yl)acetyl]piperazin-1-yl}benzamide;

1-(4-{2-[2-(4-hydroxypiperidin-1-yl)pyrimidin-5-yl]-4-(trifluoromethyl)phenyl}-2-methylpiperazin-1-yl)-2-(1H-pyrrolo[2,3-b]pyridin-1-yl)ethanone;

1-[4-(4-fluoro-2-{2-[4-(methylsulfonyl)piperidin-1-yl]pyrimidin-5-yl}phenyl)piperazin-1-yl]-2-(3H-imidazo[4,5-b]pyridin-3-yl)ethanone and the pharmaceutically acceptable salts thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorus, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ cycloalkyl" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ cycloalkyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

As used herein, the term "aryl" refers to an aromatic hydrocarbon rings containing from six to ten carbon ring atoms (e.g., a $C_{6-10}$ aryl). The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "heterocyclyl" refers to a "5 to 11-membered heterocycle" and includes stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1λ$^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

As used herein, the term "heteroaryl" refers to a "5 to 11-membered heteroaryl" and includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl.

It will be understood that when a heterocyclyl or heteroaryl contains a S ring atom, such S ring atom can be present in the ring in its divalent, tetravalent, or hexavalent form, i.e., —S—, —S(O)— or —S(O)$_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art. It will be understood that one to three carbon ring moieties in the each of the $C_{3-10}$ carbocyclic rings, the 5 to 11-membered heterocyclic rings, the nonaromatic portion of the bicyclic aryl or heteroaryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above. The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula (I) may be made using the general synthetic methods described below, which also constitute part of the invention.

General Synthetic Methods

The compounds of the invention may be prepared by the methods described below. In each of the schemes below, the groups R$^1$ to R$^5$, A, B, D and X are as defined above for general formula (I) unless noted otherwise. Optimum reaction conditions and reaction times may vary depending on the particular reactants used. Unless otherwise specified, solvents, temperatures, pressures and other reaction conditions may be readily selected by one of ordinary skill in the art. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carboxylic acid and an amine in the presence of 1-(3-dimethylaminopropyl)-3-ethylcarbodiimide (EDC) and 1-hydroxybenzotriazole. Specific procedures are provided in the Synthetic Examples section. Typically, reaction progress may be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature. Initial products of formula (I) may be modified further by methods known in the art to produce additional compounds of formula (I).

Compounds of formula (I) where A is N and where ----- is a single bond may be prepared as shown in Scheme 1

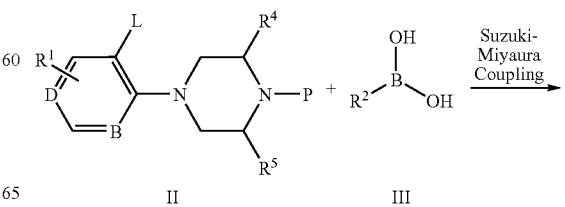

Scheme 1

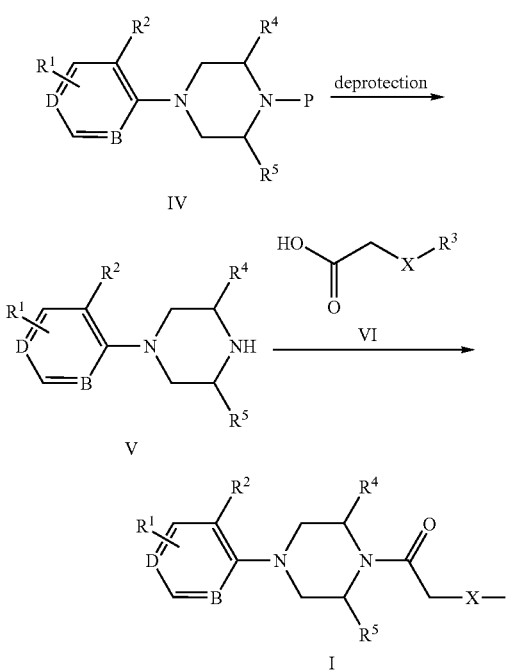

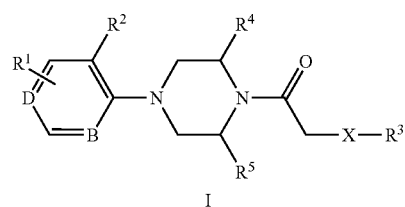

As illustrated in Scheme 1, intermediate II, where P is a suitable amine protecting group such as a t-Boc (tert-butoxycarbonyl) group, is reacted with intermediate III, a boronic acid bearing R², under Suzuki-Miyaura coupling conditions (see for example, F. Bellina et al., Synthesis, 2004, 2419-2440) to provide intermediate IV. Removal of the protecting group, for example by treatment with acid if P is a t-Boc group, provides intermediate V. Coupling intermediate V with carboxylic acid intermediate VI under peptide coupling conditions known in the art, for example by reacting in the presence of O-(Benzotriazol-1-yl)-N,N,N',N'-tetramethyluronium tetrafluoroborate (TBTU) and a suitable base such as di-isopropylethylamine in a suitable solvent such as methylene chloride provides the desired compound of formula (I).

Compounds of formula (I) may also be made by a variation of this method illustrated in Scheme 2.

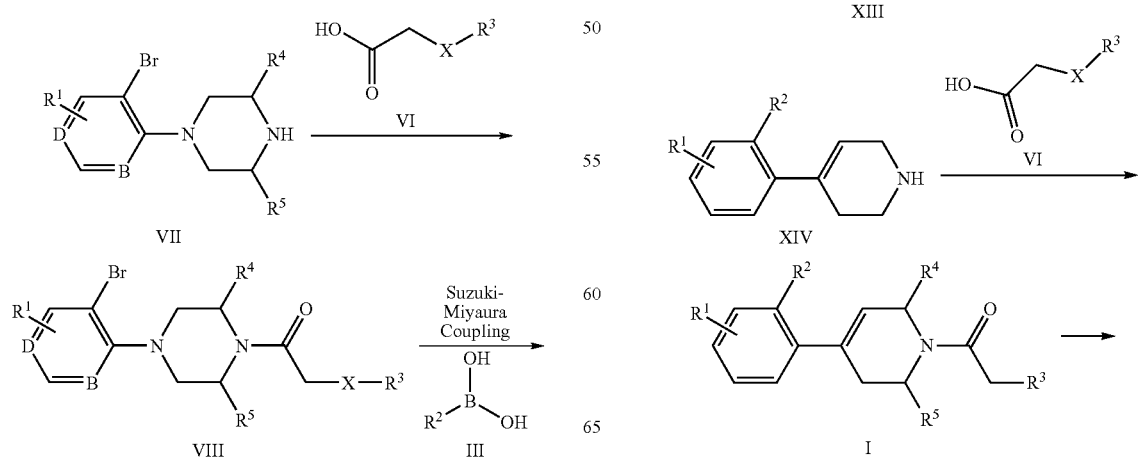

As illustrated above, the peptide coupling with carboxylic acid may be carried out with intermediate VII bearing a Br substituent or similar functionality capable of undergoing the Suzuki-Miyaura coupling, for example a Cl, I or triflate substituent, providing intermediate VIII. Intermediate VIII is then coupled with intermediate III to provide the desired compound of formula (I).

Compounds of formula (I) where A is C may be prepared as described in Scheme 3.

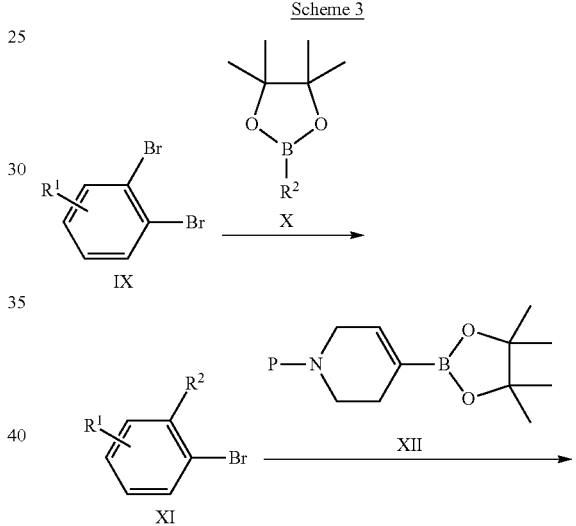

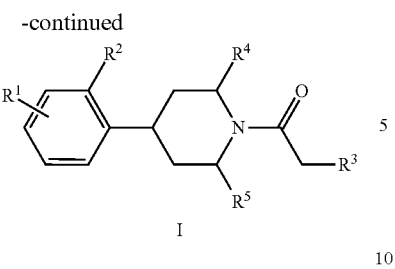

I

As illustrated above 1,2-dibromobenzene, optionally substituted with R¹ is reacted with a boron ester bearing R², such as the pinacol ester shown, under Suzuki-Miyaura coupling conditions to provide intermediate XI. Intermediate XI then undergoes a second Suzuki-Miyaura coupling reaction with intermediate XII, where P is an amine protecting group such as a t-Boc group, to provide intermediate XIII Deprotection, as described above in Scheme 1, provides intermediate XIV. Intermediate XIV then undergoes peptide coupling with intermediate VI as described in Scheme 1 to provide the compound of formula (I) where A is C and ----- is a double bond. Reduction of the double bond by methods well known in the art, for example by treating with hydrogen in the presence of Pd on carbon, provides the compound of formula (I) where A is C and ----- is a single bond.

Scheme 4 illustrates an alternate procedure, useful for preparing compounds of formula (I) where R² is benzoimidazole, benzooxazole or benzothiazole.

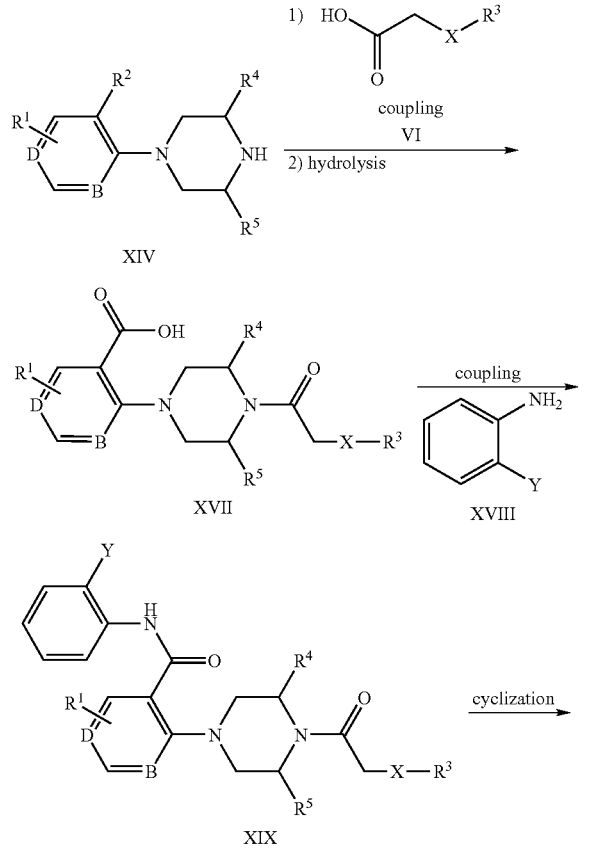

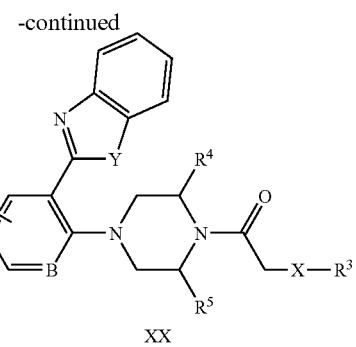

XX

As illustrated above, intermediate VI is coupled with intermediate XIV, where R is an alkyl group such as methyl or ethyl, as described in Scheme 2, followed by hydrolysis of the ester, for example, by treatment with aqueous NaOH in THF/MeOH, to provide XVII. Intermediate XVII is then coupled with intermediate XVII, where Y is NH₂, OH, or SH, to provide intermediate XIX. Cyclization, for example by heating in a suitable solvent such as dichloroethane in the presence of a suitable catalyst such as p-TsOH, provides the desired compound of formula (I) where Y is NH, O, or S.

All of the compounds in Table I were prepared by the methods illustrated above and in the Synthetic Examples section below.

SYNTHETIC EXAMPLES

Example 1

Synthesis of 1-{4-[2-(2-Methoxy-pyrimidin-5-yl)-phenyl]-piperazin-1-yl}-2-pyrrolo[2,3-b]pyridin-1-yl-ethanone

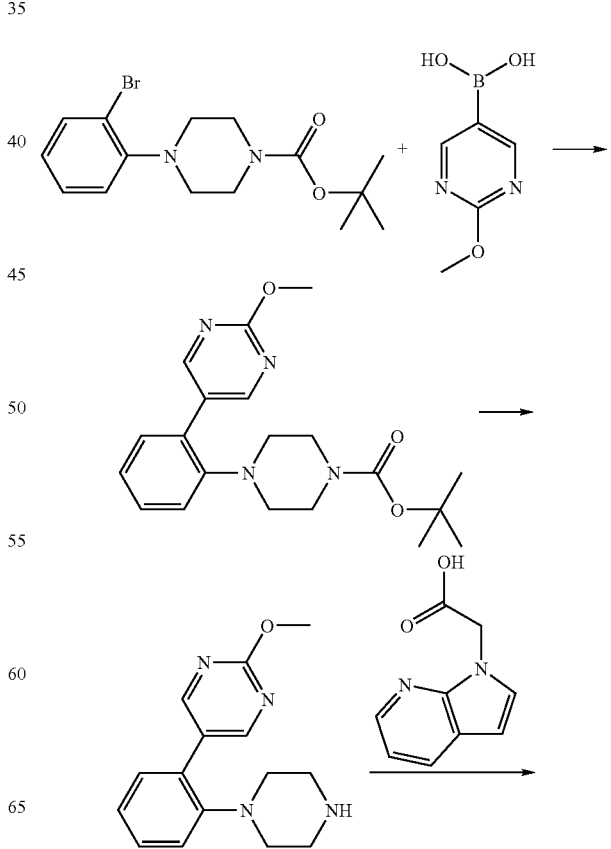

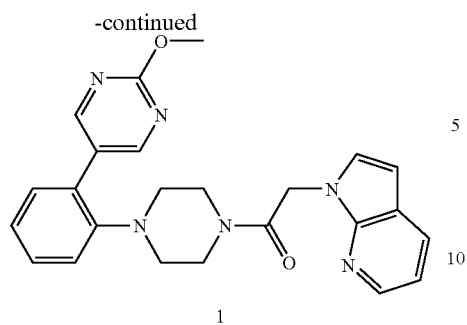

1

4-(2-Bromophenyl)-piperazine-1-carboxylic acid, t-butyl ester (10 g, 29.30 mmol) and 2-methoxypyrimidine-5-boronic acid (5 g, 32.48 mmol) are dissolved in DMF (200 mL) under a stream of nitrogen. To this mixture is added a 2M aqueous solution of sodium carbonate (73.26 mL, 150 mmol) followed by bis(triphenylphosphine)palladium (II) chloride (2.06 g, 2.93 mmol). The resulting mixture is allowed to stir at 100° C. for 30 min. A precipitate forms. Water is added and the resulting mixture is filtered to provide a gray colored solid which is air dried. The solid is then re-dissolved in dichloromethane (20 mL) and loaded on a 340 g Biotage SNAP column and eluted with 35% ethyl acetate in hexanes to provide 4-[2-(2-methoxy-pyrimidin-5-yl)-phenyl]-piperazine-1-carboxylic acid t-butyl ester (5.87 g, 54% yield).

To a solution of the above ester (5.67 g, 15.31 mmol) dissolved in dichloromethane (50 mL) is added TFA (10 mL, 129.80 mmol). The reaction is stirred at ambient temperature for 20 h. The reaction is then concentrated by rotary evaporation and the residue is reconstituted with EtOAc (200 mL) and washed with 1N aqueous NaOH solution (2×150 mL). The organic solution is dried with magnesium sulfate, filtered and concentrated by rotary evaporation to provide 2-methoxy-5-(2-piperazin-1-yl-phenyl)-pyrimidine (3.85 g, 14.24 mmol, 93% yield) as a brown solid.

To 2-methoxy-5-(2-piperazin-1-yl-phenyl)-pyrimidine (7.4 g, 27.37 mmol) dissolved in dichloromethane (100 mL) is added pyrrolo[2,3-b]pyridin-1-yl-acetic acid (4.82 g, 27.37 mmol), TBTU (8.79 g, 27.37 mmol), and DIPEA (14.66 mL, 82.12 mmol). The reaction is stirred for 16 h at ambient temperature. The product is purified on a 100 g Biotage SNAP column with 40% EtOAc in hexanes to provide the title compound (8.3 g, 19.37 mmol, 71% yield).

Example 2

Synthesis of 1-{4-[2-(2-Methoxy-pyrimidin-5-yl)-4-trifluoromethyl-phenyl]-piperazin-1-yl}-2-pyrrolo[2,3-b]pyridin-1-yl-ethanone

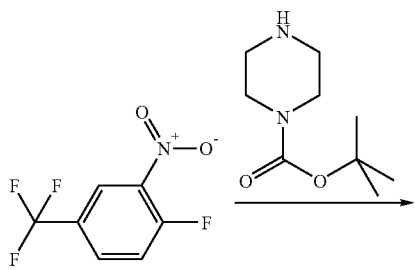

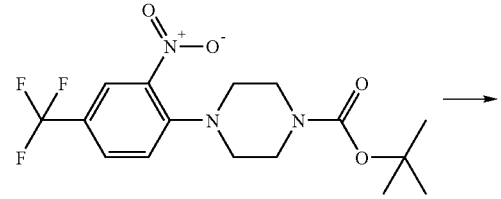

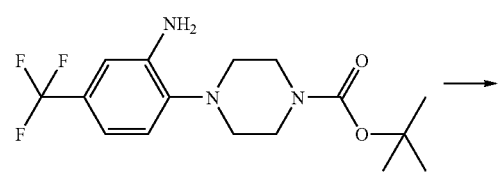

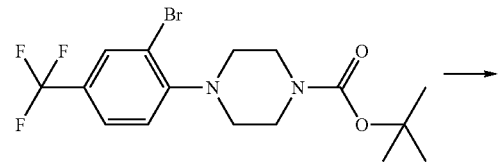

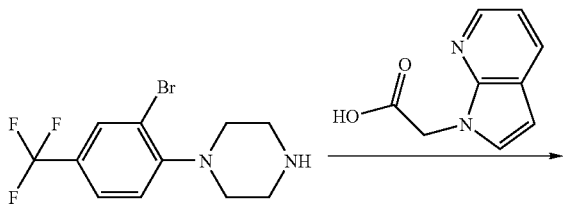

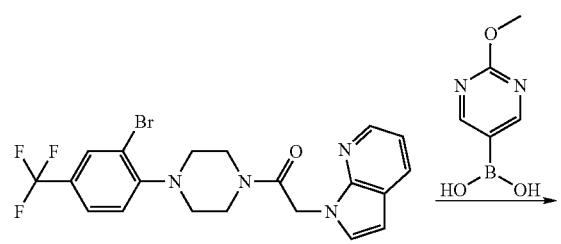

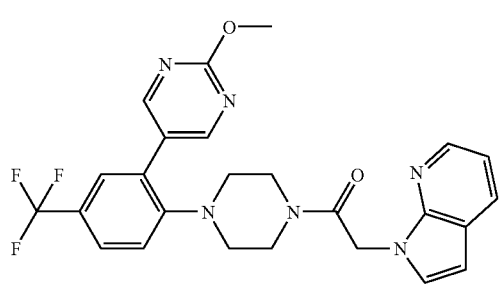

2

To a solution of 2-fluoro-4-trifluoromethylnitrobenzene (1 g, 4.78 mmol) and Hunig's base (2.45 mL, 14.35 mmol) in DMF (10 mL) is added 1-Boc-piperazine (1.14 g, 7.17 mmol). The resulting reaction is allowed to stir at 80° C. in an oil bath for 1 h. Water (30 mL) is added and mixture is extracted with EtOAc. The organic layer is washed with water, brine, dried (Na$_2$SO$_4$) and concentrated. The resulting 4-(2-nitro-4-trifluoromethyl-phenyl)-piperazine-1-carboxylic acid t-butyl ester is isolated as an orange oil (1.80 g, 100%) and is used in the next step without further purification.

To a solution of the above intermediate (1.80 g, 4.80 mmol) in EtOH (25 mL) is added Pd/C (5% on activated carbon, 100 mg) and the mixture is purged and back filled with H₂ three times via a H₂ balloon. The resulting reaction is allowed to stir at ambient temperature overnight. The reaction mixture is then filtered through a thin pad of diatomaceous earth and washed with MeOH (10 mL). The filtrate is concentrated to give a dark oil. The crude oil is purified using biotage chromatography eluting with 0-30% EtOAc/hexane. Removal of the solvent provides 4-(2-amino-4-trifluoromethyl-phenyl)-piperazine-1-carboxylic acid t-butyl ester as a colorless solid (1.65 g, 99%).

Isoamyl nitrite (0.76 mL, 5.68 mmol) is added dropwise to an ice-bath cooled solution of the above amine intermediate (1.40 g, 4.05 mmol) in dried acetonitrile (20 mL) under nitrogen. The resulting mixture turns light yellow during addition. The reaction is allowed to stir at 0° C. for 20 min. Then CuBr (872 mg, 6.08 mmol) is added in small portions. The reaction gradually turns to dark green. It is allowed to warm up to ambient temperature in 30 min and stirred overnight.

Water (20 mL) is added and mixture is extracted with EtOAc. The organic layer is washed with water, brine, dried (Na₂SO₄) and concentrated. The resulting dark red oil is purified using biotage chromatography eluting with 0-25% EtOAc/hexane. Removal of the solvent provides 4-(2-bromo-4-trifluoromethyl-phenyl)-piperazine-1-carboxylic acid t-butyl ester red oil (1.03 g, 62%).

TFA (1 mL) is added dropwise to a solution of the above intermediate (550 mg, 1.34 mmol) in methylene chloride (5 mL). The reaction is allowed to stir at ambient temperature for 2 h. Solvent is removed by rotavap and to the residue is added 2N NaOH to adjust pH >12. The resulting solution is extracted with EtOAc. The organic layer is washed with water, brine, dried (Na₂SO₄) and concentrated to provide 1-(2-bromo-4-trifluoromethyl-phenyl)-piperazine as a red oil (415 mg, 99%). The product is used in the next step without further purification.

1-(2-Bromo-4-trifluoromethyl-phenyl)-piperazine (225 mg, 0.73 mmol), pyrrolo[2,3-b]pyridin-1-yl-acetic acid (154 mg, 0.87 mmol), TBTU (304 mg, 0.95 mmol) and triethylamine (304 µl, 2.18 mmol) are combined in dichloromethane (3 mL). The resulting reaction is allowed to stir at ambient temperature for 2 h. Water is added and the mixture is extracted with EtOAc. The organic layer is washed with water, brine, dried (Na₂SO₄) and concentrated. The crude product is purified using biotage chromatography eluting with 0-50% EtOAc/hexane. Removal of the solvent provides 1-[4-(2-bromo-4-trifluoromethyl-phenyl)-piperazin-1-yl]-2-pyrrolo[2,3-b]pyridin-1-yl-ethanone as a colorless foam (268 mg, 79%).

The above intermediate (150 mg, 0.32 mmol), 2-(methoxy) pyrimidine-5-boronic acid (70 mg, 0.38 mmol), bis(triphenylphosphine)palladium (II) chloride (23 mg, 0.032 mmol), aqueous Na₂CO₃ solution (2N, 803 µl, 1.6 mmol) and dimethylformamide (2 mL) are added to a 2-5 mL microwave tube. The reaction is carried out in a microwave oven at 100° C. for 30 min. The mixture turns black. The reaction mixture is filtered and washed with a bit MeOH/water (1/0.1 mL). The clear filtrate is purified through prep-HPLC. Removal of the solvent gives the title compound as a colorless foam (110 mg, 69%).

Example 3

Synthesis of 2-(3,5-dimethyl-pyrazol-1-yl)-1-{4-[2-(2-morpholin-4-yl-pyrimidin-5-yl)-phenyl]-piperidin-1-yl}-ethanone

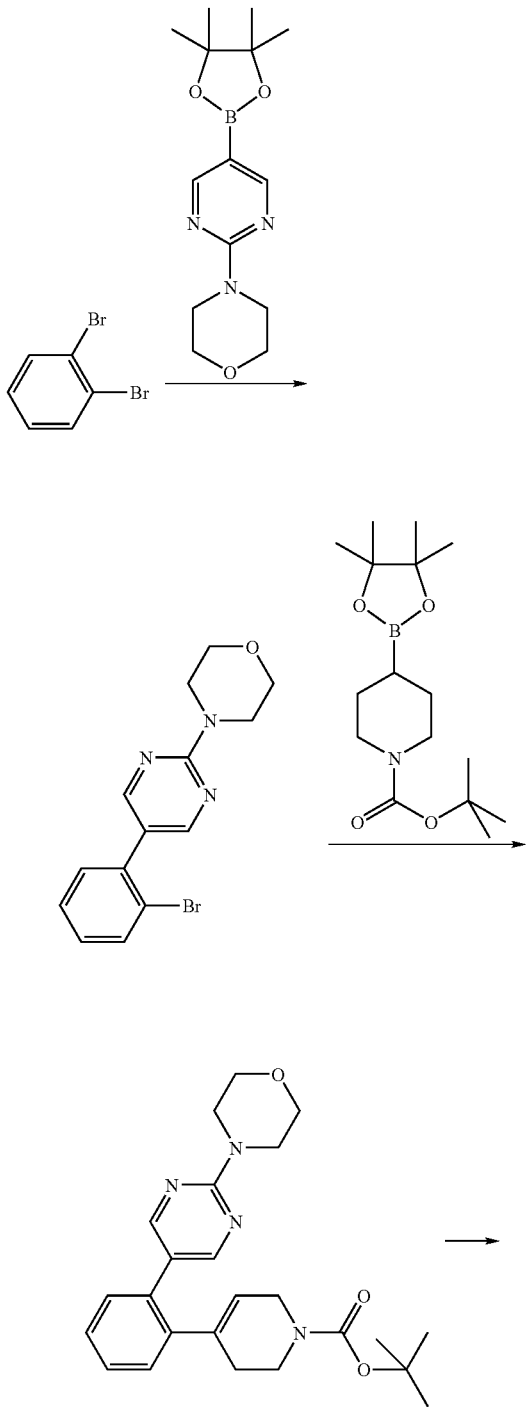

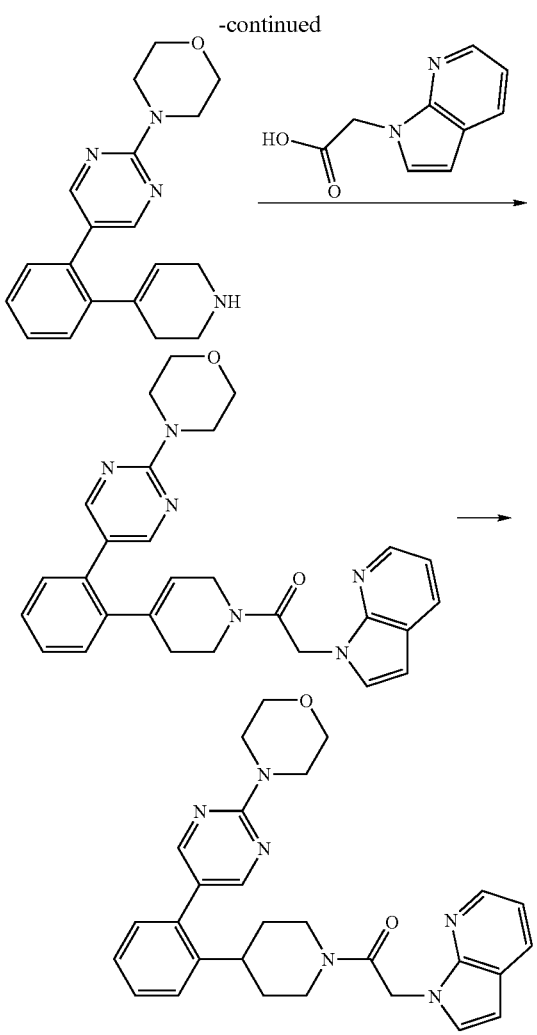

2-(4-Morpholino)pyrimidine-5-boronic acid pinacol ester (300 mg, 1.03 mmol), 1,2-dibromobenzene (243 mg, 1.03 mmol), Bis(triphenylphosphine)palladium (II) chloride (72 mg, 0.10 mmol), aqueous Na₂CO₃ (2N, 2.58 mL, 5.15 mmol) and DMF (5 mL) are added to a 10 mL microwave tube. Reaction is carried out in a microwave oven at 100° C. for 30 min. The reaction mixture turns black. The mixture is poured into water and extracted with EtOAc. The organic layers are washed with water, brine, dried (Na₂SO₄) and concentrated. The crude product is purified using biotage eluting with 0-30% EtOAc/Hexane. The desired mono-coupled product elutes at 30% EtOAc. The di-coupled by-product elutes earlier. Removal of the solvent gives 4-[5-(2-bromo-phenyl)-pyrimidin-2-yl]-morpholine as a white solid (130 mg, 39%).

The above intermediate (150 mg, 0.47 mmol), 3,6-dihydro-2H-pyridine-1-tert-butoxycarbonyl-4-boronic acid, pinacol ester (174 mg, 0.56 mmol), bis(triphenylphosphine)palladium (II) chloride (33 mg, 0.05 mmol), aqueous Na₂CO₃ (2N, 1.17 mL, 2.34 mmol) and DMF (4 mL) are added to a 10 mL microwave tube. The reaction is carried out in a microwave oven at 100° C. for 30 min. The mixture turns black. The reaction mixture is poured into water and a precipitate forms. The mixture is filtered and the cake is washed with water. The solid is dissolved and washed with dichloromethane/MeOH (1/1) and the dark solution is filtered and collected. The solvent is removed from the filtrate by rotavap and the residue, dissolved with a bit of methylene chloride is purified using biotage chromatography eluting with 0-30% EtOAc/hexane to provide 4-[2-(2-morpholin-4-yl-pyrimidin-5-yl)-phenyl]-3,6-dihydro-2H-pyridine-1-carboxylic acid tert-butyl ester as a colorless foam (195 mg, 98%).

TFA (1 mL) is added dropwise to a solution of the above t-butyl ester (195 mg, 0.46 mmol) in methylene chloride (5 mL). The reaction is allowed to stir at ambient temperature for 2 h. Solvent is removed by rotavap and to the residue is added 2N NaOH to adjust pH>12. The resulting solution is extracted with EtOAc. The organic layer is washed with water, brine, dried (Na₂SO₄) and concentrated. The crude 4-{5-[2-(1,2,3,6-tetrahydro-pyridin-4-yl)-phenyl]-pyrimidin-2-yl}-morpholine is isolated as a red oil (149 mg, 100%) and is used in the next step without further purification.

The above intermediate (60 mg, 0.19 mmol), pyrrolo[2,3-b]pyridin-1-yl-acetic acid (36 mg, 0.21 mmol), TBTU (78 mg, 0.24 mmol) and triethylamine (78 μl, 0.56 mmol) are combined in dichloromethane (3 mL). The resulting reaction is allowed to stir at ambient temperature for 2 h. Water is added and the mixture is extracted with EtOAc. The organic layer is washed with water, brine, dried (Na₂SO₄) and concentrated. The crude product is purified using biotage chromatography eluting with 0-100% EtOAc/hexane. Removal of the solvent provides 1-{4-[2-(2-morpholin-4-yl-pyrimidin-5-yl)-phenyl]-3,6-dihydro-2H-pyridin-1-yl}-2-pyrrolo[2,3-b]pyridin-1-yl-ethanone as a colorless foam (55 mg, 61%).

To the solution of the above intermediate (55 mg, 0.11 mmol) in EtOH (5 mL) is added Pd/C (5% on activated carbon, 5 mg) and the mixture is purged and back filled with H₂ three times using a H₂ balloon. The resulting reaction is allowed to stir at ambient temperature overnight then is filtered and the solid is washed with a bit MeOH (5 mL). The filtrate is collected and concentrated on a rotavap. The residue is re-dissolved in a minimum amount of DMSO/water. It was then purified using prep-HPLC. Removal of the solvent gave the title compound as a white solid (25 mg, 45%).

Example 4

Synthesis of 1-{4-[2-(1H-benzoimidazol-2-yl)-phenyl]-piperazin-1-yl}-2-(3,5-dimethyl-pyrazol-1-yl)-ethanone

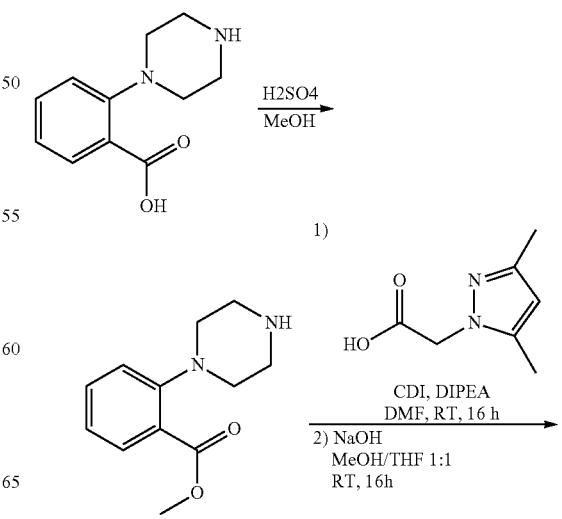

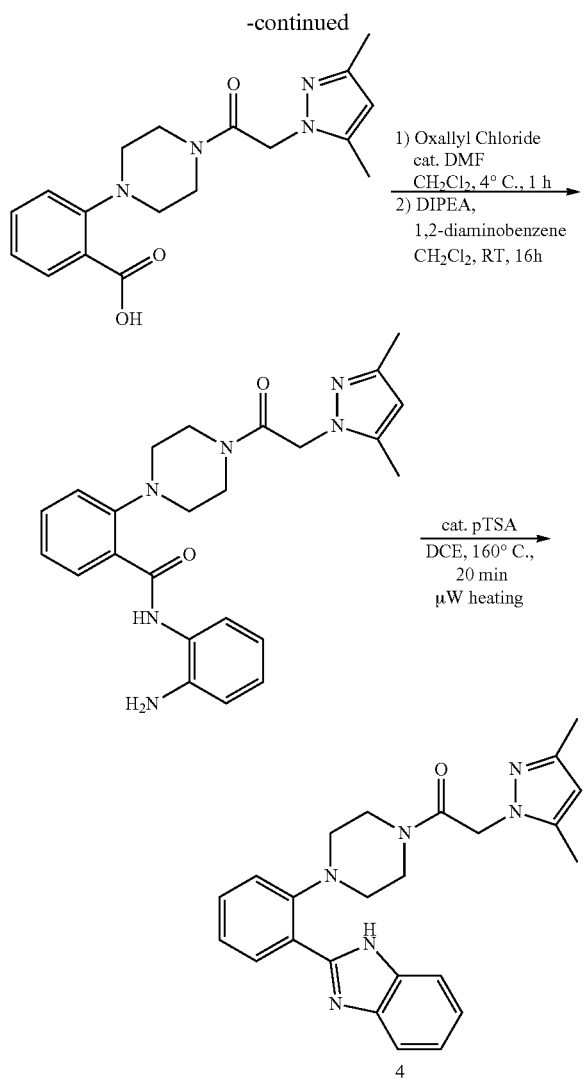

2-Piperazin-1-yl-benzoic acid (1.00 g, 4.89 mmol) is suspended in 10 mL of MeOH. To this is added 5 mL of conc. H₂SO₄. The mixture is stirred for 16 h resulting in a white precipitate. The reaction volume is increased by an additional 210 mL of MeOH and 65 mL of H₂SO₄. The mixture stirred for 2 h at room temperature and then heated at reflux for 12 h. The reaction volume is concentrated to approximately 175 mL and applied to an ion exchange column, eluting with 5×200 mL of 10% NH₃/MeOH. The product fractions are concentrated and then co-evaporated with toluene to remove residual water providing 0.667 g of 2-piperazin-1-yl-benzoic acid methyl ester.

To a vial containing the 2-piperazin-1-yl-benzoic acid methyl ester (0.667 g, 3.03 mmol) is added a pre-mixed solution containing (3,5-dimethyl-pyrazol-1-yl)-acetic acid (0.428 g, 2.78 mmol) and carbonyl diimidazole (0.567 g, 3.50 mmol). The mixture is stirred overnight and then diluted with 200 mL of EtOAc followed by 200 mL of sat. NH₄Cl. The organic phase is washed with 2×200 mL of H₂O and 1×200 mL of brine. The organic phase is dried with MgSO₄, filtered and concentrated to give 0.849 g of 2-{4-[2-(3,5-dimethyl-pyrazol-1-yl)-acetyl]-piperazin-1-yl}-benzoic acid methyl ester.

2-{4-[2-(3,5-dimethyl-pyrazol-1-yl)-acetyl]-piperazin-1-yl}-benzoic acid methyl ester (0.848 g, 2.38 mmol) is dissolved in 10 mL of 1:1 THF/MeOH. 2 mL of 15% aq NaOH is added and the mixture is stirred overnight. The mixture is concentrated to dryness and suspended in 50 mL of H₂O. The pH of the solution is adjusted to 4 by careful addition of conc. HCl. The aqueous phase is extracted with 3×100 mL of CH₂Cl₂. The organic phase is dried with MgSO₄, filtered and concentrated to give 0.730 g of {4-[2-(3,5-dimethyl-pyrazol-1-yl)-acetyl]-piperazin-1-yl}-benzoic acid in 90% yield.

2-{4-[2-(3,5-dimethyl-pyrazol-1-yl)-acetyl]-piperazin-1-yl}-benzoic acid (0.107 g, 0.296 mmol) is dissolved into 5 mL of dry CH₂Cl₂ under argon. The mixture is cooled to 4° C. and a 2 M solution of oxallyl chloride (0.150 mL, 0.300 mmol) is added in a dropwise fashion resulting in gas evolution. The reaction is stirred for 30 min at 4° C. and then 1 drop of DMF is added. The mixture is stirred at room temperature for 30 min, cooled to 4° C. and 1,2-diaminobenzene (0.048 g, 0.444 mmol) is added. The reaction is warmed to room temperature and stirred for 1 h. The reaction is then diluted with 50 mL CH₂Cl₂ followed by 20 mL of sat. NH₄Cl. The mixture is extracted with 3×20 mL of CH₂Cl₂.

The organic phase is dried with MgSO₄, filtered and concentrated. The crude product is applied to a SiO2 prep plate and eluted with (2.5% MeOH/CH2Cl2) to give 58.4 mg of N-(2-amino-phenyl)-2-{4-[2-(3,5-dimethyl-pyrazol-1-yl)-acetyl]-piperazin-1-yl}-benzamide.

The N-(2-amino-phenyl)-2-{4-[2-(3,5-dimethyl-pyrazol-1-yl)-acetyl]-piperazin-1-yl}-benzamide (0.050 g, 0.116 mmol) is dissolved into 2 mL of dichloroethane and placed in a microwave tube. To this is added a catalytic amt. of p-TsOH. The mixture is heated in a microwave at 130° C. for 20 min and then 160° C. for 30 min. The reaction mixture is concentrated to dryness and the product is purified using a Gilson Prep HPLC system eluting with 20%-100% CH₃CN/H₂O) to give 43 mg of desired product. Impure fractions are concentrated and purified using a SiO2 prep plate eluting with (5% MeOH/CH₂Cl₂) to give an additional 17.5 mg of 1-{4-[2-(1H-benzoimidazol-2-yl)-phenyl]-piperazin-1-yl}-2-(3,5-dimethyl-pyrazol-1-yl)-ethanone.

1-[4-(2-Benzooxazol-2-yl-phenyl)-piperazin-1-yl]-2-(3,5-dimethyl-pyrazol-1-yl)-ethanone is prepared in an analogous fashion.

Example 5

Synthesis of intermediate 4-(2-carboxy-phenyl)-piperazine-1-carboxylic acid tert-butyl ester

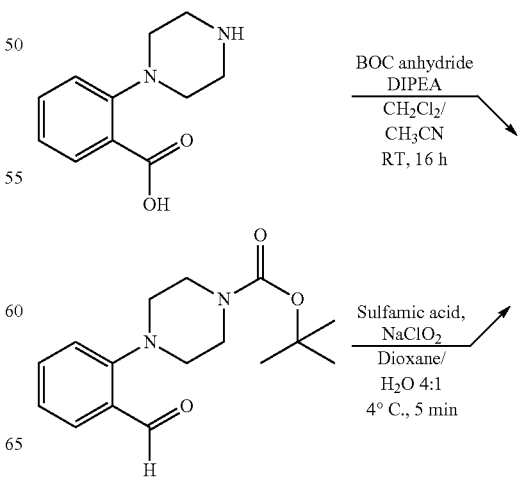

-continued

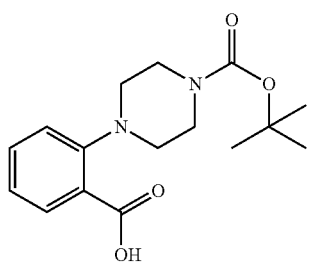

Method A.

Piperazin-1-yl-benzoic acid (2.00 g, 9.79 mmol) is suspended in 100 mL of $CH_2Cl_2$. To this is added diisopropylethyl amine (2.22 mL, 12.00 mmol) and BOC anhydride (2.07 g, 9.50 mmol). The mixture remains heterogeneous after 1 h. An additional 100 mL of anhydrous $CH_3CN$ is added and the mixture stirred overnight. The mixture is diluted with 250 mL of EtOAc followed by 250 mL of sat. $NH_4Cl$. The organic phase is washed with 2×250 mL of $H_2O$ and 1×250 mL of brine and then is dried with $MgSO_4$, filtered and concentrated to give 2.37 g of 4-(2-carboxy-phenyl)-piperazine-1-carboxylic acid tert-butyl ester.

Method B 4-(2-Formyl-phenyl)-piperazine-1-carboxylic acid tert-butyl ester (0.50 g, 1.72 mmol) is dissolved in 80 mL of dioxane and 20 mL of $H_2O$. The mixture is cooled to 4° C. and then sulfamic acid (1.36 g, 14.00 mmol) is added in one portion. The mixture is stirred for an additional 30 min and then 3 mL of a solution of $NaClO_2$ (0.343 g, 3.80 mmol) is added in a drop-wise portion. The reaction is quenched by the addition of 50 mL of $H_2O$ and 50 mL of brine. The resulting mixture is extracted with 3×100 mL of $CH_2Cl_2$. The combined organic phase is washed with 2×50 mL of brine, dried with $MgSO_4$, filtered and concentrated to give 500 mg of 4-(2-carboxy-phenyl)-piperazine-1-carboxylic acid tert-butyl ester.

Example 6

Synthesis of 2-(3,5-dimethyl-pyrazol-1-yl)-1-{4-[2-(5-trifluoromethyl-1H-benzoimidazol-2-yl)-phenyl]-piperazin-1-yl}-ethanone

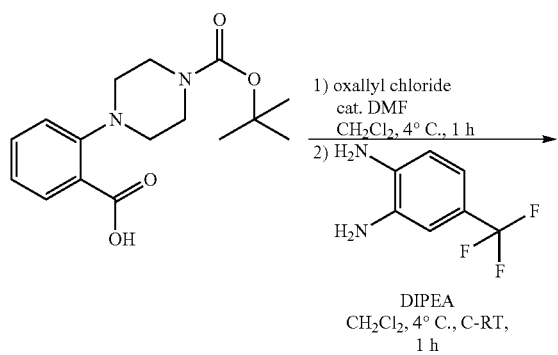

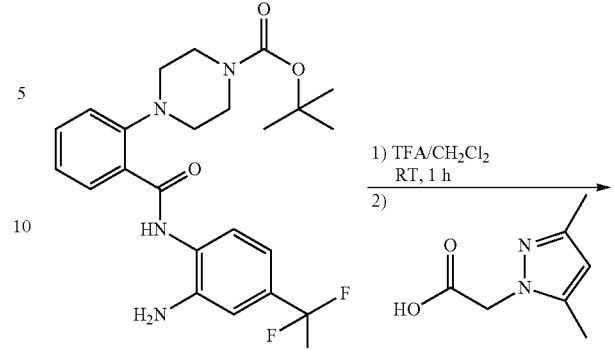

4-(2-Carboxy-phenyl)-piperazine-1-carboxylic acid tert-butyl ester, (0.060 g, 0.195 mmol) is dissolved in 5 mL of dry $CH_2Cl_2$ under argon. The solution is cooled to 4° C. and a 2 M solution of oxallyl chloride (0.10 mL, 0.21 mmol) is added in a drop-wise fashion resulting in gas evolution. After stirring the mixture for 30 min, 1 drop of DMF is added and the mixture is stirred at room temperature for 30 min. The reaction mixture is cooled to 4° C. and 4-trifluoromethyl-benzene-1,2-diamine (0.069 g, 0.390 mmol) and diisopropylethyl amine (0.092 mL, 0.500 mmol) are added. The reaction is warmed to room temperature and stirred for 1 h. The mixture is diluted with 50 mL EtOAc followed by 20 mL of sat. $NH_4Cl$. The organic phase is washed with 2×20 mL of $H_2O$ and 1×20 mL of brine. The organic phase is dried with $MgSO_4$, filtered and concentrated. The residue is applied to a $SiO_2$ prep plate and eluted with 50% EtOAc/hexanes to give 0.045 g of 4-[2-(2-amino-4-trifluoromethyl-phenylcarbamoyl)-phenyl]-piperazine-1-carboxylic acid tert-butyl ester.

The above tert-butyl ester (0.045 g, 0.097 mmol) in a vial is dissolved in 1 mL of CH$_2$Cl$_2$ and 1 mL of TFA. The mixture is stirred for 1 h. and then concentrated to dryness to give crude N-(2-amino-4-trifluoromethyl-phenyl)-2-piperazin-1-yl-benzamide trifluoroacetamide. To a vial containing the amine salt is added 1.0 mL of a premixed (1 hr) solution containing (3,5-dimethyl-pyrazol-1-yl)-acetic acid (0.016 g, 0.104 mmol) and carbonyl diimidazole (0.017 g, 0.104 mmol). The mixture is stirred overnight and then 20 mL of sat. NH$_4$Cl is added followed by 50 mL of CH$_2$Cl$_2$. The mixture is washed with 2×20 mL of H$_2$O and 1×20 mL of brine. The organic phase is dried with MgSO$_4$, filtered and concentrated to give 52 mg of N-(2-amino-4-trifluoromethyl-phenyl)-2-{4-[2-(3,5-dimethyl-pyrazol-1-yl)-acetyl]-piperazin-1-yl}-benzamide.

The above benzamide (0.049 g, 0.090 mmol) is dissolved in 2 mL of CH$_2$Cl$_2$ and placed in a microwave vial. A catalytic amount of p-TsOH is added and then the mixture is heated in the microwave oven for 20 min at 160° C. The mixture is then concentrated under a stream of N$_2$. The residue is dissolved in MeOH and purified using a Gilson Prep HPLC system eluting with 20%-80% CH$_3$CN/H$_2$O to give 36.3 mg of 2-(3,5-dimethyl-pyrazol-1-yl)-1-{4-[2-(5-trifluoromethyl-1H-benzoimidazol-2-yl)-phenyl]-piperazin-1-yl}-ethanone in 77% yield.

The following compounds are prepared analogously:

2-(3,5-Dimethyl-pyrazol-1-yl)-1-{4-[2-(1H-imidazo[4,5-c]pyridin-2-yl)-phenyl]-piperazin-1-yl}-ethanone;

1-{4-[2-(5-Chloro-1H-benzoimidazol-2-yl)-phenyl]-piperazin-1-yl}-2-(3,5-dimethyl-pyrazol-1-yl)-ethanone; and 2-(2-{4-[2-(3,5-Dimethyl-pyrazol-1-yl)-acetyl]-piperazin-1-yl}-phenyl)-1H-benzoimidazole-5-carbonitrile.

Example 7

Synthesis of 2-(3,5-dimethyl-pyrazol-1-yl)-1-{4-[2-(2-methylamino-pyrimidin-5-yl)-phenyl]-piperazin-1-yl}-ethanone

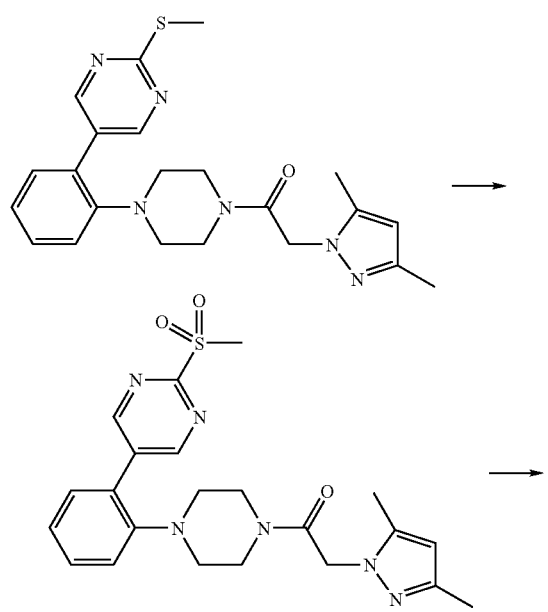

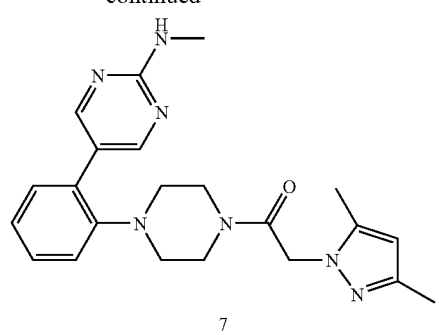

7

To a solution of 2-(3,5-dimethyl-pyrazol-1-yl)-1-{4-[2-(2-methylsulfanyl-pyrimidin-5-yl)-phenyl]-piperazin-1-yl}-ethanone (210 mg, 0.497 mmol) in THF (5 mL) is added a solution of oxone (611 mg, 0.994 mmol) in water (5 mL). The mixture is allowed to stir at room temperature for 4 h. Water (10 mL) is added and the mixture is extracted with EtOAc 3×. The organic extracts are washed with water, brine, dried (Na$_2$SO$_4$) and concentrated. The residue is re-dissolved in dichloromethane (3 mL) and loaded on a 10 g Biotage SNAP column and eluted with 100% EtOAc to provide 2-(3,5-dimethyl-pyrazol-1-yl)-1-{4-[2-(2-methanesulfonyl-pyrimidin-5-yl)-phenyl]-piperazin-1-yl}-ethanone (102 mg).

The above sulfone (40 mg, 0.088 mmol) is added to a 0.5-2 mL Biotage microwave tube followed by methylamine (2M in THF, 0.22 mL, 0.44 mmol), Hunig's base (0.045 mL, 0.264 mmol) and isopropanol (1 mL). The reaction is carried out in a microwave oven at 175° C. for 15 min. After cooling, the mixture is filtered and purified via prep-HPLC. Removal of the solvent gives the title compound as colorless foam (15 mg).

Example 8

Synthesis of 4-amino-N-[2-(4-biphenyl-2-yl-piperazin-1-yl)-2-oxo-ethyl]-3-methoxy-benzamide

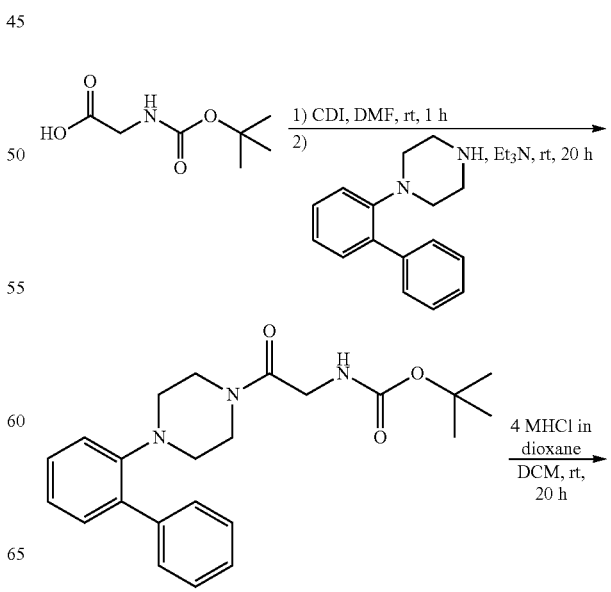

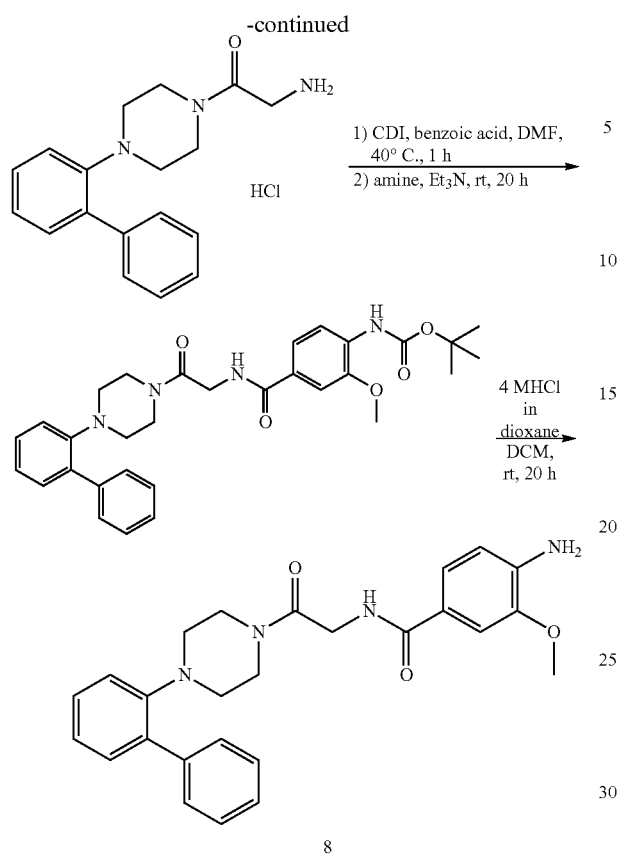

8

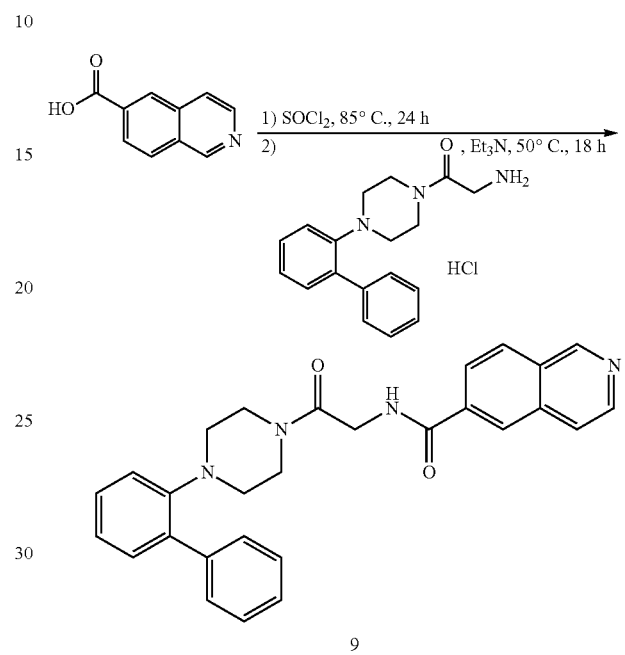

A solution of N-Boc-glycine (1.31 g, 7.33 mmol) and carbonyl diimidazole (1.21 mg, 7.33 mmol) in DMF (50 mL) is stirred at room temperature for 45 min. To the solution is added the biphenylpiperazine intermediate (2.28 g, 7.33 mmol) and triethylamine (5.13 mL, 36.63 mmol) and the solution stirred at room temperature for 24 h. The reaction is diluted with EtOAc (600 mL) and washed with sat. NH$_4$Cl (600 mL), NaHCO$_3$ (600 mL), then brine (100 mL). The aqueous layers are extracted again with more EtOAc (600 mL). The organics are dried (Na$_2$SO$_4$) and concentrated to give a solid. Trituration in diethyl ether and hexane followed by filtration afforded 2.32 g of the desired amide intermediate.

To a solution of the above amide intermediate (5.17 g, 12.94 mmol) in dichloromethane (200 mL) is added 4M HCl/dioxane (33 mL, 129.4 mmol) and the suspension stirred vigorously at room temperature for 20 h with periodic venting. The suspension is diluted with Et$_2$O (350 mL) and hexane (350 mL) and stirred 1 h. The hydroscopic white solid is filtered washing with Et$_2$O and hexane, then dried in vacuo under P$_2$O$_5$ to afford 4.84 g of the desired amine intermediate A solution of Boc-4-amino-3-methoxybenzoic acid (56 mg, 0.204 mmol) and carbonyl diimidazole (33 mg, 0.204 mmol) in DMF (2 mL) is stirred at 50° C. for 1 h. To the solution is added the above amine intermediate (75 mg, 0.204 mmol) and triethylamine (0.143 mL, 1.02 mmol) and the solution stirred at room temperature 24 h. The reaction is concentrated to a crude gum by nitrogen flow and used in the next reaction without further purification.

The crude coupling product from above is dissolved in trifluoroacetic acid (4 mL) and stirred at ambient temperature for 20 h. The reaction is concentrated in vacuo at 40° C. to a residue. The reaction is diluted with DMF (2 mL) and water (1 mL) and purified by reverse-phase preparative HPLC (10-100% CH$_3$CN/H$_2$O) to give 24 mg of the title compound.

Example 9

Synthesis of isoquinoline-6-carboxylic acid [2-(4-biphenyl-2-yl-piperazin-1-yl)-2-oxo-ethyl]-amide

9

A solution of isoquinoline-6-carboxylic acid (24 mg, 0.136 mmol) in excess thionyl chloride (3 mL) is stirred in a sealed vial at 85° C. for 24 h. The thionyl chloride is blown off by argon flow and to the solid residue is added the glycine amine intermediate (50 mg, 0.136 mmol) followed by DMF (1.5 mL) and triethylamine (0.250 mL, 1.79 mmol). The reaction is stirred at 50° C. for 18 h. The reaction is diluted with DMF (1 mL) and water (1 mL), quenched with trifluoroacetic acid (0.2 mL) and purified by reverse-phase preparative HPLC (20-100% CH$_3$CN/H$_2$O) to give 51 mg of the title compound.

Example 10

Synthesis of 3,4-dimethoxy-N-(2-{4-[2-(2-morpholin-4-yl-pyrimidin-5-yl)-phenyl]-piperazin-1-yl}-2-oxo-ethyl)-benzamide

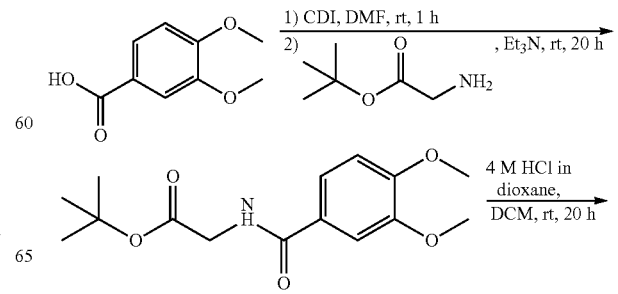

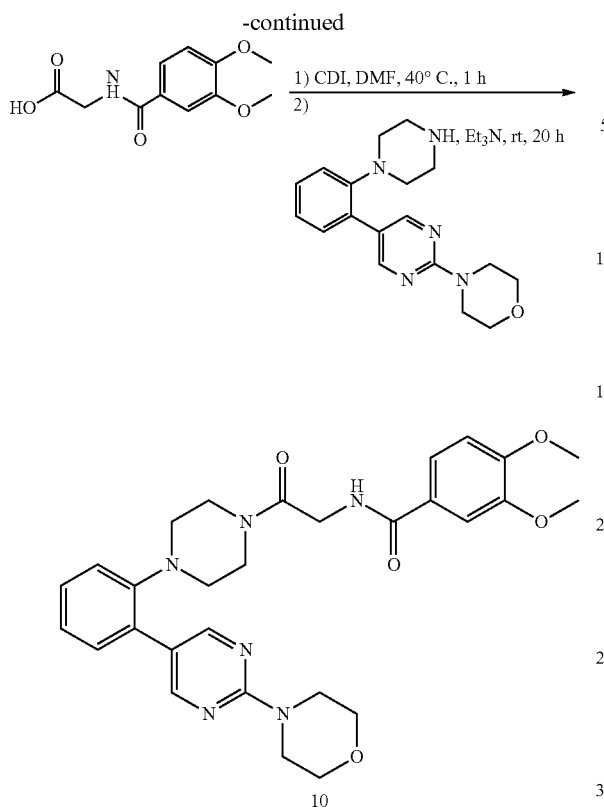

A solution of 3,4-dimethoxybenzoic acid (2.80 g, 15.25 mmol) and carbonyl diimidazole (2.50 g, 15.25 mmol) in DMF (20 mL) is stirred at room temperature for 30 min. To this is added glycine t-butyl ester HCl (2.00 g, 15.25 mmol) at room temperature and Hunig's base (2.7 mL, 15.25 mmol) and the solution stirred at room temperature for 72 h. The reaction is diluted with EtOAc (500 mL) and washed with 0.05M HCl (500 mL), sat. NaHCO$_3$ (500 mL) then water (500 mL). The aqueous layers are extracted again with more EtOAc (500 mL), and the organics dried (Na$_2$SO$_4$) and concentrated to give the 3.92 g of the desired amide intermediate as a gum in 84% yield.

To a solution of the above amide intermediate (3.92 g, 13.14 mmol) in dichloromethane (100 mL) at 0° C. is added trifluoroacetic acid (50 mL) and the reaction stirred at room temperature for 72 h with periodic venting. The reaction is concentrated at 40° C. and the resulting oil dissolved in dichloromethane and concentrated again. The oil is slurried in EtOAc (150 mL). The resulting precipitate is filtered, washing with EtOAc to give 2.72 g of the carboxylic acid intermediate in 85% yield A solution of the above carboxylic acid intermediate (38 mg, 0.154 mmol) and carbonyl diimidazole (26 mg, 0.154 mmol) in DMF (2 mL) is stirred at room temperature for 1 h. To the solution is added the substituted piperazine intermediate (50 mg, 0.154 mmol) and triethylamine (0.151 mL, 1.08 mmol) and the solution stirred at room temperature 18 h. The reaction is diluted with DMF (1 mL) and water (1 mL), quenched with trifluoroacetic acid (0.2 mL) and purified by reverse-phase preparative HPLC (15-100% CH$_3$CN/H$_2$O) to give 70 mg of the title compound.

Example 11

Synthesis of 1-((S)-4-Biphenyl-2-yl-2-methyl-piperazin-1-yl)-2-(3,5-dimethyl-pyrazol-1-yl)-ethanone

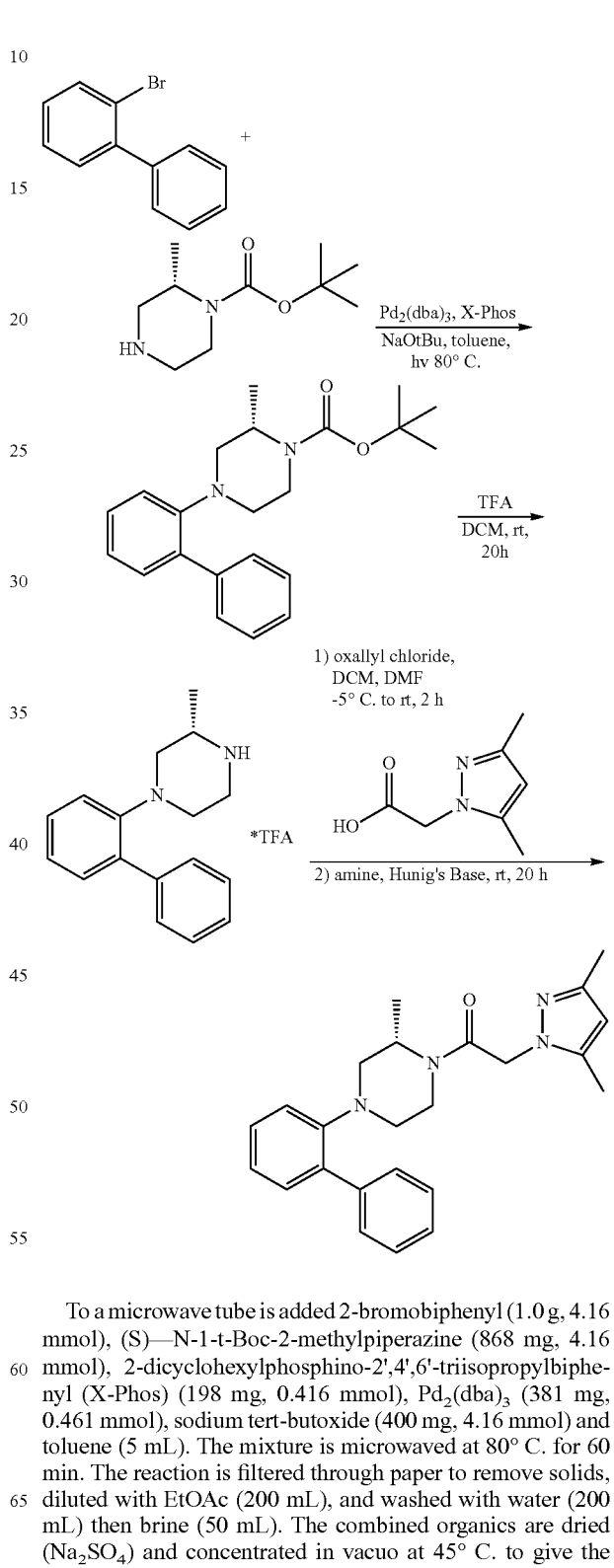

To a microwave tube is added 2-bromobiphenyl (1.0 g, 4.16 mmol), (S)—N-1-t-Boc-2-methylpiperazine (868 mg, 4.16 mmol), 2-dicyclohexylphosphino-2',4',6'-triisopropylbiphenyl (X-Phos) (198 mg, 0.416 mmol), Pd$_2$(dba)$_3$ (381 mg, 0.461 mmol), sodium tert-butoxide (400 mg, 4.16 mmol) and toluene (5 mL). The mixture is microwaved at 80° C. for 60 min. The reaction is filtered through paper to remove solids, diluted with EtOAc (200 mL), and washed with water (200 mL) then brine (50 mL). The combined organics are dried (Na$_2$SO$_4$) and concentrated in vacuo at 45° C. to give the desired t-Boc-piperazine intermediate as a crude brown gum. This is reacted without further purification.

To a solution of the above crude t-Boc-piperazine in dichloromethane (10 mL) is added TFA (50 mL) and the solution is stirred for 2 h. The reaction is concentrated in vacuo at 45° C. to give a brown oil, which is diluted in EtOAc (200 mL) and washed with saturated NaHCO$_3$ (200 mL), water (200 mL) and brine (50 mL). The organic layer is concentrated to a brown oil at 45° C. and purified by silica gel chromatography eluting with a gradient of 100% dichloromethane to 25% MeOH/dichloromethane. Fractions containing product are pooled and concentrated in vacuo to afford 128 mg of the desired piperazine intermediate as a brown solid.

(3,5-Dimethyl-1H-pyrazol-1-yl)acetic acid (21 mg, 0.125 mmol) is dissolved in dichloromethane (1 mL) and cooled to −5° C. To this is added oxalyl chloride solution (2 M in dichloromethane, 0.063 mL, 0.125 mmol), followed by 0.02 mL DMF. The mixture is stirred for 2 h warming to room temperature. To the acid chloride solution is then added a solution of the above piperazine intermediate (30 mg, 0.119 mmol) and Hunig's base (0.104 mL, 0.595 mmol) in dichloromethane (1 mL) and the reaction is stirred at ambient temp for 20 h. The reaction is concentrated in vacuo at 40° C. to a residue. The residue is diluted with DMF (2 mL), water (1 mL) and TFA (0.2 mL) and purified by reverse-phase preparative HPLC (10-100% CH$_3$CN/H$_2$O) to give 21 mg of the title compound.

Assessment of Biological Properties

Compounds are assessed for the ability to block the interaction of CXCR3 and IP-10 in a functional cellular assay measuring calcium flux in CXCR3 transfected cells.

Cyno-CHO cells, stably expressing recombinant CXCR3 and G-alpha-16 are grown in F12 medium (Mediatech #45000-360) supplemented with 10% (V/V) FBS (Mediatech #35-01500), 1% Geneticin (Invitrogen #10131-027) and 0.2% Zeocin (Invitrogen #R250-05). The cells are spun down and re-suspended in growth media to a concentration of 4.8 ES cells/mL. 25 microL of cell suspension is added to each well of a BD-384-well TC treated plate, providing 12,000 cells/well. The plate is incubated at 37° C./5% CO$_2$ overnight. On the day of the assay, the plates are removed, the media is flicked out and 25 microL of Ca-4 dye in assay buffer (HBSS, 10 mM HEPES ph 7.4), containing 2 mM probenacid is added to each well. The cell assay plates are then incubated at 37° C./5% CO$_2$ for one hour.

Test compounds are dissolved in DMSO and diluted to 1.045 mM in DMSO. Just prior to assay, 2.75 microL of appropriately diluted test compound are added to each well of a 384 well plate containing 45 microL of HBSS buffer. After mixing, 5 microL of diluted compound are added to each well of the cell assay plate for a final assay concentration of 10 microM. The plate is incubated at room temperature for 15 min. 10 microL of IP-10 stock solution in HBSS (4× EC80 concentration) are added to each well of the cell assay plate except those cells reserved as blank wells containing buffer only. Intracellular calcium flux is recorded on the HAMAMTSU FDSS6000, using excitation at 480 nm and emission at 540 nm. Data are analyzed using Activity Base software.

In general, the preferred potency range (IC$_{50}$) of compounds in the above assay is between 1 nM to 3 μM, and the most preferred potency range is 1 nM to 200 nM. The following table shows IC$_{50}$s for representative compounds of the invention in the above assay.

TABLE II

| Compound | IC$_{50}$, nM |
|---|---|
| 1-{4-[2-(2-Methylsulfanyl-pyrimidin-5-yl)-4-trifluoromethyl-phenyl]-piperazin-1-yl}-2-pyrrolo[2,3-b]pyridin-1-yl-ethanone | 9 |
| 1-{4-[2-(2-Piperidin-1-yl-pyrimidin-5-yl)-phenyl]-piperazin-1-yl}-2-pyrrolo[2,3-b]pyridin-1-yl-ethanone | 11 |
| 1-{4-[2-(2-Morpholin-4-yl-pyrimidin-5-yl)-phenyl]-piperidin-1-yl}-2-pyrrolo[2,3-b]pyridin-1-yl-ethanone | 11 |
| 1-{4-[2-(2-Methanesulfonyl-pyrimidin-5-yl)-4-trifluoromethyl-phenyl]-piperazin-1-yl}-2-pyrrolo[2,3-b]pyridin-1-yl-ethanone | 13 |
| 3-(2-Methylsulfanyl-pyrimidin-5-yl)-4-[4-(2-pyrrolo[2,3-b]pyridin-1-yl-acetyl)-piperazin-1-yl]-benzonitrile | 4 |
| 2-(3,5-Dimethyl-pyrazol-1-yl)-1-{4-[2-(2-methylsulfanyl-pyrimidin-5-yl)-4-trifluoromethyl-phenyl]-piperazin-1-yl}-ethanone | 5 |
| 2-(3,5-Dimethyl-pyrazol-1-yl)-1-{4-[2-(2-morpholin-4-yl-pyrimidin-5-yl)-4-trifluoromethyl-phenyl]-piperazin-1-yl}-ethanone | 8 |
| 3,4-Dimethoxy-N-(2-{4-[2-(2-morpholin-4-yl-pyrimidin-5-yl)-phenyl]-piperazin-1-yl}-2-oxo-ethyl)-benzamide | 68 |
| 5-(2-{4-[2-(Thiazol-2-ylamino)-acetyl]-piperazin-1-yl}-phenyl)-pyridine-2-carbonitrile | 47 |
| 2-(3,5-Dimethyl-pyrazol-1-yl)-1-{4-[2-(2-methanesulfonyl-pyrimidin-5-yl)-4-trifluoromethyl-phenyl]-piperazin-1-yl}-ethanone | 54 |
| 2-(3,5-Dimethyl-pyrazol-1-yl)-1-[4-(3'-methoxy-biphenyl-2-yl)-piperazin-1-yl]-ethanone | 56 |
| 1-{4-[2-(2-Ethylamino-pyrimidin-5-yl)-phenyl]-piperazin-1-yl}-2-pyrrolo[2,3-b]pyridin-1-yl-ethanone | 9 |
| 5-{2-[4-(2-Pyrrolo[2,3-b]pyridin-1-yl-acetyl)-piperazin-1-yl]-phenyl}-pyridine-2-carbonitrile | 5 |
| 2-(3,5-Dimethyl-pyrazol-1-yl)-1-{4-[2-(2-methylamino-pyrimidin-5-yl)-4-trifluoromethyl-phenyl]-piperazin-1-yl}-ethanone | 7 |
| 1-{4-[2-(2-Methylamino-pyrimidin-5-yl)-4-trifluoromethyl-phenyl]-piperazin-1-yl}-2-pyrrolo[2,3-b]pyridin-1-yl-ethanone | 5 |
| 1-(4-{2-[2-(2,6-Dimethyl-morpholin-4-yl)-pyrimidin-5-yl]-phenyl}-piperazin-1-yl)-2-(3,5-dimethyl-pyrazol-1-yl)-ethanone | 6 |
| 2-Indol-1-yl-1-{4-[2-(2-methoxy-pyrimidin-5-yl)-phenyl]-piperazin-1-yl}-ethanone | 44 |
| 2'-{4-[2-(3,5-Dimethyl-pyrazol-1-yl)-acetyl]-piperazin-1-yl}-biphenyl-4-carbonitrile | 100 |

TABLE II-continued

| Compound | IC$_{50}$, nM |
|---|---|
| 1-{4-[2-(2-Morpholin-4-yl-pyrimidin-5-yl)-phenyl]-piperazin-1-yl}-2-pyrrolo[2,3-b]pyridin-1-yl-ethanone | 6 |
| 2-(3,5-Dimethyl-pyrazol-1-yl)-1-{4-[2-(2-pyrrolidin-1-yl-pyrimidin-5-yl)-phenyl]-piperazin-1-yl}-ethanone | 7 |
| 1-{4-[2-(6-Chloro-pyridin-3-yl)-phenyl]-piperazin-1-yl}-2-pyrrolo[2,3-b]pyridin-1-yl-ethanone | 31 |
| 1-{3-[2-(2-Methoxy-pyrimidin-5-yl)-phenyl]-3,8-diaza-bicyclo[3.2.1]oct-8-yl}-2-pyrrolo[2,3-b]pyridin-1-yl-ethanone | 7 |
| 2-(3,5-Dimethyl-pyrazol-1-yl)-1-{4-[2-(1-methyl-1H-indol-6-yl)-phenyl]-piperazin-1-yl}-ethanone | 19 |
| 1-{4-[2-(2-Morpholin-4-yl-pyrimidin-5-yl)-phenyl]-3,6-dihydro-2H-pyridin-1-yl}-2-pyrrolo[2,3-b]pyridin-1-yl-ethanone | 20 |
| 1-{4-[2-(2-Morpholin-4-yl-pyrimidin-5-yl)-phenyl]-piperazin-1-yl}-2-(pyridin-4-ylamino)-ethanone | 27 |
| 2-(3,5-Dimethyl-pyrazol-1-yl)-1-{4-[2-(2-piperidin-1-yl-pyrimidin-5-yl)-phenyl]-piperazin-1-yl}-ethanone | 7 |
| 3-(2-Methoxy-pyrimidin-5-yl)-4-[4-(2-pyrrolo[2,3-b]pyridin-1-yl-acetyl)-piperazin-1-yl]-benzonitrile | 7 |
| 1-{4-[2-Fluoro-6-(2-morpholin-4-yl-pyrimidin-5-yl)-phenyl]-piperazin-1-yl}-2-pyrrolo[2,3-b]pyridin-1-yl-ethanone | 27 |
| 2-Indazol-2-yl-1-{4-[2-(2-methoxy-pyrimidin-5-yl)-phenyl]-piperazin-1-yl}-ethanone | 28 |
| 1-(4-{2-[2-((2R,6R)-2,6-Dimethyl-morpholin-4-yl)-pyrimidin-5-yl]-phenyl}-piperazin-1-yl)-2-pyrrolo[2,3-b]pyridin-1-yl-ethanone | 7 |
| 1-[4-(3'-Chloro-biphenyl-2-yl)-piperazin-1-yl]-2-(3,5-dimethyl-pyrazol-1-yl)-ethanone | 111 |
| 1-{4-[2-(2-Methanesulfonyl-pyrimidin-5-yl)-phenyl]-piperazin-1-yl}-2-pyrrolo[2,3-b]pyridin-1-yl-ethanone | 115 |
| 3-(2-Methylamino-pyrimidin-5-yl)-4-[4-(2-pyrrolo[2,3-b]pyridin-1-yl-acetyl)-piperazin-1-yl]-benzonitrile | 8 |
| 2-(3,5-Dimethyl-pyrazol-1-yl)-1-{4-[2-(6-methoxy-pyridin-3-yl)-phenyl]-piperazin-1-yl}-ethanone | 58 |
| 2-(3,5-Dimethyl-pyrazol-1-yl)-1-{4-[2-(2-methyl-pyrimidin-5-yl)-phenyl]-piperazin-1-yl}-ethanone | 67 |
| 1-{4-[2-(2-Methoxy-pyrimidin-5-yl)-phenyl]-piperazin-1-yl}-2-pyrrolo[2,3-c]pyridin-1-yl-ethanone | 9 |
| 1-{4-[2-(2-Pyrrolidin-1-yl-pyrimidin-5-yl)-phenyl]-piperazin-1-yl}-2-pyrrolo[2,3-b]pyridin-1-yl-ethanone | 9 |
| 1-{4-[2-(2-Morpholin-4-yl-pyrimidin-5-yl)-phenyl]-piperazin-1-yl}-2-(thiazol-2-ylamino)-ethanone | 35 |
| 2-(3,5-Dimethyl-pyrazol-1-yl)-1-{4-[2-(2-methylsulfanyl-pyrimidin-5-yl)-phenyl]-piperazin-1-yl}-ethanone | 10 |
| 1-(4-{2-[2-(4-Methyl-piperazin-1-yl)-pyrimidin-5-yl]-phenyl}-piperazin-1-yl)-2-pyrrolo[2,3-b]pyridin-1-yl-ethanone | 11 |
| 1-{4-[2-(2-Methylamino-pyrimidin-5-yl)-phenyl]-piperazin-1-yl}-2-pyrrolo[2,3-b]pyridin-1-yl-ethanone | 7 |
| 1-{4-[2-(2-Dimethylamino-pyrimidin-5-yl)-phenyl]-piperazin-1-yl}-2-(3,5-dimethyl-pyrazol-1-yl)-ethanone | 7 |
| 1-{4-[4-Chloro-2-(2-morpholin-4-yl-pyrimidin-5-yl)-phenyl]-piperazin-1-yl}-2-pyrrolo[2,3-b]pyridin-1-yl-ethanone | 13 |
| 5-{2-[4-(2-Pyrrolo[2,3-b]pyridin-1-yl-acetyl)-piperazin-1-yl]-phenyl}-pyrimidine-2-carbonitrile | 13 |
| 2-Imidazo[4,5-b]pyridin-3-yl-1-{4-[2-(2-methoxy-pyrimidin-5-yl)-phenyl]-piperazin-1-yl}-ethanone | 15 |
| 1-{4-[2-(2-Morpholin-4-yl-pyrimidin-5-yl)-4-trifluoromethyl-phenyl]-piperazin-1-yl}-2-pyrrolo[2,3-b]pyridin-1-yl-ethanone | 15 |
| 5-(2-{4-[2-(3,5-Dimethyl-pyrazol-1-yl)-acetyl]-piperazin-1-yl}-phenyl)-pyridine-2-carbonitrile | 18 |
| 1-{4-[2-(2-Methylsulfanyl-pyrimidin-5-yl)-phenyl]-piperazin-1-yl}-2-pyrrolo[2,3-b]pyridin-1-yl-ethanone | 4 |
| 5-(2-{4-[2-(5-Methyl-3-trifluoromethyl-pyrazol-1-yl)-acetyl]-piperazin-1-yl}-phenyl)-pyridine-2-carbonitrile | 71 |
| 2-(3,5-Dimethyl-pyrazol-1-yl)-1-{4-[2-(1H-indol-6-yl)-phenyl]-piperazin-1-yl}-ethanone | 81 |
| 1-{4-[2-(2-Methoxy-pyrimidin-5-yl)-phenyl]-piperazin-1-yl}-2-pyrrolo[2,3-b]pyridin-1-yl-ethanone | 6 |
| 1-{4-[2-(2-Dimethylamino-pyrimidin-5-yl)-phenyl]-piperazin-1-yl}-2-pyrrolo[2,3-b]pyridin-1-yl-ethanone | 6 |
| 2-(3,5-Dimethyl-pyrazol-1-yl)-1-{4-[2-(2-ethoxy-pyrimidin-5-yl)-phenyl]-piperazin-1-yl}-ethanone | 18 |
| 4-{4-[2-(3,5-Dimethyl-pyrazol-1-yl)-acetyl]-piperazin-1-yl}-3-(2-morpholin-4-yl-pyrimidin-5-yl)-benzonitrile | 18 |
| 1-{4-[2-(2-Methoxy-pyrimidin-5-yl)-4-trifluoromethyl-phenyl]-piperazin-1-yl}-2-pyrrolo[2,3-b]pyridin-1-yl-ethanone | 8 |
| 2-(3,5-Dimethyl-pyrazol-1-yl)-1-{4-[2-(2-morpholin-4-yl-pyrimidin-5-yl)-phenyl]-piperazin-1-yl}-ethanone | 9 |
| 3-(2-Morpholin-4-yl-pyrimidin-5-yl)-4-[4-(2-pyrrolo[2,3-b]pyridin-1-yl-acetyl)-piperazin-1-yl]-benzonitrile | 8 |

TABLE II-continued

| Compound | IC$_{50}$, nM |
|---|---|
| 1-{4-[2-(6-Methoxy-pyridin-3-yl)-phenyl]-piperazin-1-yl}-2-pyrrolo[2,3-b]pyridin-1-yl-ethanone | 34 |
| 2-(3,5-Dimethyl-pyrazol-1-yl)-1-{4-[2-(2-methylamino-pyrimidin-5-yl)-phenyl]-piperazin-1-yl}-ethanone | 34 |
| 2-Indazol-1-yl-1-{4-[2-(2-methoxy-pyrimidin-5-yl)-phenyl]-piperazin-1-yl}-ethanone | 35 |
| 2-(3,5-Dimethyl-pyrazol-1-yl)-1-{4-[2-(2-methoxy-pyrimidin-5-yl)-phenyl]-piperazin-1-yl}-ethanone | 46 |
| 1-(4-{2-[2-((2R,6S)-2,6-Dimethyl-morpholin-4-yl)-pyrimidin-5-yl]-phenyl}-piperazin-1-yl)-2-pyrrolo[2,3-b]pyridin-1-yl-ethanone | 10 |
| 4-{4-[2-(3,5-Dimethyl-pyrazol-1-yl)-acetyl]-piperazin-1-yl}-3-(2-methylsulfanyl-pyrimidin-5-yl)-benzonitrile | 36 |
| 2-(3,5-Dimethyl-pyrazol-1-yl)-1-{4-[2-(2-phenoxy-pyrimidin-5-yl)-phenyl]-piperazin-1-yl}-ethanone | 39 |
| 2-(3,5-Dimethyl-pyrazol-1-yl)-1-(4-{2-[2-(4-methyl-piperazin-1-yl)-pyrimidin-5-yl]-phenyl}-piperazin-1-yl)-ethanone | 40 |
| 5-(2-{4-[2-(3,5-Dimethyl-pyrazol-1-yl)-acetyl]-piperazin-1-yl}-phenyl)-pyrimidine-2-carbonitrile | 43 |
| 1-{4-[2-(2-[1,4]Oxazepan-4-yl-pyrimidin-5-yl)-phenyl]-piperazin-1-yl}-2-pyrrolo[2,3-b]pyridin-1-yl-ethanone | 9 |
| 1-(2-{4-[2-(2-Morpholin-4-yl-pyrimidin-5-yl)-phenyl]-piperazin-1-yl}-2-oxo-ethyl)-1,3-dihydro-benzoimidazol-2-one | 10 |
| 5-(2-{4-[2-(2,4-Dimethyl-imidazol-1-yl)-acetyl]-piperazin-1-yl}-phenyl)-pyridine-2-carbonitrile | 47 |
| 4-{4-[2-(3,5-Dimethyl-pyrazol-1-yl)-acetyl]-piperazin-1-yl}-3-(2-methoxy-pyrimidin-5-yl)-benzonitrile | 150 |
| 1-{4-[4-Methoxy-2-(2-morpholin-4-yl-pyrimidin-5-yl)-phenyl]-piperazin-1-yl}-2-pyrrolo[2,3-b]pyridin-1-yl-ethanone | 9 |
| 2-(3,5-Dimethyl-pyrazol-1-yl)-1-(4-{2-[2-(pyridin-3-yloxy)-pyrimidin-5-yl]-phenyl}-piperazin-1-yl)-ethanone | 56 |
| 1-[2-(4-Biphenyl-2-yl-piperazin-1-yl)-2-oxo-ethyl]-1,3-dihydro-benzoimidazol-2-one | 140 |
| 2-(3,5-Dimethyl-pyrazol-1-yl)-1-{4-[2-(2-methoxy-pyrimidin-5-yl)-4-trifluoromethyl-phenyl]-piperazin-1-yl}-ethanone | 8 |
| 2-(3,5-Dimethyl-pyrazol-1-yl)-1-[4-(4'-methyl-biphenyl-2-yl)-piperazin-1-yl]-ethanone | 70 |
| 1-(4-{2-[2-(3,5-Dimethyl-piperidin-1-yl)-pyrimidin-5-yl]-phenyl}-piperazin-1-yl)-2-(3,5-dimethyl-pyrazol-1-yl)-ethanone | 14 |
| 2-(3,5-Dimethyl-pyrazol-1-yl)-1-(4-{2-[2-(4-hydroxy-piperidin-1-yl)-pyrimidin-5-yl]-phenyl}-piperazin-1-yl)-ethanone | 7 |
| 1-[5-(2-{4-[2-(3,5-Dimethyl-pyrazol-1-yl)-acetyl]-piperazin-1-yl}-phenyl)-pyrimidin-2-yl]-piperidine-3-carboxylic acid amide | 9 |
| 2-(3,5-Dimethyl-pyrazol-1-yl)-1-(4-{2-[2-(octahydro-isoquinolin-2-yl)-pyrimidin-5-yl]-phenyl}-piperazin-1-yl)-ethanone | 21 |
| 1-(4-{2-[2-(4-Dimethylamino-piperidin-1-yl)-pyrimidin-5-yl]-phenyl}-piperazin-1-yl)-2-(3,5-dimethyl-pyrazol-1-yl)-ethanone | 31 |
| 1-[5-(2-{4-[2-(3,5-Dimethyl-pyrazol-1-yl)-acetyl]-piperazin-1-yl}-phenyl)-pyrimidin-2-yl]-piperidine-4-carboxylic acid amide | 6 |
| 1-(4-{2-[2-((R)-3-Dimethylamino-pyrrolidin-1-yl)-pyrimidin-5-yl]-phenyl}-piperazin-1-yl)-2-(3,5-dimethyl-pyrazol-1-yl)-ethanone | 4 |
| 1-[5-(2-{4-[2-(3,5-Dimethyl-pyrazol-1-yl)-acetyl]-piperazin-1-yl}-phenyl)-pyrimidin-2-yl]-piperidine-4-carboxylic acid methylamide | 9 |
| 2-(3,5-Dimethyl-pyrazol-1-yl)-1-(4-{2-[2-(4-fluoro-piperidin-1-yl)-pyrimidin-5-yl]-phenyl}-piperazin-1-yl)-ethanone | 10 |
| 1-(4-{2-[2-(3,3-Difluoro-piperidin-1-yl)-pyrimidin-5-yl]-phenyl}-piperazin-1-yl)-2-(3,5-dimethyl-pyrazol-1-yl)-ethanone | 9 |
| 2-(3,5-Dimethyl-pyrazol-1-yl)-1-(4-{2-[2-(3-trifluoromethyl-piperidin-1-yl)-pyrimidin-5-yl]-phenyl}-piperazin-1-yl)-ethanone | 12 |
| 2-(3,5-Dimethyl-pyrazol-1-yl)-1-{4-[2-(2-ethylamino-pyrimidin-5-yl)-phenyl]-piperazin-1-yl}-ethanone | 10 |
| 1-(4-{2-[2-(4,4-Difluoro-piperidin-1-yl)-pyrimidin-5-yl]-phenyl}-piperazin-1-yl)-2-(3,5-dimethyl-pyrazol-1-yl)-ethanone | 22 |
| 2-(3,5-Dimethyl-pyrazol-1-yl)-1-(4-{2-[2-(3-fluoro-piperidin-1-yl)-pyrimidin-5-yl]-phenyl}-piperazin-1-yl)-ethanone | 8 |
| 2-(3,5-Dimethyl-pyrazol-1-yl)-1-(4-{2-[2-(4-methoxy-4-methyl-piperidin-1-yl)-pyrimidin-5-yl]-phenyl}-piperazin-1-yl)-ethanone | 33 |
| 2-(3,5-Dimethyl-pyrazol-1-yl)-1-(4-{2-[2-(4-methanesulfonyl-piperidin-1-yl)-pyrimidin-5-yl]-phenyl}-piperazin-1-yl)-ethanone | 6 |
| 2-(3,5-Dimethyl-pyrazol-1-yl)-1-(4-{2-[2-(3-hydroxy-pyrrolidin-1-yl)-pyrimidin-5-yl]-phenyl}-piperazin-1-yl)-ethanone | 9 |
| 2-(3,5-Dimethyl-pyrazol-1-yl)-1-{4-[2-(2-[1,4]oxazepan-4-yl-pyrimidin-5-yl)-phenyl]-piperazin-1-yl}-ethanone | 11 |
| 2-(3,5-Dimethyl-pyrazol-1-yl)-1-[4-(2-{2-[4-(1-hydroxy-1-methyl-ethyl)-piperidin-1-yl]-pyrimidin-5-yl}-phenyl)-piperazin-1-yl]-ethanone | 12 |
| 2-(3,5-Dimethyl-pyrazol-1-yl)-1-(4-{2-[2-((S)-2-methoxymethyl-pyrrolidin-1-yl)-pyrimidin-5-yl]-phenyl}-piperazin-1-yl)-ethanone | 12 |
| 1-(4-{2-[2-(4,4-Dimethyl-piperidin-1-yl)-pyrimidin-5-yl]-phenyl}-piperazin-1-yl)-2-(3,5-dimethyl-pyrazol-1-yl)-ethanone | 12 |

TABLE II-continued

| Compound | IC$_{50}$, nM |
|---|---|
| 2-(3,5-Dimethyl-pyrazol-1-yl)-1-(4-{2-[(1S,4S)-2-(2-oxa-5-aza-bicyclo[2.2.1]hept-5-yl)-pyrimidin-5-yl]-phenyl}-piperazin-1-yl)-ethanone | 14 |
| 1-(4-{2-[(1R,4S)-2-(2-Aza-bicyclo[2.2.1]hept-2-yl)-pyrimidin-5-yl]-phenyl}-piperazin-1-yl)-2-(3,5-dimethyl-pyrazol-1-yl)-ethanone | 4 |
| 1-(4-{2-[2-(3,3-Difluoro-azetidin-1-yl)-pyrimidin-5-yl]-phenyl}-piperazin-1-yl)-2-(3,5-dimethyl-pyrazol-1-yl)-ethanone | 7 |
| 2-(3,5-Dimethyl-pyrazol-1-yl)-1-{4-[4-fluoro-2-(2-morpholin-4-yl-pyrimidin-5-yl)-phenyl]-piperazin-1-yl}-ethanone | 5 |
| 1-{2-Methyl-4-[2-(2-morpholin-4-yl-pyrimidin-5-yl)-phenyl]-piperazin-1-yl}-2-pyrrolo[2,3-b]pyridin-1-yl-ethanone | 13 |
| 1-{3-Methyl-4-[2-(2-morpholin-4-yl-pyrimidin-5-yl)-phenyl]-piperazin-1-yl}-2-pyrrolo[2,3-b]pyridin-1-yl-ethanone | 11 |
| 2-(5-Fluoro-pyrrolo[2,3-b]pyridin-1-yl)-1-{4-[2-(2-methoxy-pyrimidin-5-yl)-phenyl]-piperazin-1-yl}-ethanone | 8 |
| 1-{4-[4-Chloro-2-(2-methoxy-pyrimidin-5-yl)-phenyl]-piperazin-1-yl}-2-pyrrolo[2,3-b]pyridin-1-yl-ethanone | 7 |
| 1-{4-[2-(2-Methoxy-pyridin-4-yl)-phenyl]-piperazin-1-yl}-2-pyrrolo[2,3-b]pyridin-1-yl-ethanone | 24 |
| 1-{4-[2-(2-Morpholin-4-yl-pyridin-4-yl)-phenyl]-piperazin-1-yl}-2-pyrrolo[2,3-b]pyridin-1-yl-ethanone | 16 |
| 2-(7-Chloro-pyrrolo[2,3-c]pyridin-1-yl)-1-{4-[2-(2-methoxy-pyrimidin-5-yl)-phenyl]-piperazin-1-yl}-ethanone | 16 |
| 2-(4-Chloro-pyrrolo[2,3-d]pyrimidin-7-yl)-1-{4-[2-(2-methoxy-pyrimidin-5-yl)-phenyl]-piperazin-1-yl}-ethanone | 48 |
| 1-{4-[4-Chloro-2-(2-methylsulfanyl-pyrimidin-5-yl)-phenyl]-piperazin-1-yl}-2-pyrrolo[2,3-b]pyridin-1-yl-ethanone | 8 |
| 2-(2-{4-[2-(2-Methoxy-pyrimidin-5-yl)-phenyl]-piperazin-1-yl}-2-oxo-ethyl)-2,3-dihydro-isoindol-1-one | 17 |
| 1-{4-[4-Chloro-2-(2-methoxy-pyrimidin-5-yl)-phenyl]-piperazin-1-yl}-2-(3,5-dimethyl-pyrazol-1-yl)-ethanone | 12 |
| 1-(2-{4-[2-(2-Methoxy-pyrimidin-5-yl)-phenyl]-piperazin-1-yl}-2-oxo-ethyl)-3-methyl-1,3-dihydro-benzoimidazol-2-one | 11 |
| 1-{4-[4-Chloro-2-(2-methanesulfonyl-pyrimidin-5-yl)-phenyl]-piperazin-1-yl}-2-pyrrolo[2,3-b]pyridin-1-yl-ethanone | 24 |
| 1-{4-[4-Chloro-2-(2-morpholin-4-yl-pyrimidin-5-yl)-phenyl]-piperazin-1-yl}-2-(3,5-dimethyl-pyrazol-1-yl)-ethanone | 11 |
| 1-{4-[4-Chloro-2-(2-methylsulfanyl-pyrimidin-5-yl)-phenyl]-piperazin-1-yl}-2-(3,5-dimethyl-pyrazol-1-yl)-ethanone | 7 |
| 1-{4-[4-Chloro-2-(2-methylamino-pyrimidin-5-yl)-phenyl]-piperazin-1-yl}-2-pyrrolo[2,3-b]pyridin-1-yl-ethanone | 6 |
| 1-{4-[4-Chloro-2-(2-methylamino-pyrimidin-5-yl)-phenyl]-piperazin-1-yl}-2-(3,5-dimethyl-pyrazol-1-yl)-ethanone | 13 |
| 2-(4-Chloro-3,5-dimethyl-pyrazol-1-yl)-1-{4-[2-(2-methoxy-pyrimidin-5-yl)-phenyl]-piperazin-1-yl}-ethanone | 10 |
| 2-{2-[4-(2-Pyrrolo[2,3-b]pyridin-1-yl-acetyl)-piperazin-1-yl]-phenyl}-2,3-dihydro-isoindol-1-one | 48 |
| 2-(3,5-Dimethyl-pyrazol-1-yl)-1-{4-[4-fluoro-2-(2-methoxy-pyrimidin-5-yl)-phenyl]-piperazin-1-yl}-ethanone | 14 |
| 5-fluoro-N-(2-methoxypyridin-4-yl)-2-[(3S)-3-methyl-4-(1H-pyrrolo[2,3-c]pyridin-1-ylacetyl)piperazin-1-yl]benzamide | 6 |
| 1-{2-[4-(4-fluoro-2-{2-[4-(methylsulfonyl)piperidin-1-yl]pyrimidin-5-yl}phenyl)piperazin-1-yl]-2-oxoethyl}-1,3-dihydro-2H-benzimidazol-2-one | 7 |
| 2-(3,5-dimethyl-1H-pyrazol-1-yl)-1-{2-methyl-4-[2-{2-[4-(methylsulfonyl)piperidin-1-yl]pyrimidin-5-yl}-4-(trifluoromethyl)phenyl]piperazin-1-yl}ethanone | 7 |
| 1-(4-{2-[2-(4-hydroxypiperidin-1-yl)pyrimidin-5-yl]-4-(trifluoromethyl)phenyl}-2-methylpiperazin-1-yl)-2-(1H-pyrrolo[2,3-c]pyridin-1-yl)ethanone | 7 |
| 5-fluoro-2-[(3R)-4-(3H-imidazo[4,5-b]pyridin-3-ylacetyl)-3-methylpiperazin-1-yl]-N-(2-methoxypyridin-4-yl)benzamide | 7 |
| 1-{2-methyl-4-[2-{2-[4-(methylsulfonyl)piperidin-1-yl]pyrimidin-5-yl}-4-(trifluoromethyl)phenyl]piperazin-1-yl}-2-(1H-pyrrolo[2,3-c]pyridin-1-yl)ethanone | 7 |
| 2-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-2,3-dihydro-1H-isoindol-1-one | 7 |
| 5-fluoro-N-(2-methoxypyridin-4-yl)-2-{(3R)-3-methyl-4-[(1-oxo-1,3-dihydro-2H-isoindol-2-yl)acetyl]piperazin-1-yl}benzamide | 7 |
| 2-(3H-imidazo[4,5-b]pyridin-3-yl)-1-{2-methyl-4-[2-{2-[4-(methylsulfonyl)piperidin-1-yl]pyrimidin-5-yl}-4-(trifluoromethyl)phenyl]piperazin-1-yl}ethanone | 7 |
| 1-[2-methyl-4-(2-{2-[4-(methylsulfonyl)piperidin-1-yl]pyrimidin-5-yl}phenyl)piperazin-1-yl]-2-(1H-pyrrolo[2,3-c]pyridin-1-yl)ethanone | 8 |
| 1-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)-1,3-dihydro-2H-benzimidazol-2-one | 8 |

TABLE II-continued

| Compound | IC$_{50}$, nM |
|---|---|
| 2-{(3R)-4-[(3,5-dimethyl-1H-pyrazol-1-yl)acetyl]-3-methylpiperazin-1-yl}-5-fluoro-N-(2-methoxypyridin-4-yl)benzamide | 8 |
| 1-(4-{4-fluoro-2-[2-(4-hydroxypiperidin-1-yl)pyrimidin-5-yl]phenyl}piperazin-1-yl)-2-(1H-pyrrolo[2,3-b]pyridin-1-yl)ethanone | 8 |
| 1-(4-{4-fluoro-2-[2-(4-hydroxypiperidin-1-yl)pyrimidin-5-yl]phenyl}piperazin-1-yl)-2-(3H-imidazo[4,5-b]pyridin-3-yl)ethanone | 8 |
| 1-[4-(4-fluoro-2-{2-[4-(methylsulfonyl)piperidin-1-yl]pyrimidin-5-yl}phenyl)piperazin-1-yl]-2-(1H-pyrrolo[2,3-c]pyridin-1-yl)ethanone | 8 |
| 1-[2-(4-{4-fluoro-2-[2-(4-hydroxypiperidin-1-yl)pyrimidin-5-yl]phenyl}piperazin-1-yl)-2-oxoethyl]-1,3-dihydro-2H-benzimidazol-2-one | 8 |
| 1-[4-(4-fluoro-2-{2-[4-(methylsulfonyl)piperidin-1-yl]pyrimidin-5-yl}phenyl)-2-methylpiperazin-1-yl]-2-(1H-pyrrolo[2,3-c]pyridin-1-yl)ethanone | 8 |
| 2-(3,5-dimethyl-1H-pyrazol-1-yl)-1-(4-{2-[2-(4-hydroxypiperidin-1-yl)pyrimidin-5-yl]-4-(trifluoromethyl)phenyl}-2-methylpiperazin-1-yl)ethanone | 8 |
| 1-[4-(4-fluoro-2-{2-[4-(methylsulfonyl)piperidin-1-yl]pyrimidin-5-yl}phenyl)-2-methylpiperazin-1-yl]-2-(1H-pyrrolo[2,3-b]pyridin-1-yl)ethanone | 8 |
| 5-fluoro-N-(2-methoxypyridin-4-yl)-2-{(3S)-3-methyl-4-[(2-oxopiperidin-1-yl)acetyl]piperazin-1-yl}benzamide | 8 |
| 1-[2-(4-{2-[2-(4-hydroxypiperidin-1-yl)pyrimidin-5-yl]phenyl}-2-methylpiperazin-1-yl)-2-oxoethyl]-1,3-dihydro-2H-benzimidazol-2-one | 8 |
| 1-(4-{2-[2-(4-hydroxypiperidin-1-yl)pyrimidin-5-yl]phenyl}-2-methylpiperazin-1-yl)-2-(1H-pyrrolo[2,3-c]pyridin-1-yl)ethanone | 8 |
| 5-fluoro-N-(2-methoxypyridin-4-yl)-2-{(3R)-3-methyl-4-[(2-oxo-2,3-dihydro-1H-benzimidazol-1-yl)acetyl]piperazin-1-yl}benzamide | 8 |
| 5-fluoro-N-(2-methoxypyridin-4-yl)-2-[(3R)-3-methyl-4-(1H-pyrrolo[2,3-c]pyridin-1-ylacetyl)piperazin-1-yl]benzamide | 9 |
| 5-fluoro-N-(2-methoxypyridin-4-yl)-2-{(3R)-3-methyl-4-[N-methyl-N-(2-methylpropanoyl)glycyl]piperazin-1-yl}benzamide | 9 |
| 1-[4-(4-fluoro-2-{2-[4-(methylsulfonyl)piperidin-1-yl]pyrimidin-5-yl}phenyl)piperazin-1-yl]-2-(1H-pyrrolo[2,3-b]pyridin-1-yl)ethanone | 9 |
| 1-(4-{2-[2-(4-hydroxypiperidin-1-yl)pyrimidin-5-yl]phenyl}-2-methylpiperazin-1-yl)-2-(1H-pyrrolo[2,3-b]pyridin-1-yl)ethanone | 9 |
| 2-{2-[4-(4-fluoro-2-{2-[4-(methylsulfonyl)piperidin-1-yl]pyrimidin-5-yl}phenyl)piperazin-1-yl]-2-oxoethyl}-2,3-dihydro-1H-isoindol-1-one | 9 |
| 1-[2-methyl-4-(2-{2-[4-(methylsulfonyl)piperidin-1-yl]pyrimidin-5-yl}phenyl)piperazin-1-yl]-2-(1H-pyrrolo[2,3-b]pyridin-1-yl)ethanone | 9 |
| 1-{2-[4-(4-fluoro-2-{2-[4-(methylsulfonyl)piperidin-1-yl]pyrimidin-5-yl}phenyl)-2-methylpiperazin-1-yl]-2-oxoethyl}-1,3-dihydro-2H-benzimidazol-2-one | 9 |
| 5-fluoro-N-(2-methoxypyridin-4-yl)-2-[(3R)-3-methyl-4-(1H-pyrrolo[2,3-b]pyridin-1-ylacetyl)piperazin-1-yl]benzamide | 9 |
| 2-(3,5-dimethyl-1H-pyrazol-1-yl)-1-(4-{4-fluoro-2-[2-(4-hydroxypiperidin-1-yl)pyrimidin-5-yl]phenyl}piperazin-1-yl)ethanone | 9 |
| 2-[2-(4-{2-[2-(4-hydroxypiperidin-1-yl)pyrimidin-5-yl]-4-(trifluoromethyl)phenyl}-2-methylpiperazin-1-yl)-2-oxoethyl]-2,3-dihydro-1H-isoindol-1-one | 9 |
| 2-[2-(4-{4-fluoro-2-[2-(4-hydroxypiperidin-1-yl)pyrimidin-5-yl]phenyl}piperazin-1-yl)-2-oxoethyl]-2,3-dihydro-1H-isoindol-1-one | 9 |
| 2-(3,5-dimethyl-1H-pyrazol-1-yl)-1-[2-methyl-4-(2-{2-[4-(methylsulfonyl)piperidin-1-yl]pyrimidin-5-yl}phenyl)piperazin-1-yl]ethanone | 9 |
| 1-[2-(4-{2-[2-(4-hydroxypiperidin-1-yl)pyrimidin-5-yl]-4-(trifluoromethyl)phenyl}-2-methylpiperazin-1-yl)-2-oxoethyl]-1,3-dihydro-2H-benzimidazol-2-one | 9 |
| 5-fluoro-N-(2-methoxypyridin-4-yl)-2-{(3S)-3-methyl-4-[(2-oxo-2,3-dihydro-1H-benzimidazol-1-yl)acetyl]piperazin-1-yl}benzamide | 9 |
| 1-(4-{4-fluoro-2-[2-(4-hydroxypiperidin-1-yl)pyrimidin-5-yl]phenyl}piperazin-1-yl)-2-(1H-pyrrolo[2,3-c]pyridin-1-yl)ethanone | 10 |
| 2-[2-(4-{2-[2-(4-hydroxypiperidin-1-yl)pyrimidin-5-yl]phenyl}-2-methylpiperazin-1-yl)-2-oxoethyl]-2,3-dihydro-1H-isoindol-1-one | 10 |
| 2-(3,5-dimethyl-1H-pyrazol-1-yl)-1-[4-(4-fluoro-2-{2-[4-(methylsulfonyl)piperidin-1-yl]pyrimidin-5-yl}phenyl)-2-methylpiperazin-1-yl]ethanone | 10 |
| 2-{2-[4-(4-fluoro-2-{2-[4-(methylsulfonyl)piperidin-1-yl]pyrimidin-5-yl}phenyl)-2-methylpiperazin-1-yl]-2-oxoethyl}-2,3-dihydro-1H-isoindol-1-one | 10 |
| 5-fluoro-N-(2-methoxypyridin-4-yl)-2-{(3R)-3-methyl-4-[(2-oxopiperidin-1-yl)acetyl]piperazin-1-yl}benzamide | 10 |
| 1-(4-{2-[2-(4-hydroxypiperidin-1-yl)pyrimidin-5-yl]-4-(trifluoromethyl)phenyl}-2-methylpiperazin-1-yl)-2-(1H-pyrrolo[2,3-b]pyridin-1-yl)ethanone | 10 |

TABLE II-continued

| Compound | IC$_{50}$, nM |
|---|---|
| 1-[4-(4-fluoro-2-{2-[4-(methylsulfonyl)piperidin-1-yl]pyrimidin-5-yl}phenyl)piperazin-1-yl]-2-(3H-imidazo[4,5-b]pyridin-3-yl)ethanone | 10 |
| 1-{4-[4-fluoro-2-(2-methoxypyrimidin-5-yl)phenyl]piperazin-1-yl}-2-(1H-pyrrolo[2,3-b]pyridin-1-yl)ethanone | 11 |
| 1-[2-(4-{2-[2-(4-hydroxypiperidin-1-yl)pyrimidin-5-yl]-4-(trifluoromethyl)phenyl}-2-methylpiperazin-1-yl)-2-oxoethyl]piperidin-2-one | 11 |
| 5-fluoro-2-[(3S)-4-(3H-imidazo[4,5-b]pyridin-3-ylacetyl)-3-methylpiperazin-1-yl]-N-(2-methoxypyridin-4-yl)benzamide | 11 |
| 1-(2-{2-methyl-4-[2-{2-[4-(methylsulfonyl)piperidin-1-yl]pyrimidin-5-yl}-4-(trifluoromethyl)phenyl]piperazin-1-yl}-2-oxoethyl)piperidin-2-one | 11 |
| 1-(4-{2-[2-(4-hydroxypiperidin-1-yl)pyrimidin-5-yl]-4-(trifluoromethyl)phenyl}-2-methylpiperazin-1-yl)-2-(3H-imidazo[4,5-b]pyridin-3-yl)ethanone | 11 |
| 1-[2-(4-{4-fluoro-2-[2-(morpholin-4-yl)pyrimidin-5-yl]phenyl}piperazin-1-yl)-2-oxoethyl]-1,3-dihydro-2H-benzimidazol-2-one | 11 |
| 2-(3,5-dimethyl-1H-pyrazol-1-yl)-1-[4-(4-fluoro-2-{2-[4-(methylsulfonyl)piperidin-1-yl]pyrimidin-5-yl}phenyl)piperazin-1-yl]ethanone | 11 |
| 1-{2-[2-methyl-4-(2-{2-[4-(methylsulfonyl)piperidin-1-yl]pyrimidin-5-yl}phenyl)piperazin-1-yl]-2-oxoethyl}-1,3-dihydro-2H-benzimidazol-2-one | 11 |
| N-{2-[(2S)-4-{4-fluoro-2-[(2-methoxypyridin-4-yl)carbamoyl]phenyl}-2-methylpiperazin-1-yl]-2-oxoethyl}-N,5-dimethyl-1,3-oxazole-4-carboxamide | 11 |
| 5-fluoro-N-(2-methoxypyridin-4-yl)-2-{(3S)-3-methyl-4-[N-methyl-N-(2-methylpropanoyl)glycyl]piperazin-1-yl}benzamide | 11 |
| 1-(4-{2-[2-(4-hydroxypiperidin-1-yl)pyrimidin-5-yl]phenyl}-2-methylpiperazin-1-yl)-2-(3H-imidazo[4,5-b]pyridin-3-yl)ethanone | 11 |
| 5-fluoro-2-{(3S)-3-methyl-4-[(2-oxo-2,3-dihydro-1H-benzimidazol-1-yl)acetyl]piperazin-1-yl}-N-(5-methyl-4,5,6,7-tetrahydro[1,3]thiazolo[5,4-c]pyridin-2-yl)benzamide | 12 |
| 2-{(3S)-4-[(3,5-dimethyl-1H-pyrazol-1-yl)acetyl]-3-methylpiperazin-1-yl}-5-fluoro-N-(2-methoxypyridin-4-yl)benzamide | 12 |
| N-{2-[(2R)-4-{4-fluoro-2-[(2-methoxypyridin-4-yl)carbamoyl]phenyl}-2-methylpiperazin-1-yl]-2-oxoethyl}-N,5-dimethyl-1,3-oxazole-4-carboxamide | 12 |
| 2-{(3S)-4-[(3,5-dimethyl-1H-pyrazol-1-yl)acetyl]-3-methylpiperazin-1-yl}-5-fluoro-N-(5-methyl-4,5,6,7-tetrahydro[1,3]thiazolo[5,4-c]pyridin-2-yl)benzamide | 12 |
| 1-[4-(4-fluoro-2-{2-[4-(methylsulfonyl)piperidin-1-yl]pyrimidin-5-yl}phenyl)-2-methylpiperazin-1-yl]-2-(3H-imidazo[4,5-b]pyridin-3-yl)ethanone | 13 |
| 1-(2-{4-[4-fluoro-2-(2-methoxypyrimidin-5-yl)phenyl]piperazin-1-yl}-2-oxoethyl)-1,3-dihydro-2H-benzimidazol-2-one | 13 |
| 5-fluoro-N-(2-methoxypyridin-4-yl)-2-{(3S)-3-methyl-4-[(1-oxo-1,3-dihydro-2H-isoindol-2-yl)acetyl]piperazin-1-yl}benzamide | 13 |
| 1-{4-[4-fluoro-2-(2-methoxypyrimidin-5-yl)phenyl]piperazin-1-yl}-2-(1H-pyrrolo[2,3-c]pyridin-1-yl)ethanone | 13 |
| 2-(3,5-dimethyl-1H-pyrazol-1-yl)-1-(4-{2-[2-(4-hydroxypiperidin-1-yl)pyrimidin-5-yl]phenyl}-2-methylpiperazin-1-yl)ethanone | 13 |
| 1-(4-{4-fluoro-2-[2-(morpholin-4-yl)pyrimidin-5-yl]phenyl}piperazin-1-yl)-2-(1H-pyrrolo[2,3-c]pyridin-1-yl)ethanone | 13 |
| 1-[2-(4-{4-fluoro-2-[2-(4-methylpiperazin-1-yl)pyrimidin-5-yl]phenyl}piperazin-1-yl)-2-oxoethyl]-1,3-dihydro-2H-benzimidazol-2-one | 14 |
| 1-(4-{4-fluoro-2-[2-(pyrrolidin-1-yl)pyrimidin-5-yl]phenyl}piperazin-1-yl)-2-(3H-imidazo[4,5-b]pyridin-3-yl)ethanone | 14 |
| 1-[2-(4-{4-fluoro-2-[2-(pyrrolidin-1-yl)pyrimidin-5-yl]phenyl}piperazin-1-yl)-2-oxoethyl]-1,3-dihydro-2H-benzimidazol-2-one | 14 |
| 5-fluoro-2-{(3S)-3-methyl-4-[N-methyl-N-(2-methylpropanoyl)glycyl]piperazin-1-yl}-N-(5-methyl-4,5,6,7-tetrahydro[1,3]thiazolo[5,4-c]pyridin-2-yl)benzamide | 14 |
| 2-(3H-imidazo[4,5-b]pyridin-3-yl)-1-[2-methyl-4-(2-{2-[4-(methylsulfonyl)piperidin-1-yl]pyrimidin-5-yl}phenyl)piperazin-1-yl]ethanone | 14 |
| 1-(4-{4-fluoro-2-[2-(pyrrolidin-1-yl)pyrimidin-5-yl]phenyl}piperazin-1-yl)-2-(1H-pyrrolo[2,3-c]pyridin-1-yl)ethanone | 14 |
| 1-{2-[4-(4-fluoro-2-{2-[4-(methylsulfonyl)piperidin-1-yl]pyrimidin-5-yl}phenyl)-2-methylpiperazin-1-yl]-2-oxoethyl}piperidin-2-one | 14 |
| 1-(4-{4-fluoro-2-[2-(morpholin-4-yl)pyrimidin-5-yl]phenyl}piperazin-1-yl)-2-(1H-pyrrolo[2,3-b]pyridin-1-yl)ethanone | 14 |
| 5-fluoro-2-{(3S)-3-methyl-4-[(1-oxo-1,3-dihydro-2H-isoindol-2-yl)acetyl]piperazin-1-yl}-N-(5-methyl-4,5,6,7-tetrahydro[1,3]thiazolo[5,4-c]pyridin-2-yl)benzamide | 15 |
| 5-fluoro-2-[(3S)-4-(3H-imidazo[4,5-b]pyridin-3-ylacetyl)-3-methylpiperazin-1-yl]-N-(5-methyl-4,5,6,7-tetrahydro[1,3]thiazolo[5,4-c]pyridin-2-yl)benzamide | 15 |

TABLE II-continued

| Compound | IC$_{50}$, nM |
|---|---|
| 1-{2-[4-(4-fluoro-2-{2-[4-(methylsulfonyl)piperidin-1-yl]pyrimidin-5-yl}phenyl)piperazin-1-yl]-2-oxoethyl}piperidin-2-one | 15 |
| 2-{(3R)-4-[(3,5-dimethyl-1H-pyrazol-1-yl)acetyl]-3-methylpiperazin-1-yl}-5-fluoro-N-(5-methyl-4,5,6,7-tetrahydro[1,3]thiazolo[5,4-c]pyridin-2-yl)benzamide | 15 |
| 5-fluoro-2-[(3R)-4-(3H-imidazo[4,5-b]pyridin-3-ylacetyl)-3-methylpiperazin-1-yl]-N-(5-methyl-4,5,6,7-tetrahydro[1,3]thiazolo[5,4-c]pyridin-2-yl)benzamide | 15 |
| 2-[2-(4-{4-fluoro-2-[2-(pyrrolidin-1-yl)pyrimidin-5-yl]phenyl}piperazin-1-yl)-2-oxoethyl]-2,3-dihydro-1H-isoindol-1-one | 15 |
| 1-(4-{4-fluoro-2-[2-(pyrrolidin-1-yl)pyrimidin-5-yl]phenyl}piperazin-1-yl)-2-(1H-pyrrolo[2,3-b]pyridin-1-yl)ethanone | 15 |
| 5-fluoro-2-{(3R)-3-methyl-4-[(1-oxo-1,3-dihydro-2H-isoindol-2-yl)acetyl]piperazin-1-yl}-N-(5-methyl-4,5,6,7-tetrahydro[1,3]thiazolo[5,4-c]pyridin-2-yl)benzamide | 15 |
| 1-[2-(4-{4-fluoro-2-[2-(4-hydroxypiperidin-1-yl)pyrimidin-5-yl]phenyl}piperazin-1-yl)-2-oxoethyl]piperidin-2-one | 16 |
| 2-(3,5-dimethyl-1H-pyrazol-1-yl)-1-(4-{4-fluoro-2-[2-(pyrrolidin-1-yl)pyrimidin-5-yl]phenyl}piperazin-1-yl)ethanone | 16 |
| 5-fluoro-2-[(3S)-3-methyl-4-(1H-pyrrolo[2,3-b]pyridin-1-ylacetyl)piperazin-1-yl]-N-(5-methyl-4,5,6,7-tetrahydro[1,3]thiazolo[5,4-c]pyridin-2-yl)benzamide | 17 |
| 5-fluoro-2-{(3S)-3-methyl-4-[(2-oxopiperidin-1-yl)acetyl]piperazin-1-yl}-N-(5-methyl-4,5,6,7-tetrahydro[1,3]thiazolo[5,4-c]pyridin-2-yl)benzamide | 17 |
| 5-fluoro-2-{(3R)-3-methyl-4-[(2-oxo-2,3-dihydro-1H-benzimidazol-1-yl)acetyl]piperazin-1-yl}-N-(5-methyl-4,5,6,7-tetrahydro[1,3]thiazolo[5,4-c]pyridin-2-yl)benzamide | 18 |
| 5-fluoro-N-(2-methoxypyridin-4-yl)-2-[(3S)-3-methyl-4-(1H-pyrrolo[2,3-b]pyridin-1-ylacetyl)piperazin-1-yl]benzamide | 18 |
| 1-[2-(4-{2-[2-(4-hydroxypiperidin-1-yl)pyrimidin-5-yl]phenyl}-2-methylpiperazin-1-yl)-2-oxoethyl]piperidin-2-one | 19 |
| 5-fluoro-2-{(3R)-3-methyl-4-[N-methyl-N-(2-methylpropanoyl)glycyl]piperazin-1-yl}-N-(5-methyl-4,5,6,7-tetrahydro[1,3]thiazolo[5,4-c]pyridin-2-yl)benzamide | 19 |
| 1-[2-(2-methyl-4-{2-[2-(methylsulfonyl)pyrimidin-5-yl]-4-(trifluoromethyl)phenyl}piperazin-1-yl)-2-oxoethyl]-1,3-dihydro-2H-benzimidazol-2-one | 20 |
| 5-fluoro-2-[(3R)-3-methyl-4-(1H-pyrrolo[2,3-b]pyridin-1-ylacetyl)piperazin-1-yl]-N-(5-methyl-4,5,6,7-tetrahydro[1,3]thiazolo[5,4-c]pyridin-2-yl)benzamide | 20 |
| 1-(4-{4-fluoro-2-[2-(4-methylpiperazin-1-yl)pyrimidin-5-yl]phenyl}piperazin-1-yl)-2-(1H-pyrrolo[2,3-b]pyridin-1-yl)ethanone | 20 |
| 5-fluoro-2-{(3R)-3-methyl-4-[(2-oxopiperidin-1-yl)acetyl]piperazin-1-yl}-N-(5-methyl-4,5,6,7-tetrahydro[1,3]thiazolo[5,4-c]pyridin-2-yl)benzamide | 20 |
| N-{2-[(2S)-4-{4-fluoro-2-[(5-methyl-4,5,6,7-tetrahydro[1,3]thiazolo[5,4-c]pyridin-2-yl)carbamoyl]phenyl}-2-methylpiperazin-1-yl]-2-oxoethyl}-N,5-dimethyl-1,3-oxazole-4-carboxamide | 21 |
| 2-[2-(4-{4-fluoro-2-[2-(morpholin-4-yl)pyrimidin-5-yl]phenyl}piperazin-1-yl)-2-oxoethyl]-2,3-dihydro-1H-isoindol-1-one | 23 |
| 1-[2-(4-{4-fluoro-2-[2-(pyrrolidin-1-yl)pyrimidin-5-yl]phenyl}piperazin-1-yl)-2-oxoethyl]piperidin-2-one | 23 |
| 1-(4-{4-fluoro-2-[2-(morpholin-4-yl)pyrimidin-5-yl]phenyl}piperazin-1-yl)-2-(3H-imidazo[4,5-b]pyridin-3-yl)ethanone | 24 |
| 2-[2-(4-{4-fluoro-2-[2-(4-methylpiperazin-1-yl)pyrimidin-5-yl]phenyl}piperazin-1-yl)-2-oxoethyl]-2,3-dihydro-1H-isoindol-1-one | 26 |
| 1-(2-methyl-4-{2-[2-(methylsulfonyl)pyrimidin-5-yl]phenyl}piperazin-1-yl)-2-(1H-pyrrolo[2,3-b]pyridin-1-yl)ethanone | 27 |
| 1-(2-methyl-4-{2-[2-(methylsulfonyl)pyrimidin-5-yl]-4-(trifluoromethyl)phenyl}piperazin-1-yl)-2-(1H-pyrrolo[2,3-b]pyridin-1-yl)ethanone | 30 |
| 1-[2-(4-{4-fluoro-2-[2-(morpholin-4-yl)pyrimidin-5-yl]phenyl}piperazin-1-yl)-2-oxoethyl]piperidin-2-one | 30 |
| 1-{2-[2-methyl-4-(2-{2-[4-(methylsulfonyl)piperidin-1-yl]pyrimidin-5-yl}phenyl)piperazin-1-yl]-2-oxoethyl}piperidin-2-one | 34 |
| N-{2-[(2R)-4-{4-fluoro-2-[(5-methyl-4,5,6,7-tetrahydro[1,3]thiazolo[5,4-c]pyridin-2-yl)carbamoyl]phenyl}-2-methylpiperazin-1-yl]-2-oxoethyl}-N,5-dimethyl-1,3-oxazole-4-carboxamide | 35 |
| 2-(3,5-dimethyl-1H-pyrazol-1-yl)-1-(4-{4-fluoro-2-[2-(4-methylpiperazin-1-yl)pyrimidin-5-yl]phenyl}piperazin-1-yl)ethanone | 40 |
| 1-(4-{4-fluoro-2-[2-(4-methylpiperazin-1-yl)pyrimidin-5-yl]phenyl}piperazin-1-yl)-2-(3H-imidazo[4,5-b]pyridin-3-yl)ethanone | 43 |
| 1-[2-(4-{4-fluoro-2-[2-(methylsulfonyl)pyrimidin-5-yl]phenyl}piperazin-1-yl)-2-oxoethyl]-1,3-dihydro-2H-benzimidazol-2-one | 47 |

TABLE II-continued

| Compound | IC$_{50}$, nM |
|---|---|
| 1-(4-{4-fluoro-2-[2-(methylsulfonyl)pyrimidin-5-yl]phenyl}-2-methylpiperazin-1-yl)-2-(1H-pyrrolo[2,3-b]pyridin-1-yl)ethanone | 48 |
| 1-{4-[4-fluoro-2-(2-methoxypyrimidin-5-yl)phenyl]piperazin-1-yl}-2-(3H-imidazo[4,5-b]pyridin-3-yl)ethanone | 53 |
| 2-(3,5-dimethyl-1H-pyrazol-1-yl)-1-(2-methyl-4-{2-[2-(methylsulfonyl)pyrimidin-5-yl]-4-(trifluoromethyl)phenyl}piperazin-1-yl)ethanone | 56 |
| 1-[2-(4-{4-fluoro-2-[2-(methylsulfonyl)pyrimidin-5-yl]phenyl}-2-methylpiperazin-1-yl)-2-oxoethyl]-1,3-dihydro-2H-benzimidazol-2-one | 60 |
| 1-[2-(2-methyl-4-{2-[2-(methylsulfonyl)pyrimidin-5-yl]phenyl}piperazin-1-yl)-2-oxoethyl]-1,3-dihydro-2H-benzimidazol-2-one | 63 |
| 1-(4-{4-fluoro-2-[2-(methylsulfonyl)pyrimidin-5-yl]phenyl}piperazin-1-yl)-2-(1H-pyrrolo[2,3-b]pyridin-1-yl)ethanone | 67 |
| 1-[2-(4-{4-fluoro-2-[2-(4-methylpiperazin-1-yl)pyrimidin-5-yl]phenyl}piperazin-1-yl)-2-oxoethyl]piperidin-2-one | 94 |
| 2-[2-(2-methyl-4-{2-[2-(methylsulfonyl)pyrimidin-5-yl]-4-(trifluoromethyl)phenyl}piperazin-1-yl)-2-oxoethyl]-2,3-dihydro-1H-isoindol-1-one | 101 |
| 2-(3,5-dimethyl-1H-pyrazol-1-yl)-1-(4-{4-fluoro-2-[2-(methylsulfonyl)pyrimidin-5-yl]phenyl}-2-methylpiperazin-1-yl)ethanone | 157 |
| 1-(2-{4-[4-fluoro-2-(2-methoxypyrimidin-5-yl)phenyl]piperazin-1-yl}-2-oxoethyl)piperidin-2-one | 174 |
| 2-(3H-imidazo[4,5-b]pyridin-3-yl)-1-(2-methyl-4-{2-[2-(methylsulfonyl)pyrimidin-5-yl]-4-(trifluoromethyl)phenyl}piperazin-1-yl)ethanone | 189 |
| 2-[2-(4-{4-fluoro-2-[2-(methylsulfonyl)pyrimidin-5-yl]phenyl}-2-methylpiperazin-1-yl)-2-oxoethyl]-2,3-dihydro-1H-isoindol-1-one | 245 |
| 2-[2-(4-{4-fluoro-2-[2-(methylsulfonyl)pyrimidin-5-yl]phenyl}piperazin-1-yl)-2-oxoethyl]-2,3-dihydro-1H-isoindol-1-one | 249 |
| 2-(3,5-dimethyl-1H-pyrazol-1-yl)-1-(4-{4-fluoro-2-[2-(methylsulfonyl)pyrimidin-5-yl]phenyl}piperazin-1-yl)ethanone | 278 |
| 2-[2-(2-methyl-4-{2-[2-(methylsulfonyl)pyrimidin-5-yl]phenyl}piperazin-1-yl)-2-oxoethyl]-2,3-dihydro-1H-isoindol-1-one | 293 |
| 1-[2-(2-methyl-4-{2-[2-(methylsulfonyl)pyrimidin-5-yl]-4-(trifluoromethyl)phenyl}piperazin-1-yl)-2-oxoethyl]piperidin-2-one | 310 |
| 2-(3H-imidazo[4,5-b]pyridin-3-yl)-1-(2-methyl-4-{2-[2-(methylsulfonyl)pyrimidin-5-yl]phenyl}piperazin-1-yl)ethanone | 434 |
| 1-(4-{4-fluoro-2-[2-(methylsulfonyl)pyrimidin-5-yl]phenyl}piperazin-1-yl)-2-(3H-imidazo[4,5-b]pyridin-3-yl)ethanone | 488 |

Methods of Use

The compounds of the invention are effective antagonists of the interaction of CXCR3 and its ligands and thus inhibit CXCR3 activation. Therefore, in one embodiment of the invention, there is provided methods of treating CXCR3-mediated disorders using compounds of the invention. In another embodiment, there is provided methods of treating inflammatory, autoimmune and cardiovascular diseases using compounds of the invention.

Without wishing to be bound by theory, by inhibiting the activity of CXCR3 the compounds of the invention block the migration of T-cells and other leukocytes that express CXCR3. Thus, the inhibition of CXCR3 activity is an attractive means for preventing and treating a variety of autoimmune and immunological diseases exacerbated by the influx of these leukocytes. These include multiple sclerosis, rheumatoid arthritis, psoriasis inflammatory bowel disease, chronic obstructive pulmonary disease (COPD) and kidney disease. Furthermore, a genetic deletion study and a study in LDL receptor KO mice with a CXCR3 antagonist have both shown that inhibition of CXCR3 activity attenuates atherosclerotic lesion formation. Thus inhibition of CXCR3 activity is also an attractive means for treating and preventing atherosclerosis and secondary atherothrombotic events such as myocardial infarction and stroke.

For treatment of the above-described diseases and conditions, a therapeutically effective dose will generally be in the range of approximately 0.01 mg to about 100 mg/kg of body weight per dosage of a compound of the invention; preferably, from about 0.1 mg to about 20 mg/kg of body weight per dosage. For example, for administration to a 70 kg person, the dosage range would be approximately 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula (I):

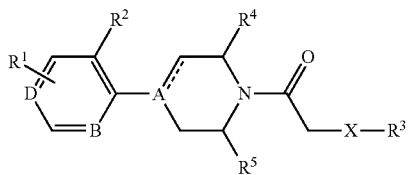

(I)

wherein:
A is N;
B is C;
D is C;
X is absent;
$R^1$ is H or F;
$R^2$ is benzoimidazolyl, benzooxazolyl, benzo[b]thiophenyl, dibenzofuranyl, dibenzothiophenyl, furanyl, imidazolyl, 1H-imidazo[4,5-c]pyridinyl, indolyl, isoindolyl, isoquinolinyl, isoxazolyl, oxazolyl, phenyl, pyranyl, pyrazinyl, pyrazolyl, pyridazinyl, pyridinyl, pyrimidinyl, pyrrolyl, quinolinyl, thiadiazolyl, thiazolyl, thienyl or triazinyl, each optionally substituted with one to three $R^6$;
$R^3$ is benzoimidazolyl, benzo[d]isothiazolyl, benzo[b]thiophenyl, benzotriazolyl, furanyl, imidazo[4,5-b]pyridinyl, imidazolyl, indazolyl, indolyl, isoindolyl, isoquinolinyl, isothiazolyl, phenyl, phthalazinyl, pyrazolyl, pyridinyl, pyrrolo[2,3-b]pyridinyl, pyrrolo[2,3-c]pyridinyl, pyrrolo[3,2-c]pyridinyl, pyrrolo[3,2-b]pyridinyl, pyrrolo[2,3-d]pyrimidinyl, pyrrolyl, quinazolinyl, thiadiazolyl or thiazolyl, each optionally substituted with one to three $R^7$;
$R^4$ and $R^5$ are;
each $R^6$ is independently —OH, oxo, hydroxy$C_{1-6}$alkyl, halogen, —$(CH_2)_m$—CN, nitro, $C_{1-6}$ alkyl, $C_{2-6}$ alkenyl, $C_{2-6}$ alkynyl, $C_{3-10}$ cycloalkyl, $C_{1-6}$ alkoxy, phenoxy, pyridyloxy, $C_{1-6}$ alkoxycarbonyl, carboxyl, —C(O)$C_{1-6}$alkyl, —$(CH_2)_m$—$NR_8R_9$, —S(O)$_n C_{1-6}$alkyl, —NHS(O)$_2 C_{1-6}$alkyl, —NHC(O)$C_{1-6}$alkyl, —S(O)$_2 NR_8R_9$, —C(O)$NR_8R_9$, thienyl, morpholinyl, pyrrolidinyl, piperidinyl, [1,3]-oxazepan-1-yl, piperazinyl, azabicyclo[2.2.1]heptyl, 2-oxa-5-azabicyclo[2.2.1]heptyl, octahydroisoquinolinyl, [1,4]-oxazepanyl, azetidinyl phenyl or benzyl, wherein each alkyl, alkenyl or alkynyl of said $R^6$ is optionally partially or fully halogenated and each heterocyclyl, heteroaryl, phenyl or benzyl of said $R^6$ is optionally substituted with one to three $CH_3$, —$OCH_3$, halogen, —CN, —$CF_3$, —C(O)$CH_3$, $NR^8R^9$, —C(O)$NH_2$, —C(O)$NHCH_3$, —OH, —$CH_2OCH_3$, —C(OH)($CH_3$)$CH_3$, —$SCH_3$, pyrrolidinyl or —S(O)$_2CH_3$;
each $R^7$ is independently $C_{1-6}$ alkyl, $C_{2-6}$ alkenyl, $C_{2-6}$ alkynyl, $C_{3-10}$ cycloalkyl, $C_{1-6}$ alkoxy, halogen, oxo, —CN, carboxy, —$(CH_2)_m$—$NR_8R_9$, phenyl or pyridyl, wherein each alkyl, alkenyl or alkynyl of said $R^7$ is optionally partially or fully halogenated;
$R^8$ and $R^9$ are each independently hydrogen, $C_{1-6}$ alkyl, $C_{1-6}$ acyl or $C_{3-10}$ cycloalkyl;
m is an integer from 0 to 3;
n is an integer from 0 to 2; and
------- is a single bond;
or a pharmaceutically acceptable salt thereof.

2. The compound of claim 1, wherein:
$R^2$ is benzoimidazolyl, benzooxazolyl, imidazolyl, 1H-imidazo[4,5-c]pyridinyl, indolyl, isoindolyl, isoquinolinyl, isoxazolyl, oxazolyl, phenyl, pyrazinyl, pyrazolyl, pyridazinyl, pyridinyl, pyrimidinyl, quinolinyl, thiadiazolyl, thiazolyl or thienyl, wherein each of the foregoing is optionally substituted by one to three $R^6$;
$R^3$ is benzoimidazolyl, benzotriazolyl, imidazolyl, imidazo[4,5-b]pyridinyl, indazolyl, indolyl, isoindolyl, isothiazolyl, pyrazolyl, pyridinyl, pyrrolo[2,3-b]pyridinyl, pyrrolo[2,3-c]pyridinyl, pyrrolo[3,2-c]pyridinyl, pyrrolo[3,2-b]pyridinyl, pyrrolo[2,3-d]pyrimidinyl, pyrrolyl, thiadiazolyl or thiazolyl wherein each of the foregoing is optionally substituted with one to three $R^7$;
each $R^6$ is independently —$CH_2OH$, —Cl, —F, —CN, oxo, $C_{1-6}$ alkyl, $C_{3-6}$ cycloalkyl, $C_{1-2}$ alkoxy, phenoxy, pyridyloxy, —C(O)$CH_3$, —$(CH_2)_m$—$NR_8R_9$, —S(O)$_n CH_3$, —NHS(O)$_2CH_3$, —NH(CO)$CH_3$, —S(O)$_2NR_8R_9$, —C(O)$NR_8R_9$, thienyl, morpholinyl, pyrrolidinyl, piperidinyl, [1,3]-oxazepan-1-yl, piperazinyl, phenyl or benzyl, wherein each alkyl of said $R^6$ is optionally partially or fully halogenated and each heterocyclyl or phenyl of said $R^6$ is optionally substituted with one to three $CH_3$, —$OCH_3$, halogen, —CN, —$CF_3$, $N(CH_3)_2$, —C(O)$NH_2$, —C(O)$NHCH_3$, —OH, —$CH_2OCH_3$, —C(OH)($CH_3$)$CH_3$, pyrrolidinyl or S(O)$_2CH_3$;
each $R^7$ is independently $C_{1-3}$ alkyl, —$OCH_3$, $CF_3$, oxo, —CN, —Cl or —F;
$R^8$ and $R^9$ are each independently hydrogen, $C_{1-6}$ alkyl, $C_{1-3}$ acyl or $C_{3-6}$ cycloalkyl;
or a pharmaceutically acceptable salt thereof.

3. The compound of claim 1 wherein:
$R^3$ is benzoimidazolyl, benzotriazolyl, imidazolyl, imidazo[4,5-b]pyridinyl, indazolyl, indolyl, isoindolyl, pyrazolyl, pyrrolo[2,3-b]pyridinyl, pyrrolo[2,3-c]pyridinyl, pyrrolo[3,2-c]pyridinyl, pyrrolo[3,2-b]pyridinyl or pyrrolyl, wherein each of the foregoing is optionally substituted with one to three R⁷;

or a pharmaceutically acceptable salt thereof.

4. A method of treating rheumatoid arthritis comprising administering a therapeutically effective amount of a compound of claim 1, or a pharmaceutically acceptable salt thereof, to patient in need thereof.

5. A compound selected from:

1-{4-[2-(2-Methylsulfanyl-pyrimidin-5-yl)-phenyl]-piperazin-1-yl}-2-pyrrolo[2,3-b]pyridin-1-yl-ethanone;
5-{2-[4-(2-Pyrrolo[2,3-b]pyridin-1-yl-acetyl)-piperazin-1-yl]-phenyl}-pyridine-2-carbonitrile;
1-(4-Biphenyl-2-yl-piperazin-1-yl)-2-piperidin-1-yl-ethanone;
1-(4-{2-[2-(2,6-Dimethyl-morpholin-4-yl)-pyrimidin-5-yl]-phenyl}-piperazin-1-yl)-2-(3,5-dimethyl-pyrazol-1-yl)-ethanone;
1-{4-[2-(2-Methoxy-pyrimidin-5-yl)-phenyl]-piperazin-1-yl}-2-pyrrolo[2,3-b]pyridin-1-yl-ethanone;
1-{4-[2-(2-Dimethylamino-pyrimidin-5-yl)-phenyl]-piperazin-1-yl}-2-pyrrolo[2,3-b]pyridin-1-yl-ethanone;
1-{4-[2-(2-Morpholin-4-yl-pyrimidin-5-yl)-phenyl]-piperazin-1-yl}-2-pyrrolo[2,3-b]pyridin-1-yl-ethanone;
2-(3,5-Dimethyl-pyrazol-1-yl)-1-{4-[2-(2-pyrrolidin-1-yl-pyrimidin-5-yl)-phenyl]-piperazin-1-yl}-ethanone;
1-(2-{4-[2-(2-Morpholin-4-yl-pyrimidin-5-yl)-phenyl]-piperazin-1-yl}-2-oxo-ethyl)-imidazolidin-2-one;
1-[4-(4'-Dimethylaminomethyl-biphenyl-2-yl)-piperazin-1-yl]-2-(3,5-dimethyl-pyrazol-1-yl)-ethanone;
1-[2-(4-Biphenyl-2-yl-piperazin-1-yl)-2-oxo-ethyl]-1H-benzoimidazole-5-carboxylic acid;
2-(3,5-Dimethyl-pyrazol-1-yl)-1-{4-[2-(2-piperidin-1-yl-pyrimidin-5-yl)-phenyl]-piperazin-1-yl}-ethanone;
1-(4-{2-[2-((2R,6R)-2,6-Dimethyl-morpholin-4-yl)-pyrimidin-5-yl]-phenyl}-piperazin-1-yl)-2-pyrrolo[2,3-b]pyridin-1-yl-ethanone;
1-{4-[2-(2-Methylamino-pyrimidin-5-yl)-phenyl]-piperazin-1-yl}-2-pyrrolo[2,3-b]pyridin-1-yl-ethanone;
1-{4-[2-(2-Dimethylamino-pyrimidin-5-yl)-phenyl]-piperazin-1-yl}-2-(3,5-dimethyl-pyrazol-1-yl)-ethanone;
1-Biphenyl-2-yl-4-[2-(3,5-dimethyl-pyrazol-1-yl)-ethyl]-piperazine;
3-[2-(4-Biphenyl-2-yl-piperazin-1-yl)-2-oxo-ethyl]-3H-benzoimidazole-5-carboxylic acid;
2-(3,5-Dimethyl-pyrazol-1-yl)-1-{4-[2-(2-morpholin-4-yl-pyrimidin-5-yl)-phenyl]-piperazin-1-yl}-ethanone;
1-{4-[2-(2-Methoxy-pyrimidin-5-yl)-phenyl]-piperazin-1-yl}-2-pyrrolo[2,3-c]pyridin-1-yl-ethanone;
1-{4-[2-(2-[1,4]-oxazepan-4-yl-pyrimidin-5-yl)-phenyl]-piperazin-1-yl}-2-pyrrolo[2,3-b]pyridin-1-yl-ethanone;
1-{4-[2-(2-Ethylamino-pyrimidin-5-yl)-phenyl]-piperazin-1-yl}-2-pyrrolo[2,3-b]pyridin-1-yl-ethanone;
1-{4-[2-(2-Pyrrolidin-1-yl-pyrimidin-5-yl)-phenyl]-piperazin-1-yl}-2-pyrrolo[2,3-b]pyridin-1-yl-ethanone;
1-(2-{4-[2-(2-Morpholin-4-yl-pyrimidin-5-yl)-phenyl]-piperazin-1-yl}-2-oxo-ethyl)-1,3-dihydro-benzoimidazol-2-one;
2-(3,5-Dimethyl-pyrazol-1-yl)-1-{4-[2-(2-methylsulfanyl-pyrimidin-5-yl)-phenyl]-piperazin-1-yl}-ethanone;
1-(4-{2-[2-((2R,6S)-2,6-Dimethyl-morpholin-4-yl)-pyrimidin-5-yl]-phenyl}-piperazin-1-yl)-2-pyrrolo[2,3-b]pyridin-1-yl-ethanone;
1-(4-{2-[2-(4-Methyl-piperazin-1-yl)-pyrimidin-5-yl]-phenyl}-piperazin-1-yl)-2-pyrrolo[2,3-b]pyridin-1-yl-ethanone;
1-{4-[2-(2-Piperidin-1-yl-pyrimidin-5-yl)-phenyl]-piperazin-1-yl}-2-pyrrolo[2,3-b]pyridin-1-yl-ethanone;
5-{2-[4-(2-Pyrrolo[2,3-b]pyridin-1-yl-acetyl)-piperazin-1-yl]-phenyl}-pyrimidine-2-carbonitrile;
2-Imidazo[4,5-b]pyridin-3-yl-1-{4-[2-(2-methoxy-pyrimidin-5-yl)-phenyl]-piperazin-1-yl}-ethanone;
5-(2-{4-[2-(3,5-Dimethyl-pyrazol-1-yl)-acetyl]-piperazin-1-yl}-phenyl)-pyridine-2-carbonitrile;
2-(3,5-Dimethyl-pyrazol-1-yl)-1-{4-[2-(2-ethoxy-pyrimidin-5-yl)-phenyl]-piperazin-1-yl}-ethanone;
2-(3,5-Dimethyl-pyrazol-1-yl)-1-{4-[2-(1-methyl-1H-indol-6-yl)-phenyl]-piperazin-1-yl}-ethanone;
5-{2-[4-(2-Pyrrolo[2,3-b]pyridin-1-yl-acetyl)-piperazin-1-yl]-phenyl}-pyridine-2-carboxylic acid amide;
1-{4-[2-Fluoro-6-(2-morpholin-4-yl-pyrimidin-5-yl)-phenyl]-piperazin-1-yl}-2-pyrrolo[2,3-b]pyridin-1-yl-ethanone;
2-Indazol-2-yl-1-{4-[2-(2-methoxy-pyrimidin-5-yl)-phenyl]-piperazin-1-yl}-ethanone;
2-(2,4-Dimethyl-imidazol-1-yl)-1-{4-[2-(2-morpholin-4-yl-pyrimidin-5-yl)-phenyl]-piperazin-1-yl}-ethanone;
1-{4-[2-(6-Chloro-pyridin-3-yl)-phenyl]-piperazin-1-yl}-2-pyrrolo[2,3-b]pyridin-1-yl-ethanone;
2-(3,5-Dimethyl-pyrazol-1-yl)-1-{4-[2-(6-trifluoromethyl-pyridin-3-yl)-phenyl]-piperazin-1-yl}-ethanone;
1-{4-[2-(6-Methoxy-pyridin-3-yl)-phenyl]-piperazin-1-yl}-2-pyrrolo[2,3-b]pyridin-1-yl-ethanone;
2-(3,5-Dimethyl-pyrazol-1-yl)-1-{4-[2-(2-methylamino-pyrimidin-5-yl)-phenyl]-piperazin-1-yl}-ethanone;
2-Indazol-1-yl-1-{4-[2-(2-methoxy-pyrimidin-5-yl)-phenyl]-piperazin-1-yl}-ethanone;
2-(3,5-Dimethyl-pyrazol-1-yl)-1-[4-(4'-trifluoromethyl-biphenyl-2-yl)-piperazin-1-yl]-ethanone;
2-(3,5-Dimethyl-pyrazol-1-yl)-1-{4-[2-(2-phenoxy-pyrimidin-5-yl)-phenyl]-piperazin-1-yl}-ethanone;
2-(3,5-Dimethyl-pyrazol-1-yl)-1-(4-{2-[2-(4-methyl-piperazin-1-yl)-pyrimidin-5-yl]-phenyl}-piperazin-1-yl)-ethanone;
5-(2-{4-[2-(3,5-Dimethyl-pyrazol-1-yl)-acetyl]-piperazin-1-yl}-phenyl)-pyrimidine-2-carbonitrile;
2-Indol-1-yl-1-{4-[2-(2-methoxy-pyrimidin-5-yl)-phenyl]-piperazin-1-yl}-ethanone 2-(3,5-Dimethyl-pyrazol-1-yl)-1-{4-[2-(2-methoxy-pyrimidin-5-yl)-phenyl]-piperazin-1-yl}-ethanone;
5-(2-{4-[2-(2,4-Dimethyl-imidazol-1-yl)-acetyl]-piperazin-1-yl}-phenyl)-pyridine-2-carbonitrile;
1-[4-(2-Benzo[b]thiophen-2-yl-phenyl)-piperazin-1-yl]-2-(3,5-dimethyl-pyrazol-1-yl)-ethanone;
2-(3,5-Dimethyl-pyrazol-1-yl)-1-[4-(3'-methoxy-biphenyl-2-yl)-piperazin-1-yl]-ethanone;
2-(3,5-Dimethyl-pyrazol-1-yl)-1-(4-{2-[2-(pyridin-3-yloxy)-pyrimidin-5-yl]-phenyl}-piperazin-1-yl)-ethanone;
2-(3,5-Dimethyl-pyrazol-1-yl)-1-{4-[2-(6-methoxy-pyridin-3-yl)-phenyl]-piperazin-1-yl}-ethanone;
2-(2,4-Dimethyl-imidazol-1-yl)-1-{4-[2-(2-methoxy-pyrimidin-5-yl)-phenyl]-piperazin-1-yl}-ethanone;
2-(3,5-Dimethyl-pyrazol-1-yl)-1-{4-[2-(2-methyl-pyrimidin-5-yl)-phenyl]-piperazin-1-yl}-ethanone;
2-(3,5-Dimethyl-pyrazol-1-yl)-1-[4-(4'-methyl-biphenyl-2-yl)-piperazin-1-yl]-ethanone;
5-(2-{4-[2-(5-Methyl-3-trifluoromethyl-pyrazol-1-yl)-acetyl]-piperazin-1-yl}-phenyl)-pyridine-2-carbonitrile;
2-(3,5-Dimethyl-pyrazol-1-yl)-1-{4-[2-(1H-indol-6-yl)-phenyl]-piperazin-1-yl}-ethanone;

1-[4-(4'-Chloro-biphenyl-2-yl)-piperazin-1-yl]-2-(3,5-dimethyl-pyrazol-1-yl)-ethanone;
2-(3,5-Dimethyl-pyrazol-1-yl)-1-[4-(4'-methoxy-biphenyl-2-yl)-piperazin-1-yl]-ethanone;
2'-{4-[2-(3,5-Dimethyl-pyrazol-1-yl)-acetyl]-piperazin-1-yl}-biphenyl-4-carbonitrile
1-[4-(4'-tert-Butyl-biphenyl-2-yl)-piperazin-1-yl]-2-(3,5-dimethyl-pyrazol-1-yl)-ethanone;
1-{4-[2-(2-Methoxy-pyrimidin-5-yl)-phenyl]-piperazin-1-yl}-2-(5-methyl-3-trifluoromethyl-pyrazol-1-yl)-ethanone;
2-(3,5-Dimethyl-pyrazol-1-yl)-1-[4-(4'-isopropyl-biphenyl-2-yl)-piperazin-1-yl]-ethanone;
1-[4-(3'-Chloro-biphenyl-2-yl)-piperazin-1-yl]-2-(3,5-dimethyl-pyrazol-1-yl)-ethanone;
1-{4-[2-(2-Methoxy-pyrimidin-5-yl)-phenyl]-piperazin-1-yl}-2-(3,4,5-trimethyl-pyrazol-1-yl)-ethanone;
1-{4-[2-(2-Methanesulfonyl-pyrimidin-5-yl)-phenyl]-piperazin-1-yl}-2-pyrrolo[2,3-b]pyridin-1-yl-ethanone;
2-(3,5-Dimethyl-pyrazol-1-yl)-1-(4-[1,1';4',1'']terphenyl-2-yl-piperazin-1-yl)-ethanone;
1-[2-(4-Biphenyl-2-yl-piperazin-1-yl)-2-oxo-ethyl]-1,3-dihydro-benzoimidazol-2-one;
1-{4-[2-(2-Cyclopropylamino-pyrimidin-5-yl)-phenyl]-piperazin-1-yl}-2-(3,5-dimethyl-pyrazol-1-yl)-ethanone;
1-(4-Biphenyl-2-yl-piperazin-1-yl)-2-pyrrolo[2,3-h]pyridin-1-yl-ethanone;
1-{4-[2-(2-tert-Butyl-thiazol-4-yl)-phenyl]-piperazin-1-yl}-2-(3,5-dimethyl-pyrazol-1-yl)-ethanone;
2-(3,5-Dimethyl-pyrazol-1-yl)-1-[4-(4'-fluoro-biphenyl-2-yl)-piperazin-1-yl]-ethanone;
2-(3,5-Dimethyl-pyrazol-1-yl)-1-[4-(3'-trifluoromethyl-biphenyl-2-yl)-piperazin-1-yl]-ethanone;
2-Benzotriazol-1-yl-1-{4-[2-(2-methoxy-pyrimidin-5-yl)-phenyl]-piperazin-1-yl}-ethanone;
1-(4-Biphenyl-2-yl-piperazin-1-yl)-2-(2,5-dimethyl-imidazol-1-yl)-ethanone;
2-(3,5-Dimethyl-pyrazol-1-yl)-1-{4-[2-(1H-indol-5-yl)-phenyl]-piperazin-1-yl}-ethanone;
N-(2'-{4-[2-(3,5-Dimethyl-pyrazol-1-yl)-acetyl]-piperazin-1-yl}-biphenyl-4-yl)-methanesulfonamide;
5-(2-{4-[2-(5-Methyl-3-trifluoromethyl-pyrazol-1-yl)-acetyl]-piperazin-1-yl}-phenyl)-pyridine-2-carboxylic acid amide;
2-(3,5-Dimethyl-pyrazol-1-yl)-1-[4-(2-pyrimidin-5-yl-phenyl)-piperazin-1-yl]-ethanone;
1-[4-(3',5'-Bis-trifluoromethyl-biphenyl-2-yl)-piperazin-1-yl]-2-(3,5-dimethyl-pyrazol-1-yl)-ethanone;
1-{4-[2-(2-Amino-pyrimidin-5-yl)-phenyl]-piperazin-1-yl}-2-(3,5-dimethyl-pyrazol-1-yl)-ethanone;
2-(3,5-Dimethyl-pyrazol-1-yl)-1-[4-(4'-methanesulfonyl-biphenyl-2-yl)-piperazin-1-yl]-ethanone;
2'-{4-[2-(3,5-Dimethyl-pyrazol-1-yl)-acetyl]-piperazin-1-yl}-biphenyl-4-sulfonic acid amide;
1-(4-Biphenyl-2-yl-piperazin-1-yl)-2-imidazo[4,5-b]pyridin-1-yl-ethanone;
1-[4-(2'-Chloro-biphenyl-2-yl)-piperazin-1-yl]-2-(3,5-dimethyl-pyrazol-1-yl)-ethanone;
2-(3,5-Dimethyl-pyrazol-1-yl)-1-[4-(4'-hydroxymethyl-biphenyl-2-yl)-piperazin-1-yl]-ethanone;
2-(3,5-Dimethyl-pyrazol-1-yl)-1-[4-(4'-hydroxy-biphenyl-2-yl)-piperazin-1-yl]-ethanone;
2-(3,5-Dimethyl-pyrazol-1-yl)-1-(4-[1,1';3',1'']terphenyl-2-yl-piperazin-1-yl)-ethanone;
2'-{4-[2-(3,5-Dimethyl-pyrazol-1-yl)-acetyl]-piperazin-1-yl}-biphenyl-4-carboxylic acid amide;
2-[2-(4-Biphenyl-2-yl-piperazin-1-yl)-2-oxo-ethyl]-isoindole-1,3-dione;
N-(2'-{4-[2-(3,5-Dimethyl-pyrazol-1-yl)-acetyl]-piperazin-1-yl}-biphenyl-4-yl)-acetamide;
2-Benzoimidazol-1-yl-1-(4-biphenyl-2-yl-piperazin-1-yl)-ethanone;
2-(2,4-Dimethyl-pyrrol-1-yl)-1-{4-[2-(2-methoxy-pyrimidin-5-yl)-phenyl]-piperazin-1-yl}-ethanone;
2-(3,5-Dimethyl-pyrazol-1-yl)-1-[4-(2-pyridin-3-yl-phenyl)-piperazin-1-yl]-ethanone;
1-{4-[2-(2-Methoxy-pyrimidin-5-yl)-phenyl]-piperazin-1-yl}-2-(4-methyl-pyrazol-1-yl)-ethanone;
1-(4-Biphenyl-2-yl-piperazin-1-yl)-2-(3-methyl-pyrazol-1-yl)-ethanone;
2-(3,5-Dimethyl-pyrazol-1-yl)-1-[4-(2-pyridin-4-yl-phenyl)-piperazin-1-yl]-ethanone;
1-(4-Biphenyl-2-yl-piperazin-1-yl)-2-(5-methyl-3-trifluoromethyl-pyrazol-1-yl)-ethanone;
2-(3,5-Dimethyl-pyrazol-1-yl)-1-{4-[2-(1-methyl-1H-pyrazol-4-yl)-phenyl]-piperazin-1-yl}-ethanone;
2-(3,5-Dimethyl-pyrazol-1-yl)-1-{4-[2-(2-methanesulfonyl-pyrimidin-5-yl)-phenyl]-piperazin-1-yl}-ethanone;
2-(3,5-Dimethyl-pyrazol-1-yl)-1-[4-(2'-trifluoromethyl-biphenyl-2-yl)-piperazin-1-yl]-ethanone;
1-(4-Biphenyl-2-yl-piperazin-1-yl)-2-(3H-imidazo[4,5-b]pyridin-4-yl)-ethanone;
1-(4-Biphenyl-2-yl-piperazin-1-yl)-2-(4-phenyl-imidazol-1-yl)-ethanone;
1-(4-Biphenyl-2-yl-piperazin-1-yl)-2-imidazo[4,5-b]pyridin-3-yl-ethanone;
1-[4-(3',4'-Dimethoxy-biphenyl-2-yl)-piperazin-1-yl]-2-(3,5-dimethyl-pyrazol-1-yl)-ethanone;
2-(3,5-Dimethyl-pyrazol-1-yl)-1-[4-(2-quinolin-3-yl-phenyl)-piperazin-1-yl]-ethanone;
2-(3,5-Dimethyl-pyrazol-1-yl)-1-{4-[2-(6-ethoxy-pyridin-3-yl)-phenyl]-piperazin-1-yl}-ethanone;
2-(3,5-Dimethyl-pyrazol-1-yl)-1-{4-[2-(5-methoxy-pyrazin-2-yl)-phenyl]-piperazin-1-yl}-ethanone;
2-(3,5-Dimethyl-pyrazol-1-yl)-1-{4-[2-(6-morpholin-4-yl-pyridin-3-yl)-phenyl]-piperazin-1-yl}-ethanone;
2-(3,5-Dimethyl-pyrazol-1-yl)-1-[4-(4'-ethoxy-biphenyl-2-yl)-piperazin-1-yl]-ethanone;
1-[4-(3'-Acetyl-biphenyl-2-yl)-piperazin-1-yl]-2-(3,5-dimethyl-pyrazol-1-yl)-ethanone;
2-(3,5-Dimethyl-pyrazol-1-yl)-1-{4-[2-(1-methyl-1H-indol-5-yl)-phenyl]-piperazin-1-yl}-ethanone;
2-(3,5-Dimethyl-pyrazol-1-yl)-1-[4-(2-quinolin-6-yl-phenyl)-piperazin-1-yl]-ethanone;
1-[4-(4'-Acetyl-biphenyl-2-yl)-piperazin-1-yl]-2-(3,5-dimethyl-pyrazol-1-yl)-ethanone;
2-(3,5-Dimethyl-pyrazol-1-yl)-1-[4-(3'-ethoxy-biphenyl-2-yl)-piperazin-1-yl]-ethanone;
4-(2-{4-[2-(3,5-Dimethyl-pyrazol-1-yl)-acetyl]-piperazin-1-yl}-phenyl)-pyridine-2-carboxylic acid methyl ester;
5-(2-{4-[2-(3,5-Dimethyl-pyrazol-1-yl)-acetyl]-piperazin-1-yl}-phenyl)-nicotinic acid ethyl ester;
1-{4-[2-(1-Benzyl-1H-pyrazol-4-yl)-phenyl]-piperazin-1-yl}-2-(3,5-dimethyl-pyrazol-1-yl)-ethanone;
2-(3,5-Dimethyl-pyrazol-1-yl)-1-[4-(4'-thiophen-2-yl-biphenyl-2-yl)-piperazin-1-yl]-ethanone;
2'-{4-[2-(3,5-Dimethyl-pyrazol-1-yl)-acetyl]-piperazin-1-yl}-biphenyl-4-sulfonic acid dimethylamide;
2-(3,5-Dimethyl-pyrazol-1-yl)-1-{4-[2-(5-phenyl-thiophen-2-yl)-phenyl]-piperazin-1-yl}-ethanone;

2'-{4-[2-(3,5-Dimethyl-pyrazol-1-yl)-acetyl]-piperazin-1-yl}-biphenyl-3-carboxylic acid methylamide;
1-[4-(4'-Benzyl-biphenyl-2-yl)-piperazin-1-yl]-2-(3,5-dimethyl-pyrazol-1-yl)-ethanone;
N-(2'-{4-[2-(3,5-Dimethyl-pyrazol-1-yl)-acetyl]-piperazin-1-yl}-biphenyl-3-yl)-acetamide;
5-(2-{4-[2-(3,5-Dimethyl-pyrazol-1-yl)-acetyl]-piperazin-1-yl}-phenyl)-pyridine-2-carboxylic acid methyl ester;
1-[4-(3'-Benzyl-biphenyl-2-yl)-piperazin-1-yl]-2-(3,5-dimethyl-pyrazol-1-yl)-ethanone;
1-[4-(2-Benzo[b]thiophen-3-yl-phenyl)-piperazin-1-yl]-2-(3,5-dimethyl-pyrazol-1-yl)-ethanone;
2'-{4-[2-(3,5-Dimethyl-pyrazol-1-yl)-acetyl]-piperazin-1-yl}-biphenyl-4-carboxylic acid dimethylamide;
2'-{4-[2-(3,5-Dimethyl-pyrazol-1-yl)-acetyl]-piperazin-1-yl}-biphenyl-3-sulfonic acid dimethylamide;
2'-{4-[2-(3,5-Dimethyl-pyrazol-1-yl)-acetyl]-piperazin-1-yl}-biphenyl-4-carboxylic acid methylamide;
2'-{4-[2-(3,5-Dimethyl-pyrazol-1-yl)-acetyl]-piperazin-1-yl}-biphenyl-3-carboxylic acid dimethylamide;
1-{4-[2-(1H-Benzoimidazol-2-yl)-phenyl]-piperazin-1-yl}-2-(3,5-dimethyl-pyrazol-1-yl)-ethanone;
1-[4-(2-Benzooxazol-2-yl-phenyl)-piperazin-1-yl]-2-(3,5-dimethyl-pyrazol-1-yl)-ethanone;
1-{4-[2-(5-Chloro-1H-benzoimidazol-2-yl)-phenyl]-piperazin-1-yl}-2-(3,5-dimethyl-pyrazol-1-yl)-ethanone;
2-(2-{4-[2-(3,5-Dimethyl-pyrazol-1-yl)-acetyl]-piperazin-1-yl}-phenyl)-1H-benzoimidazole-5-carbonitrile;
2-(3,5-Dimethyl-pyrazol-1-yl)-1-{4-[2-(5-trifluoromethyl-1H-benzoimidazol-2-yl)-phenyl]-piperazin-1-yl}-ethanone;
1-(4-{2-[2-((R)-3-Dimethylamino-pyrrolidin-1-yl)-pyrimidin-5-yl]-phenyl}-piperazin-1-yl)-2-(3,5-dimethyl-pyrazol-1-yl)-ethanone;
1-(4-{2-[(1R,4S)-2-(2-Aza-bicyclo[2.2.1]hept-2-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-{4-[4-fluoro-2-(2-morpholin-4-yl-pyrimidin-5-yl)-phenyl]-piperazin-1-yl}-ethanone;
2-(3,5-Dimethyl-pyrazol-1-yl)-1-(4-{2-[2-(4-methanesulfonyl-piperidin-1-yl)-pyrimidin-5-yl]-phenyl}-piperazin-1-yl)-ethanone;
1-[5-(2-{4-[2-(3,5-Dimethyl-pyrazol-1-yl)-acetyl]-piperazin-1-yl}-phenyl)-pyrimidin-2-yl]-piperidine-4-carboxylic acid amide;
2-(3,5-Dimethyl-pyrazol-1-yl)-1-(4-{2-[2-(4-hydroxy-piperidin-1-yl)-pyrimidin-5-yl]-phenyl}-piperazin-1-yl)-ethanone;
1-(4-{2-[2-(3,3-Difluoro-azetidin-1-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-(4-{2-[2-(3-fluoro-piperidin-1-yl)-pyrimidin-5-yl]-phenyl}-piperazin-1-yl)-ethanone;
2-(5-Fluoro-pyrrolo[2,3-b]pyridin-1-yl)-1-{4-[2-(2-methoxy-pyrimidin-5-yl)-phenyl]-piperazin-1-yl}-ethanone;
1-[5-(2-{4-[2-(3,5-Dimethyl-pyrazol-1-yl)-acetyl]-piperazin-1-yl}-phenyl)-pyrimidin-2-yl]-piperidine-3-carboxylic acid amide;
1-[5-(2-{4-[2-(3,5-Dimethyl-pyrazol-1-yl)-acetyl]-piperazin-1-yl}-phenyl)-pyrimidin-2-yl]-piperidine-4-carboxylic acid methylamide;
1-(4-{2-[2-(3,3-Difluoro-piperidin-1-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-(4-{2-[2-(3-hydroxy-pyrrolidin-1-yl)-pyrimidin-5-yl]-phenyl}-piperazin-1-yl)-ethanone;
2-(3,5-Dimethyl-pyrazol-1-yl)-1-(4-{2-[2-(4-fluoro-piperidin-1-yl)-pyrimidin-5-yl]-phenyl}-piperazin-1-yl)-ethanone;
2-(4-Chloro-3,5-dimethyl-pyrazol-1-yl)-1-{4-[2-(2-methoxy-pyrimidin-5-yl)-phenyl]-piperazin-1-yl}-ethanone;
2-(3,5-Dimethyl-pyrazol-1-yl)-1-{4-[2-(2-ethylamino-pyrimidin-5-yl)-phenyl]-piperazin-1-yl}-ethanone;
2-(3,5-Dimethyl-pyrazol-1-yl)-1-{4-[2-(2-[1,4]-oxazepan-4-yl-pyrimidin-5-yl)-phenyl]-piperazin-1-yl}-ethanone;
1-(2-{4-[2-(2-Methoxy-pyrimidin-5-yl)-phenyl]-piperazin-1-yl}-2-oxo-ethyl)-3-methyl-1,3-dihydro-benzoimidazol-2-one;
2-(3,5-Dimethyl-pyrazol-1-yl)-1-(4-{2-[2-(3-trifluoromethyl-piperidin-1-yl)-pyrimidin-5-yl]-phenyl}-piperazin-1-yl)-ethanone;
1-(4-{2-[2-(4,4-Dimethyl-piperidin-1-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-(4-{2-[2-((S)-2-methoxymethyl-pyrrolidin-1-yl)-pyrimidin-5-yl]-phenyl}-piperazin-1-yl)-ethanone;
2-(3,5-Dimethyl-pyrazol-1-yl)-1-[4-(2-{2-[4-(1-hydroxy-1-methyl-ethyl)-piperidin-1-yl]-pyrimidin-5-yl}-phenyl)-piperazin-1-yl]-ethanone;
2-(3,5-Dimethyl-pyrazol-1-yl)-1-(4-{2-[(1S,4S)-2-(2-oxa-5-aza-bicyclo[2.2.1]hept-5-yl)-pyrimidin-5-yl]-phenyl}-piperazin-1-yl)-ethanone;
1-(4-{2-[2-(3,5-Dimethyl-piperidin-1-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-{4-[4-fluoro-2-(2-methoxy-pyrimidin-5-yl)-phenyl]-piperazin-1-yl}-ethanone;
2-(7-Chloro-pyrrolo[2,3-c]pyridin-1-yl)-1-{4-[2-(2-methoxy-pyrimidin-5-yl)-phenyl]-piperazin-1-yl}-ethanone;
1-{4-[2-(2-Morpholin-4-yl-pyridin-4-yl)-phenyl]-piperazin-1-yl}-2-pyrrolo[2,3-b]pyridin-1-yl-ethanone;
2-(2-{4-[2-(2-Methoxy-pyrimidin-5-yl)-phenyl]-piperazin-1-yl}-2-oxo-ethyl)-2,3-dihydro-isoindol-1-one;
2-(3,5-Dimethyl-pyrazol-1-yl)-1-(4-{2-[2-(octahydro-isoquinolin-2-yl)-pyrimidin-5-yl]-phenyl}-piperazin-1-yl)-ethanone;
1-(4-{2-[2-(4,4-Difluoro-piperidin-1-yl)-pyrimidin-5-yl]-phenyl}-piperazin-1-yl)-2-(3,5-dimethyl-pyrazol-1-yl)-ethanone;
1-{4-[2-(2-Methoxy-pyridin-4-yl)-phenyl]-piperazin-1-yl}-2-pyrrolo[2,3-b]pyridin-1-yl-ethanone;
1-(4-{2-[2-(4-Dimethylamino-piperidin-1-yl)-pyrimidin-5-yl]-phenyl}-piperazin-1-yl)-2-(3,5-dimethyl-pyrazol-1-yl)-ethanone;
2-(3,5-Dimethyl-pyrazol-1-yl)-1-(4-{2-[2-(4-methoxy-4-methyl-piperidin-1-yl)-pyrimidin-5-yl]-phenyl}-piperazin-1-yl)-ethanone;
2-(3,5-Dimethyl-pyrazol-1-yl)-1-(4-{2-[2-(4-pyrrolidin-1-yl-piperidin-1-yl)-pyrimidin-5-yl]-phenyl}-piperazin-1-yl)-ethanone;

2-(4-Chloro-pyrrolo[2,3-d]pyrimidin-7-yl)-1-{4-[2-(2-methoxy-pyrimidin-5-yl)-phenyl]-piperazin-1-yl}-ethanone;
2-(4-Chloro-pyrrolo[3,2-c]pyridin-1-yl)-1-{4-[2-(2-methoxy-pyrimidin-5-yl)-phenyl]-piperazin-1-yl}-ethanone;
4-(2-{4-[2-(3,5-Dimethyl-pyrazol-1-yl)-acetyl]-piperazin-1-yl}-phenyl)-pyridine-2-carboxylic acid methylamide;
1-{4-[2-(2-Methoxy-pyrimidin-5-yl)-phenyl]-piperazin-1-yl}-2-pyrrolo[3,2-c]pyridin-1-yl-ethanone;
2-(5-Chloro-pyrrolo[3,2-b]pyridin-1-yl)-1-{4-[2-(2-methoxy-pyrimidin-5-yl)-phenyl]-piperazin-1-yl}-ethanone;
2-(3,5-Dimethyl-pyrazol-1-yl)-1-(4-{2-[2-(4-methoxy-piperidin-1-yl)-pyrimidin-5-yl]-phenyl}-piperazin-1-yl)-ethanone;
2-(2-{4-[2-(2-Methoxy-pyrimidin-5-yl)-phenyl]-piperazin-1-yl}-2-oxo-ethyl)-2H-phthalazin-1-one;
1-(2-{4-[2-(2-Methoxy-pyrimidin-5-yl)-phenyl]-piperazin-1-yl}-2-oxo-ethyl)-1H-indole-2,3-dione;
3-(2-{4-[2-(2-Methoxy-pyrimidin-5-yl)-phenyl]-piperazin-1-yl}-2-oxo-ethyl)-3H-quinazolin-4-one;
2-(6-Bromo-pyrrolo[3,2-c]pyridin-1-yl)-1-{4-[2-(2-methoxy-pyrimidin-5-yl)-phenyl]-piperazin-1-yl}-ethanone;
N-[5-(2-{4-[2-(3,5-Dimethyl-pyrazol-1-yl)-acetyl]-piperazin-1-yl}-phenyl)-pyrimidin-2-yl]-N-methyl-acetamide;
1-(2-{4-[2-(2-Methoxy-pyrimidin-5-yl)-phenyl]-piperazin-1-yl}-2-oxo-ethyl)-1H-pyrrolo[2,3-b]pyridine-4-carbonitrile;
(R)-1-[5-(2-{4-[2-(3,5-Dimethyl-pyrazol-1-yl)-acetyl]-piperazin-1-yl}-phenyl)-pyrimidin-2-yl]-pyrrolidine-2-carboxylic acid amide;
1-{4-[2-(2-Methoxy-pyrimidin-5-yl)-phenyl]-piperazin-1-yl}-2-(5-methoxy-pyrrolo[2,3-b]pyridin-1-yl)-ethanone;
1-{4-[2-(2-Methoxy-pyrimidin-5-yl)-phenyl]-piperazin-1-yl}-2-(3-methyl-benzo[b]thiophen-2-yl)-ethanone;
2-{2-[4-(2-Pyrrolo[2,3-b]pyridin-1-yl-acetyl)-piperazin-1-yl]-phenyl}-2H-isoquinolin-1-one;
2-(2-{4-[2-(2-Methoxy-pyrimidin-5-yl)-phenyl]-piperazin-1-yl}-2-oxo-ethyl)-1,1-dioxo-1,2-dihydro-1l6-benzo[d]isothiazol-3-one;
2-(4,5-Dichloro-imidazol-1-yl)-1-{4-[2-(2-methoxy-pyrimidin-5-yl)-phenyl]-piperazin-1-yl}-ethanone;
(S)-1-[5-(2-{4-[2-(3,5-Dimethyl-pyrazol-1-yl)-acetyl]-piperazin-1-yl}-phenyl)-pyrimidin-2-yl]-pyrrolidine-2-carboxylic acid methylamide;
2-{2-[4-(2-Pyrrolo[2,3-b]pyridin-1-yl-acetyl)-piperazin-1-yl]-phenyl}-isoindole-1,3-dione;
5-(2-{4-[2-(3,5-Dimethyl-pyrazol-1-yl)-acetyl]-piperazin-1-yl}-phenyl)-pyridine-2-carboxylic acid methylamide;
2-{2-[4-(2-Pyrrolo[2,3-b]pyridin-1-yl-acetyl)-piperazin-1-yl]-phenyl}-3,4-dihydro-2H-isoquinolin-1-one;
1-{4-[2-(2-Methoxy-pyrimidin-5-yl)-phenyl]-piperazin-1-yl}-2-(5-methoxy-pyrrolo[3,2-b]pyridin-1-yl)-ethanone;
2-(2-{4-[2-(3,5-Dimethyl-pyrazol-1-yl)-acetyl]-piperazin-1-yl}-phenyl)-2,3-dihydro-isoindol-1-one;
4-(2-{4-[2-(3,5-Dimethyl-pyrazol-1-yl)-acetyl]-piperazin-1-yl}-phenyl)-pyridine-2-carboxylic acid dimethylamide;
5-(2-{4-[2-(3,5-Dimethyl-pyrazol-1-yl)-acetyl]-piperazin-1-yl}-phenyl)-N-methyl-nicotinamide;
1-{2-[4-(4-fluoro-2-{2-[4-(methylsulfonyl)piperidin-1-yl]pyrimidin-5-yl}phenyl)piperazin-1-yl]-2-oxoethyl}-1,3-dihydro-2H-benzimidazol-2-one;
1-(4-{4-fluoro-2-[2-(4-hydroxypiperidin-1-yl)pyrimidin-5-yl]phenyl}piperazin-1-yl)-2-(1H-pyrrolo[2,3-b]pyridin-1-yl)ethanone;
1-(4-{4-fluoro-2-[2-(4-hydroxypiperidin-1-yl)pyrimidin-5-yl]phenyl}piperazin-1-yl)-2-(3H-imidazo[4,5-b]pyridin-3-yl)ethanone;
1-[4-(4-fluoro-2-{2-[4-(methylsulfonyl)piperidin-1-yl]pyrimidin-5-yl}phenyl)piperazin-1-yl]-2-(1H-pyrrolo[2,3-c]pyridin-1-yl)ethanone;
1-[2-(4-{4-fluoro-2-[2-(4-hydroxypiperidin-1-yl)pyrimidin-5-yl]phenyl}piperazin-1-yl)-2-oxoethyl]-1,3-dihydro-2H-benzimidazol-2-one;
1-[4-(4-fluoro-2-{2-[4-(methylsulfonyl)piperidin-1-yl]pyrimidin-5-yl}phenyl)piperazin-1-yl]-2-(1H-pyrrolo[2,3-b]pyridin-1-yl)ethanone;
2-{2-[4-(4-fluoro-2-{2-[4-(methylsulfonyl)piperidin-1-yl]pyrimidin-5-yl}phenyl)piperazin-1-yl]-2-oxoethyl}-2,3-dihydro-1H-isoindol-1-one;
2-(3,5-dimethyl-1H-pyrazol-1-yl)-1-(4-{4-fluoro-2-[2-(4-hydroxypiperidin-1-yl)pyrimidin-5-yl]phenyl}piperazin-1-yl)ethanone;
2-[2-(4-{4-fluoro-2-[2-(4-hydroxypiperidin-1-yl)pyrimidin-5-yl]phenyl}piperazin-1-yl)-2-oxoethyl]-2,3-dihydro-1H-isoindol-1-one;
1-(4-{4-fluoro-2-[2-(4-hydroxypiperidin-1-yl)pyrimidin-5-yl]phenyl}piperazin-1-yl)-2-(1H-pyrrolo[2,3-c]pyridin-1-yl)ethanone;
1-[4-(4-fluoro-2-{2-[4-(methylsulfonyl)piperidin-1-yl]pyrimidin-5-yl}phenyl)piperazin-1-yl]-2-(3H-imidazo[4,5-b]pyridin-3-yl)ethanone;
1-{4-[4-fluoro-2-(2-methoxypyrimidin-5-yl)phenyl]piperazin-1-yl}-2-(1H-pyrrolo[2,3-b]pyridin-1-yl)ethanone;
1-[2-(4-{4-fluoro-2-[2-(morpholin-4-yl)pyrimidin-5-yl]phenyl}piperazin-1-yl)-2-oxoethyl]-1,3-dihydro-2H-benzimidazol-2-one;
2-(3,5-dimethyl-1H-pyrazol-1-yl)-1-[4-(4-fluoro-2-{2-[4-(methylsulfonyl)piperidin-1-yl]pyrimidin-5-yl}phenyl)piperazin-1-yl]ethanone;
1-(2-{4-[4-fluoro-2-(2-methoxypyrimidin-5-yl)phenyl]piperazin-1-yl}-2-oxoethyl)-1,3-dihydro-2H-benzimidazol-2-one;
1-{4-[4-fluoro-2-(2-methoxypyrimidin-5-yl)phenyl]piperazin-1-yl}-2-(1H-pyrrolo[2,3-c]pyridin-1-yl)ethanone;
1-(4-{4-fluoro-2-[2-(morpholin-4-yl)pyrimidin-5-yl]phenyl}piperazin-1-yl)-2-(1H-pyrrolo[2,3-c]pyridin-1-yl)ethanone;
1-[2-(4-{4-fluoro-2-[2-(4-methylpiperazin-1-yl)pyrimidin-5-yl]phenyl}piperazin-1-yl)-2-oxoethyl]-1,3-dihydro-2H-benzimidazol-2-one;
1-(4-{4-fluoro-2-[2-(pyrrolidin-1-yl)pyrimidin-5-yl]phenyl}piperazin-1-yl)-2-(3H-imidazo[4,5-b]pyridin-3-yl)ethanone;
1-[2-(4-{4-fluoro-2-[2-(pyrrolidin-1-yl)pyrimidin-5-yl]phenyl}piperazin-1-yl)-2-oxoethyl]-1,3-dihydro-2H-benzimidazol-2-one;
1-(4-{4-fluoro-2-[2-(pyrrolidin-1-yl)pyrimidin-5-yl]phenyl}piperazin-1-yl)-2-(1H-pyrrolo[2,3-c]pyridin-1-yl)ethanone;
1-(4-{4-fluoro-2-[2-(morpholin-4-yl)pyrimidin-5-yl]phenyl}piperazin-1-yl)-2-(1H-pyrrolo[2,3-b]pyridin-1-yl)ethanone;

1-{2-[4-(4-fluoro-2-{2-[4-(methylsulfonyl)piperidin-1-yl]pyrimidin-5-yl}phenyl)piperazin-1-yl]-2-oxoethyl}piperidin-2-one;

2-[2-(4-{4-fluoro-2-[2-(pyrrolidin-1-yl)pyrimidin-5-yl]phenyl}piperazin-1-yl)-2-oxoethyl]-2,3-dihydro-1H-isoindol-1-one;

1-(4-{4-fluoro-2-[2-(pyrrolidin-1-yl)pyrimidin-5-yl]phenyl}piperazin-1-yl)-2-(1H-pyrrolo[2,3-b]pyridin-1-yl)ethanone;

1-[2-(4-{4-fluoro-2-[2-(4-hydroxypiperidin-1-yl)pyrimidin-5-yl]phenyl}piperazin-1-yl)-2-oxoethyl]piperidin-2-one;

2-(3,5-dimethyl-1H-pyrazol-1-yl)-1-(4-{4-fluoro-2-[2-(pyrrolidin-1-yl)pyrimidin-5-yl]phenyl}piperazin-1-yl)ethanone;

1-(4-{4-fluoro-2-[2-(4-methylpiperazin-1-yl)pyrimidin-5-yl]phenyl}piperazin-1-yl)-2-(1H-pyrrolo[2,3-b]pyridin-1-yl)ethanone;

2-[2-(4-{4-fluoro-2-[2-(morpholin-4-yl)pyrimidin-5-yl]phenyl}piperazin-1-yl)-2-oxoethyl]-2,3-dihydro-1H-isoindol-1-one;

1-[2-(4-{4-fluoro-2-[2-(pyrrolidin-1-yl)pyrimidin-5-yl]phenyl}piperazin-1-yl)-2-oxoethyl]piperidin-2-one;

1-(4-{4-fluoro-2-[2-(morpholin-4-yl)pyrimidin-5-yl]phenyl}piperazin-1-yl)-2-(3H-imidazo[4,5-b]pyridin-3-yl)ethanone;

2-[2-(4-{4-fluoro-2-[2-(4-methylpiperazin-1-yl)pyrimidin-5-yl]phenyl}piperazin-1-yl)-2-oxoethyl]-2,3-dihydro-1H-isoindol-1-one;

1-[2-(4-{4-fluoro-2-[2-(morpholin-4-yl)pyrimidin-5-yl]phenyl}piperazin-1-yl)-2-oxoethyl]piperidin-2-one;

2-(3,5-dimethyl-1H-pyrazol-1-yl)-1-(4-{4-fluoro-2-[2-(4-methylpiperazin-1-yl)pyrimidin-5-yl]phenyl}piperazin-1-yl)ethanone;

1-(4-{4-fluoro-2-[2-(4-methylpiperazin-1-yl)pyrimidin-5-yl]phenyl}piperazin-1-yl)-2-(3H-imidazo[4,5-b]pyridin-3-yl)ethanone;

1-[2-(4-{4-fluoro-2-[2-(methylsulfonyl)pyrimidin-5-yl]phenyl}piperazin-1-yl)-2-oxoethyl]-1,3-dihydro-2H-benzimidazol-2-one;

1-{4-[4-fluoro-2-(2-methoxypyrimidin-5-yl)phenyl]piperazin-1-yl}-2-(3H-imidazo[4,5-b]pyridin-3-yl)ethanone;

1-(4-{4-fluoro-2-[2-(methylsulfonyl)pyrimidin-5-yl]phenyl}piperazin-1-yl)-2-(1H-pyrrolo[2,3-b]pyridin-1-yl)ethanone;

1-[2-(4-{4-fluoro-2-[2-(4-methylpiperazin-1-yl)pyrimidin-5-yl]phenyl}piperazin-1-yl)-2-oxoethyl]piperidin-2-one;

1-(2-{4-[4-fluoro-2-(2-methoxypyrimidin-5-yl)phenyl]piperazin-1-yl}-2-oxoethyl)piperidin-2-one;

2-[2-(4-{4-fluoro-2-[2-(methylsulfonyl)pyrimidin-5-yl]phenyl}piperazin-1-yl)-2-oxoethyl]-2,3-dihydro-1H-isoindol-1-one;

2-(3,5-dimethyl-1H-pyrazol-1-yl)-1-(4-{4-fluoro-2-[2-(methylsulfonyl)pyrimidin-5-yl]phenyl}piperazin-1-yl)ethanone;

1-(4-{4-fluoro-2-[2-(methylsulfonyl)pyrimidin-5-yl]phenyl}piperazin-1-yl)-2-(3H-imidazo[4,5-b]pyridin-3-yl)ethanone;

1-[2-(4-{4-fluoro-2-[2-(methylsulfonyl)pyrimidin-5-yl]phenyl}piperazin-1-yl)-2-oxoethyl]piperidin-2-one;

or a pharmaceutically acceptable salt thereof.

\* \* \* \* \*